US011248234B2

(12) United States Patent
Tresch et al.

(10) Patent No.: US 11,248,234 B2
(45) Date of Patent: *Feb. 15, 2022

(54) HERBICIDE-RESISTANT HYDROXYPHENYLPYRUVATE DIOXYGENASES

(71) Applicant: BASF SE, Ludwigshafen (DE)

(72) Inventors: Stefan Tresch, Neustadt Hambach (DE); Maciej Pasternak, Ludwigshafen (DE); Liliana Parra Rapado, Offenburg (DE); Jill M. Paulik, Apex, NC (US); Jens Lerchl, Limburgerhof (DE); Gilbert Besong, Bad Duerkheim (DE); Markus Kordes, Frankenthal (DE); Thomas Mietzner, Annweiler (DE); Eva Stauffer, Maxdorf (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/549,499

(22) PCT Filed: Feb. 10, 2016

(86) PCT No.: PCT/EP2016/052835
§ 371 (c)(1),
(2) Date: Aug. 8, 2017

(87) PCT Pub. No.: WO2016/128470
PCT Pub. Date: Aug. 18, 2016

(65) Prior Publication Data
US 2018/0023060 A1  Jan. 25, 2018

Related U.S. Application Data

(60) Provisional application No. 62/114,618, filed on Feb. 11, 2015.

(51) Int. Cl.
*C12N 15/82* (2006.01)
*C12N 9/02* (2006.01)

(52) U.S. Cl.
CPC ....... *C12N 15/8274* (2013.01); *C12N 9/0069* (2013.01)

(58) Field of Classification Search
None
See application file for complete search history.

(56) References Cited

U.S. PATENT DOCUMENTS

| | | | |
|---|---|---|---|
| 5,349,127 A | 9/1994 | Dean et al. | |
| 6,121,512 A | 9/2000 | Siminszky et al. | |
| 6,245,968 B1 | 6/2001 | Boudec et al. | |
| 6,300,544 B1 | 10/2001 | Halkier et al. | |
| 6,380,465 B1 | 4/2002 | Barrett | |
| 6,649,814 B2 | 11/2003 | Halkier et al. | |
| 6,653,529 B2 | 11/2003 | Peng et al. | |
| 10,619,138 B2 * | 4/2020 | Tresch | A01N 43/80 |
| 2009/0011936 A1 | 1/2009 | Hawkes et al. | |
| 2009/0049567 A1 | 2/2009 | Olhoft et al. | |
| 2009/0172831 A1 | 7/2009 | Andrews et al. | |
| 2011/0023180 A1 * | 1/2011 | Hawkes | C12N 9/0004 800/278 |
| 2011/0039706 A1 * | 2/2011 | Busch | C12Y 113/11027 504/348 |
| 2013/0053243 A1 * | 2/2013 | Mietzner | C12N 15/8274 504/130 |
| 2014/0259213 A1 * | 9/2014 | Lange | C12N 9/0008 800/278 |
| 2016/0376567 A1 * | 12/2016 | Tresch | C12N 9/0069 504/271 |

FOREIGN PATENT DOCUMENTS

| | | |
|---|---|---|
| EP | 0173657 A2 | 3/1986 |
| WO | WO-1996/38567 A2 | 12/1996 |
| WO | WO-2007/000077 A1 | 1/2007 |
| WO | WO-2008/124495 A2 | 10/2008 |
| WO | WO-2011/035874 A1 | 3/2011 |
| WO | WO-2012/028579 A1 | 3/2012 |
| WO | WO-2013/064964 A1 | 5/2013 |
| WO | WO-2013/072300 A1 | 5/2013 |
| WO | WO-2013/072402 A1 | 5/2013 |
| WO | WO-2013/076315 A2 | 5/2013 |
| WO | WO-2013/083859 A2 | 6/2013 |
| WO | WO-2013/092551 A1 | 6/2013 |

(Continued)

OTHER PUBLICATIONS

International Patent Application No. PCT/EP2016/052835, International Search Report and Written Opinion, 19 pp., dated Jul. 4, 2016.
International Patent Application No. PCT/EP2016/052835, International Preliminary Report on Patentability, dated Aug. 15, 2017.
Matringe et al., p-Hydroxyphenylpyruvate dioxygenase inhibitor-resistant plants, Pest Manag. Sci., 61(3):269-76 (2005).
Mitchell et al., Mesotrione: a new selective herbicide for use in maize, Pest Manag. Sci., 57(2):120-8 (2001).
Schulz et al., SC-0051, a 2-benzoyl-cyclohexane-1,3-dione bleaching herbicide, is a potent inhibitor of the enzyme p-hydroxyphenylpyruvate dioxygenase, FEBS Lett., 318(2):162-6 (1993).

*Primary Examiner* — Ashley K Buran
(74) *Attorney, Agent, or Firm* — Marshall, Gerstein & Borun LLP

(57) ABSTRACT

The present invention refers to method for producing a transgenic plant with increased herbicide tolerance or resistance as compared to a corresponding non-transformed wild type plant, comprising transforming a plant cell or a plant cell nucleus or a plant tissue with a nucleic acid molecule encoding a mutated HPPD polypeptide, as well as to the nucleic acid, and plants with increased HPPD-inhibiting herbicide tolerance or resistance comprising the nucleic acid of the invention.

7 Claims, 7 Drawing Sheets
Specification includes a Sequence Listing.

(56) References Cited

FOREIGN PATENT DOCUMENTS

WO   WO-2014/177992  A2   11/2014
WO   WO-2015/022634  A2   2/2015

* cited by examiner

Figure 1

```
                            10        20        30        40        50        60        70
Scenedesmus        .......................MGAGGAQGPKVELVGYANFVRNNPRSDKFPVHKFHHIEFWCADATN
ScenedesmusShort   .......................MGAGGAQGPKVELVGYANFVRNNPRSDKFPVHKFHHIEFWCADATN
Helianthus         ............MG.TEATVAAVVAGDESDHPTSAFKLVGFKNFIRTNPMSDKFTVKNFHHIEFWCSDATN
HelianthusMutant   ............MG.TEATVAAVVAGDESDHPTSAFKLVGFKNFIRTNPMSDKFTVKNFHHIEFWCSDATN
Lemna              ........MAEEEGVEARAAKLDDSVNSGAAADGFQLVGFSNFVRRNPRSDRFHAKSFHHVEFWCADATN
Belliella          ....................................MEQDFLPLLGTDYVELYVGNAKQ
Nitritalea         ....................................MEQDFLPINGTDYVEFYVGNAKQ
Pontibacter        ....................................MATDILPLNGTDHIEFYVGNAKQ
Ferroplasma        ....................................MYNNDELFKKINHIEFYVSSAKT
Microscilla        ....................................MEQAHDFLPIIGTDHLEFYVGNAKQ
Algoriphagus       ....................................MTEDFLPINGTDYVELYVGNAKQ
Frankia            .............MSTEVTLTGQERSAELDVDQLRQLVGLVEHDPAGDPFPVSGWDAVVWVGNAKQ
Herpetosiphon      ....................MTMAEQETTNAHDPLALRGIDYVEMYVGNARQ
Mucilaginibacter   MTLTTITDTLSLTNPELAEQLKQTKHTITYMETTFVNALPAVENLGQLNNDFLPLNGTDYVEFYVGNAKQ
Acidobacterium     .....................................MSTLVHPEVATQKDFLPLNGTDHVEFYVGNAKQ
Geodermatophilus|  .............MSLEQALNDDERLAQLDLDQLKQLVGLVEYDASGDPFPVSGWDALVWVGNATQ
Hordeum            ...........MPPTPTTPAATGAAAAVTPEHARPHRMVRFNPRSDRFHTLSFHHVEFWCADAAS
Arabidopsis        ..........MGHQNAAVSENQNHDDGAASSPGFKLVGFSKFVRKNPKSDKFKVKRFHHIEFWCGDATN 80        90        100       110       120       130       140
Scenedesmus        TFKRFQHGLGMTLVAKSDHSTGNSKYCSYVLQSNDLVFTFTAPYSRKCAAAAP..SSSEPLPDYDQQQAF
ScenedesmusShort   TFKRFQHGLGMTLVAKSDHSTGNSKYCSYVLQSNDLVFTFTAPYSRKCAAAAP..SSSEPLPDYDQQQAF
Helianthus         TARRFSWGLGMPIIFKSDLSTGNSTHASYLLRSGHLNFLFTAPYSPSISP....TTTTASIPTFSHSASR
HelianthusMutant   TARRFSWGLGMPIIFKSDLSTGNSTHASYLLRSGQLNFLFTAPYSPSIS.....TTTTASIPTFSHSASR
Lemna              VSRRFSFGLGMPLAAKSDLSTGNSSHASYMIRSRDLRFLFTAPLSSSAAD......SKSAIPSFDSDACR
Belliella          SALYYQYAFGYELIAYAGPETGIKDRASYVLKQDKIRLVLTTPLQ..................ENHPIA
Nitritalea         SALYYQYAFGYELIAYAGPETGVKDRASYVLKQDKIRLVLTTALQ..................AEHPIA
Pontibacter        AAHFYQTAFGFKLIAYAGPETGVRDRASYVLQQEKIRLVLTTSLD..................PNSDIA
Ferroplasma        WSYFMERGLGLDLKAYSGLETGNRGKSSYVLNKGDINLVFSSSME..................KHSEIN
Microscilla        SAYFYQSAFGYQLVGYAGPETGVRDRASYVLKQGKVRLVLTTAMH..................PSSEVS
Algoriphagus       SALYYQYAFGFELIAYAGPETGIKDRASYVLKQDKIRIVLTTPLS..................PDNPIT
Frankia            AAHYYQSAFGMDLVAYSGPETGQPDHCSYVLTSGAVRFVFKGGVR..................PDSPLL
Herpetosiphon      AAHYYRTAFGFTPVAYAGLETGTRDRVSFVMQQRNIRLVLTGALN..................PDSPIA
Mucilaginibacter   AAHFYKTAFGFQSLAYAGPETGVRDRASYVLQQDKIRLVLTTPMH..................SDHPIA
Acidobacterium     AAYFYRVAFGFQLVAYAGPETGVRDRASYVLQQNKIRFVLTTPLR..................PDGEIA
Geodermatophilus   AAHFHQSAFGMELVAYSGPETGNRDHLAYVLESGAARFVVRGAYD..................PASPLA
Hordeum            AAGRFAFALGAPLAARSDLSTGNSAHASQLLRSGSLAFLFTAPYANGCDA......ATASLPSFSADAAR
Arabidopsis        VARRFSWGLGMRFSAKSDLSTGNMVHASYLLTSGDLRFLFTAPYSPSLSAGEIKPTTTASIPSFDHGSCR 150       160       170       180       190       200       210
Scenedesmus        EFICTHGLAARAVGLQVGDAAQAYEVSVANGAKGVRPPTKLEDGGGCAVVSEVLLYCDVVLRYISGK...
ScenedesmusShort   EFICTHGLAARAVGLQVGDAAQAYEVSVANGAKGVRPPTKLEDGGGCAVVSEVLLYCDVVLRYISGK...
Helianthus         HFTATHGLAVRAIAVEVEDAETAFAVSVANGAKPSSPPVTLGH..NDVVLSEVKLYCDVVLRYVSYKNNT
HelianthusMutant   HFTATHGLAVRAIAVEVEDAETAFAVSVANGAKPSSPPVTLGH..NDVVLSEVKLYCDVVLRYVSYKNNT
Lemna              RFSNLHGLAVRAVALQVADAAAAFHVSVQNGARPAFPPADLG....GAVISEVELYCDVVLRFLSLG...
Belliella          DHIKKHGDGVKVLALWVEDAKKSWLETTSRGAVSYEEPRTIKDENGEVVVASIRTYCETIHTFIERK...
Nitritalea         EHVKTHGDGVKVLALWVDDARKSFEETTKRGAKAYQEPTVLQDEHGEVVISGIHTYCETVHLFVERS...
Pontibacter        QHVHQHGDGVKVLALWVDDAEASFRGTVERGAKPAMEPKTLTDEHGEKVVASIHTYCDTIHTFVERK...
Ferroplasma        DSISLHGDGVRDISLEVDDIEFTKKHLESRNIKVS.SIKEEKDDNGKIRRAVMQTYCDTIHTMIEKG...
Microscilla        EHVKKHGDGVKVLAIQVENAYQAYEETVKRGAKSAIEPHTLTDEYGEIKIAAIHIYCETIHKFVERT...
Algoriphagus       QHIAKHGDGVKVLALWVDDAEKSWKETTSRGAQSAIEPHVLSDANGEVKVASIKTYCETIHTFVERK...
Frankia            DHHRRHGDGVVDIALEVPDVDRCIAHARAQGARVIEEPHELRDEHGVVRLAAIAAYCRTRHTLVDRS...
Herpetosiphon      EHVKLHGDGVKDIALEVENATAAFEAALARGATAVLEPTVLESKWGKVVKATIRTYCHTVHTFVERD...
Mucilaginibacter   EHIKKHGDGVKVLALWVDDAYDAFKQTVSRGAKPFQEPQTITDEHGEVRTSGIYLYCETVHLFVERK...
Acidobacterium     AHIHLHGDGIRDVALWVDDARQAWKETTKRGARSVREPFELKDEHGTVKMASIAAYCDTVHTFVERG...
Geodermatophilus   DHHRKHGDGIVDIALSVPDVDRCIAHAAAQGATVLEQPHDISDEFGTVRIGAIATYCDTRHTLVDRS...
Hordeum            RFSADHGIAVRSVALRVADAAEAFRASVDGGARPAFAPVDLG...RGFGFAEVELYCDVVLRFVSHP...
Arabidopsis        SFFSSHGLGVRAVAIEVEDAESAFSISVANGAIPSSPPIVLN..EAVTIAEVKLYCDVVLRYVSYK...
```

Figure 1 continued

```
                       220       230       240       250       260       270       280
Scenedesmus       ........WEGPYLPGYTATP...DEPQICYG..LHRLDHAVGNVP..KLIEHLEHVIGFTGFHEFAEFV
ScenedesmusShort  ........WEGPYLPGYTATP...DEPQICYG..LHRLDHAVGNVP..KLIEHLEHVIGFTGFHEFAEFV
Helianthus        NNNNNNDNDNYIFLPGFEAMDKTSSFQELDYG..IRRLDHAVGNVP..ELAPAVDYVKSFTGFHEFAEFT
HelianthusMutant  NNDNNNDNDNYIFLPGFEAMDKTSSFQELDYG..IRRLDHAVGNVP..ELAPAVDYVKSFTGFHEFAEFT
Lemna             ......SGEKFQFLPGFEDLSP..NSADLDYG..IRRLDHAVGNVP..ELAPAAAYVKKFTGFHEFAEFT
Belliella         .......NYHGIFLPGYKPRKSEYKPTSIG....LKYIDHCVGNVGWGEMNKWVKFYEDVMGFKLLITFD
Nitritalea        .......NYSGIFLPGYVPRQSTYKPEPIG....LKYIDHCVGNVGWGEMNTWVEFYEKVMGFNLLITFD
Pontibacter       .......NYNGVFMPGYVARQSQLDIESVG....LKYVDHCVGNVELGQMNEWVKFYEDVMGFKLLLTFD
Ferroplasma       .......DYKG.FLPGY..REEDTHTADTG....IYKVDHVVGNVYEGEMDQWVNYYIKNMNFSQLVTFD
Microscilla       .......NYNGVFMPGYEPREG.IKANPVG....LKHVDHCVGNVELGEMDKWVKFYEDVMGFKLLLTFD
Algoriphagus      .......NYNGTFLPGYIPRKSLYNSQSIG....LKYIDHCVGNVELGEMNRWVKFYEDVMGFKLLITFD
Frankia           .......RYSGCYLPGYVERRSGHVRRPGAPRSLFQALDHVVGNVELGAMDEWVAFYNRVMGFTNLAEFI
Herpetosiphon     .......GYTGTFMPGYNKVKNPAKAEPTG....LAAVDHIVGNVELGKMDEWVNFYARILGFSQLQQFT
Mucilaginibacter  .......NYNGPFLPGYQKMKSTYNPEPTG....LLYVDHCVGNVGWNKMNQWVNFYEDVLGFKNILTFD
Acidobacterium    .......SYHGVFLPGYRAEAEDTIARPTG....LLHVDHMVGNVGWNEMNRWVDFYADIMGFSLYQHFD
Geodermatophilus  .......RYTGPYLPGYVERRSSHVKRDGAPKRLFQAVDHVVGNVELGAMDRWVEFYNRVMGFTNMAEFV
Hordeum           ......DGTDVPFLPGFEGVT...NPDAVDYG..LTRFDHVVGNVP..ELAPAAAYIAGFTGFHEFAEFT
Arabidopsis       ....AEDTEKSEFLPGFERVEDASSFP.LDYG..IRRLDHAVGNVP..ELGPALTYVAGFTGFHQFAEFT 290       300       310       320       330       340       350
Scenedesmus       AEDVGTVDSGLNSMVLASNNEMVLLPMNEPTFGTKRKSQIQTYLEQNEGPGLQHLALKTHDILSTMREMH
ScenedesmusShort  AEDVGTVDSGLNSMVLASNNEMVLLPMNEPTFGTKRKSQIQTYLEQNEGPGLQHLALKTHDILSTMREMH
Helianthus        AEDVGTSESGLNSVVLACNSEMVLIPMNEPVYGTKRKSQIQTYLEHNEGAGVQHLALASEDIFRTLREMR
HelianthusMutant  AEDVGTSESGLNSVVLACNSEMVLIPMNEPVYGTKRKSQIQTYLEHNEGAGVQHLALASEDIFRTLREMR
Lemna             ADDVGTAESGLNSVVLANNDENVLLPLNEPVHGTPRRSQIQTYLDHNEGPGLQHLALSSEDVIATLRKMR
Belliella         DKDISTEYSALMSKVVSNGNGYIKFPINEPAEGK.KKSQIEEYLDFYNGSGVQHMAIATDDIVHTVSELR
Nitritalea        DKDISTDYTALMSKVVSNGNGFIKFPINEPAEGK.KKSQIEEYIDFYQGAGVQHLAIATDDIIHTVSELR
Pontibacter       DKDISTEYTALMSKVVSNGNGYIKFPINEPAEGK.KKSQIEDEYLEFYKGAGVQHIAVATNDILHTVAELR
Ferroplasma       DKMIRTDYSALRSKVVKYNDN.IVFPINEPAQGL.KKSQIQEYLDYYNSQGVQHIALKTDNIIETVSKMK
Microscilla       DKDISTEYTALMSKVVSNGNGYIKFPINEPAEGR.KKSQIEEYLDFYQGAGVQHIAVATDDILHTVGELR
Algoriphagus      DSDISTEYSALMSKVVSNGNGYIKFPINEPAEGK.KKSQIEEYLDFYHGPGVQHMAIATDDIIYTVSELR
Frankia           GGDIATRYSALMSKVVASGNHRVKFPLNEPAPGR.RKSQIAEYLEFHGGPGAQHLALATGDILASVDAMR
Herpetosiphon     DDDISTEYSALMSKVVQNGTGRIKFPINEPAEGR.KKSQIDEYLDYYRGPGAQHIALITPDIIKTVQQLR
Mucilaginibacter  DKAISTEYSALMSKVMSNGNGYVKFPINEPAEGK.KKSQIEEYLEFYEGEGVQHLALATHDIVDTVTKLQ
Acidobacterium    DKDISTEYSALMSKVMANGNGRVKFPLNEPAEGR.RKSQIEEYLEFYHGPGVQHVAMATHDILETVSKLQ
Geodermatophilus  GEDIATDYSALMSKVVANGNHRVKFPLNEPAIGK.KKSQIDEYLEFYGGPGAQHVALATNDILTTVDALR
Hordeum           AEDVGITESGLNSVVLANNSEGVLLPLNEPVHGTKRRSQIQTFLEHHGGPGVQHIAVASSDVLRTLRKMR
Arabidopsis       ADDVGTAESGLNSAVLASNDEMVLLPINEPVHGTKRKSQIQTYLEHNEGAGLQHLALMSEDIFRTLREMR 360       370       380       390       400       410       420
Scenedesmus       ARSRCGGFELQAAPGHDYYKRVAEKVGDVLSPEEWAAVEQLGILVDQDDQGVLLQIFTKPLGDRPTIFIE
ScenedesmusShort  ARSRCGGFELQAAPGHDYYKRVAEKVGDVLSPEEWAAVEQLGILVDQDDQGVLLQIFTKPLGDRPTIFIE
Helianthus        KRSGVGGFELMPSPPPTYYRNLKSRAGDVLSDEQIKECEELGILVDRDDQGTLLQIFTKPVGDRPTIFIE
HelianthusMutant  KRSGVGGFELMPSPPPTYYRNLKSRAGDVLSDEQIKECEELGILVDRDDQGTLLQIFTKPVGDRPTIFIE
Lemna             AASALGGFELMPPPPPTYYRNLRKRAKDVLTEDQMVACEELGILVDRDDQGILLQIFTKPVGDRPTIFLE
Belliella         KR....GVEFLEVP.SSYYDD..LLDRVGKIDEDLQPLKDLNILVDRDDEGYLLQIFTKPIQDRPTLFFE
Nitritalea        RR....GVEFLEVP.NTYYDD..LLDRVGSIDEDLQPLKDLNILVDRDDEGYLLQIFTKPVQDRPTVFYE
Pontibacter       RR....GVEFLYVP.ETYYED..LIERIGHIDEDMEDLRKLNILVDRDDEGYLLQIFTKPVEDRPTVFYE
Ferroplasma       QN....GIQFLQTP.ASYYDT..LTERVGNVDEDIEELKKLNILVDRDDDGYLLQIFTKPLTDRPTVFFE
Microscilla       NR....GVDFLHVP.DNYYED..LEQRVGKVDEDMDDLRKLNILVDRDDEGYLLQIFTKPVGDRPTVFYE
Algoriphagus      KR....GVEFLEVP.QSYYDD..LLDRVGKIDEDLQPLKDLNILVDRDDEGYLLQIFTKPVQDRPTLFFE
Frankia           AG....GVEFLDTP.DTYYDDPALWARVGEVRAPVEELRRRRILVDRDDEGYLLQIFTKPLCDRPTVFFE
Herpetosiphon     DN....GVEFLRTP.DTYYSA..LAGRVGHIDEDYNTLQQLGILVDRDDEGYLLQIFTKPVGDRPTVFYE
Mucilaginibacter  SR....GIEFLTVP.TTYYDT..LTERVGHIDENLEPLKQLGILVDRDDEGYLLQIFTKPVEDRPTVFFE
Acidobacterium    AQ....GVAFLKVP.HSYYTE..LEGRVGKIDEPIEELEKLGILVDRDDEGYMLQIFTKPVEDRPTLFYE
Geodermatophilus  AE....GIEFLATP.DSYYEDPELRARIGEVRAPIEELQERGVLVDRDEDGYLLQIFTKPLCDRPTVFFE
Hordeum           ARSAMGGFDFLPPPLPKYYEGVRRLAGDVLSEAQIKECQELGVLVDRDDQGVLLQIFTKPVGDRPTLFLE
Arabidopsis       KRSSIGGFDFMPSPPPTYYQNLKKRVGDVLSDDQIKECEELGILVDRDDQGTLLQIFTKPLGDRPTIFIE
```

Figure 1 continued

```
                      430       440       450       460       470       480       490
Scenedesmus       IIERRCCLKESAAQAGSAAAAAAEPTAAGGDADADGAAAAVADKFKDIVQVREDGVVVEQAAGCGGFGKG
ScenedesmusShort  IIERRCCLKESAAQAGSAAAA............................VEQAAGCGGFGKG
Helianthus        IIQRVCCMVKDDEGK..................................VQQKAGCGGFGKG
HelianthusMutant  IIQRVCCMVKDDEGK..................................VQQKAGCGGFGKG
Lemna             IIQRICCMMKDEAGK..................................EYQKGGCGGFGKG
Belliella         IIQRKCAK..........................................................SFGKG
Nitritalea        IIQRKCAK..........................................................SFGKG
Pontibacter       IIQRKCAK..........................................................SFGKG
Ferroplasma       VIERKCAK..........................................................SFGAG
Microscilla       IIQRKCAK..........................................................SFGKG
Algoriphagus      IIQRKCAK..........................................................SFGKG
Frankia           LIERHCSL..........................................................GFGKG
Herpetosiphon     IIQRKCSR..........................................................CFGAG
Mucilaginibacter  IIQRKCAK..........................................................SFGAG
Acidobacterium    IIQRKCSR..........................................................SFGKG
Geodermatophilus  LIERHCSL..........................................................GFGIG
Hordeum           MIQRICCMEKDERGE..................................EYQKGGCGGFGKG
Arabidopsis       IIQRVCCMMKDEEGK..................................AYQSGGCGGFGKG 500       510
Scenedesmus       NFSELFKSIEEYERTLQV......... SEQ ID NO:2
ScenedesmusShort  NFSELFKSIEEYERTLQV......... SEQ ID NO:4
Helianthus        NFSELFKSIEEYEKTLEARSTTAAA.. SEQ ID NO:6
HelianthusMutant  NFSELFKSIEEYEKTLEARSTTAAA.. SEQ ID NO:8
Lemna             NFTELFKSIEDYEKSLEAKQAGTRF.. SEQ ID NO:10
Belliella         NFKALFEAIEREQELRGNL........ SEQ ID NO:12
Nitritalea        NFKALFEAIEREQELRGNL........ SEQ ID NO:14
Pontibacter       NFKALFEAIEREQALRGNL........ SEQ ID NO:16
Ferroplasma       NFKALFESIERDQAMRGNL........ SEQ ID NO:18
Microscilla       NFKALFEAIEREQAVRGNL........ SEQ ID NO:20
Algoriphagus      NFKALFEAIEREQELRGNL........ SEQ ID NO:22
Frankia           NFQALFEAIEREQERRGNL........ SEQ ID NO:24
Herpetosiphon     NFKALFEAIEREQAKRGNL........ SEQ ID NO:26
Mucilaginibacter  NFKALFEAIEREQELRGNL........ SEQ ID NO:28
Acidobacterium    NFKALFEAIEREQELRGNL........ SEQ ID NO:30
Geodermatophilus  NFKALFEAIEREQHKRGNF........ SEQ ID NO:32
Hordeum           NFSELFKSIEDYEKSLEAKQSAAVQGS SEQ ID NO:40
Arabidopsis       NFSELFKSIEEYEKTLEAKQLVG.... SEQ ID NO:42
```

X non conserved
X ≥ 50% conserved
X all match

SEQUENCE LISTING

```
<160> NUMBER OF SEQ ID NOS: 46

<210> SEQ ID NO 1
<211> LENGTH: 1395
<212> TYPE: DNA
<213> ORGANISM: Scenedesmus

<400> SEQUENCE: 1
atgggcgcag gtggagctca gggcccgaag gttgagctgg ttggctacgc caatttcgtt      60
cgcaacaacc ctcgcagcga taagttccct gtgcacaagt ttcaccacat cgagttttgg     120
tgcgcggacg ccaccaacac cttcaagcgc ttccagcatg gcctgggcat gaccctagtg     180
gccaagtccg accacagcac aggcaacagc aagtactgca gctacgtctt gcaaagcaac     240
gacctcgtgt tcaccttcac agcaccctac tcgcgcaagt gcgcagcagc agcgccttct     300
agcagcgagc cgctgccaga ttatgaccag cagcaggcct ttgaattcat ctgcacccac     360
ggcctggcgg caagggctgt aggcctgcag gtgggcgatg cagcgcaggc gtacgaggtt     420
tctgtggcaa acggcgcgaa gggtgtgcgt ccacccacca agctggagga tggcggcggc     480
tgtgctgtgg tcagcgaggt gctgctgtat ggtgacgtgg tgctgcgcta catcagcggc     540
aagtgggagg gcccctacct gccgggctac acagccacgc ctgatgagcc gcagatctgc     600
tacggcctgc accgcctgga ccacgccgtg ggcaatgtgc ccaagctcat cgagcacttg     660
gagcacgtca ttggcttcac aggcttccac gagtttgccg agtttgtggc ggaggacgtg     720
ggcactgtgg acagcgggct gaacagcatg gtgctggcca gcaacaacga gatggtgctg     780
ctgcccatga cgagcccac ctttggcacc aagcgcaagt cgcagatcca gacgtacctg     840
gagcagaacg agggccccgg gctgcagcac ctggcgctga gacgcacga catcctgtcc     900 accatgcgcg agatgcacgc acgctcgcgc tgcggcggct tcgagttcca ggcggcaccc     960
gggcacgact actacaagcg cgtggcggag aaagtgggtg acgtgctgtc cccggaggag    1020
tgggcagccg ttgagcagct gggcatcctg gtggaccagg acgaccaggg cgtgctgctg    1080
cagatcttca ccaagccgct ggggacagg cccaccatct tcattgagat cattgagcgg    1140
```

```
cgcggctgcc tcaaggagag cgcggcacag gcaggcagtg cggcagcagc agcagcagag    1200
cctacagcag ctggcggtga tgcagatgca gatggagcag cagcagcagt ggctgacaag    1260
ttcaaagaca tcgtgcaggt gcgtgaggat ggcgtggttg tggagcaagc tgctggctgt    1320
ggaggcttcg gcaaaggcaa cttcagcgag ctgttcaaaa gcattgagga gtacgagcgc    1380
acgctgcagg tgtaa                                                     1395
```

<210> SEQ ID NO 2
<211> LENGTH: 464
<212> TYPE: PRT
<213> ORGANISM: Scenedesmus

<400> SEQUENCE: 2

```
Met Gly Ala Gly Gly Ala Gln Gly Pro Lys Val Glu Leu Val Gly Tyr
1               5                   10                  15

Ala Asn Phe Val Arg Asn Asn Pro Arg Ser Asp Lys Phe Pro Val His
                20                  25                  30

Lys Phe His His Ile Glu Phe Trp Cys Ala Asp Ala Thr Asn Thr Phe
            35                  40                  45

Lys Arg Phe Gln His Gly Leu Gly Met Thr Leu Val Ala Lys Ser Asp
50                  55                  60

His Ser Thr Gly Asn Ser Lys Tyr Cys Ser Tyr Val Leu Gln Ser Asn
65                  70                  75                  80

Asp Leu Val Phe Thr Phe Thr Ala Pro Tyr Ser Arg Lys Cys Ala Ala
                85                  90                  95

Ala Ala Pro Ser Ser Ser Glu Pro Leu Pro Asp Tyr Asp Gln Gln Gln
            100                 105                 110

Ala Phe Glu Phe Ile Cys Thr His Gly Leu Ala Ala Arg Ala Val Gly
        115                 120                 125

Leu Gln Val Gly Asp Ala Ala Gln Ala Tyr Glu Val Ser Val Ala Asn
130                 135                 140

Gly Ala Lys Gly Val Arg Pro Pro Thr Lys Leu Glu Asp Gly Gly Gly
145                 150                 155                 160

Cys Ala Val Val Ser Glu Val Leu Leu Tyr Gly Asp Val Val Leu Arg
                165                 170                 175

Tyr Ile Ser Gly Lys Trp Glu Gly Pro Tyr Leu Pro Gly Tyr Thr Ala
            180                 185                 190

Thr Pro Asp Glu Pro Gln Ile Cys Tyr Gly Leu His Arg Leu Asp His
        195                 200                 205

Ala Val Gly Asn Val Pro Lys Leu Ile Glu His Leu Glu His Val Ile
210                 215                 220

Gly Phe Thr Gly Phe His Glu Phe Ala Glu Phe Val Ala Glu Asp Val
225                 230                 235                 240

Gly Thr Val Asp Ser Gly Leu Asn Ser Met Val Leu Ala Ser Asn Asn
                245                 250                 255

Glu Met Val Leu Leu Pro Met Asn Glu Pro Thr Phe Gly Thr Lys Arg
            260                 265                 270

Lys Ser Gln Ile Gln Thr Tyr Leu Glu Gln Asn Glu Gly Pro Gly Leu
        275                 280                 285

Gln His Leu Ala Leu Lys Thr His Asp Ile Leu Ser Thr Met Arg Glu
290                 295                 300

Met His Ala Arg Ser Arg Cys Gly Gly Phe Glu Phe Gln Ala Ala Pro
305                 310                 315                 320
```

```
Gly His Asp Tyr Tyr Lys Arg Val Ala Glu Lys Val Gly Asp Val Leu
                325                 330                 335

Ser Pro Glu Glu Trp Ala Ala Val Glu Gln Leu Gly Ile Leu Val Asp
        340                 345                 350

Gln Asp Asp Gln Gly Val Leu Leu Gln Ile Phe Thr Lys Pro Leu Gly
    355                 360                 365

Asp Arg Pro Thr Ile Phe Ile Glu Ile Ile Glu Arg Arg Gly Cys Leu
370                 375                 380

Lys Glu Ser Ala Ala Gln Ala Gly Ser Ala Ala Ala Ala Ala Ala Glu
385                 390                 395                 400

Pro Thr Ala Ala Gly Gly Asp Ala Asp Ala Asp Gly Ala Ala Ala Ala
                405                 410                 415

Val Ala Asp Lys Phe Lys Asp Ile Val Gln Val Arg Glu Asp Gly Val
                420                 425                 430

Val Val Glu Gln Ala Ala Gly Cys Gly Gly Phe Gly Lys Gly Asn Phe
            435                 440                 445

Ser Glu Leu Phe Lys Ser Ile Glu Glu Tyr Glu Arg Thr Leu Gln Val
        450                 455                 460
```

<210> SEQ ID NO 3
<211> LENGTH: 1395
<212> TYPE: DNA
<213> ORGANISM: Scenedesmus

<400> SEQUENCE: 3

```
atgggcgcag gtggagctca gggcccgaag gttgagctgg ttggctacgc caatttcgtt      60
cgcaacaacc ctcgcagcga taagttccct gtgcacaagt tcaccacat cgagttttgg      120
tgcgcggacg ccaccaacac cttcaagcgc ttccagcatg gcctgggcat gaccctagtg     180
gccaagtccg accacagcac aggcaacagc aagtactgca gctacgtctt gcaaagcaac     240
gacctcgtgt tcaccttcac agcaccctac tcgcgcaagt gcgcagcagc agcgccttct     300
agcagcgagc cgctgccaga ttatgaccag cagcaggcct ttgaattcat ctgcacccac     360
ggcctggcgg caagggctgt aggcctgcag gtgggcgatg cagcgcaggc gtacgaggtt     420
tctgtggcaa acggcgcgaa gggtgtgcgt ccacccacca agctggagga tggcggcggc     480
tgtgctgtgg tcagcgaggt gctgctgtat ggtgacgtgg tgctgcgcta catcagcggc     540
aagtgggagg cccctacct gccgggctac acagccacgc ctgatgagcc gcagatctgc     600
tacggcctgc accgcctgga ccacgccgtg gcaatgtgc ccaagctcat cgagcacttg     660
gagcacgtca ttggcttcac aggcttccac gagtttgccg agtttgtggc ggaggacgtg     720
ggcactgtgg acagcgggct gaacagcatg gtgctggcca gcaacaacga tggtgctg      780
ctgcccatga cgagcccac ctttggcacc aagcgcaagt cgcagatcca gacgtacctg     840
gagcagaacg agggccccgg gctgcagcac ctggcgctga gacgcacga catcctgtcc     900
accatgcgcg agatgcacgc acgctcgcgc tgcggcggct tcgagttcca ggcggcaccc     960
gggcacgact actacaagcg cgtggcggag aaagtgggtg acgtgctgtc cccggaggag    1020
tgggcagccg ttgagcagct gggcatcctg gtgaccagg acgaccaggg cgtgctgctg     1080
cagatcttca ccaagccgct gggggacagg cccaccatct tcattgagat cattgagcgg    1140
cgcggctgcc tcaaggagag cgcggcacag gcaggcagtg cggcagcagc agcagcagag    1200
cctacagcag ctggcggtga tgcagatgca gatggagcag cagcagcagt ggctgacaag    1260
ttcaaagaca tcgtgcaggt gcgtgaggat ggcgtggttg tggagcaagc tgctggctgt    1320
```
ggaggcttcg gcaaaggcaa cttcagcgag ctgttcaaaa gcattgagga gtacgagcgc    1380
acgctgcagg tgtaa    1395

<210> SEQ ID NO 4
<211> LENGTH: 428
<212> TYPE: PRT
<213> ORGANISM: Scenedesmus

<400> SEQUENCE: 4

Met Gly Ala Gly Gly Ala Gln Gly Pro Lys Val Glu Leu Val Gly Tyr
1               5                   10                  15

Ala Asn Phe Val Arg Asn Asn Pro Arg Ser Asp Lys Phe Pro Val His
            20                  25                  30

Lys Phe His His Ile Glu Phe Trp Cys Ala Asp Ala Thr Asn Thr Phe
        35                  40                  45

Lys Arg Phe Gln His Gly Leu Gly Met Thr Leu Val Ala Lys Ser Asp
    50                  55                  60

His Ser Thr Gly Asn Ser Lys Tyr Cys Ser Tyr Val Leu Gln Ser Asn
65                  70                  75                  80

Asp Leu Val Phe Thr Phe Thr Ala Pro Tyr Ser Arg Lys Cys Ala Ala
                85                  90                  95

Ala Ala Pro Ser Ser Ser Glu Pro Leu Pro Asp Tyr Asp Gln Gln Gln
            100                 105                 110

Ala Phe Glu Phe Ile Cys Thr His Gly Leu Ala Ala Arg Ala Val Gly
        115                 120                 125

Leu Gln Val Gly Asp Ala Ala Gln Ala Tyr Glu Val Ser Val Ala Asn
    130                 135                 140

Gly Ala Lys Gly Val Arg Pro Pro Thr Lys Leu Glu Asp Gly Gly Gly
145                 150                 155                 160

Cys Ala Val Val Ser Glu Val Leu Leu Tyr Gly Asp Val Val Leu Arg
                165                 170                 175

Tyr Ile Ser Gly Lys Trp Glu Gly Pro Tyr Leu Pro Gly Tyr Thr Ala
            180                 185                 190

Thr Pro Asp Glu Pro Gln Ile Cys Tyr Gly Leu His Arg Leu Asp His
        195                 200                 205

Ala Val Gly Asn Val Pro Lys Leu Ile Glu His Leu Glu His Val Ile
    210                 215                 220

Gly Phe Thr Gly Phe His Glu Phe Ala Glu Phe Val Ala Glu Asp Val
225                 230                 235                 240

Gly Thr Val Asp Ser Gly Leu Asn Ser Met Val Leu Ala Ser Asn Asn
                245                 250                 255

Glu Met Val Leu Leu Pro Met Asn Glu Pro Thr Phe Gly Thr Lys Arg
            260                 265                 270

Lys Ser Gln Ile Gln Thr Tyr Leu Glu Gln Asn Glu Gly Pro Gly Leu
        275                 280                 285

Gln His Leu Ala Leu Lys Thr His Asp Ile Leu Ser Thr Met Arg Glu
    290                 295                 300

Met His Ala Arg Ser Arg Cys Gly Gly Phe Glu Phe Gln Ala Ala Pro
305                 310                 315                 320

Gly His Asp Tyr Tyr Lys Arg Val Ala Glu Lys Val Gly Asp Val Leu
                325                 330                 335

Ser Pro Glu Glu Trp Ala Ala Val Glu Gln Leu Gly Ile Leu Val Asp
            340                 345                 350

Gln Asp Asp Gln Gly Val Leu Leu Gln Ile Phe Thr Lys Pro Leu Gly

```
                355                 360                 365
Asp Arg Pro Thr Ile Phe Ile Glu Ile Ile Glu Arg Arg Gly Cys Leu
            370                 375                 380

Lys Glu Ser Ala Ala Gln Ala Gly Ser Ala Ala Ala Val Glu Gln
385                 390                 395                 400

Ala Ala Gly Cys Gly Phe Gly Lys Gly Asn Phe Ser Glu Leu Phe
                405                 410                 415

Lys Ser Ile Glu Glu Tyr Glu Arg Thr Leu Gln Val
            420                 425
```

<210> SEQ ID NO 5
<211> LENGTH: 1356
<212> TYPE: DNA
<213> ORGANISM: Helianthus

<400> SEQUENCE: 5

```
atgggaacgg aagctaccgt cgccgccgtc gtcgccggag atgaatccga tcaccccacc    60
tccgccttca agcttgtagg cttcaaaaac ttcatccgta ccaaccccat gtcggacaaa   120
ttcaccgtca aaaacttcca ccacatcgag ttctggtgct ccgacgccac caacaccgcc   180
cgccgcttct cctggggcct cggcatgccc atcatcttca atccgatct ctccaccggc    240
aactccaccc acgcctccta tctcctccgc tccggccacc tcaacttcct cttcaccgcc   300
ccttattccc cctccatctc ccccaccacc accaccgctt ccatcccac cttctcccac    360
tccgcctccc gccacttcac cgctaccac ggtctcgccg tccgcgccat cgccgttgaa    420
gtcgaagacg ccgaaaccgc cttcgccgtt agcgtcgcta acggcgccaa accctcgtct   480
cccccagtca ccctcggtca acgacgtc gtgttgtcag aagttaaatt atacggcgac    540
gtcgttttgc gttatgttag ttacaaaaat aatactaata acaataataa caatgataat   600
gataattata tattttttgcc tggatttgaa gctatggaca aaacgtcgtc gtttcaggag   660
ctagactacg gcatccgccg gctcgatcac gcggtgggga acgtgccgga gctagctcca   720
gcggtggact atgtgaaatc tttcaccggg tttcacgagt tcgctgagtt cactgctgag   780
gacgttggaa cgagtgaaag cgggctcaac tcggtggttt tagcgtgtaa cagtgagatg   840
gttttgatac cgatgaacga ccagtgtac gggacgaaga ggaagagtca gatacagacg   900
tatttggagc ataatgaagg ggctggggtg cagcatttgg cgttggctag tgaggatata   960
tttaggactt tgagagagat gaggaaacgg agtgggggttg ggggggtttga gtttatgccg   1020
tctccgccac ctacttatta taggaatttg aagagtcgag cgggcgatgt gttgtcggat   1080
gagcagatta aggagtgtga agagttgggg atattggtgg atagagatga tcagggggact   1140
ttgcttcaga ttttttactaa gcctgtgggt gataggccga cgatattcat agagataata   1200
caaagagtag ggtgcatggt aaaggatgat gaaggaaagg tgcagcagaa ggcagggtgt   1260
ggagggtttg gcaaagggaa cttctcggag ctttttaaat ctattgagga atatgagaag   1320
acacttgaag caagaagcac cactgctgct gcataa                             1356
```

<210> SEQ ID NO 6
<211> LENGTH: 451
<212> TYPE: PRT
<213> ORGANISM: Helianthus

<400> SEQUENCE: 6

```
Met Gly Thr Glu Ala Thr Val Ala Ala Val Val Ala Gly Asp Glu Ser
1               5                   10                  15
```

```
Asp His Pro Thr Ser Ala Phe Lys Leu Val Gly Phe Lys Asn Phe Ile
            20                  25                  30

Arg Thr Asn Pro Met Ser Asp Lys Phe Thr Val Lys Asn Phe His His
        35                  40                  45

Ile Glu Phe Trp Cys Ser Asp Ala Thr Asn Thr Ala Arg Arg Phe Ser
 50                  55                  60

Trp Gly Leu Gly Met Pro Ile Ile Phe Lys Ser Asp Leu Ser Thr Gly
 65                  70                  75                  80

Asn Ser Thr His Ala Ser Tyr Leu Leu Arg Ser Gly His Leu Asn Phe
                85                  90                  95

Leu Phe Thr Ala Pro Tyr Ser Pro Ser Ile Ser Pro Thr Thr Thr Thr
            100                 105                 110

Ala Ser Ile Pro Thr Phe Ser His Ser Ala Ser Arg His Phe Thr Ala
        115                 120                 125

Thr His Gly Leu Ala Val Arg Ala Ile Ala Val Glu Val Glu Asp Ala
130                 135                 140

Glu Thr Ala Phe Ala Val Ser Val Ala Asn Gly Ala Lys Pro Ser Ser
145                 150                 155                 160

Pro Pro Val Thr Leu Gly His Asn Asp Val Val Leu Ser Glu Val Lys
                165                 170                 175

Leu Tyr Gly Asp Val Val Leu Arg Tyr Val Ser Tyr Lys Asn Asn Thr
            180                 185                 190

Asn Asn Asn Asn Asn Asn Asp Asn Asp Asn Tyr Ile Phe Leu Pro Gly
        195                 200                 205

Phe Glu Ala Met Asp Lys Thr Ser Ser Phe Gln Glu Leu Asp Tyr Gly
210                 215                 220

Ile Arg Arg Leu Asp His Ala Val Gly Asn Val Pro Glu Leu Ala Pro
225                 230                 235                 240

Ala Val Asp Tyr Val Lys Ser Phe Thr Gly Phe His Glu Phe Ala Glu
                245                 250                 255

Phe Thr Ala Glu Asp Val Gly Thr Ser Glu Ser Gly Leu Asn Ser Val
            260                 265                 270

Val Leu Ala Cys Asn Ser Glu Met Val Leu Ile Pro Met Asn Glu Pro
        275                 280                 285

Val Tyr Gly Thr Lys Arg Lys Ser Gln Ile Gln Thr Tyr Leu Glu His
290                 295                 300

Asn Glu Gly Ala Gly Val Gln His Leu Ala Leu Ala Ser Glu Asp Ile
305                 310                 315                 320

Phe Arg Thr Leu Arg Glu Met Arg Lys Arg Ser Gly Val Gly Gly Phe
                325                 330                 335

Glu Phe Met Pro Ser Pro Pro Thr Tyr Tyr Arg Asn Leu Lys Ser
            340                 345                 350

Arg Ala Gly Asp Val Leu Ser Asp Glu Gln Ile Lys Glu Cys Glu Glu
        355                 360                 365

Leu Gly Ile Leu Val Asp Arg Asp Gln Gly Thr Leu Leu Gln Ile
370                 375                 380

Phe Thr Lys Pro Val Gly Asp Arg Pro Thr Ile Phe Ile Glu Ile Ile
385                 390                 395                 400

Gln Arg Val Gly Cys Met Val Lys Asp Asp Glu Gly Lys Val Gln Gln
                405                 410                 415

Lys Ala Gly Cys Gly Gly Phe Gly Lys Gly Asn Phe Ser Glu Leu Phe
            420                 425                 430

Lys Ser Ile Glu Glu Tyr Glu Lys Thr Leu Glu Ala Arg Ser Thr Thr
```

Ala Ala Ala
    450

<210> SEQ ID NO 7
<211> LENGTH: 1353
<212> TYPE: DNA
<213> ORGANISM: Helianthus

<400> SEQUENCE: 7

```
atgggcactg aagcgactgt tgcagccgtt gttgctggcg acgaatctga tcatccgacc    60
agcgcgttca aactggtggg tttcaaaaac tttatccgca ccaacccaat gtccgataaa   120
ttcaccgtca aaacttcca ccacatcgaa ttctggtgct ctgacgccac taacactgct   180
cgccgctttt cctggggcct gggtatgcca atcattttca atctgaccct gagcaccggt   240
aactctacgc atgcgtccta tctgctgcgt tccggtcagc tgaactttct gtttaccgct   300
ccgtattccc cgtctatttc taccactacc acggcttcta ttccgacctt cagccactcc   360
gcgtctcgtc atttcacggc cactcatggt ctggctgttc gtgcaattgc cgttgaagtg   420
gaggatgcag aaactgcgtt tgcggtgagc gtagccaacg tgcaaaaacc aagctctccg   480
ccagtgaccc tgggtcacaa cgatgtagtg ctgtctgaag tcaaactgta cggtgacgtc   540
gtactccgtt atgtgtccta caaaaacaac accaacaacg ataacaacaa cgacaacgac   600
aactacatct tcctgccagg cttcgaagct atggacaaaa ccagctcttt tcaggaactg   660
gactacggca ttcgccgcct cgatcacgct gttggtaacg taccggaact ggcaccagcg   720
gttgactacg taaaaagctt caccggtttc cacgaattcg cggaattcac tgccgaagac   780
gtaggtactt ccgaatccgg tctgaactct gttgtgctgg cgtgcaactc tgaaatggtc   840
ctgattccga tgaacgaacc ggtgtacggc accaaacgta atcccagat ccagacgtac   900
ctgaacacac acgaaggtgc tggtgttcag cacctggctc tggcgtctga agatatcttc   960
cgtaccctgc gtgaaatgcg taaacgctct ggtgttggcg gtttcgaatt tatgccgtct  1020
ccaccgccaa cctactatcg caacctgaaa tctcgtgcag cgacgttct gagcgatgaa  1080
cagatcaaag agtgcgaaga gctgggtatc ctggttgatc gtgatgatca gggtaccctg  1140
ctgcagatct ttaccaaacc ggtaggtgac cgtccgacga tcttcattga aatcatccag  1200
cgtgttggct gtatggtgaa agacgatgag gcaaagttca gcagaaagc aggctgtggt  1260
ggcttcggca aaggcaactt cagcgagctg ttcaaatcta tcgaggaata cgagaaaacc  1320
ctggaggcac gttctaccac tgcagctgcg taa                                1353
```

<210> SEQ ID NO 8
<211> LENGTH: 450
<212> TYPE: PRT
<213> ORGANISM: Helianthus

<400> SEQUENCE: 8

```
Met Gly Thr Glu Ala Thr Val Ala Ala Val Val Ala Gly Asp Glu Ser
1               5                   10                  15

Asp His Pro Thr Ser Ala Phe Lys Leu Val Gly Phe Lys Asn Phe Ile
            20                  25                  30

Arg Thr Asn Pro Met Ser Asp Lys Phe Thr Val Lys Asn Phe His His
        35                  40                  45

Ile Glu Phe Trp Cys Ser Asp Ala Thr Asn Thr Ala Arg Arg Phe Ser
    50                  55                  60
```

```
Trp Gly Leu Gly Met Pro Ile Ile Phe Lys Ser Asp Leu Ser Thr Gly
 65                  70                  75                  80

Asn Ser Thr His Ala Ser Tyr Leu Leu Arg Ser Gly Gln Leu Asn Phe
                 85                  90                  95

Leu Phe Thr Ala Pro Tyr Ser Pro Ser Ile Ser Thr Thr Thr Thr Ala
            100                 105                 110

Ser Ile Pro Thr Phe Ser His Ser Ala Ser Arg His Phe Thr Ala Thr
        115                 120                 125

His Gly Leu Ala Val Arg Ala Ile Ala Val Glu Val Glu Asp Ala Glu
    130                 135                 140

Thr Ala Phe Ala Val Ser Val Ala Asn Gly Ala Lys Pro Ser Ser Pro
145                 150                 155                 160

Pro Val Thr Leu Gly His Asn Asp Val Val Leu Ser Glu Val Lys Leu
                165                 170                 175

Tyr Gly Asp Val Val Leu Arg Tyr Val Ser Tyr Lys Asn Asn Thr Asn
            180                 185                 190

Asn Asp Asn Asn Asn Asp Asn Asp Asn Tyr Ile Phe Leu Pro Gly Phe
        195                 200                 205

Glu Ala Met Asp Lys Thr Ser Ser Phe Gln Glu Leu Asp Tyr Gly Ile
    210                 215                 220

Arg Arg Leu Asp His Ala Val Gly Asn Val Pro Glu Leu Ala Pro Ala
225                 230                 235                 240

Val Asp Tyr Val Lys Ser Phe Thr Gly Phe His Glu Phe Ala Glu Phe
                245                 250                 255

Thr Ala Glu Asp Val Gly Thr Ser Glu Ser Gly Leu Asn Ser Val Val
            260                 265                 270

Leu Ala Cys Asn Ser Glu Met Val Leu Ile Pro Met Asn Glu Pro Val
        275                 280                 285

Tyr Gly Thr Lys Arg Lys Ser Gln Ile Gln Thr Tyr Leu Glu His Asn
    290                 295                 300

Glu Gly Ala Gly Val Gln His Leu Ala Leu Ala Ser Glu Asp Ile Phe
305                 310                 315                 320

Arg Thr Leu Arg Glu Met Arg Lys Arg Ser Gly Val Gly Gly Phe Glu
                325                 330                 335

Phe Met Pro Ser Pro Pro Thr Tyr Tyr Arg Asn Leu Lys Ser Arg
            340                 345                 350

Ala Gly Asp Val Leu Ser Asp Glu Gln Ile Lys Glu Cys Glu Glu Leu
        355                 360                 365

Gly Ile Leu Val Asp Arg Asp Asp Gln Gly Thr Leu Leu Gln Ile Phe
    370                 375                 380

Thr Lys Pro Val Gly Asp Arg Pro Thr Ile Phe Ile Glu Ile Ile Gln
385                 390                 395                 400

Arg Val Gly Cys Met Val Lys Asp Asp Glu Gly Lys Val Gln Gln Lys
                405                 410                 415

Ala Gly Cys Gly Gly Phe Gly Lys Gly Asn Phe Ser Glu Leu Phe Lys
            420                 425                 430

Ser Ile Glu Glu Tyr Glu Lys Thr Leu Glu Ala Arg Ser Thr Thr Ala
        435                 440                 445

Ala Ala
    450

<210> SEQ ID NO 9
<211> LENGTH: 1323
<212> TYPE: DNA
```

<213> ORGANISM: Lemna

<400> SEQUENCE: 9

```
atggccgagg aggaaggggt agaagctcgc gccgcgaagc tcgacgattc cgtcaatagc      60
ggagccgctg cggacggctt ccagctcgtc ggattctcca atttcgtccg cagaaatcct     120
cgcagcgaca gattccacgc gaaaagcttc caccacgtcg aattctggtg cgcggacgcc     180
acgaacgtct ccagaaggtt ctccttcggc ctcggcatgc cgctggccgc caaatcggat     240
ctctccaccg gaaattccag ccacgcctct tacatgatca gatccagaga tctccgattt     300
ctattcaccg cgccgttatc gtcctccgcc gcggattcca atccgcgat tccgtccttc      360
gattccgacg cctgccgccg gttctcgaac ctccacggcc tcgccgtccg cgcggtggcg     420
ctgcaggtcg ccgacgccgc cgccgccttc acgtcagcg tccagaacgg cgcgcggccg      480
gcgtttcccc cggcggatct cggcggcgcg gtaatttccg aggtggagct ctacggcgac     540
gtcgtcctac gcttcctcag cctcggatcc ggcgagaaat tccaattcct ccctggattt     600
gaggatctga gccctaattc cgccgatctg gactacggaa ttaggcgtct ggaccacgcc     660
gtcggaaacg tgccggagct cgcgccggcg gcggcgtacg tcaagaaatt cacaggattc     720
cacgaattcg cggagttcac ggcggatgac gtcggcacgg cggagagcgg cctcaattcc     780
gtcgtcctgg cgaacaacga cgagaatgtc ctcctccctc tgaacgagcc ggtccacgga     840
actcctcgga gaagccagat ccagacctac ctcgatcaca cgaaggtcc ggggctgcag      900
catctggcgc tctccagcga agatgttatt gcgacgctga ggaagatgcg agctgcttct     960
gccttggggg ggtttgaatt tatgcctccg ccgcctccca cctattatcg gaatctgagg    1020
aagagggcca aggatgtgct cacggaggat cagatggtgg cttgcgagga gctgggaatt    1080
ctcgttgata gagatgatca gggaattctg ctccagatat tcaccaagcc cgttggagat    1140
agaccaacaa tattcctgga gatcatccag aggatcggat gcatgatgaa ggacgaggcg    1200
gggaaggagt atcagaaggg agggtgcgga ggatttggaa aggggaattt caccgagctc    1260
ttcaaatcga tcgaggacta cgagaaatct ctcgaggcga agcaagcagg tacgcgattc    1320
tag                                                                   1323
```

<210> SEQ ID NO 10
<211> LENGTH: 440
<212> TYPE: PRT
<213> ORGANISM: Lemna

<400> SEQUENCE: 10

```
Met Ala Glu Glu Gly Val Glu Ala Arg Ala Ala Lys Leu Asp Asp
1               5                   10                  15

Ser Val Asn Ser Gly Ala Ala Asp Gly Phe Gln Leu Val Gly Phe
                20                  25                  30

Ser Asn Phe Val Arg Arg Asn Pro Arg Ser Asp Arg Phe His Ala Lys
        35                  40                  45

Ser Phe His His Val Glu Phe Trp Cys Ala Asp Ala Thr Asn Val Ser
    50                  55                  60

Arg Arg Phe Ser Phe Gly Leu Gly Met Pro Leu Ala Ala Lys Ser Asp
65                  70                  75                  80

Leu Ser Thr Gly Asn Ser Ser His Ala Ser Tyr Met Ile Arg Ser Arg
                85                  90                  95

Asp Leu Arg Phe Leu Phe Thr Ala Pro Leu Ser Ser Ser Ala Ala Asp
            100                 105                 110
```

Ser Lys Ser Ala Ile Pro Ser Phe Asp Ser Asp Ala Cys Arg Arg Phe
              115                 120                 125

Ser Asn Leu His Gly Leu Ala Val Arg Ala Val Ala Leu Gln Val Ala
        130                 135                 140

Asp Ala Ala Ala Phe His Val Ser Val Gln Asn Gly Ala Arg Pro
145                 150                 155                 160

Ala Phe Pro Pro Ala Asp Leu Gly Gly Ala Val Ile Ser Glu Val Glu
                165                 170                 175

Leu Tyr Gly Asp Val Val Leu Arg Phe Leu Ser Leu Ser Gly Glu
        180                 185                 190

Lys Phe Gln Phe Leu Pro Gly Phe Glu Asp Leu Ser Pro Asn Ser Ala
        195                 200                 205

Asp Leu Asp Tyr Gly Ile Arg Arg Leu Asp His Ala Val Gly Asn Val
210                 215                 220

Pro Glu Leu Ala Pro Ala Ala Tyr Val Lys Lys Phe Thr Gly Phe
225                 230                 235                 240

His Glu Phe Ala Glu Phe Thr Ala Asp Asp Val Gly Thr Ala Glu Ser
                245                 250                 255

Gly Leu Asn Ser Val Val Leu Ala Asn Asn Asp Glu Asn Val Leu Leu
        260                 265                 270

Pro Leu Asn Glu Pro Val His Gly Thr Pro Arg Arg Ser Gln Ile Gln
        275                 280                 285

Thr Tyr Leu Asp His Asn Glu Gly Pro Gly Leu Gln His Leu Ala Leu
        290                 295                 300

Ser Ser Glu Asp Val Ile Ala Thr Leu Arg Lys Met Arg Ala Ala Ser
305                 310                 315                 320

Ala Leu Gly Gly Phe Glu Phe Met Pro Pro Pro Pro Thr Tyr Tyr
                325                 330                 335

Arg Asn Leu Arg Lys Arg Ala Lys Asp Val Leu Thr Glu Asp Gln Met
        340                 345                 350

Val Ala Cys Glu Glu Leu Gly Ile Leu Val Asp Arg Asp Gln Gly
        355                 360                 365

Ile Leu Leu Gln Ile Phe Thr Lys Pro Val Gly Asp Arg Pro Thr Ile
        370                 375                 380

Phe Leu Glu Ile Ile Gln Arg Ile Gly Cys Met Met Lys Asp Glu Ala
385                 390                 395                 400

Gly Lys Glu Tyr Gln Lys Gly Cys Gly Phe Gly Lys Gly Asn
                405                 410                 415

Phe Thr Glu Leu Phe Lys Ser Ile Glu Asp Tyr Glu Lys Ser Leu Glu
        420                 425                 430

Ala Lys Gln Ala Gly Thr Arg Phe
        435                 440

<210> SEQ ID NO 11
<211> LENGTH: 1095
<212> TYPE: DNA
<213> ORGANISM: Belliella

<400> SEQUENCE: 11
atggaacagg atttcctgcc gctgctgggt actgattacg ttgaactgta cgtaggtaac     60
gcgaaacagt ctgctctgta ttatcagtac gccttcggct acgaactgat tgcgtatgct    120
ggtccggaaa ctggtatcaa agaccgtgct agctacgtgc tgaaacagga caaaattcgt    180
ctggttctga ccactccgct gcaggaaaac cacccaattg cggatcacat caaaaaacac    240

-continued

```
ggcgatggtg tgaaagtgct cgcactgtgg gtcgaagacg ctaaaaaatc ttggctggaa      300
acgacctctc gtggtgcagt ttcctacgaa gaaccgcgta cgatcaaaga cgagaacggt      360
gaagtagtag ttgcgtctat ccgtacttac ggtgagacga tccataccct tatcgagcgc      420
aaaaactacc acggcatttt cctgccgggt tataaaccac gcaaatccga gtacaaaccg      480
acctccattg gcctgaaata catcgatcac tgcgttggta acgtcggttg gggtgaaatg      540
aacaaatggg tgaaattcta tgaagacgtg atgggcttca aactgctgat caccttcgac      600
gacaaagata tcagcactga gtactctgcc ctgatgagca agttgtctc taacggcaac       660
ggctacatca aattcccgat caacgaaccg gcagagggca aaaaaaaatc tcagatcgaa      720
gagtatctgg acttctataa cggctccggt gttcagcata tggcgatcgc aaccgatgat      780
atcgttcaca ccgtatccga actgcgtaaa cgtggtgttg aattcctgga agtgccgtct      840
agctactatg acgatctcct ggaccgtgtt ggtaaaatcg acgaagatct gcagccgctg      900
aaagacctga acattctggt agatcgtgac gatgaaggct acctgctgca gattttttacc     960
aaaccgattc aggaccgccc aaccctgttt ttcgagatta ccagcgcaa aggtgcgaaa       1020
agctttggca aaggcaactt caaagccctc ttcgaagcta tcgaacgtga acaggaactg     1080
cgtggtaacc tgtaa                                                       1095
```

<210> SEQ ID NO 12
<211> LENGTH: 364
<212> TYPE: PRT
<213> ORGANISM: Belliella

<400> SEQUENCE: 12

```
Met Glu Gln Asp Phe Leu Pro Leu Leu Gly Thr Asp Tyr Val Glu Leu
 1               5                  10                  15

Tyr Val Gly Asn Ala Lys Gln Ser Ala Leu Tyr Tyr Gln Tyr Ala Phe
            20                  25                  30

Gly Tyr Glu Leu Ile Ala Tyr Ala Gly Pro Glu Thr Gly Ile Lys Asp
        35                  40                  45

Arg Ala Ser Tyr Val Leu Lys Gln Asp Lys Ile Arg Leu Val Leu Thr
    50                  55                  60

Thr Pro Leu Gln Glu Asn His Pro Ile Ala Asp His Ile Lys Lys His
65                  70                  75                  80

Gly Asp Gly Val Lys Val Leu Ala Leu Trp Val Glu Asp Ala Lys Lys
                85                  90                  95

Ser Trp Leu Glu Thr Thr Ser Arg Gly Ala Val Ser Tyr Glu Glu Pro
            100                 105                 110

Arg Thr Ile Lys Asp Glu Asn Gly Glu Val Val Ala Ser Ile Arg
        115                 120                 125

Thr Tyr Gly Glu Thr Ile His Thr Phe Ile Glu Arg Lys Asn Tyr His
    130                 135                 140

Gly Ile Phe Leu Pro Gly Tyr Lys Pro Arg Lys Ser Glu Tyr Lys Pro
145                 150                 155                 160

Thr Ser Ile Gly Leu Lys Tyr Ile Asp His Cys Val Gly Asn Val Gly
                165                 170                 175

Trp Gly Glu Met Asn Lys Trp Val Lys Phe Tyr Glu Asp Val Met Gly
            180                 185                 190

Phe Lys Leu Leu Ile Thr Phe Asp Asp Lys Asp Ile Ser Thr Glu Tyr
        195                 200                 205

Ser Ala Leu Met Ser Lys Val Val Ser Asn Gly Asn Gly Tyr Ile Lys
    210                 215                 220
```

```
Phe Pro Ile Asn Glu Pro Ala Glu Gly Lys Lys Ser Gln Ile Glu
225                 230                 235                 240

Glu Tyr Leu Asp Phe Tyr Asn Gly Ser Gly Val Gln His Met Ala Ile
            245                 250                 255

Ala Thr Asp Asp Ile Val His Thr Val Ser Glu Leu Arg Lys Arg Gly
        260                 265                 270

Val Glu Phe Leu Glu Val Pro Ser Ser Tyr Tyr Asp Asp Leu Leu Asp
    275                 280                 285

Arg Val Gly Lys Ile Asp Glu Asp Leu Gln Pro Leu Lys Asp Leu Asn
290                 295                 300

Ile Leu Val Asp Arg Asp Asp Glu Gly Tyr Leu Leu Gln Ile Phe Thr
305                 310                 315                 320

Lys Pro Ile Gln Asp Arg Pro Thr Leu Phe Phe Glu Ile Ile Gln Arg
                325                 330                 335

Lys Gly Ala Lys Ser Phe Gly Lys Gly Asn Phe Lys Ala Leu Phe Glu
            340                 345                 350

Ala Ile Glu Arg Glu Gln Glu Leu Arg Gly Asn Leu
        355                 360

<210> SEQ ID NO 13
<211> LENGTH: 1095
<212> TYPE: DNA
<213> ORGANISM: Nitritalea

<400> SEQUENCE: 13
atggaacagg acttcctgcc gatcaacggt actgattacg tcgagttcta cgtcggtaac     60
gccaaacagt ctgcgctgta ctatcagtac gcgtttggct atgaactgat tgcgtatgct    120
ggcccggaaa ctggtgtgaa agaccgtgca agctacgttc tgaaacagga caaaattcgc    180
ctggttctga ccactgctct gcaggcagaa catccaatcg cggaacacgt gaaaacgcac    240
ggcgatggtg ttaaagtact ggcactgtgg gttgatgacg cacgcaaatc tttcgaggaa    300
actaccaaac gtggtgccaa agcctatcag gaaccgactg tactccagga tgaacacggt    360
gaggtagtga tttctggtat ccacacgtac ggcgagactg ttcatctgtt tgttgagcgc    420
tccaactact ctggcatctt tctgccgggt tatgtcccac gtcagtctac ctacaaaccg    480
gaaccgattg tctgaaaata catcgatcac tgcgttggca acgtcggttg gggtgaaatg    540
aacacctggg tggagttcta tgagaaagtg atgggcttca acctgctcat taccttcgac    600
gacaaagata tctccaccga ctacaccgcg ctgatgagca agtggtaag caacggtaac    660 ggcttcatca aattcccgat taacgaaccg gctgaaggca aaaaaaaatc ccagatcgaa    720
gagtatatcg acttctacca gggtgctggt gttcagcacc tggctatcgc aaccgacgat    780
atcatccata cggtatctga actgcgtcgt cgtggtgttg aattcctgga agtgccgaac    840
acctactatg acgatctgct ggatcgtgtt ggttccattg acgaagacct gcagccactg    900
aaagacctga catcctggt agatcgtgat gacgaaggct acctgctgca gatctttacc    960
aaaccagttc aggatcgccc aaccgtgttc tacgaaatca tccagcgtaa aggtgccaaa   1020
tcttttggca aggcaacttc caaagcgctg ttcgaagcta ttgaacgcga acaggaactg   1080
cgtggcaacc tgtaa                                                    1095

<210> SEQ ID NO 14
<211> LENGTH: 364
<212> TYPE: PRT
<213> ORGANISM: Nitritalea
```

<400> SEQUENCE: 14

```
Met Glu Gln Asp Phe Leu Pro Ile Asn Gly Thr Asp Tyr Val Glu Phe
1               5                   10                  15

Tyr Val Gly Asn Ala Lys Gln Ser Ala Leu Tyr Tyr Gln Tyr Ala Phe
            20                  25                  30

Gly Tyr Glu Leu Ile Ala Tyr Ala Gly Pro Glu Thr Gly Val Lys Asp
        35                  40                  45

Arg Ala Ser Tyr Val Leu Lys Gln Asp Lys Ile Arg Leu Val Leu Thr
    50                  55                  60

Thr Ala Leu Gln Ala Glu His Pro Ile Ala Glu His Val Lys Thr His
65                  70                  75                  80

Gly Asp Gly Val Lys Val Leu Ala Leu Trp Val Asp Ala Arg Lys
                85                  90                  95

Ser Phe Glu Glu Thr Thr Lys Arg Gly Ala Lys Ala Tyr Gln Glu Pro
            100                 105                 110

Thr Val Leu Gln Asp Glu His Gly Glu Val Val Ile Ser Gly Ile His
        115                 120                 125

Thr Tyr Gly Glu Thr Val His Leu Phe Val Glu Arg Ser Asn Tyr Ser
130                 135                 140

Gly Ile Phe Leu Pro Gly Tyr Val Pro Arg Gln Ser Thr Tyr Lys Pro
145                 150                 155                 160

Glu Pro Ile Gly Leu Lys Tyr Ile Asp His Cys Val Gly Asn Val Gly
                165                 170                 175

Trp Gly Glu Met Asn Thr Trp Val Glu Phe Tyr Glu Lys Val Met Gly
            180                 185                 190

Phe Asn Leu Leu Ile Thr Phe Asp Asp Lys Asp Ile Ser Thr Asp Tyr
        195                 200                 205

Thr Ala Leu Met Ser Lys Val Val Ser Asn Gly Asn Gly Phe Ile Lys
    210                 215                 220

Phe Pro Ile Asn Glu Pro Ala Glu Gly Lys Lys Lys Ser Gln Ile Glu
225                 230                 235                 240

Glu Tyr Ile Asp Phe Tyr Gln Gly Ala Gly Val Gln His Leu Ala Ile
                245                 250                 255

Ala Thr Asp Asp Ile Ile His Thr Val Ser Glu Leu Arg Arg Gly
            260                 265                 270

Val Glu Phe Leu Glu Val Pro Asn Thr Tyr Tyr Asp Asp Leu Leu Asp
        275                 280                 285

Arg Val Gly Ser Ile Asp Glu Asp Leu Gln Pro Leu Lys Asp Leu Asn
    290                 295                 300

Ile Leu Val Asp Arg Asp Asp Glu Gly Tyr Leu Leu Gln Ile Phe Thr
305                 310                 315                 320

Lys Pro Val Gln Asp Arg Pro Thr Val Phe Glu Ile Ile Gln Arg
                325                 330                 335

Lys Gly Ala Lys Ser Phe Gly Lys Gly Asn Phe Lys Ala Leu Phe Glu
            340                 345                 350

Ala Ile Glu Arg Glu Gln Glu Leu Arg Gly Asn Leu
        355                 360
```

<210> SEQ ID NO 15
<211> LENGTH: 1095
<212> TYPE: DNA
<213> ORGANISM: Pontibacter

<400> SEQUENCE: 15

```
atggcaaccg atattctgcc actgaacggc accgaccata tcgagttta cgtcggtaac    60
gccaaacagg cggcacattt ttatcagacc gcgttcggct tcaaactgat tgcatacgct   120
ggtccggaaa ctggtgttcg tgaccgtgca tcttacgttc tgcagcagga gaaaatccgt   180
ctggtgctga ccacttctct ggacccaaac tctgatatcg ctcagcacgt gcaccagcat   240
ggtgatggcg ttaaagtcct ggcactgtgg gtggatgacg ctgaagcgtc ttttcgcggt   300
actgtagaac gtggtgcgaa accagcgatg gaaccgaaaa ctctgaccga tgaacacggt   360
gaagtaaaag tcgccagcat ccacacttac ggtgatacca tccacacgtt cgttgagcgc   420
aaaaactaca acggcgtgtt tatgccgggt tatgtagctc gtcagtctca gctggatatc   480
gaatccgtgg gcctgaaata cgttgatcac tgcgttggca acgtagaact gggtcagatg   540
aacgagtggg tgaaattcta tgaagacgtg atgggcttca aactcctgct gaccttcgac   600
gacaaagata tctccacgga atacaccgcc ctgatgtcta agttgtatc caacggcaac   660
ggctacatca aattcccgat caacgaaccg gctgaaggca aaaaaaaaag ccagatcgac   720
gagtatctgg agttctacaa aggtgcaggt gttcagcaca ttgcggttgc gaccaacgat   780
attctgcaca ctgttgctga actgcgtcgt cgtggtgttg aattcctgta cgtgccggag   840
acctactatg aagacctgat tgagcgtatc ggtcacatcg acgaagacat ggaggatctg   900
cgcaaactga acatcctggt tgaccgcgac gatgaaggtt atctcctgca gatcttcacc   960
aaaccagtcg aagaccgccc gacggtattt tacgaaatta ccagcgcaa aggtgcgaaa  1020
agcttcggca aaggcaactt caaagccctg ttcgaagcta ttgaacgtga acaggctctg  1080
cgtggtaacc tgtaa                                                  1095

<210> SEQ ID NO 16
<211> LENGTH: 364
<212> TYPE: PRT
<213> ORGANISM: Pontibacter

<400> SEQUENCE: 16

Met Ala Thr Asp Ile Leu Pro Leu Asn Gly Thr Asp His Ile Glu Phe
1               5                   10                  15

Tyr Val Gly Asn Ala Lys Gln Ala Ala His Phe Tyr Gln Thr Ala Phe
            20                  25                  30

Gly Phe Lys Leu Ile Ala Tyr Ala Gly Pro Glu Thr Gly Val Arg Asp
        35                  40                  45

Arg Ala Ser Tyr Val Leu Gln Gln Glu Lys Ile Arg Leu Val Leu Thr
    50                  55                  60

Thr Ser Leu Asp Pro Asn Ser Asp Ile Ala Gln His Val His Gln His
65                  70                  75                  80

Gly Asp Gly Val Lys Val Leu Ala Leu Trp Val Asp Asp Ala Glu Ala
                85                  90                  95

Ser Phe Arg Gly Thr Val Glu Arg Gly Ala Lys Pro Ala Met Glu Pro
            100                 105                 110

Lys Thr Leu Thr Asp Glu His Gly Glu Val Lys Val Ala Ser Ile His
        115                 120                 125

Thr Tyr Gly Asp Thr Ile His Thr Phe Val Glu Arg Lys Asn Tyr Asn
    130                 135                 140

Gly Val Phe Met Pro Gly Tyr Val Ala Arg Gln Ser Gln Leu Asp Ile
145                 150                 155                 160

Glu Ser Val Gly Leu Lys Tyr Val Asp His Cys Val Gly Asn Val Glu
                165                 170                 175
```

Leu Gly Gln Met Asn Glu Trp Val Lys Phe Tyr Glu Asp Val Met Gly
            180                 185                 190

Phe Lys Leu Leu Leu Thr Phe Asp Lys Asp Ile Ser Thr Glu Tyr
            195                 200                 205

Thr Ala Leu Met Ser Lys Val Val Ser Asn Gly Asn Gly Tyr Ile Lys
210                 215                 220

Phe Pro Ile Asn Glu Pro Ala Glu Gly Lys Lys Lys Ser Gln Ile Asp
225                 230                 235                 240

Glu Tyr Leu Glu Phe Tyr Lys Gly Ala Gly Val Gln His Ile Ala Val
            245                 250                 255

Ala Thr Asn Asp Ile Leu His Thr Val Ala Glu Leu Arg Arg Arg Gly
            260                 265                 270

Val Glu Phe Leu Tyr Val Pro Glu Thr Tyr Tyr Glu Asp Leu Ile Glu
            275                 280                 285

Arg Ile Gly His Ile Asp Glu Asp Met Glu Asp Leu Arg Lys Leu Asn
            290                 295                 300

Ile Leu Val Asp Arg Asp Asp Glu Gly Tyr Leu Leu Gln Ile Phe Thr
305                 310                 315                 320

Lys Pro Val Glu Asp Arg Pro Thr Val Phe Tyr Glu Ile Ile Gln Arg
            325                 330                 335

Lys Gly Ala Lys Ser Phe Gly Lys Gly Asn Phe Lys Ala Leu Phe Glu
            340                 345                 350

Ala Ile Glu Arg Glu Gln Ala Leu Arg Gly Asn Leu
            355                 360

<210> SEQ ID NO 17
<211> LENGTH: 1083
<212> TYPE: DNA
<213> ORGANISM: Ferroplasma

<400> SEQUENCE: 17
atggcgtaca acaacgatga gctgttcaaa aaaatcaacc acatcgaatt ctacgtgtct      60
tccgccaaaa cctggtctta ctttatggaa cgcggtctcg gtctggatct gaaagcttac     120
agcggtctgg aaactggtaa ccgcggcaaa tctagctacg ttctcaacaa aggcgacatt     180
aacctggtct ttagctcctc tatggagaaa cattccgaga tcaacgattc tatctccctg     240
cacggtgacg gtgttcgtga tatctctctg gaagtggatg acatcgaatt caccaaaaaa     300
catctggaat cccgtaacat caaagtgagc tccatcaaag aggaaaaaga cgataacggc     360
aaaatccgcc gtgcagtaat gcagacttat ggcgacacga ttcacactat gatcgagaaa     420
ggcgattaca aggtttcct gccaggctat cgtgaagaag acactcacac tgcagatacc     480
ggtatctata aagtcgatca cgtggtaggc aacgtttacg aaggtgagat ggaccagtgg     540
gtcaactact acatcaaaaa catgaacttc tctcagctgg ttacgtttga cacaaaatg     600 attcgtacgg actattctgc cctgcgtagc aaagtggtta atacaacga acatcgtt       660 ttcccgatca acgaaccagc gcagggtctg aaaaaatctc agattcagga gtacctggac     720
tactataact ctcagggcgt tcagcacatt gcgctgaaaa ccgacaacat tatcgagacc     780
gtgagcaaaa tgaaacagaa cggtattcag ttcctgcaga ctccggcttc ctattacgac     840
accctgaccg aacgtgtagg caacgttgac gaagatatcg aggagctgaa aaaactgaac     900
attctggtgg atcgtgatga cgatggttat ctgctgcaga tctttaccaa accgctgacc     960
gatcgtccga ccgttttctt tgaagtaatc gagcgcaaag gtgctaaatc tttcggtgct    1020

-continued

```
ggcaacttca aagcactgtt cgaatctatt gaacgtgacc aggcgatgcg cggtaacctg    1080
taa                                                                  1083
```

<210> SEQ ID NO 18
<211> LENGTH: 359
<212> TYPE: PRT
<213> ORGANISM: Ferroplasma

<400> SEQUENCE: 18

```
Met Tyr Asn Asn Asp Glu Leu Phe Lys Lys Ile Asn His Ile Glu Phe
1               5                   10                  15

Tyr Val Ser Ser Ala Lys Thr Trp Ser Tyr Phe Met Glu Arg Gly Leu
            20                  25                  30

Gly Leu Asp Leu Lys Ala Tyr Ser Gly Leu Glu Thr Gly Asn Arg Gly
        35                  40                  45

Lys Ser Ser Tyr Val Leu Asn Lys Gly Asp Ile Asn Leu Val Phe Ser
    50                  55                  60

Ser Ser Met Glu Lys His Ser Glu Ile Asn Asp Ser Ile Ser Leu His
65                  70                  75                  80

Gly Asp Gly Val Arg Asp Ile Ser Leu Glu Val Asp Ile Glu Phe
                85                  90                  95

Thr Lys Lys His Leu Glu Ser Arg Asn Ile Lys Val Ser Ser Ile Lys
            100                 105                 110

Glu Glu Lys Asp Asp Asn Gly Lys Ile Arg Arg Ala Val Met Gln Thr
        115                 120                 125

Tyr Gly Asp Thr Ile His Thr Met Ile Glu Lys Gly Asp Tyr Lys Gly
    130                 135                 140

Phe Leu Pro Gly Tyr Arg Glu Glu Asp Thr His Thr Ala Asp Thr Gly
145                 150                 155                 160

Ile Tyr Lys Val Asp His Val Val Gly Asn Val Tyr Glu Gly Glu Met
                165                 170                 175

Asp Gln Trp Val Asn Tyr Tyr Ile Lys Asn Met Asn Phe Ser Gln Leu
            180                 185                 190

Val Thr Phe Asp Asp Lys Met Ile Arg Thr Asp Tyr Ser Ala Leu Arg
        195                 200                 205

Ser Lys Val Val Lys Tyr Asn Asp Asn Ile Val Phe Pro Ile Asn Glu
    210                 215                 220

Pro Ala Gln Gly Leu Lys Lys Ser Gln Ile Gln Glu Tyr Leu Asp Tyr
225                 230                 235                 240

Tyr Asn Ser Gln Gly Val Gln His Ile Ala Leu Lys Thr Asp Asn Ile
                245                 250                 255

Ile Glu Thr Val Ser Lys Met Lys Gln Asn Gly Ile Gln Phe Leu Gln
            260                 265                 270

Thr Pro Ala Ser Tyr Tyr Asp Thr Leu Thr Glu Arg Val Gly Asn Val
        275                 280                 285

Asp Glu Asp Ile Glu Glu Leu Lys Lys Leu Asn Ile Leu Val Asp Arg
    290                 295                 300

Asp Asp Asp Gly Tyr Leu Leu Gln Ile Phe Thr Lys Pro Leu Thr Asp
305                 310                 315                 320

Arg Pro Thr Val Phe Phe Glu Val Ile Glu Arg Lys Gly Ala Lys Ser
                325                 330                 335

Phe Gly Ala Gly Asn Phe Lys Ala Leu Phe Glu Ser Ile Glu Arg Asp
            340                 345                 350

Gln Ala Met Arg Gly Asn Leu
```

<210> SEQ ID NO 19
<211> LENGTH: 1098
<212> TYPE: DNA
<213> ORGANISM: Microscilla

<400> SEQUENCE: 19

```
atggaacagg cacatgactt tctgccgatt atcggtaccg accatctgga attctatgtc    60
ggcaacgcca aacagtctgc gtacttttac cagtctgcgt ttggttacca gctggtaggt   120
tacgcaggtc cagaaactgg tgttcgtgac cgcgccagct atgttctgaa acagggcaaa   180
gtacgtctgg tcctgactac cgcgatgcat ccatcttctg aagtgtccga gcacgtgaaa   240
aaacacggtg atggcgtgaa agtactcgct atccaggttg agaacgctta ccaggcttat   300
gaggaaaccg ttaaacgcgg tgcgaaatcc gctatcgaac cacatacsct gactgacgaa   360
tacggcgaaa tcaaaattgc agctatccac acctacggtg aaacgatcca caaattcgtc   420
gaacgtacga actacaacgg tgtctttatg ccgggctacg aaccgcgtga aggtatcaaa   480
gcaaacccgg taggcctgaa acacgttgat cactgcgttg gtaacgttga actgggcgag   540
atggacaaat gggtgaaatt ctatgaagac gtgatgggct caaactgct gctgaccttc   600
gatgacaaag atatctccac cgagtacacc gctctgatga gcaaagttgt aagcaacggc   660
aacggctaca ttaaattccc gattaacgaa ccggctgaag tcgcaaaaa atctcagatc   720
gaagagtatc tggacttcta tcagggtgcg ggtgttcagc acattgccgt gcaactgat   780
gacatcctgc acaccgtagg tgaactccgt aaccgtggtg ttgatttcct gcacgtgccg   840
gacaactact atgaagatct ggaacagcgc gttggtaaag tggacgaaga catggatgat   900
ctgcgtaaac tgaacattct ggtggatcgt gacgatgagg ttacctgct gcagattttc   960
accaaaccag tggaagaccg tccgactgta ttctacgaga tcatccagcg caaaggtgcc  1020
aaatcttttcg gcaaaggcaa cttcaaagcg ctgtttgaag cgatcgaacg tgaacaggca  1080
gttcgtggca acctgtaa                                                1098
```

<210> SEQ ID NO 20
<211> LENGTH: 365
<212> TYPE: PRT
<213> ORGANISM: Microscilla

<400> SEQUENCE: 20

```
Met Glu Gln Ala His Asp Phe Leu Pro Ile Ile Gly Thr Asp His Leu
1               5                   10                  15

Glu Phe Tyr Val Gly Asn Ala Lys Gln Ser Ala Tyr Phe Tyr Gln Ser
            20                  25                  30

Ala Phe Gly Tyr Gln Leu Val Gly Tyr Ala Gly Pro Glu Thr Gly Val
        35                  40                  45

Arg Asp Arg Ala Ser Tyr Val Leu Lys Gln Gly Lys Val Arg Leu Val
    50                  55                  60

Leu Thr Thr Ala Met His Pro Ser Ser Glu Val Ser Glu His Val Lys
65                  70                  75                  80

Lys His Gly Asp Gly Val Lys Val Leu Ala Ile Gln Val Glu Asn Ala
                85                  90                  95

Tyr Gln Ala Tyr Glu Glu Thr Val Lys Arg Gly Ala Lys Ser Ala Ile
            100                 105                 110

Glu Pro His Thr Leu Thr Asp Glu Tyr Gly Glu Ile Lys Ile Ala Ala
        115                 120                 125
```

Ile His Thr Tyr Gly Glu Thr Ile His Lys Phe Val Glu Arg Thr Asn
    130                 135                 140

Tyr Asn Gly Val Phe Met Pro Gly Tyr Glu Pro Arg Glu Gly Ile Lys
145                 150                 155                 160

Ala Asn Pro Val Gly Leu Lys His Val Asp His Cys Val Gly Asn Val
                165                 170                 175

Glu Leu Gly Glu Met Asp Lys Trp Val Lys Phe Tyr Glu Asp Val Met
            180                 185                 190

Gly Phe Lys Leu Leu Leu Thr Phe Asp Asp Lys Asp Ile Ser Thr Glu
        195                 200                 205

Tyr Thr Ala Leu Met Ser Lys Val Val Ser Asn Gly Asn Gly Tyr Ile
    210                 215                 220

Lys Phe Pro Ile Asn Glu Pro Ala Glu Gly Arg Lys Lys Ser Gln Ile
225                 230                 235                 240

Glu Glu Tyr Leu Asp Phe Tyr Gln Gly Ala Gly Val Gln His Ile Ala
                245                 250                 255

Val Ala Thr Asp Asp Ile Leu His Thr Val Gly Glu Leu Arg Asn Arg
            260                 265                 270

Gly Val Asp Phe Leu His Val Pro Asp Asn Tyr Tyr Glu Asp Leu Glu
        275                 280                 285

Gln Arg Val Gly Lys Val Asp Glu Asp Met Asp Asp Leu Arg Lys Leu
    290                 295                 300

Asn Ile Leu Val Asp Arg Asp Asp Glu Gly Tyr Leu Leu Gln Ile Phe
305                 310                 315                 320

Thr Lys Pro Val Glu Asp Arg Pro Thr Val Phe Tyr Glu Ile Ile Gln
                325                 330                 335

Arg Lys Gly Ala Lys Ser Phe Gly Lys Gly Asn Phe Lys Ala Leu Phe
            340                 345                 350

Glu Ala Ile Glu Arg Glu Gln Ala Val Arg Gly Asn Leu
        355                 360                 365

<210> SEQ ID NO 21
<211> LENGTH: 1098
<212> TYPE: DNA
<213> ORGANISM: Algoriphagus

<400> SEQUENCE: 21
atggccaccg aagactttct gccgatcaac ggcacggact atgttgaact gtatgtgggc      60
aacgcaaaac agtccgctct gtactatcag tacgcgtttg gctttgaact gatcgcttac     120
gctggtccgg aaactggtat caaagaccgt gcgtcctacg tgctgaaaca ggacaaaatc     180
cgtattgtcc tgaccacgcc gctgtctccg ataacccga ttactcagca cattgcgaaa      240
cacggtgacg gtgtaaaagt tctggccctg tgggttgatg acgcggaaaa aagctggaaa     300
gaaaccactt ctcgtggtgc acagagcgct attgaaccac acgtactgtc tgacgctaac     360
ggcgaggtaa aagtcgcctc tatcaaaacc tacggcgaaa cgatccacac cttcgtcgaa     420
cgcaaaaact acaacggtac cttcctgcca ggttacatcc acgtaaatc tctgtacaac      480 agccagtcca ttggcctgaa atatatcgat cactgcgtgg gtaacgttga actgggtgag     540
atgaaccgtt gggtgaaatt ctacgaggac gtgatgggct tcaaactgct gatcaccttc     600
gacgattctg acatctccac tgagtattct gcgctgatgt ccaaagtagt tagcaacggt     660
aacggttata tcaaattccc gatcaacgag ccggcagaag gcaaaaaaaa atcccagatc     720
gaggaatacc tggatttcta ccacggtccg ggtgttcagc atatggcaat cgcgaccgat     780

```
gatattatct acaccgtgag cgaactgcgc aaacgtggcg ttgaattcct cgaagtaccg    840
cagtcttatt acgatgacct cctggatcgt gttggtaaaa tcgacgaaga tctgcagccg    900
ctgaaagacc tgaacattct ggtggatcgt gacgatgaag gttacctcct gcagatcttt    960
accaaaccgg ttcaggaccg tccgactctg ttctttgaaa tcattcagcg caaaggtgcg   1020
aaatctttcg gcaaaggcaa cttcaaagct ctgttcgaag caattgaacg cgagcaggaa   1080
ctgcgcggca acctgtaa                                                 1098
```

<210> SEQ ID NO 22
<211> LENGTH: 364
<212> TYPE: PRT
<213> ORGANISM: Algoriphagus

<400> SEQUENCE: 22

```
Met Thr Glu Asp Phe Leu Pro Ile Asn Gly Thr Asp Tyr Val Glu Leu
1               5                   10                  15

Tyr Val Gly Asn Ala Lys Gln Ser Ala Leu Tyr Tyr Gln Tyr Ala Phe
                20                  25                  30

Gly Phe Glu Leu Ile Ala Tyr Ala Gly Pro Glu Thr Gly Ile Lys Asp
            35                  40                  45

Arg Ala Ser Tyr Val Leu Lys Gln Asp Lys Ile Arg Ile Val Leu Thr
        50                  55                  60

Thr Pro Leu Ser Pro Asp Asn Pro Ile Thr Gln His Ile Ala Lys His
65                  70                  75                  80

Gly Asp Gly Val Lys Val Leu Ala Leu Trp Val Asp Ala Glu Lys
                85                  90                  95

Ser Trp Lys Glu Thr Thr Ser Arg Gly Ala Gln Ser Ala Ile Glu Pro
            100                 105                 110

His Val Leu Ser Asp Ala Asn Gly Glu Val Lys Val Ala Ser Ile Lys
        115                 120                 125

Thr Tyr Gly Glu Thr Ile His Thr Phe Val Glu Arg Lys Asn Tyr Asn
    130                 135                 140

Gly Thr Phe Leu Pro Gly Tyr Ile Pro Arg Lys Ser Leu Tyr Asn Ser
145                 150                 155                 160

Gln Ser Ile Gly Leu Lys Tyr Ile Asp His Cys Val Gly Asn Val Glu
                165                 170                 175

Leu Gly Glu Met Asn Arg Trp Val Lys Phe Tyr Glu Asp Val Met Gly
            180                 185                 190

Phe Lys Leu Leu Ile Thr Phe Asp Asp Ser Asp Ile Ser Thr Glu Tyr
        195                 200                 205

Ser Ala Leu Met Ser Lys Val Val Ser Asn Gly Asn Gly Tyr Ile Lys
    210                 215                 220

Phe Pro Ile Asn Glu Pro Ala Glu Gly Lys Lys Lys Ser Gln Ile Glu
225                 230                 235                 240

Glu Tyr Leu Asp Phe Tyr His Gly Pro Val Gln His Met Ala Ile
                245                 250                 255

Ala Thr Asp Asp Ile Ile Tyr Thr Val Ser Glu Leu Arg Lys Arg Gly
            260                 265                 270

Val Glu Phe Leu Glu Val Pro Gln Ser Tyr Tyr Asp Asp Leu Leu Asp
        275                 280                 285

Arg Val Gly Lys Ile Asp Glu Asp Leu Gln Pro Leu Lys Asp Leu Asn
    290                 295                 300

Ile Leu Val Asp Arg Asp Asp Glu Gly Tyr Leu Leu Gln Ile Phe Thr
```

```
                305                 310                 315                 320
Lys Pro Val Gln Asp Arg Pro Thr Leu Phe Phe Glu Ile Ile Gln Arg
                    325                 330                 335

Lys Gly Ala Lys Ser Phe Gly Lys Gly Asn Phe Lys Ala Leu Phe Glu
                340                 345                 350

Ala Ile Glu Arg Glu Gln Glu Leu Arg Gly Asn Leu
            355                 360

<210> SEQ ID NO 23
<211> LENGTH: 1209
<212> TYPE: DNA
<213> ORGANISM: Frankia

<400> SEQUENCE: 23
atggcttcca ccgaagttac cctgaccggt caggaacgta gcgctgaact ggatgtggat      60
cagctgcgtc agctggtggg tctggttgaa cacgatccag cgggcgaccc atttccggta     120
agcggttggg acgctgttgt gtgggtggtc ggtaacgcca acaggctgc gcactactac      180 cagagcgcct ttggcatgga tctggtagcg tatagcggtc agaaactgg ccagccggac      240 cattgctctt atgtcctgac gtccggcgct gtccgcttcg tattcaaagg tggcgttcgt     300
ccggactctc cactcctgga ccatcatcgc cgtcacggtg acggtgtagt ggacatcgcg     360
ctggaggtac agatgttga ccgctgcatt gcacacgcac gcgcacaggg tgcacgcgtt      420
atcgaagaac cgcacgaact gcgtgacgaa cacggtgtag tccgtctggc agcgattgcg     480
gcttacggtc gtactcgcca cactctggtc gatcgctctc gttattctgg ctgttacctg     540
ccgggctacg ttgaacgccg ttccggtcat gtgcgccgtc cgggtgctcc acgctccctg     600
tttcaggcgc tggatcacgt agtgggcaac gttgaactgg gcgcgatgga cgagtgggtg     660
gcgttctata ccgtgtgat gggctttacc aacctggccg agttcattgg tggtgatatc      720
gccactcgct actccgcact gatgtccaaa gtggttgcgt ccggtaacca ccgcgtcaaa     780
ttcccgctga cgaaccagc accaggtcgc cgtaaatctc agatcgcgga gtacctggaa      840
ttccacggcg gtccgggtgc tcagcatctg gcgctcgcta cgggcgatat cctggcaagc     900
gttgacgcaa tgcgtgctgg cggtgtagag ttcctgacca cgccggatac ctactatgat     960
gatccggccc tgtgggctcg tgtaggcgaa gttcgcgctc cagttgaaga gctgcgccgt    1020
cgccgtatcc tggttgaccg tgacgaagac ggctacctcc tgcagatctt cactcgtccg    1080
ctgggcgatc gtccgaccgt gttctttgaa ctgattgaac gccacggttc tctgggtttc    1140
ggcaaaggta acttccaggc cctgttcgaa gcaatcgaac gtgaacagga gcgccgtggc    1200
aacctgtaa                                                           1209

<210> SEQ ID NO 24
<211> LENGTH: 401
<212> TYPE: PRT
<213> ORGANISM: Frankia

<400> SEQUENCE: 24

Met Ser Thr Glu Val Thr Leu Thr Gly Gln Glu Arg Ser Ala Glu Leu
1               5                   10                  15

Asp Val Asp Gln Leu Arg Gln Leu Val Gly Leu Val Glu His Asp Pro
                20                  25                  30

Ala Gly Asp Pro Phe Pro Val Ser Gly Trp Asp Ala Val Val Trp Val
            35                  40                  45

Val Gly Asn Ala Lys Gln Ala Ala His Tyr Tyr Gln Ser Ala Phe Gly
```

```
            50                  55                  60
Met Asp Leu Val Ala Tyr Ser Gly Pro Glu Thr Gly Gln Pro Asp His
 65                  70                  75                  80

Cys Ser Tyr Val Leu Thr Ser Gly Ala Val Arg Phe Val Phe Lys Gly
                 85                  90                  95

Gly Val Arg Pro Asp Ser Pro Leu Leu Asp His His Arg His Arg Gly
                100                 105                 110

Asp Gly Val Val Asp Ile Ala Leu Glu Val Pro Asp Val Asp Arg Cys
                115                 120                 125

Ile Ala His Ala Arg Ala Gln Gly Ala Arg Val Ile Glu Glu Pro His
            130                 135                 140

Glu Leu Arg Asp Glu His Gly Val Val Arg Leu Ala Ala Ile Ala Ala
145                 150                 155                 160

Tyr Gly Arg Thr Arg His Thr Leu Val Asp Arg Ser Arg Tyr Ser Gly
                165                 170                 175

Cys Tyr Leu Pro Gly Tyr Val Glu Arg Arg Ser Gly His Val Arg Arg
                180                 185                 190

Pro Gly Ala Pro Arg Ser Leu Phe Gln Ala Leu Asp His Val Val Gly
                195                 200                 205

Asn Val Glu Leu Gly Ala Met Asp Glu Trp Val Ala Phe Tyr Asn Arg
210                 215                 220

Val Met Gly Phe Thr Asn Leu Ala Glu Phe Ile Gly Asp Ile Ala
225                 230                 235                 240

Thr Arg Tyr Ser Ala Leu Met Ser Lys Val Val Ala Ser Gly Asn His
                245                 250                 255

Arg Val Lys Phe Pro Leu Asn Glu Pro Ala Pro Gly Arg Arg Lys Ser
                260                 265                 270

Gln Ile Ala Glu Tyr Leu Glu Phe His Gly Gly Pro Gly Ala Gln His
                275                 280                 285

Leu Ala Leu Ala Thr Gly Asp Ile Leu Ala Ser Val Asp Ala Met Arg
290                 295                 300

Ala Gly Gly Val Glu Phe Leu Asp Thr Pro Asp Thr Tyr Tyr Asp Asp
305                 310                 315                 320

Pro Ala Leu Trp Ala Arg Val Gly Glu Val Arg Ala Pro Val Glu Glu
                325                 330                 335

Leu Arg Arg Arg Arg Ile Leu Val Asp Arg Asp Glu Asp Gly Tyr Leu
                340                 345                 350

Leu Gln Ile Phe Thr Arg Pro Leu Gly Asp Arg Pro Thr Val Phe Phe
                355                 360                 365

Glu Leu Ile Glu Arg His Gly Ser Leu Gly Phe Gly Lys Gly Asn Phe
370                 375                 380

Gln Ala Leu Phe Glu Ala Ile Glu Arg Glu Gln Glu Arg Gly Asn
385                 390                 395                 400

Leu

<210> SEQ ID NO 25
<211> LENGTH: 1125
<212> TYPE: DNA
<213> ORGANISM: Herpetosiphon

<400> SEQUENCE: 25
atggcgacta tggctgaaca ggaaaccacc aacgctcatg atccactggc actgcgtggc    60
atcgattatg tcgagatgta cgtaggtaac gcgcgtcagg ctgcccacta ctatcgtacc   120
```

```
gctttcggct ttactccggt tgcgtacgca ggtctggaaa ctggtactcg cgaccgcgta    180
tcttttgtca tgcagcagcg taacatccgt ctcgttctga ctggtgcgct gaacccggat    240
agcccaatcg ctgaacacgt gaaactgcac ggcgacggcg ttaaagatat cgccctggaa    300
gttgaaaacg cgactgctgc ctttgaagca gcgctggctc gtggtgcaac cgcagtactg    360
gaaccgaccg tcctggaatc taaatggggt aaagttgtga aagcgactat ccgcacctac    420
ggtcataccg tgcataccttt cgttgaacgt gacggctata ccggtacctt catgccaggc    480
tacaacaaag tgaaaaaccc ggcaaaagcc gaaccaaccg gtctggcagc tgtagatcac    540
atcgttggca acgtggagct gggcaaaatg gacgagtggg tgaacttcta cgcgcgtatt    600
ctgggtttct ctcagctgca gcagttcacg gatgacgata tctccaccga atacagcgct    660
ctgatgtcca aagttgtcca gaacggcacc ggtcgtatca aattcccgat taacgaaccg    720
gcggaaggcc gcaaaaaatc tcagattgac gagtacctcg actactatcg cggtccaggt    780
gctcagcaca ttgcactgat cactccggac attatcaaaa cggttcagca gctgcgcgac    840
aacggcgttg agtttctgcg tactccggat acgtattatt ccgcgctggc tggtcgtgtt    900
ggccacatcg atgaagacta caacaccctg cagcagctgg gtattctggt agaccgtgac    960
gatgaaggct acctgctcca gatcttcacg aaaccggtag gtgatcgccc aaccgtgttc    1020
tacgagatta tccagcgtaa aggttctcgc ggcttcggtg caggtaactt caaagccctg    1080
ttcgaagcca tcaacgtgac acaggcgaaa cgtggtaacc tgtaa    1125
```

<210> SEQ ID NO 26
<211> LENGTH: 373
<212> TYPE: PRT
<213> ORGANISM: Herpetosiphon

<400> SEQUENCE: 26

Met Thr Met Ala Glu Gln Glu Thr Thr Asn Ala His Asp Pro Leu Ala
1               5                   10                  15

Leu Arg Gly Ile Asp Tyr Val Glu Met Tyr Val Gly Asn Ala Arg Gln
            20                  25                  30

Ala Ala His Tyr Tyr Arg Thr Ala Phe Gly Phe Thr Pro Val Ala Tyr
        35                  40                  45

Ala Gly Leu Glu Thr Gly Thr Arg Asp Arg Val Ser Phe Val Met Gln
    50                  55                  60

Gln Arg Asn Ile Arg Leu Val Leu Thr Gly Ala Leu Asn Pro Asp Ser
65                  70                  75                  80

Pro Ile Ala Glu His Val Lys Leu His Gly Asp Gly Val Lys Asp Ile
                85                  90                  95

Ala Leu Glu Val Glu Asn Ala Thr Ala Ala Phe Glu Ala Ala Leu Ala
            100                 105                 110

Arg Gly Ala Thr Ala Val Leu Glu Pro Thr Val Leu Glu Ser Lys Trp
        115                 120                 125

Gly Lys Val Val Lys Ala Thr Ile Arg Thr Tyr Gly His Thr Val His
    130                 135                 140

Thr Phe Val Glu Arg Asp Gly Tyr Thr Gly Thr Phe Met Pro Gly Tyr
145                 150                 155                 160

Asn Lys Val Lys Asn Pro Ala Lys Ala Glu Pro Thr Gly Leu Ala Ala
                165                 170                 175

Val Asp His Ile Val Gly Asn Val Glu Leu Gly Lys Met Asp Glu Trp
            180                 185                 190

Val Asn Phe Tyr Ala Arg Ile Leu Gly Phe Ser Gln Leu Gln Gln Phe

```
              195                 200                 205
Thr Asp Asp Ile Ser Thr Glu Tyr Ser Ala Leu Met Ser Lys Val
    210                 215                 220
Val Gln Asn Gly Thr Gly Arg Ile Lys Phe Pro Ile Asn Glu Pro Ala
225                 230                 235                 240
Glu Gly Arg Lys Lys Ser Gln Ile Asp Glu Tyr Leu Asp Tyr Tyr Arg
                245                 250                 255
Gly Pro Gly Ala Gln His Ile Ala Leu Ile Thr Pro Asp Ile Ile Lys
                260                 265                 270
Thr Val Gln Gln Leu Arg Asp Asn Gly Val Glu Phe Leu Arg Thr Pro
    275                 280                 285
Asp Thr Tyr Tyr Ser Ala Leu Ala Gly Arg Val Gly His Ile Asp Glu
290                 295                 300
Asp Tyr Asn Thr Leu Gln Gln Leu Gly Ile Leu Val Ala Arg Asp Asp
305                 310                 315                 320
Glu Gly Tyr Leu Leu Gln Ile Phe Thr Lys Pro Val Gly Asp Arg Pro
                325                 330                 335
Thr Val Phe Tyr Glu Ile Ile Gln Arg Lys Gly Ser Arg Gly Phe Gly
                340                 345                 350
Ala Gly Asn Phe Lys Ala Leu Phe Glu Ala Ile Glu Arg Glu Gln Ala
    355                 360                 365
Lys Arg Gly Asn Leu
    370

<210> SEQ ID NO 27
<211> LENGTH: 1146
<212> TYPE: DNA
<213> ORGANISM: Mucilaginibacter

<400> SEQUENCE: 27
atggaaacca cgtttgttaa cgccctgcca gctgttgaaa acctgggtca gctgaacaac      60
gactttctgc cactcaacgg cactgattac gtcgaattct acgtgggcaa cgcaaaacag     120
gctgcccatt tctacaaaac ggcgttcggt tttcagagcc tggcttacgc aggtccagaa     180
actggtgtcc gtgaccgtgc gagctatgtt ctgcagcagg gtaaaattcg tctggttctg     240
accactccga tgcactctga tcacccaatc gcggaacaca tcaaaaaaca tggcgatggc     300
gtgaaagtac tggcactgtg ggttgatgac gcctacgacg ctttcaaaca gaccgtatcc     360
cgcggcgcaa accatttcag gaaccacag acgatcactg acgaacatgg cgaagttcgc     420
actagcggta tctacctgta tggtgaaacg gtgcacctgt tcgtggagcg caaaaactat     480
aacggcccgt ttctgccggg ttaccagaaa atgaaatcca cctacaaccc agaaccgact     540
ggcctgctct acgtagatca ctgtgttggt aacgtcggct ggaacaaaat gaaccagtgg     600
gtgaacttct atgaggacgt gctgggtttc aaaaacatcc tgactttcga cgacaaagcg     660
atctctaccg aatactctgc tctgatgtcc aaagttatgt ctaacggcaa cggctacgtc     720
aaattcccaa tcaacgagcc ggcagagggc aaaaaaaaat ctcagatcga gagtatctg     780 gaattctacg aaggtgaggg tgtacagcac ctggctctgg caacccacga tatcgtggat     840
accgttacca aactgcagtc ccgtggtatt gaattcctga ccgtaccgac tacctactat     900
gataccctga ccgaacgtgt tggtcacatc gatgaaaacc tggaaccgct gaaacagctg     960
ggtattctgg tggaccgtga tgacgaaggt tatctgctgc agatcttcac caaaccggtt    1020
gaagaccgtc caaccgtatt cttcgagatt attcagcgca aaggtgcgaa atcttttggc    1080
```

```
gctggcaact tcaaagcgct gtttgaagcg attgaacgtg agcaggaact ccgtggtaac    1140
ctgtaa                                                                1146

<210> SEQ ID NO 28
<211> LENGTH: 411
<212> TYPE: PRT
<213> ORGANISM: Mucilaginibacter

<400> SEQUENCE: 28

Met Thr Leu Thr Thr Ile Thr Asp Thr Leu Ser Leu Thr Asn Pro Glu
1               5                   10                  15

Leu Ala Glu Gln Leu Lys Gln Thr Lys His Thr Ile Thr Tyr Met Glu
            20                  25                  30

Thr Thr Phe Val Asn Ala Leu Pro Ala Val Glu Asn Leu Gly Gln Leu
        35                  40                  45

Asn Asn Asp Phe Leu Pro Leu Asn Gly Thr Asp Tyr Val Glu Phe Tyr
    50                  55                  60

Val Gly Asn Ala Lys Gln Ala Ala His Phe Tyr Lys Thr Ala Phe Gly
65                  70                  75                  80

Phe Gln Ser Leu Ala Tyr Ala Gly Pro Glu Thr Gly Val Arg Asp Arg
                85                  90                  95

Ala Ser Tyr Val Leu Gln Gln Gly Lys Ile Arg Leu Val Leu Thr Thr
            100                 105                 110

Pro Met His Ser Asp His Pro Ile Ala Glu His Ile Lys Lys His Gly
        115                 120                 125

Asp Gly Val Lys Val Leu Ala Leu Trp Val Asp Ala Tyr Asp Ala
    130                 135                 140

Phe Lys Gln Thr Val Ser Arg Gly Ala Lys Pro Phe Gln Glu Pro Gln
145                 150                 155                 160

Thr Ile Thr Asp Glu His Gly Glu Val Arg Thr Ser Gly Ile Tyr Leu
                165                 170                 175

Tyr Gly Glu Thr Val His Leu Phe Val Glu Arg Lys Asn Tyr Asn Gly
            180                 185                 190

Pro Phe Leu Pro Gly Tyr Gln Lys Met Lys Ser Thr Tyr Asn Pro Glu
        195                 200                 205

Pro Thr Gly Leu Leu Tyr Val Asp His Cys Val Gly Asn Val Gly Trp
    210                 215                 220

Asn Lys Met Asn Gln Trp Val Asn Phe Tyr Glu Asp Val Leu Gly Phe
225                 230                 235                 240

Lys Asn Ile Leu Thr Phe Asp Asp Lys Ala Ile Ser Thr Glu Tyr Ser
                245                 250                 255

Ala Leu Met Ser Lys Val Met Ser Asn Gly Asn Gly Tyr Val Lys Phe
            260                 265                 270

Pro Ile Asn Glu Pro Ala Glu Gly Lys Lys Ser Gln Ile Glu Glu
        275                 280                 285

Tyr Leu Glu Phe Tyr Glu Gly Glu Gly Val Gln His Leu Ala Leu Ala
    290                 295                 300

Thr His Asp Ile Val Asp Thr Val Thr Lys Leu Gln Ser Arg Gly Ile
305                 310                 315                 320

Glu Phe Leu Thr Val Pro Thr Thr Tyr Tyr Asp Thr Leu Thr Glu Arg
                325                 330                 335

Val Gly His Ile Asp Glu Asn Leu Glu Pro Leu Lys Gln Leu Gly Ile
            340                 345                 350

Leu Val Asp Arg Asp Asp Glu Gly Tyr Leu Leu Gln Ile Phe Thr Lys
```

```
            355                 360                 365
Pro Val Glu Asp Arg Pro Thr Val Phe Phe Glu Ile Ile Gln Arg Lys
    370                 375                 380

Gly Ala Lys Ser Phe Gly Ala Gly Asn Phe Lys Ala Leu Phe Glu Ala
385                 390                 395                 400

Ile Glu Arg Glu Gln Glu Leu Arg Gly Asn Leu
                405                 410

<210> SEQ ID NO 29
<211> LENGTH: 1128
<212> TYPE: DNA
<213> ORGANISM: Acidobacterium

<400> SEQUENCE: 29
atggcgagca ccctggtgca tccagaggta gctacccaga agatttcct gccgctgaac      60 ggcaccgatc acgttgaatt ctatgtaggt aacgccaaac aggcggccta tttctaccgc    120
gttgcctttg gtttccagct cgttgcttac gctggtccgg aaactggtgt acgtgaccgt    180
gctagctatg tcctgcagca gaacaaaatt cgtttcgtac tgactacccc actgcgccca    240
gacggtgaaa tcgcagcgca tatccacctg cacggcgacg gtatccgcga tgtcgctctg    300
tgggttgacg acgcacgtca ggcttggaaa gaaactacga acgtggcgc acgctctgta     360 cgtgagccat tcgaactgaa agacgaacac ggcacggtga aatggcttc tatcgctgcg     420 tacggtgata ccgttcacac ctttgtcgag cgtggctctt atcacggtgt tttcctcccg    480
ggttatcgtg ctgaagcgga agataccatc gcacgtccaa ccggtctgct gcacgtggat    540
cacatggtgg gtaacgtcgg ttggaacgaa atgaaccgtt gggttgactt ctacgcagac    600
attatgggct tttcccctgta ccagcacttc gatgacaaag acatctctac tgagtattcc    660
gcactgatgt ccaaagtgat ggctaacggt aacggtcgcg tgaaattccc gattaacgaa    720
ccggcggaag tcgccgtaa atcccagatt gaagaatacc tggagtttta ccacggccca    780
ggcgttcagc atgttgcaat ggcgactcac gacattctgg agacggtatc taaactgcag    840
gcacagggtg tcgcgtttct gaaagtgccg catagctact acaccgaact ggaaggccgt    900
gtgggcaaaa ttgatgagcc aatcgaagag ctggaaaaac tcggtatcct ggttgatcgt    960
gatgacgaag ctacatgct gcagatcttc actaaaccag ttgaagaccg tccgaccctg    1020
ttctacgaaa ttatccagcg taaaggctct cgttctttcg gcaaaggtaa cttcaaagcg   1080
ctgtttgaag ctattgaacg cgaacaggaa ctgcgcggca acctgtaa                1128

<210> SEQ ID NO 30
<211> LENGTH: 374
<212> TYPE: PRT
<213> ORGANISM: Acidobacterium

<400> SEQUENCE: 30

Met Ser Thr Leu Val His Pro Glu Val Ala Thr Gln Lys Asp Phe Leu
1               5                   10                  15

Pro Leu Asn Gly Thr Asp His Val Glu Phe Tyr Val Gly Asn Ala Lys
            20                  25                  30

Gln Ala Ala Tyr Phe Tyr Arg Val Ala Phe Gly Phe Gln Leu Val Ala
        35                  40                  45

Tyr Ala Gly Pro Glu Thr Gly Val Arg Asp Arg Ala Ser Tyr Val Leu
    50                  55                  60

Gln Gln Asn Lys Ile Arg Phe Val Leu Thr Thr Pro Leu Arg Pro Asp
65                  70                  75                  80
```

Gly Glu Ile Ala Ala His Ile His Leu His Gly Asp Gly Ile Arg Asp
                85                  90                  95

Val Ala Leu Trp Val Asp Asp Ala Arg Gln Ala Trp Lys Glu Thr Thr
                100                 105                 110

Lys Arg Gly Ala Arg Ser Val Arg Glu Pro Phe Glu Leu Lys Asp Glu
                115                 120                 125

His Gly Thr Val Lys Met Ala Ser Ile Ala Ala Tyr Gly Asp Thr Val
            130                 135                 140

His Thr Phe Val Glu Arg Gly Ser Tyr His Gly Val Phe Leu Pro Gly
145                 150                 155                 160

Tyr Arg Ala Glu Ala Glu Asp Thr Ile Ala Arg Pro Thr Gly Leu Leu
                165                 170                 175

His Val Asp His Met Val Gly Asn Val Gly Trp Asn Glu Met Asn Arg
                180                 185                 190

Trp Val Asp Phe Tyr Ala Asp Ile Met Gly Phe Ser Leu Tyr Gln His
                195                 200                 205

Phe Asp Asp Lys Asp Ile Ser Thr Glu Tyr Ser Ala Leu Met Ser Lys
210                 215                 220

Val Met Ala Asn Gly Asn Gly Arg Val Lys Phe Pro Ile Asn Glu Pro
225                 230                 235                 240

Ala Glu Gly Arg Arg Lys Ser Gln Ile Glu Glu Tyr Leu Glu Phe Tyr
                245                 250                 255

His Gly Pro Gly Val Gln His Val Ala Met Ala Thr His Asp Ile Leu
                260                 265                 270

Glu Thr Val Ser Lys Leu Gln Ala Gln Gly Val Ala Phe Leu Lys Val
                275                 280                 285

Pro His Ser Tyr Tyr Thr Glu Leu Glu Gly Arg Val Gly Lys Ile Asp
                290                 295                 300

Glu Pro Ile Glu Glu Leu Glu Lys Leu Gly Ile Leu Val Asp Arg Asp
305                 310                 315                 320

Asp Glu Gly Tyr Met Leu Gln Ile Phe Thr Lys Pro Val Glu Asp Arg
                325                 330                 335

Pro Thr Leu Phe Tyr Glu Ile Ile Gln Arg Lys Gly Ser Arg Ser Phe
                340                 345                 350

Gly Lys Gly Asn Phe Lys Ala Leu Phe Glu Ala Ile Glu Arg Glu Gln
                355                 360                 365

Glu Leu Arg Gly Asn Leu
                370

<210> SEQ ID NO 31
<211> LENGTH: 1209
<212> TYPE: DNA
<213> ORGANISM: Geodermatophilus

<400> SEQUENCE: 31
atggcgagcc tggaacaggc actgaacgac gatgaacgtc tggcgcagct ggatctggac    60
cagctgaaac agctggtggg tctggttgaa tacgacgcct ccggtgatcc gtttccggtt   120
agcggttggg atgcgctcgt atgggttgta ggtaacgcta tcaggctgc gcacttccac    180 cagtccgcct ttggtatgga actcgtcgcc tattctggcc agaaaccgg taaccgcgat    240 cacctggcct atgttctgga atctggcgca gcgcgttttg tagtgcgtgg tgcttacgat    300
ccagcttctc cactggcaga ccaccatcgc aaacatggcg acggtatcgt tgacattgcg    360
ctctccgtac cggacgtaga tcgttgcatt gcgcacgcag ctgctcaggg tgcaaccgtt    420

```
ctggaacagc cgcacgacat tagcgacgaa ttcggcaccg ttcgtatcgg tgctattgcg    480
acctacggcg ataccgtca cactctggtt gatcgctctc gttacactgg cccatacctg    540
ccaggctacg ttgaacgccg ttcctctcac gtcaaacgcg acggtgctcc gaaacgtctg    600
ttccaggcgg ttgatcacgt cgtgggtaac gtagaactgg gcgcgatgga tcgctgggtt    660 gaatttaca accgcgtgat gggcttcacc aacatggcgg aattcgtcgg tgaggatatc    720
gccaccgatt acagcgcact gatgtctaaa gtggttgcga acggcaacca tcgcgtgaaa    780
ttcccactga acgaaccggc aatcggcaaa aaaaaatctc agatcgacga gtatctggag    840
ttctacggcg gtccaggcgc tcagcatgtg gcactggcta ccaacgatat cctgactacc    900
gttgacgcac tgcgtgccga aggtatcgaa ttcctggcta ctccggactc ctactatgag    960
gacccagaac tgcgtgcacg tattggtgaa gtgcgtgctc cgattgaaga gctgcaggaa   1020
cgtggtgtac tggttgaccg tgacgaagac ggctatctgc tgcagatctt cacgaaaccg   1080
ctgggtgatc gtccgacggt gttctttgaa ctgatcgagc gtcacggtag cctgggtttc   1140
ggtatcggca acttcaaagc gctgttcgaa gcaatcgagc gtgagcagca caaacgcggc   1200
aacttctaa                                                            1209
```

<210> SEQ ID NO 32
<211> LENGTH: 401
<212> TYPE: PRT
<213> ORGANISM: Geodermatophilus

<400> SEQUENCE: 32

```
Met Ser Leu Glu Gln Ala Leu Asn Asp Asp Glu Arg Leu Ala Gln Leu
1               5                   10                  15

Asp Leu Asp Gln Leu Lys Gln Leu Val Gly Leu Val Glu Tyr Asp Ala
            20                  25                  30

Ser Gly Asp Pro Phe Pro Val Ser Gly Trp Asp Ala Leu Val Trp Val
        35                  40                  45

Val Gly Asn Ala Thr Gln Ala Ala His Phe His Gln Ser Ala Phe Gly
    50                  55                  60

Met Glu Leu Val Ala Tyr Ser Gly Pro Glu Thr Gly Asn Arg Asp His
65                  70                  75                  80

Leu Ala Tyr Val Leu Glu Ser Gly Ala Ala Arg Phe Val Val Arg Gly
                85                  90                  95

Ala Tyr Asp Pro Ala Ser Pro Leu Ala Asp His His Arg Lys His Gly
            100                 105                 110

Asp Gly Ile Val Asp Ile Ala Leu Ser Val Pro Asp Val Asp Arg Cys
        115                 120                 125

Ile Ala His Ala Ala Gln Gly Ala Thr Val Leu Glu Gln Pro His
    130                 135                 140

Asp Ile Ser Asp Glu Phe Gly Thr Val Arg Ile Gly Ala Ile Ala Thr
145                 150                 155                 160

Tyr Gly Asp Thr Arg His Thr Leu Val Asp Arg Ser Arg Tyr Thr Gly
                165                 170                 175

Pro Tyr Leu Pro Gly Tyr Val Glu Arg Arg Ser Ser His Val Lys Arg
            180                 185                 190

Asp Gly Ala Pro Lys Arg Leu Phe Gln Ala Val Asp His Val Val Gly
        195                 200                 205

Asn Val Glu Leu Gly Ala Met Asp Arg Trp Val Glu Phe Tyr Asn Arg
    210                 215                 220
```

| | | | | | | | | | | | | | |
|---|---|---|---|---|---|---|---|---|---|---|---|---|---|
|Val|Met|Gly|Phe|Thr|Asn|Met|Ala|Glu|Phe|Val|Gly|Glu|Asp|Ile|Ala|
|225| | | | |230| | | | |235| | | | |240|

Thr Asp Tyr Ser Ala Leu Met Ser Lys Val Val Ala Asn Gly Asn His
                    245                    250                    255

Arg Val Lys Phe Pro Leu Asn Glu Pro Ala Ile Gly Lys Lys Lys Ser
         260                    265                    270

Gln Ile Asp Glu Tyr Leu Glu Phe Tyr Gly Gly Pro Gly Ala Gln His
    275                    280                    285

Val Ala Leu Ala Thr Asn Asp Ile Leu Thr Thr Val Asp Ala Leu Arg
         290                    295                    300

Ala Glu Gly Ile Glu Phe Leu Ala Thr Pro Asp Ser Tyr Tyr Glu Asp
305                    310                    315                    320

Pro Glu Leu Arg Ala Arg Ile Gly Glu Val Arg Ala Pro Ile Glu Glu
                  325                    330                    335

Leu Gln Glu Arg Gly Val Leu Val Asp Arg Asp Glu Asp Gly Tyr Leu
            340                    345                    350

Leu Gln Ile Phe Thr Lys Pro Leu Gly Asp Arg Pro Thr Val Phe Phe
               355                    360                    365

Glu Leu Ile Glu Arg His Gly Ser Leu Gly Phe Gly Ile Gly Asn Phe
370                    375                    380

Lys Ala Leu Phe Glu Ala Ile Glu Arg Glu Gln His Lys Arg Gly Asn
385                    390                    395                    400

Phe

<210> SEQ ID NO 33
<211> LENGTH: 1395
<212> TYPE: DNA
<213> ORGANISM: Scenedesmus

<400> SEQUENCE: 33

```
atgggagctg gtggtgctca aggacctaag gttgaacttg tgggatacgc taacttcgtg      60
aggaacaacc ctaggtctga taagttccct gtgcacaagt ccaccacat cgagttctgg      120
tgtgctgatg ctaccaacac cttcaagaga ttccagcacg gactcggaat gactctcgtg    180
gctaagtctg atcactctac cggaaactct aagtactgct cttacgtgct ccagtctaac    240
gatctcgtgt tcactttcac cgctccatac tctagaaagt gcgctgctgc tgctccatct    300
tcttcagaac tctctcccaga ttacgatcag cagcaggctt tcgagttcat ctgcactcat    360
ggacttgctg ctagagctgt tggactccaa gttggagatg ctgctcaggc ttacgaggtt    420
tcagttgcta atggtgctaa gggtgtgagg cctcctacta agcttgaaga tggtggtgga    480
tgcgctgtgg tttctgaggt tttgctctac ggtgatgttg tgctcagata tatcagtgga    540
aagtgggagg gaccttacct ccctggatat actgctactc ctgatgagcc tcagatctgc    600
tacggactcc atagactcga tcacgctgtt ggaaacgtgc aaagcttat cgagcatctc    660
gagcacgtga tcggattcac tggattccat gagttcgctg agttcgtggc tgaggatgtt    720
ggaactgttg attctggact caactctatg gtgctcgctt ctaacaacga tggtgctc    780
ttgcctatga acgagcctac cttcggaact aagaggaagt ctcagatcca gacctacctc    840
gagcaaaatg agggacctgg acttcagcat ctcgctctca agactcacga tatcctctca    900
accatgagag agatgcacgc taggtctaga tgcggaggat tgagtttca agctgctcct    960
ggacacgatt actacaagag agtggcagag aaagttggtg atgtgctttc tccagaagag   1020
tgggctgctg ttgagcagtt gggaatcctt gtggatcagg atgatcaggg tgttctcctc   1080
```

```
cagatcttca ctaagcctct cggagatagg cctactatct tcattgagat catcgagaga      1140 agggatgcc tcaaagagtc tgctgctcaa gctggatctg ctgctgctgc agctgctgaa       1200
cctactgctg ctggtggtga tgcagatgct gatggtgctg ctgctgctgt ggctgataag     1260
ttcaaggata ttgtgcaggt tagggaagat ggtgtggtgg ttgaacaagc tgctggttgt     1320
ggtggattcg gaaagggaaa cttctctgag cttttcaagt ctatcgaaga gtacgagagg     1380
accctccagg tgtga                                                       1395

<210> SEQ ID NO 34
<211> LENGTH: 1287
<212> TYPE: DNA
<213> ORGANISM: Scenedesmus

<400> SEQUENCE: 34
atgggagctg gtggtgctca aggacctaag gttgaacttg tgggatacgc taacttcgtg     60
aggaacaacc ctaggtctga taagttccct gtgcacaagt tccaccacat cgagttctgg    120
tgtgctgatg ctaccaacac cttcaagaga ttccagcacg gactcggaat gactctcgtg    180
gctaagtctg atcactctac cggaaactct aagtactgct cttacgtgct ccagtctaac   240
gatctcgtgt tcactttcac cgctccatac tctagaaagt gcgctgctgc tgctccatct   300
tcttcagaac ctctcccaga ttacgatcag cagcaggctt tcgagttcat ctgcactcat   360
ggacttgctc tagagctgt tggactccaa gttgagatg ctgctcaggc ttacgaggtt      420
tcagttgcta atggtgctaa gggtgtgagg cctcctacta agcttgaaga tggtggtgga    480
tgcgctgtgg tttctgaggt tttgctctac ggtgatgttg tgctcagata tatcagtgga    540
aagtgggagg gaccttacct ccctggatat actgctactc ctgatgagcc tcagatctgc   600 tacgactcc atagactcga tcacgctgtt ggaaacgtgc caaagcttat cgagcatctc    660
gagcacgtga tcggattcac tggattccat gagttcgctg agttcgtggc tgaggatgtt   720
ggaactgttg attctggact caactctatg gtgctcgctt caacaacga gatggtgctc    780 ttgcctatga acgagcctac cttcggaact aagaggaagt ctcagatcca gacctacctc   840
gagcaaaatg agggacctgg acttcagcat ctcgctctca agactcacga tatcctctca   900
accatgagag agatgcacgc taggtctaga tgcggaggat ttgagtttca agctgctcct   960
ggacacgatt actacaagag agtggcagag aaagttggtg atgtgctttc tccagaagag     1020
tgggctgctg ttgagcagtt gggaatcctt gtggatcagg atgatcaggg tgttctcctc     1080
cagatcttca ctaagcctct cggagatagg cctactatct tcattgagat catcgagaga     1140 agggatgcc tcaaagagtc tgctgctcaa gctggatctg ctgcagctgc tgtggaacaa     1200
gctgctggtt gtggtggatt tggaaaggga aacttctctg agcttttcaa gtctatcgaa    1260
gagtacgaga ggaccctcca ggtgtga                                         1287

<210> SEQ ID NO 35
<211> LENGTH: 1323
<212> TYPE: DNA
<213> ORGANISM: Lemna

<400> SEQUENCE: 35
atggctgaag aggaaggtgt tgaagctaga gctgctaagc tcgatgattc tgtgaactct     60
ggtgctgctg ctgatggatt ccagctcgtt ggattctcta acttcgtgag aagaaaccct    120
aggtctgata ggttccacgc taagtctttc caccacgttg agttcggtg cgctgatgct     180 actaacgtgt caagaaggtt ctcttttcgga ctcggaatgc ctctcgctgc taagtctgat   240
```

```
ctctctaccg gaaactctag tcacgcttct tacatgatca ggtctaggga tctcagattc      300
ctctttaccg ctcctctctc atcttctgct gcagattcta agtctgctat cccttctttc      360
gattctgatg cttgcagaag gttcagtaac ctccatggac tcgctgttag agctgttgct      420
ctccaagttg ctgatgctgc tgcagctttc catgtgtctg ttcagaatgg tgctaggcct      480
gcttttcctc ctgctgatct tggaggtgct gttatctctg aggtggaact ctacggtgat      540
gtggtgctca gattcttgtc tctcggatct ggtgagaagt tccagttcct tccaggattc      600
gaggatctct ctcctaactc tgctgatctc gattacggaa ttagaaggct cgatcacgct      660
gtgggaaacg ttccagaact tgctccagct gctgcttacg tgaagaaatt cactggattc      720
cacgagttcg ctgagttcac cgctgatgat gttggaactg ctgagtctgg actcaactct      780
gttgtgctcg ctaacaacga tgagaacgtg ctccttccac tcaacgagcc tgttcatgga      840
acccctagaa gatcacagat ccagacctac ctcgatcaca atgagggacc tggacttcag      900
catctcgctc tcagttctga ggatgtgatc gctaccctca gaaagatgag ggctgcttct      960
gctcttggtg gattcgagtt tatgcctcct cctccaccaa cctactacag aaacctcaga     1020
aaaagggcta aggatgtgct caccgaggat cagatggttg cttgtgagga acttggaatc     1080
ctcgtggata gggatgatca gggaatcctt ctccagatct tcaccaagcc tgtgggagat     1140
agacctacca tcttcctcga gatcatccag aggatcggat gcatgatgaa ggatgaggct     1200
ggaaaagagt accagaaggg aggttgcgga ggattcggaa agggaaactt caccgagctt     1260
ttcaagtcta tcgaggatta cgagaagtct ctcgaggcta agcaggctgg aactaggttt     1320
tga                                                                    1323
```

<210> SEQ ID NO 36  
<211> LENGTH: 1392  
<212> TYPE: DNA  
<213> ORGANISM: Artificial  
<220> FEATURE:  
<223> OTHER INFORMATION: Scenedesmus DNA E.coli codon-optimized

<400> SEQUENCE: 36

```
atgggtgccg gtggtgcaca gggtccgaaa gttgaactgg ttggttatgc aaattttgtg       60
cgtaataatc cgcgtagcga taaatttccg gtgcataaat ttcaccacat cgaattttgg      120
tgtgcagatg caaccaatac ctttaaacgt tttcagcatg gtctgggtat gaccctggtt      180
gcaaaaagcg atcatagcac cggtaatagc aaatattgta gctatgttct gcagagcaac      240
gatctggttt ttacctttac cgcaccgtat agccgtaaat gtgcagcagc agcaccgagc      300
agcagcgaac cgctgccgga ttatgatcag cagcaggcat ttgaatttat ctgtacacat      360
ggcctggcag cacgtgcagt tggtctgcag gttggtgatg cagcacaggc ctatgaagtt      420
agcgttgcaa atggtgcaaa aggtgttcgt ccgcctacca aactggaaga tggtggtggt      480
tgtgcagttg ttagcgaagt tctgctgtat ggtgatgttg ttctgcgtta tattagcggt      540
aaatgggaag gtccgtatct gcctggttat accgcaacac cggatgaacc gcagatttgt      600
tatggtctgc atcgtctgga tcatgccgtt ggtaatgttc gaaactgat tgaacatctg      660 gaacatgtga ttggctttac cggctttcat gaatttgcag aatttgttgc agaagatgtt      720
ggcaccgttg atagcggtct gaatagcatg gttctggcaa gcaataatga aatggttctg      780
ctgccgatga tgaaccgac ctttggcacc aaacgtaaaa gccagattca gacctacctg      840
gaacagaatg aaggtccggg tctgcagcat ctggcactga aaacccatga tattctgagc      900
```

```
accatgcgtg aaatgcatgc acgtagccgt tgtggtggtt ttgaatttca ggcagcaccg    960
ggtcatgatt attacaaacg tgttgccgaa aaagtgggtg atgttctgag tccggaagaa   1020
tgggcagcag ttgaacagct gggtattctg gttgatcagg atgatcaggg tgtactgctg   1080 cagatttttta ccaaaccgct gggtgatcgt ccgaccattt ttatcgaaat tattgaacgt   1140
cgtgggtgcc tgaaagaaag cgcagcccag gcaggtagcg cagcagccgc agctgcagaa   1200
cctaccgcag cgggtggtga tgccgatgca gatggtgcag cggcagccgt tgccgacaaa   1260
ttcaaagata ttgttcaggt tcgtgaagat ggcgttgttg ttgaacaggc agcaggttgc   1320
ggtggctttg gtaaaggcaa ttttagcgaa ctgtttaaaa gcatcgaaga gtatgaacgt   1380
accctgcagg tt                                                        1392

<210> SEQ ID NO 37
<211> LENGTH: 1356
<212> TYPE: DNA
<213> ORGANISM: Artificial
<220> FEATURE:
<223> OTHER INFORMATION: Helianthus HPPD DNA E.coli codon-optimized

<400> SEQUENCE: 37
atgggcactg aagcgactgt tgctgccgtt gttgctggcg acgaatctga tcatccgacc     60
agcgcgttca aactggtggg tttcaaaaac tttatccgta ccaacccaat gtccgataaa    120
ttcaccgtca aaaacttcca ccacatcgaa ttctggtgct ctgacgctac taacactgct    180
cgccgctttt cctggggcct gggtatgcca atcatttttca aatctgacct gagcaccggt    240
aactctacgc atgcgtccta cctgctgcgt tccggtcacc tgaactttct gttcaccgct    300
ccgtattccc catctattag cccgaccact accacggctt ctattccgac cttcagccac    360
tccgcgtctc gtcatttcac ggccactcat ggtctcgctg ttcgtgcaat tgccgttgaa    420
gtggaggatg cagaaactgc gtttgcggtg agcgtagcca acggtgcaaa accaagctct    480
ccgccagtga ccctgggtca aacgatgta gtgctgtctg aagtcaaact gtacggtgac    540
gtcgtactgc gttatgtgtc ctacaaaaac aacaccaaca caacaacaa caacgacaac    600 gacaactata tcttcctgcc aggcttcgaa gctatggaca aaactagctc ttttttcaggaa    660 ctggactacg gcattcgccg cctggatcac gctgttggta acgtaccgga actggcacca    720
gcggttgact acgtaaaaag cttcaccggt ttccacgaat ttgcggaatt cacccgccgaa    780 gacgtaggta cttccgaatc cggtctgaac tctgttgtgc tggcgtgtaa ctctgaaatg    840
gtcctgattc cgatgaacga accggtgtac ggcaccaaac gtaaatccca gatccagacg    900
tacctggaac acaacgaagg cgctggtgtt cagcacctgg ctctcgcatc tgaagatatc    960
ttccgcaccc tgcgtgaaat gcgtaaacgc tctggtgttg gcggtttcga atttatgccg   1020
tctccaccgc caacctacta tcgcaacctg aaatctcgtg caggcgacgt tctgagcgat   1080
gaacagatca aagagtgcga agagctgggt atcctggttg atcgtgatga tcagggtacc   1140
ctgctccaga tctttaccaa accggtaggt gaccgtccga cgatcttcat tgaaatcatc   1200
cagcgtgttg gctgtatggt gaaagacgat gagggcaaag ttcagcagaa agcaggctgc   1260
ggtggcttcg gcaaaggcaa cttctctgag ctgttcaaat ctatcgaaga gtacgagaaa   1320
accctggagg cacgttctac cactgcagct gcgtaa                              1356

<210> SEQ ID NO 38
<211> LENGTH: 1353
<212> TYPE: DNA
<213> ORGANISM: Artificial
```

<220> FEATURE:
<223> OTHER INFORMATION: Helianthus_mut DNA HPPD E.coli codon-optimzed

<400> SEQUENCE: 38

```
atgggcactg aagcgactgt tgcagccgtt gttgctggcg acgaatctga tcatccgacc      60
agcgcgttca aactggtggg tttcaaaaac tttatccgca ccaacccaat gtccgataaa     120
ttcaccgtca aaaacttcca ccacatcgaa ttctggtgct ctgacgccac taacactgct     180
cgccgctttt cctggggcct gggtatgcca atcattttca atctgacct gagcaccggt      240
aactctacgc atgcgtccta tctgctgcgt tccggtcagc tgaactttct gtttaccgct     300
ccgtattccc cgtctatttc taccactacc acggcttcta ttccgacctt cagccactcc     360
gcgtctcgtc atttcacggc cactcatggt ctggctgttc gtgcaattgc cgttgaagtg     420
gaggatgcag aaactgcgtt tgcggtgagc gtagccaacg tgcaaaaacc aagctctccg     480
ccagtgaccc tgggtcacaa cgatgtagtg ctgtctgaag tcaaactgta cggtgacgtc     540
gtactccgtt atgtgtccta caaaaacaac accaacaacg ataacaacaa cgacaacgac     600
aactacatct tcctgccagg cttcgaagct atggacaaaa ccagctcttt tcaggaactg     660
gactacggca ttcgccgcct cgatcacgct gttggtaacg taccggaact ggcaccagcg     720
gttgactacg taaaaagctt caccggtttc cacgaattcg cggaattcac tgccgaagac     780
gtaggtactt ccgaatccgg tctgaactct gttgtgctgg cgtgcaactc tgaaatggtc     840
ctgattccga tgaacgaacc ggtgtacggc accaaacgta atcccagat ccagacgtac       900
ctgaacacac acgaaggtgc tggtgttcag cacctggctc tggcgtctga agatatcttc     960
cgtaccctgc gtgaaatgcg taaacgctct ggtgttggcg gtttcgaatt tatgccgtct    1020
ccaccgccaa cctactatcg caacctgaaa tctcgtgcag cgacgttct gagcgatgaa     1080
cagatcaaag agtgcgaaga gctgggtatc ctggttgatc gtgatgatca gggtaccctg    1140
ctgcagatct ttaccaaacc ggtaggtgac cgtccgacga tcttcattga aatcatccag    1200
cgtgttggct gtatggtgaa agacgatgag ggcaaagttc agcagaaagc aggctgtggt    1260
ggcttcggca aaggcaactt cagcgagctg ttcaaatcta tcgaggaata cgagaaaacc    1320
ctggaggcac gttctaccac tgcagctgcg taa                                  1353
```

<210> SEQ ID NO 39
<211> LENGTH: 1305
<212> TYPE: DNA
<213> ORGANISM: Hordeum vulgare

<400> SEQUENCE: 39

```
atgccgccca cccccaccac ccccgcggct accggcgccg ccgccgcggt gacgccggag      60
cacgcgcgac cgcaccgaat ggtccgcttc aacccgcgca cgaccgctt ccacacgctc      120
tccttccacc acgtcgagtt ctggtgcgcg gacgccgcct ccgccgccgg ccgcttcgcg     180
ttcgcgctcg gcgcgccgct cgccgccagg tccgacctct ccacggggaa ctccgcgcac     240
gcctcccagc tgctccgctc gggctccctc gccttcctct tcaccgcgcc ctacgccaac     300
ggctgcgacg ccgccaccgc ctccctgccc tccttctccg ccgacgccgc gcgccggttc     360
tccgccgacc acgggatcgc ggtgcgctcc gtagcgctgc gcgtcgcaga cgccgccgag     420
gccttccgcg ccagcgtcga cggggggcgcg cgcccggcct cgccccccgt ggacctcggc     480
cgcggcttcg gcttcgcgga ggtcgagctc tacggcgacg tcgtgctccg cttcgtcagc     540
cacccggacg gcacggacgt gcccttcttg ccggggttcg agggcgtgac caacccggac    600
```

```
gccgtggact acggcctgac gcggttcgac cacgtcgtcg gcaacgtccc ggagcttgcc    660
cccgccgcag cctacatcgc cgggttcacg gggttccacg agttcgccga gttcacggcg    720
gaggacgtgg gcacgaccga gagcgggctc aactcggtgg tgctcgccaa caactcggag    780
ggcgtgctgc tgccgctcaa cgagccggtg cacggcacca agcgccggag ccagatacag    840
acgttcctgg aacaccacgg cggccgggc gtgcagcaca tcgcggtggc cagcagtgac    900
gtgctcagga cgctcaggaa gatgcgtgcg cgctccgcca tgggcggctt cgacttcctg    960
ccacccccgc tgccgaagta ctacgaaggc gtgcgacgcc ttgccgggga tgtcctctcg   1020
gaggcgcaga tcaaggaatg ccaggagctg ggtgtgctcg tcgataggga cgaccaaggg   1080
gtgttgctcc aaatcttcac caagccagta ggggacaggc cgaccttgtt cctggagatg   1140
atccagagga tcgggtgcat ggagaaggac gagagagggg aagagtacca gaagggtggc   1200
tgcggcgggt tcggcaaagg caacttctcc gagctgttca agtccattga agattacgag   1260
aagtcccttg aagccaagca atctgctgca gttcagggat catag                  1305
```

<210> SEQ ID NO 40
<211> LENGTH: 434
<212> TYPE: PRT
<213> ORGANISM: Hordeum vulgare

<400> SEQUENCE: 40

Met Pro Pro Thr Pro Thr Thr Pro Ala Ala Thr Gly Ala Ala Ala
1               5                   10                  15

Val Thr Pro Glu His Ala Arg Pro His Arg Met Val Arg Phe Asn Pro
            20                  25                  30

Arg Ser Asp Arg Phe His Thr Leu Ser Phe His His Val Glu Phe Trp
        35                  40                  45

Cys Ala Asp Ala Ala Ser Ala Ala Gly Arg Phe Ala Phe Ala Leu Gly
    50                  55                  60

Ala Pro Leu Ala Ala Arg Ser Asp Leu Ser Thr Gly Asn Ser Ala His
65                  70                  75                  80

Ala Ser Gln Leu Leu Arg Ser Gly Ser Leu Ala Phe Leu Phe Thr Ala
                85                  90                  95

Pro Tyr Ala Asn Gly Cys Asp Ala Ala Thr Ala Ser Leu Pro Ser Phe
            100                 105                 110

Ser Ala Asp Ala Ala Arg Arg Phe Ser Ala Asp His Gly Ile Ala Val
        115                 120                 125

Arg Ser Val Ala Leu Arg Val Ala Asp Ala Ala Glu Ala Phe Arg Ala
    130                 135                 140

Ser Val Asp Gly Gly Ala Arg Pro Ala Phe Ala Pro Val Asp Leu Gly
145                 150                 155                 160

Arg Gly Phe Gly Phe Ala Glu Val Glu Leu Tyr Gly Asp Val Val Leu
                165                 170                 175

Arg Phe Val Ser His Pro Asp Gly Thr Asp Val Pro Phe Leu Pro Gly
            180                 185                 190

Phe Glu Gly Val Thr Asn Pro Asp Ala Val Asp Tyr Gly Leu Thr Arg
        195                 200                 205

Phe Asp His Val Val Gly Asn Val Pro Glu Leu Ala Pro Ala Ala Ala
    210                 215                 220

Tyr Ile Ala Gly Phe Thr Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Gly Val Leu Leu Pro Leu Asn Glu Pro Val His Gly
                260                 265                 270

Thr Lys Arg Arg Ser Gln Ile Gln Thr Phe Leu Glu His Gly Gly
            275                 280                 285

Pro Gly Val Gln His Ile Ala Val Ala Ser Ser Asp Val Leu Arg Thr
            290                 295                 300

Leu Arg Lys Met Arg Ala Arg Ser Ala Met Gly Gly Phe Asp Phe Leu
305                 310                 315                 320

Pro Pro Pro Leu Pro Lys Tyr Tyr Glu Gly Val Arg Arg Leu Ala Gly
                325                 330                 335

Asp Val Leu Ser Glu Ala Gln Ile Lys Glu Cys Gln Glu Leu Gly Val
            340                 345                 350

Leu Val Asp Arg Asp Asp Gln Gly Val Leu Leu Gln Ile Phe Thr Lys
            355                 360                 365

Pro Val Gly Asp Arg Pro Thr Leu Phe Leu Glu Met Ile Gln Arg Ile
            370                 375                 380

Gly Cys Met Glu Lys Asp Glu Arg Gly Glu Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Ala Val Gln
            420                 425                 430

Gly Ser

<210> SEQ ID NO 41
<211> LENGTH: 1338
<212> TYPE: DNA
<213> ORGANISM: Arabidopsis thaliana

<400> SEQUENCE: 41
atgggccacc aaaacgccgc cgtttcagag aatcaaaacc atgatgacgg cgctgcgtcg     60
tcgccgggat tcaagctcgt cggatttttcc aagttcgtaa gaaagaatcc aaagtctgat    120
aaattcaagg ttaagcgctt ccatcacatc gagttctggt gcggcgacgc aaccaacgtc    180
gctcgtcgct tctcctgggg tctggggatg agattctccg ccaaatccga tcttttccacc    240
ggaaacatgg ttcacgcctc ttacctactc acctccggtg acctccgatt ccttttcact    300
gctccttact ctccgtctct ctccgccgga gagattaaac cgacaaccac agcttctatc    360
ccaagtttcg atcacggctc ttgtcgttcc ttcttctctt cacatggtct cggtgttaga    420
gccgttgcga ttgaagtaga agacgcagag tcagctttct ccatcagtgt agctaatggc    480
gctattcctt cgtcgcctcc tatcgtcctc aatgaagcag ttacgatcgc tgaggttaaa    540
ctatacggcg atgttgttct ccgatatgtt agttacaaag cagaagatac cgaaaaatcc    600
gaattcttgc cagggttcga gcgtgtagag atgcgtcgt cgttcccatt ggattatggt    660
atccggcggc ttgaccacgc cgtgggaaac gttcctgagc ttggtccggc tttaacttat    720
gtagcggggt tcactggttt tcaccaattc gcagagttca cagcagacga cgttggaacc    780
gccgagagcg gtttaaattc agcggtcctg gctagcaatg atgaaatggt tcttctaccg    840
attaacgagc cagtgcacgg aacaaagagg aagagtcaga ttcagacgta tttggaacat    900
aacgaaggcg cagggctaca acatctggct ctgatgagtg aagacatatt caggaccctg    960
agagagatga ggaagaggag cagtattgga ggattcgact tcatgccttc tcctccgcct   1020
acttactacc agaatctcaa gaaacgggtc ggcgacgtgc tcagcgatga tcagatcaag   1080

```
gagtgtgagg aattagggat tcttgtagac agagatgatc aagggacgtt gcttcaaatc    1140
ttcacaaaac cactaggtga caggccgacg atatttatag agataatcca gagagtagga    1200
tgcatgatga agatgagga agggaaggct taccagagtg gaggatgtgg tggttttggc    1260
aaaggcaatt tctctgagct cttcaagtcc attgaagaat acgaaaagac tcttgaagcc    1320
aaacagttag tgggatga                                                  1338
```

<210> SEQ ID NO 42
<211> LENGTH: 445
<212> TYPE: PRT
<213> ORGANISM: Arabidopsis thaliana

<400> SEQUENCE: 42

```
Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His
        35                  40                  45

His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
            100                 105                 110

Lys Pro Thr Thr Thr Ala Ser Ile Pro Ser Phe Asp His Gly Ser Cys
        115                 120                 125

Arg Ser Phe Phe Ser Ser His Gly Leu Gly Val Arg Ala Val Ala Ile
    130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
            180                 185                 190

Lys Ala Glu Asp Thr Glu Lys Ser Glu Phe Leu Pro Gly Phe Glu Arg
        195                 200                 205

Val Glu Asp Ala Ser Ser Phe Pro Leu Asp Tyr Gly Ile Arg Arg Leu
    210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
            260                 265                 270

Asn Asp Glu Met Val Leu Leu Pro Ile Asn Glu Pro Val His Gly Thr
        275                 280                 285

Lys Arg Lys Ser Gln Ile Gln Thr Tyr Leu Glu His Asn Glu Gly Ala
    290                 295                 300

Gly Leu Gln His Leu Ala Leu Met Ser Glu Asp Ile Phe Arg Thr Leu
305                 310                 315                 320
```

Arg Glu Met Arg Lys Arg Ser Ser Ile Gly Gly Phe Asp Phe Met Pro
            325                 330                 335

Ser Pro Pro Pro Thr Tyr Tyr Gln Asn Leu Lys Lys Arg Val Gly Asp
        340                 345                 350

Val Leu Ser Asp Asp Gln Ile Lys Glu Cys Glu Glu Leu Gly Ile Leu
    355                 360                 365

Val Asp Arg Asp Asp Gln Gly Thr Leu Leu Gln Ile Phe Thr Lys Pro
370                 375                 380

Leu Gly Asp Arg Pro Thr Ile Phe Ile Glu Ile Gln Arg Val Gly
385                 390                 395                 400

Cys Met Met Lys Asp Glu Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
            420                 425                 430

Glu Tyr Glu Lys Thr Leu Glu Ala Lys Gln Leu Val Gly
            435                 440                 445

<210> SEQ ID NO 43
<211> LENGTH: 9
<212> TYPE: PRT
<213> ORGANISM: Scenedesmus obliquus
<220> FEATURE:
<221> NAME/KEY: MISC_FEATURE
<222> LOCATION: (6)..(6)
<223> OTHER INFORMATION: Xaa is Ala, Met, or Val

<400> SEQUENCE: 43

Ser Gly Leu Asn Ser Xaa Val Leu Ala
1               5

<210> SEQ ID NO 44
<211> LENGTH: 9
<212> TYPE: PRT
<213> ORGANISM: Scenedesmus obliquus

<400> SEQUENCE: 44

Cys Gly Gly Phe Gly Lys Gly Asn Phe
1               5

<210> SEQ ID NO 45
<211> LENGTH: 26
<212> TYPE: PRT
<213> ORGANISM: Scenedesmus obliquus
<220> FEATURE:
<221> NAME/KEY: MISC_FEATURE
<223> OTHER INFORMATION: So_Deg HPPD Fw

<400> SEQUENCE: 45

Trp Ser Asn Gly Gly Asn Tyr Thr Asn Ala Ala Tyr Trp Ser Asn Arg
1               5                   10                  15

Tyr Asn Gly Thr Asn Tyr Thr Asn Gly Cys
            20                  25

<210> SEQ ID NO 46
<211> LENGTH: 26
<212> TYPE: PRT
<213> ORGANISM: Scenedesmus obliquus
<220> FEATURE:
<221> NAME/KEY: MISC_FEATURE
<223> OTHER INFORMATION: So_Deg HPPD Rv

<400> SEQUENCE: 46

Arg Ala Ala Arg Thr Thr Asn Cys Cys Tyr Thr Thr Asn Cys Cys Arg

-continued

```
1               5               10              15
Ala Ala Asn Cys Cys Asn Cys Cys Arg Cys
            20              25
```

HERBICIDE-RESISTANT HYDROXYPHENYLPYRUVATE DIOXYGENASES

This application is a National Stage application of International Application No. PCT/EP2016/052835, filed Feb. 10, 2016, which claims the benefit of U.S. Provisional Patent Application No. 62/114,618 filed on Feb. 11, 2015, the entire content of which is incorporated herein by reference.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "78178_Seqlisting.txt", which was created on Jul. 17, 2017 and is 105,315 bytes in size. The subject matter of the Sequence Listing is incorporated herein in its entirety by reference.

FIELD OF THE INVENTION

The present invention relates to novel hydroxyphenylpyruvate dioxygenase mutants (mutated HPPD) which are able to confer resistance to herbicides, as well as polynucleotides encoding these enzymes. The invention also relates to transgenic plants producing these enzymes which are resistant and/or tolerant to herbicide activity, when treated therewith, seeds of such plants and methods of using such plants.

BACKGROUND OF THE INVENTION

Herbicides that inhibit 4-hydroxyphenylpyruvate dioxygenase (4-HPPD; EC 1.13.11.27), a key enzyme in the biosynthesis of the prenylquinones plastoquinone and tocopherols, have been used for selective weed control since the early 1990s. They block the conversion of 4-hydroxyphenylpyruvate to homogentisate in the biosynthetic pathway (Matringe et al., 2005, Pest Manag Sci., vol. 61:269-276; Mitchell et al., 2001, Pest Manag Sci. vol 57:120-128). Plastoquinone is thought to be a necessary cofactor of the enzyme phytoene desaturase in carotenoid biosynthesis (Boeger and Sandmann, 1998, Pestic Outlook, vol 9:29-35). Its inhibition results in the depletion of the plant plastoquinone and vitamin E pools, leading to bleaching symptoms. The loss of carotenoids, particularly in their function as protectors of the photosystems against photooxidation, leads to oxidative degradation of chlorophyll and photosynthetic membranes in growing shoot tissues. Consequently, chloroplast synthesis and function are disturbed (Boeger and Sandmann, 1998). The most important chemical classes of commercial 4-HPPD-inhibiting herbicides include pyrazolones, triketones and isoxazoles. The inhibitors mimic the binding of the substrate 4-hydroxyphenylpyruvate to an enzyme-bound ferrous ion in the active site by forming a stable ion-dipole charge transfer complex. Among 4-HPPD-inhibiting herbicides, the triketone sulcotrione was the first example of this herbicide group to be used in agriculture and identified in its mechanism of action (Schulz et al., 1993, FEBS Lett. Vol 318:162-166) The triketones have been reported to be derivatives of leptospermone, a herbicidal component from the bottlebrush plant, *Callistemon* spp (Lee et al. 1997, Weed Sci. Vol 45, 162-166).

Three main strategies are available for making plants tolerant to herbicides, i.e. (1) detoxifying the herbicide with an enzyme which transforms the herbicide, or its active metabolite, into non-toxic products, such as, for example, the enzymes for tolerance to bromoxynil or to Basta (EP242236, EP337899); (2) mutating the target enzyme into a functional enzyme which is less sensitive to the herbicide, or to its active metabolite, such as, for example, the enzymes for tolerance to glyphosate (EP293356, Padgette S. R. et al., J. Biol. Chem., 266, 33, 1991); or (3) overexpressing the sensitive enzyme so as to produce quantities of the target enzyme in the plant which are sufficient in relation to the herbicide, in view of the kinetic constants of this enzyme, so as to have enough of the functional enzyme available despite the presence of its inhibitor. The third strategy was described for successfully obtaining plants which were tolerant to HPPD inhibitors (WO96/38567). US2009/0172831 discloses nucleotide sequences encoding amino acid sequences having enzymatic activity such that the amino acid sequences are resistant to HPPD inhibitor herbicidal chemicals, in particular triketone inhibitor specific HPPD mutants.

To date, the prior art has not described HPPD-inhibiting herbicide tolerant plants containing microorganism-derived mutated HPPD nucleic acid according to the present invention. What are also needed in the art are crop plants and crop plants having increased tolerance to herbicides such as HPPD-inhibiting herbicide and containing the microorganism-derived mutated HPPD nucleic acid according to the present invention. Also needed are methods for controlling weed growth in the vicinity of such crop plants or crop plants. These compositions and methods would allow for the use of spray over techniques when applying herbicides to areas containing crop plant or crop plants The present inventors have characterized various microorganism and plant species utilizing a mechanism of conferring resistance or tolerance to herbicides. Furthermore, the inventors have generated and characterized the novel herbicide-resistance conferring mutated HPPD from these microorganisms.

BRIEF DESCRIPTION OF THE DRAWINGS

FIG. 1 Amino acid sequence alignment of HPPD enzymes from *Arabidopsis thaliana* (*Arabidopsis*) (SEQ ID NO: 42), *Helianthus annus* (*Helianthus*) (SEQ ID NO: 6), *Helianthus annus* mutant (*Helianthus* Mutant) (SEQ ID NO: 8), *Hordeum vulgare* (*Hordeum*) (SEQ ID NO: 40), *Scenedesmus obliquus* (*Scenedesmus*) (SEQ ID NO: 2), *Scenedesmus obliquus* [short] (*Scenedesmus* Short) (SEQ ID NOS: 4), *Lemna paucicosata* (*Lemna*) (SEQ ID NO: 10), *Bellelia baltica* (*Belliella*) (SEQ ID NO: 12), *Nitritalea haalkaliphilla* (*Nitritalea*) (SEQ ID NO: 14), *Pontibacter* sp. (*Pontibacter*) (SEQ ID NO: 16), *Ferroplasma acidarmanus* (*Ferroplasma*) (SEQ ID NO: 18), *Microscilla marina* (*Microscilla*) (SEQ ID NO: 20), *Algoriphagus machipongonensis* (*Algoriphagus*) (SEQ ID NO: 22), *Frankia* sp. (*Frankia*) (SEQ ID NO: 24), *Herpetosiphon aurantiacus* (*Herpetosiphon*) (SEQ ID NO: 26), *Mucilaginibacter paudis* (*Mucilaginibacter*) (SEQ ID NO: 28), *Acidobacterium capsulatum* (*Acidobacterium*) (SEQ ID NO: 30) and *Geodermatophilus obscurus* (*Geodermatophilus*) (SEQ ID NO: 32). Conserved regions are indicated in light grey and black.

TABLE 1

KEY TO SEQUENCE LISTING

Figure 2:
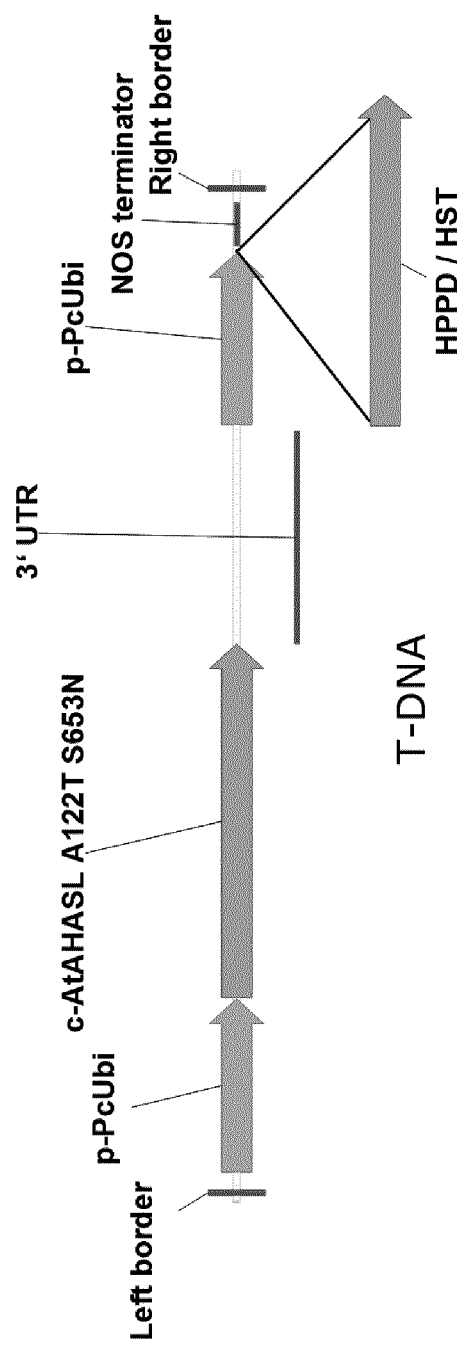
FIG. 2 shows a vector map of a plant transformation vector that is used for soybean transformation with HPPD sequences.

| Organism | Nucleic acid SEQ ID NO: | Amino acid SEQ ID NO: | Accession |
|---|---|---|---|
| Scenedesmus obliquus | 1 | 2 | |
| Scenedesmus obliquus [short] | 3 | 4 | |
| Helianthus WT | 5 | 6 | |
| Helianthus mutant | 7 | 8 | |
| Lemna | 9 | 10 | |
| Belliella | 11 | 12 | I3Z863_BELBD |
| Nitritalea | 13 | 14 | I5C6V4_9BACT |
| Pontibacter | 15 | 16 | J1FG23_9BACT |
| Ferroplasma | 17 | 18 | ZP_05569916 |
| Microscilla | 19 | 20 | A1ZF21_9BACT |
| Algoriphagus | 21 | 22 | A3HSH6_9BACT |
| Frankia | 23 | 24 | A8L2Y6_FRASN |
| Herpetosiphon | 25 | 26 | A9B1W0_HERA2 |
| Mucilaginibacter | 27 | 28 | H1Y6Y7_9SPHI |
| Acidobacterium | 29 | 30 | C1F681_ACIC5 |
| Geodermatophilus | 31 | 32 | D2SEF7_GEOOG |
| Scenedesmus codon-optimized | 33 | | |
| Scenedesmus short codon-optimized | 34 | | |
| Lemna codon-optimized | 35 | | |
| Scenedesmus codon-E. coli expression | 36 | | |
| Helianthus codon E. coli expression | 37 | | |
| Helianthus mutant codon E. coli expression | 38 | | |
| Hordeum vulgare | 39 | 40 | |
| Arabidopsis thaliana | 41 | 42 | |

SUMMARY OF THE INVENTION

Accordingly, in one embodiment, the present invention provides a method for producing a plant having an increased herbicide tolerance or resistance as compared to a corresponding wild type plant whereby the method comprises at least the following step: increasing or generating in a plant the activity of a transgenic mutated HPPD polypeptide, or a homolog or a functional equivalent thereof.

Accordingly, the invention provides a transgenic plant that over-expresses a mutated HPPD polynucleotide as defined herein, or a homolog or a functional equivalent thereof, in the sub-cellular compartment and tissue as indicated herein. The transgenic plant of the invention demonstrates an improved or increased herbicide tolerance or resistance as compared to a wild type variety of the plant.

Accordingly, the invention provides a method for producing a plant with increased herbicide tolerance or resistance as compared to a corresponding wild type plant comprising at least one of the steps selected from the group consisting of: (i) increasing or generating the activity of a mutated HPPD polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof; or (ii) increasing or generating the activity of an expression product of one or more isolated polynucleotide(s) comprising one or more polynucleotide(s) comprising a variant of the sequence of SEQ ID NO: 1, 3, 5, 7, 9, 11, 13, 15, 17, 19, 21, 23, 25, 27, 29, or 31, or a homolog or a functional equivalent thereof.

The invention further provides an isolated and/or recombinantly produced nucleic acid molecule comprising a nucleic acid molecule selected from the group consisting of:
(a) a nucleic acid molecule encoding the mutated HPPD polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof;
(b) a nucleic acid molecule comprising a variant of the sequence of SEQ ID NO: 1, 3, 5, 7, 9, 11, 13, 15, 17, 19, 21, 23, 25, 27, 29, or 31, or a homolog or a functional equivalent thereof,
(c) a nucleic acid molecule, which, as a result of the degeneracy of the genetic code, can be derived from a mutated HPPD polypeptide sequence of SEQ ID NO: 2, 4, 6, 8, 10, 12, 14, 16, 18, 20, 22, 24, 26, 28, 30, or 32, or a homolog or a functional equivalent thereof, and confers increased herbicide tolerance or resistance, as compared to a corresponding, e.g. non-transformed, wild type plant cell, a plant or a part thereof;
(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO: 1, 3, 5, 7, 9, 11, 13, 15, 17, 19, 21, 23, 25, 27, 29, or 31, ora homolog or a functional equivalent thereof, and confers increased herbicide tolerance or resistance, as compared to a corresponding, e.g. non-transformed, wild type plant cell, a plant or a part thereof;
(e) a nucleic acid molecule encoding a polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the mutated HPPD polypeptide sequence of SEQ ID NO: 2, 4, 6, 8, 10, 12, 14, 16, 18, 20, 22, 24, 26, 28, 30, or 32, and confers increased herbicide tolerance or resistance, as compared to a corresponding, e.g. non-transformed, wild type plant cell, a plant or a part thereof;
(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;

In a preferred embodiment, the encoded mutated HPPD comprises a variant of the sequence of SEQ ID NO: 4 comprising one or more of the following substitutions: the amino acid corresponding to or at position 30 is other than proline, the amino acid corresponding to or at position 39 is other than Phe, the amino acid corresponding to or at position 54 is other than Gly, the amino acid corresponding to or at position 57 is other than Met, the amino acid corresponding to or at position 84 is other than Phe, the amino acid corresponding to or at position 210 is other than Val, the amino acid corresponding to or at position 212 is other than Asn, the amino acid corresponding to or at position 223 is other than Val, the amino acid corresponding to or at position 243 is other than Val, the amino acid corresponding to or at position 247 is other than Leu, the amino acid corresponding to or at position 249 is other than Ser, the amino acid corresponding to or at position 251 is other than Val, the amino acid corresponding to or at position 264 is other than Asn, the amino acid corresponding to or at position 291 is other than Leu, the amino acid corresponding to or at position 306 is other than His, the amino acid corresponding to or at position 317 is other than Gln, the amino acid corresponding to or at position 318 is other than Ala, the amino acid corresponding to or at position 319 is other than Ala, the amino acid corresponding to or at position 321 is other than Gly, the amino acid corresponding to or at position 326 is other than Lys, the amino acid corresponding to or at position 327 is other than Arg, the amino acid corresponding to or at position 331 is other than Lys, the amino acid corresponding to or at position 341 is other than Trp, the amino acid corresponding to or at position 342 is other than Ala, the amino acid corresponding to or at position 345 is other than Glu, the amino acid corresponding to or at position 350 is other than Leu, the amino acid corresponding to or at position 363 is other than Phe, the amino acid corresponding to or at position 367 is other than Leu, the amino acid corresponding to or at position 373 is other than Ile, the amino acid corresponding to or at position 374 is other than Phe, the amino acid corresponding to or at position 375 is other than Ile, the amino acid corresponding to or at position 379 is other than Glu, the amino acid corresponding to or at position 405 is other than Gly, the amino acid corresponding to or at position 407 is other than Phe, the amino acid corresponding to or at position 410 is other than Gly, the amino acid corresponding to or at position 412 is other than Phe, the amino acid corresponding to or at position 414 is other than Glu, the amino acid corresponding to or at position 419 is other than Ile, the amino acid corresponding to or at position 421 is other than Glu, the amino acid corresponding to or at position 422 is other than Tyr.

The invention further provides a method for increasing herbicide tolerance or resistance of a crop plant, the method comprising the following steps: (i) increasing or generating of the expression of at least one polynucleotide; and/or (ii) increasing or generating the expression of an expression product encoded by at least one polynucleotide; and/or (iii) increasing or generating one or more activities of an expression product encoded by at least one polynucleotide, wherein the polynucleotide is selected from the group consisting of:

(a) an isolated and/or recombinant polynucleotide encoding the mutated HPPD polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof;
(b) an isolated and/or recombinant polynucleotide comprising a variant of the sequence of SEQ ID NO: 1, 3, 5, 7, 9, 11, 13, 15, 17, 19, 21, 23, 25, 27, 29, or 31, or a homolog or a functional equivalent thereof;
(c) an isolated and/or recombinant polynucleotide, which, as a result of the degeneracy of the genetic code, can be derived from a mutated HPPD polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof and confers an increased herbicide tolerance or resistance as compared to a corresponding, e.g. non-transformed, wild type plant cell, a transgenic plant or a part thereof;
(d) an isolated and/or recombinant polynucleotide having 30% or more identity, for example 50%, 60%, 70%, 80%, 85%, 90%, 95%, 97%, 98%, or 99% (percent) or more identity with the sequence of a polynucleotide comprising a variant of the sequence of SEQ ID NO: 1, 3, 5, 7, 9, 11, 13, 15, 17, 19, 21, 23, 25, 27, 29, or 31, or a homolog or a functional equivalent thereof and conferring an increased herbicide tolerance or resistance as compared to a corresponding, e.g. non-transformed, wild type plant cell, a transgenic plant or a part thereof;
(e) an isolated and/or recombinant polynucleotide encoding a polypeptide having 30% or more identity, for example 50%, 60%, 70%, 80%, 85%, 90%, 95%, 97%, 98%, or 99% or more identity with the amino acid sequence of the polypeptide encoded by the isolated polynucleotide of (a) to (c) and conferring an increased herbicide tolerance or resistance as compared to a corresponding, e.g. non-transformed, wild type plant cell, a transgenic plant or a part thereof;
(f) an isolated and/or recombinant polynucleotide which hybridizes with an isolated and/or recombinant polynucleotide of (a) to (c) under stringent hybridization conditions and confers an increased herbicide tolerance or resistance as compared to a corresponding, e.g. non-transformed, wild type plant cell, a transgenic plant or a part thereof;

Furthermore, the invention relates to a method for producing a transgenic plant with increased herbicide tolerance or resistance as compared to a corresponding, e.g. non-transformed, wild type plant, comprising transforming a plant cell or a plant cell nucleus or a plant tissue to produce such a plant, with an isolated and/or recombinant polynucleotide selected from the group consisting of:

(a) an isolated and/or recombinant polynucleotide encoding the mutated HPPD polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof;
(b) an isolated and/or recombinant polynucleotide comprising a variant of the sequence of SEQ ID NO: 1, 3, 5, 7, 9, 11, 13, 15, 17, 19, 21, 23, 25, 27, 29, or 31, or a homolog or a functional equivalent thereof;
(c) an isolated and/or recombinant polynucleotide, which, as a result of the degeneracy of the genetic code, can be derived from a mutated HPPD polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof and confers an increased herbicide tolerance or resistance as compared to a corresponding, e.g. non-transformed, wild type plant cell, a transgenic plant or a part thereof;
(d) an isolated and/or recombinant polynucleotide having 30 or more, for example 50%, 60%, 70%, 80%, 85%, 90%, 95%, 97%, 98%, or 99% (percent) or more identity with the sequence of a polynucleotide comprising a variant of the sequence of SEQ ID NO: 1, 3, 5, 7, 9, 11, 13, 15, 17, 19, 21, 23, 25, 27, 29, or 31, or a homolog or a functional equivalent thereof and conferring an increased herbicide tolerance or resistance as compared to a corresponding, e.g. non-transformed, wild type plant cell, a transgenic plant or a part thereof;
(e) an isolated and/or recombinant polynucleotide encoding a polypeptide having 30 or more, for example 50%, 60%, 70%, 80%, 85%, 90%, 95%, 97%, 98%, or 99% or more identity with the amino acid sequence of the polypeptide encoded by the isolated polynucleotide of (a) to (c) and conferring an increased herbicide tolerance or resistance as compared to a corresponding, e.g. non-transformed, wild type plant cell, a transgenic plant or a part thereof;

(f) an isolated and/or recombinant polynucleotide which hybridizes with an isolated and/or recombinant polynucleotide of (a) to (c) under stringent hybridization conditions and confers an increased herbicide tolerance or resistance as compared to a corresponding, e.g. non-transformed, wild type plant cell, a transgenic plant or a part thereof;

Furthermore, the invention relates to a method for controlling undesired vegetation at a plant cultivation site, the method comprising the steps of:

a) providing, at said site, a plant that comprises at least one nucleic acid comprising a nucleotide sequence encoding a mutated HPPD polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof, which is resistant or tolerant to a HPPD-inhibiting herbicide and/or b) applying to said site an effective amount of said herbicide.

In another embodiment, the invention refers to a method for growing the plant according to the present invention while controlling weeds in the vicinity of said plant, said method comprising the steps of:

a) growing said plant; and b) applying a herbicide composition comprising a HPPD-inhibiting herbicide to the plant and weeds, wherein the herbicide normally inhibits hydroxyphenylpyruvate dioxygenase, at a level of the herbicide that would inhibit the growth of a corresponding wild-type plant.

In another embodiment, the invention relates to a combination useful for weed control, comprising (a) a polynucleotide encoding mutated HPPD polypeptide according to the present invention, which polynucleotide is capable of being expressed in a plant to thereby provide to that plant tolerance to a HPPD inhibiting herbicide; and (b) a HPPD inhibiting herbicide.

In another embodiment, the invention relates to a process for preparing a combination useful for weed control comprising (a) providing a polynucleotide encoding mutated HPPD polypeptide according to the present invention, which polynucleotide is capable of being expressed in a plant to thereby provide to that plant tolerance to a HPPD inhibiting herbicide; and (b) providing a HPPD inhibiting herbicide.

In a preferred embodiment, said step of providing a polynucleotide comprises providing a plant containing the polynucleotide.

In another preferred embodiment, said step of providing a polynucleotide comprises providing a seed containing the polynucleotide.

In another preferred embodiment, said process further comprises a step of applying the HPPD inhibiting herbicide to the seed.

In another embodiment, the invention relates to the use of a combination useful for weed control, comprising (a) a polynucleotide encoding a mutated HPPD polypeptide according to the present invention, which polynucleotide is capable of being expressed in a plant to thereby provide to that plant tolerance to a HPPD inhibiting herbicide; and (b) a HPPD inhibiting herbicide, to control weeds at a plant cultivation site.

DETAILED DESCRIPTION OF THE PREFERRED EMBODIMENTS

Definition Collection

An "herbicide tolerance or resistance-increasing activity" according to the invention refers to an activity of a mutated HPPD from a microorganism or plant comprising a variant of the sequence of SEQ ID NO: 2, 4, 6, 8, 10, 12, 14, 16, 18, 20, 22, 24, 26, 28, 30, or 32, or a homolog or a functional equivalent thereof. A polypeptide conferring a herbicide tolerance or resistance-increasing activity can be encoded by a nucleic acid sequence comprising a variant of the sequence of SEQ ID NO: 1, 3, 5, 7, 9, 11, 13, 15, 17, 19, 21, 23, 25, 27, 29, or 31, or a homolog or a functional equivalent thereof, and/or comprises or consists of a polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof.

A "transgenic plant", as used herein, refers to a plant which contains a foreign nucleotide sequence inserted into either its nuclear genome or organelle genome. It encompasses further the offspring generations i.e. the T1-, T2- and consecutively generations or BC1-, BC2- and consecutively generation as well as crossbreeds thereof with non-transgenic or other transgenic plants.

A modification, i.e. an increase, can be caused by endogenous or exogenous factors. For example, an increase in activity in an organism or a part thereof can be caused by adding a gene product or a precursor or an activator or an agonist to the media or nutrition or can be caused by introducing said subjects into a organism, transient or stable. Furthermore such an increase can be reached by the introduction of the inventive nucleic acid sequence or the encoded protein in the correct cell compartment for example into the nucleus or cytoplasmic respectively or into plastids either by transformation and/or targeting.

For the purposes of the description of the present invention, the terms "cytoplasmic" and "non-targeted" shall indicate, that the nucleic acid of the invention is expressed without the addition of a non-natural transit peptide encoding sequence. A non-natural transit peptide encoding sequence is a sequence which is not a natural part of a nucleic acid of the invention, e.g. of the nucleic acids depicted in SEQ ID NO: 1, 3, 5, 7, 9, 11, 13, 15, 17, 19, 21, 23, 25, 27, 29, or 31, or a homolog or a functional equivalent thereof, but is rather added by molecular manipulation steps which are well known to the person skilled in the art or as for example described hereinafter. Therefore the terms "cytoplasmic" and "non-targeted" shall not exclude a targeted localization to any cell compartment for the products of the inventive nucleic acid sequences by their naturally occurring sequence properties within the background of the transgenic organism. The sub-cellular location of the mature polypeptide derived from the enclosed sequences can be predicted by a skilled person for the organism (plant) by using software tools like TargetP (Emanuelsson et al., (2000), Predicting sub-cellular localization of proteins based on their N-terminal amino acid sequence. J. Mol. Biol. 300, 1005-1016), ChloroP (Emanuelsson et al. (1999), ChloroP, a neural network-based method for predicting chloroplast transit peptides and their cleavage sites. Protein Science, 8: 978-984) or other predictive software tools (Emanuelsson et al. (2007), locating proteins in the cell using TargetP, SignalP, and related tools (Nature Protocols 2, 953-971).

The term "organelle" according to the invention shall mean for example "mitochondria", "plastid" or endoplasmic reticulum (ER). The term "plastid" according to the invention is intended to include various forms of plastids including proplastids, chloroplasts, chromoplasts, gerontoplasts, leucoplasts, amyloplasts, elaioplasts and etioplasts, preferably chloroplasts. They all have as a common ancestor the aforementioned proplasts.

The term "introduced" in the context of this specification shall mean the insertion of a nucleic acid sequence into the organism by means of a "transfection", "transduction" or preferably by "transformation".

A plastid, such as a chloroplast, has been "transformed" by an exogenous (preferably foreign) nucleic acid sequence if nucleic acid sequence has been introduced into the plastid that means that this sequence has crossed the membrane or the membranes of the plastid.

The foreign DNA may be integrated (covalently linked) into plastid DNA making up the genome of the plastid, or it may remain not integrated (e.g., by including a chloroplast origin of replication). "Stably" integrated DNA sequences are those, which are inherited through plastid replication, thereby transferring new plastids, with the features of the integrated DNA sequence to the progeny.

As used herein, "plant" is meant to include not only a whole plant but also a part thereof i.e., one or more cells, and tissues, including for example, leaves, stems, shoots, roots, flowers, fruits and seeds.

The term "herbicide tolerance or resistance" as used herein it is intended that a plant that is tolerant or resistant to at least one herbicide at a level that would normally kill, or inhibit the growth of, a normal or wild-type plant.

Any increase in herbicide tolerance or resistance is an improved herbicide tolerance or resistance in accordance with the invention. For example, the improvement in herbicide tolerance or resistance can comprise a 1.5×, 2×, 2.5×, 3×, 5×, 10×, 20×, 30×, 40×, 50×, 75×, 100×, 150×, 200× or greater increase in any measurable parameter, e.g. an increased tolerance factor as shown in the Examples (Table 7).

Unless otherwise specified, the terms "polynucleotides", "nucleic acid" and "nucleic acid molecule" are interchangeably in the present context. Unless otherwise specified, the terms "peptide", "polypeptide" and "protein" are interchangeably in the present context. The term "sequence" may relate to polynucleotides, nucleic acids, nucleic acid molecules, peptides, polypeptides and proteins, depending on the context in which the term "sequence" is used. The terms "gene(s)", "polynucleotide", "nucleic acid sequence", "nucleotide sequence", or "nucleic acid molecule(s)" as used herein refers to a polymeric form of nucleotides of any length, either ribonucleotides or deoxyribonucleotides. The terms "gene(s)", "polynucleotide", "nucleic acid sequence", "nucleotide sequence", or "nucleic acid molecule(s)" as used herein include known types of modifications, for example, methylation, "caps", substitutions of one or more of the naturally occurring nucleotides with an analogue. Preferably, the DNA or RNA sequence comprises a coding sequence encoding the herein defined polypeptide.

As also used herein, the terms "nucleic acid" and "nucleic acid molecule" are intended to include DNA molecules (e.g. cDNA or genomic DNA) and RNA molecules (e.g. mRNA) and analogs of the DNA or RNA generated using nucleotide analogs. The nucleic acid molecule can be single-stranded or double-stranded.

An "isolated" nucleic acid molecule is one that is substantially separated from other nucleic acid molecules, which are present in the natural source of the nucleic acid. That means other nucleic acid molecules are present in an amount less than 5% based on weight of the amount of the desired nucleic acid, preferably less than 2% by weight, more preferably less than 1% by weight, most preferably less than 0.5% by weight. Preferably, an "isolated" nucleic acid is free of some of the sequences that naturally flank the nucleic acid (i.e., sequences located at the 5' and 3' ends of the nucleic acid) in the genomic DNA of the organism from which the nucleic acid is derived. For example, in various embodiments, the isolated herbicide resistance and/or tolerance related protein encoding nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A "coding sequence" is a nucleotide sequence, which is transcribed into an RNA, e.g. a regulatory RNA, such as a miRNA, a ta-siRNA, co-suppression molecule, an RNAi, a ribozyme, etc. or into a mRNA which is translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

As used in the present context a nucleic acid molecule may also encompass the untranslated sequence located at the 3' and at the 5' end of the coding gene region, for example 2000, preferably less, e.g. 500, preferably 200, especially preferable 100, nucleotides of the sequence upstream of the 5' end of the coding region and for example 300, preferably less, e.g. 100, preferably 50, especially preferable 20, nucleotides of the sequence downstream of the 3' end of the coding gene region.

"Polypeptide" refers to a polymer of amino acid (amino acid sequence) and does not refer to a specific length of the molecule. Thus, peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring. An "isolated" polynucleotide or nucleic acid molecule is separated from other polynucleotides or nucleic acid molecules, which are present in the natural source of the nucleic acid molecule. An isolated nucleic acid molecule may be a chromosomal fragment of several kb, or preferably, a molecule only comprising the coding region of the gene. Accordingly, an isolated nucleic acid molecule of the invention may comprise chromosomal regions, which are adjacent 5' and 3' or further adjacent chromosomal regions, but preferably comprises no such sequences which naturally flank the nucleic acid molecule sequence in the genomic or chromosomal context in the organism from which the nucleic acid molecule originates (for example sequences which are adjacent to the regions encoding the 5'- and 3'-UTRs of the nucleic acid molecule). An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of a protein in which the polypeptide is separated from some of the cellular components of the cells in which it is naturally or recombinantly produced.

The terms "comprise" or "comprising" and grammatical variations thereof when used in this specification are to be taken to specify the presence of stated features, integers, steps or components or groups thereof, but not to preclude the presence or addition of one or more other features, integers, steps, components or groups thereof.

In accordance with the invention, a protein or polypeptide has the "activity of a HPPD protein if its de novo activity, or its increased expression directly or indirectly leads to and confers increased herbicide tolerance or resistance, as compared to a corresponding, e.g. non-transformed, wild type plant and the protein has the above mentioned activity of a HPPD.

Throughout the specification the activity or preferably the biological activity of such a protein or polypeptide or an nucleic acid molecule or sequence encoding such protein or polypeptide is identical or similar if it still has the biological or enzymatic activity of a protein comprising a variant of the sequence of SEQ ID NO: 2, 4, 6, 8, 10, 12, 14, 16, 18, 20, 22, 24, 26, 28, 30, or 32, or a homolog or a functional equivalent thereof, or which has 10% or more of the original enzymatic activity, preferably 20%, 30%, 40%, 50%, particularly preferably 60%, 70%, 80% most particularly preferably 90%, 95%, 98%, 99% or more in comparison to a protein comprising a variant of the sequence of SEQ ID NO: 2, 4, 6, 8, 10, 12, 14, 16, 18, 20, 22, 24, 26, 28, 30, or 32, or a homolog or a functional equivalent thereof.

In another embodiment the biological or enzymatic activity of a protein comprising a variant of the sequence of SEQ ID NO: 2, 4, 6, 8, 10, 12, 14, 16, 18, 20, 22, 24, 26, 28, 30, or 32, or a homolog or a functional equivalent thereof, has 100% or more of the original enzymatic activity, preferably 110%, 120%, 130%, 150%, particularly preferably 150%, 200%, 300% or more in comparison to a protein comprising a variant of the sequence of SEQ ID NO: 2, 4, 6, 8, 10, 12, 14, 16, 18, 20, 22, 24, 26, 28, 30, or 32, or a homolog or a functional equivalent thereof.

The terms "increased", "raised", "extended", "enhanced", "improved" or "amplified" relate to a corresponding change of a property in a plant, an organism, a part of an organism such as a tissue, seed, root, leave, flower etc. or in a cell and are interchangeable. Preferably, the overall activity in the volume is increased or enhanced in cases if the increase or enhancement is related to the increase or enhancement of an activity of a gene product, independent whether the amount of gene product or the specific activity of the gene product or both is increased or enhanced or whether the amount, stability or translation efficacy of the nucleic acid sequence or gene encoding for the gene product is increased or enhanced.

The terms "increase" include the change of said property in only parts of the subject of the present invention, for example, the modification can be found in compartment of a cell, like a organelle, or in a part of a plant, like tissue, seed, root, leave, flower etc. but is not detectable if the overall subject, i.e. complete cell or plant, is tested. Accordingly, the term "increase" means that the specific activity of an enzyme as well as the amount of a compound or metabolite, e.g. of a polypeptide, a nucleic acid molecule of the invention or an encoding mRNA or DNA, can be increased in a volume. The term "increase" includes, that a compound or an activity, especially an activity, is introduced into a cell, the cytoplasm or a sub-cellular compartment or organelle de novo or that the compound or the activity, especially an activity, has not been detected before, in other words it is "generated". Accordingly, in the following, the term "increasing" also comprises the term "generating" or "stimulating".

The increased activity manifests itself in increased herbicide tolerance or resistance, as compared to a corresponding, e.g. non-transformed, wild type plant cell, plant or part thereof.

Under "change of a property" it is understood that the activity, expression level or amount of a gene product or the metabolite content is changed in a specific volume relative to a corresponding volume of a control, reference or wild type, including the de novo creation of the activity or expression.

"Amount of protein or mRNA" is understood as meaning the molecule number of polypeptides or mRNA molecules in an organism, especially a plant, a tissue, a cell or a cell compartment.

"Increase" in the amount of a protein means the quantitative increase of the molecule number of said protein in an organism, especially a plant, a tissue, a cell or a cell compartment such as an organelle like a plastid or mitochondria or part thereof—for example by one of the methods described herein below—in comparison to a wild type, control or reference.

The increase in molecule number amounts preferably to 1% or more, preferably to 10% or more, more preferably to 30% or more, especially preferably to 50%, 70% or more, very especially preferably to 100%, most preferably to 500% or more. However, a de novo expression is also regarded as subject of the present invention.

The terms "wild type", "control" or "reference" are exchangeable and can be a cell or a part of organisms such as an organelle like a chloroplast or a tissue, or an organism, in particular a plant, which was not modified or treated according to the herein described process according to the invention. Accordingly, the cell or a part of organisms such as an organelle like a chloroplast or a tissue, or an organism, in particular a plant used as wild type, control or reference corresponds to the cell, organism, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property.

Preferably, any comparison is carried out under analogous conditions. The term "analogous conditions" means that all conditions such as, for example, culture or growing conditions, soil, nutrient, water content of the soil, temperature, humidity or surrounding air or soil, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, an organism, in particular a plant, which was not modified or treated according to the herein described process of the invention and is in any other property as similar to the subject matter of the invention as possible. The reference, control or wild type is in its genome, transcriptome, proteome or metabolome as similar as possible to the subject of the present invention.

Preferably, the term "reference-" "control-" or "wild type-"-organelle, -cell, -tissue or -organism, in particular plant, relates to an organelle, cell, tissue or organism, in particular plant, which is nearly genetically identical to the organelle, cell, tissue or organism, in particular plant, of the present invention or a part thereof preferably 90% or more, e.g. 95%, more preferred are 98%, even more preferred are 99.00%, in particular 99.10%, 99.30%, 99.50%, 99.70%, 99.90%, 99.99%, 99.999% or more. Most preferable the "reference", "control", or "wild type" is a subject, e.g. an organelle, a cell, a tissue, an organism, in particular a plant, which is genetically identical to the organism, in particular plant, cell, a tissue or organelle used according to the process of the invention except that the responsible or activity conferring nucleic acid molecules or the gene product encoded by them are amended, manipulated, exchanged or introduced according to the inventive process. In case, a control, reference or wild type differing from the subject of the present invention only by not being subject of the process of the invention can not be provided, a control, reference or wild type can be an organism in which the cause for the modulation of an activity conferring the enhanced tolerance or resistance to herbicides as compared to a corresponding, e.g. non-transformed, wild type plant cell, plant or part thereof or expression of the nucleic acid molecule of the invention as described herein has been switched back or off, e.g. by knocking out the expression of responsible gene product, e.g. by antisense or RNAi or miRNA inhibition, by inactivation of an activator or agonist, by activation of an inhibitor or antagonist, by inhibition through adding inhibitory antibodies, by adding active compounds as e.g. hormones, by introducing negative dominant mutants, etc. A gene production can for example be knocked out by introducing inactivating point mutations, which lead to an enzymatic activity inhibition or a destabilization or an inhibition of the ability to bind to cofactors etc. Accordingly, preferred reference subject is the starting subject of the present process of the invention. Preferably, the reference and the subject matter of the invention are compared after standardization and normalization, e.g. to the amount of total RNA, DNA, or protein or activity or expression of reference genes, like housekeeping genes, such as ubiquitin, actin or ribosomal proteins.

The term "expression" refers to the transcription and/or translation of a codogenic gene segment or gene. As a rule, the resulting product is an mRNA or a protein.

The increase or modulation according to this invention can be constitutive, e.g. due to a stable permanent transgenic expression or to a stable mutation in the corresponding endogenous gene encoding the nucleic acid molecule of the invention or to a modulation of the expression or of the behavior of a gene conferring the expression of the polypeptide of the invention, or transient, e.g. due to an transient transformation or temporary addition of a modulator such as a agonist or antagonist or inducible, e.g. after transformation with a inducible construct carrying the nucleic acid molecule of the invention under control of a inducible promoter and adding the inducer, e.g. tetracycline or as described herein below.

Less influence on the regulation of a gene or its gene product is understood as meaning a reduced regulation of the enzymatic activity leading to an increased specific or cellular activity of the gene or its product. An increase of the enzymatic activity is understood as meaning an enzymatic activity, which is increased by 10% or more, advantageously 20%, 30% or 40% or more, especially advantageously by 50%, 60% or 70% or more in comparison with the starting organism. This leads to increased herbicide tolerance or resistance, as compared to a corresponding, e.g. non-transformed, wild type plant or part thereof.

The increase in activity of the polypeptide amounts in a cell, a tissue, an organelle, an organ or an organism, preferably a plant, or a part thereof preferably to 5% or more, preferably to 20% or to 50%, especially preferably to 70%, 80%, 90% or more, very especially preferably are to 100%, 150% or 200%, most preferably are to 250% or more in comparison to the control, reference or wild type. In one embodiment the term increase means the increase in amount in relation to the weight of the organism or part thereof (w/w).

By "vectors" is meant with the exception of plasmids all other vectors known to those skilled in the art such as by way of example phages, viruses such as SV40, CMV, baculovirus, adenovirus, transposons, IS elements, phasmids, phagemids, cosmids, linear or circular DNA.

These vectors can be replicated autonomously in the host organism or be chromosomally replicated, chromosomal replication being preferred. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) are integrated into the genome of a host cell or a organelle upon introduction into the host cell, and thereby are replicated along with the host or organelle genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adenoassociated viruses), which serve equivalent functions.

As used herein, "operatively linked" is intended to mean that the nucleotide sequence of interest is linked to the regulatory sequence(s) in a manner which allows for expression of the nucleotide sequence (e.g. in an in vitro transcription/translation system or in a host cell when the vector is introduced into the host cell). The term "regulatory sequence" is intended to include promoters, enhancers, and other expression control elements (e.g. polyadenylation signals). Such regulatory sequences are described, for example, in Goeddel, Gene Expression Technology: Methods in Enzymology 185, Academic Press, San Diego, Calif. (1990), and Gruber and Crosby, in: Methods in Plant Molecular Biology and Biotechnology, eds. Glick and Thompson, Chapter 7, 89-108, CRC Press; Boca Raton, Fla., including the references therein. Regulatory sequences include those that direct constitutive expression of a nucleotide sequence in many types of host cells and those that direct expression of the nucleotide sequence only in certain host cells or under certain conditions.

"Transformation" is defined herein as a process for introducing heterologous DNA into a plant cell, plant tissue, or plant. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time. Transformed plant cells, plant tissue, or plants are understood to encompass not only the end product of a transformation process, but also transgenic progeny thereof.

The terms "transformed," "transgenic," and "recombinant" refer to a host organism such as a bacterium or a plant into which a heterologous nucleic acid molecule has been introduced. The nucleic acid molecule can be stably integrated into the genome of the host or the nucleic acid molecule can also be present as an extra-chromosomal molecule. Such an extra-chromosomal molecule can be auto-replicating. Transformed cells, tissues, or plants are understood to encompass not only the end product of a transformation process, but also transgenic progeny thereof. A "non-transformed", "non-transgenic" or "non-recombinant" host refers to a wild-type organism, e.g. a bacterium or plant, which does not contain the heterologous nucleic acid molecule.

The terms "host organism", "host cell", "recombinant (host) organism" and "transgenic (host) cell" are used here interchangeably. Of course these terms relate not only to the particular host organism or the particular target cell but also to the descendants or potential descendants of these organisms or cells. Since, due to mutation or environmental effects certain modifications may arise in successive generations, these descendants need not necessarily be identical with the parental cell but nevertheless are still encompassed by the term as used here.

For the purposes of the invention "transgenic" or "recombinant" means with regard for example to a nucleic acid sequence, an expression cassette (=gene construct, nucleic acid construct) or a vector containing the nucleic acid sequence according to the invention or an organism transformed by said nucleic acid sequences, expression cassette or vector according to the invention all those constructions produced by genetic engineering methods in which either
(a) the nucleic acid sequence comprising a variant of the sequence of SEQ ID NO: 1, 3, 5, 7, 9, 11, 13, 15, 17, 19, 21, 23, 25, 27, 29, or 31, or a homolog or a functional equivalent thereof, or its derivatives or parts thereof; or
(b) a genetic control sequence functionally linked to the nucleic acid sequence described under (a), for example a 3'- and/or 5'-genetic control sequence such as a promoter or terminator, or
(c) (a) and (b);
are not found in their natural, genetic environment or have been modified by genetic engineering methods, wherein the modification may by way of example be a substitution, addition, deletion, inversion or insertion of one or more nucleotide residues.

"Natural genetic environment" means the natural genomic or chromosomal locus in the organism of origin or inside the host organism or presence in a genomic library. In the case of a genomic library the natural genetic environment of the nucleic acid sequence is preferably retained at least in part. The environment borders the nucleic acid sequence at least on one side and has a sequence length of at least 50 bp, preferably at least 500 bp, particularly preferably at least 1,000 bp, most particularly preferably at least 5,000 bp. A naturally occurring expression cassette—for example the naturally occurring combination of the natural promoter of the nucleic acid sequence according to the invention with the corresponding gene—turns into a transgenic expression cassette when the latter is modified by unnatural, synthetic ("artificial") methods such as by way of example a mutagenation. Appropriate methods are described by way of example in U.S. Pat. No. 5,565,350 or WO 00/15815.

The term "transgenic plants" used in accordance with the invention also refers to the progeny of a transgenic plant, for example the $T_1$, $T_2$, $T_3$ and subsequent plant generations or the $BC_1$, $BC_2$, $BC_3$ and subsequent plant generations. Thus, the transgenic plants according to the invention can be raised and selfed or crossed with other individuals in order to obtain further transgenic plants according to the invention. Transgenic plants may also be obtained by propagating transgenic plant cells vegetatively. The present invention also relates to transgenic plant material, which can be derived from a transgenic plant population according to the invention. Such material includes plant cells and certain tissues, organs and parts of plants in all their manifestations, such as seeds, leaves, anthers, fibers, tubers, roots, root hairs, stems, embryo, calli, cotelydons, petioles, harvested material, plant tissue, reproductive tissue and cell cultures, which are derived from the actual transgenic plant and/or can be used for bringing about the transgenic plant. Any transformed plant obtained according to the invention can be used in a conventional breeding scheme or in in vitro plant propagation to produce more transformed plants with the same characteristics and/or can be used to introduce the same characteristic in other varieties of the same or related species. Such plants are also part of the invention. Seeds obtained from the transformed plants genetically also contain the same characteristic and are part of the invention. As mentioned before, the present invention is in principle applicable to any plant and crop that can be transformed with any of the transformation method known to those skilled in the art.

The term "homology" means that the respective nucleic acid molecules or encoded proteins are functionally and/or structurally equivalent. The nucleic acid molecules that are homologous to the nucleic acid molecules described above and that are derivatives of said nucleic acid molecules are, for example, variations of said nucleic acid molecules which represent modifications having the same biological function, in particular encoding proteins with the same or substantially the same biological function. They may be naturally occurring variations, such as sequences from other plant varieties or species, or mutations. These mutations may occur naturally or may be obtained by mutagenesis techniques. The allelic variations may be naturally occurring allelic variants as well as synthetically produced or genetically engineered variants. Structurally equivalents can, for example, be identified by testing the binding of said polypeptide to antibodies or computer based predictions. Structurally equivalent have the similar immunological characteristic, e.g. comprise similar epitopes.

As used herein, the terms "gene" and "recombinant gene" refer to nucleic acid molecules comprising an open reading frame encoding the polypeptide of the invention or comprising the nucleic acid molecule of the invention or encoding the polypeptide used in the process of the present invention, preferably from a crop plant or from a microorgansim useful for the method of the invention. Such natural variations can typically result in 1 to 5% variance in the nucleotide sequence of the gene. Any and all such nucleotide variations and resulting amino acid polymorphisms in genes encoding a polypeptide of the invention or comprising a the nucleic acid molecule of the invention that are the result of natural variation and that do not alter the functional activity as described are intended to be within the scope of the invention.

Specific Embodiments

Accordingly, this invention provides measures and methods to produce plants with increased herbicide tolerance or resistance.

Accordingly, the present invention provides transgenic plants showing increased tolerance or resistance to one or more herbicides as compared to the corresponding origin or the wild type plant and methods for producing such transgenic plants with increased herbicide tolerance or resistance. One or more enhanced herbicide tolerance-related phenotypes are increased in accordance with the invention by increasing or generating the activity of a mutated HPPD enzyme.

The nucleic acid molecule of the present invention or used in accordance with the present invention, encodes a protein conferring an activity of a mutated HPPD enzyme, i.e. conferring herbicide tolerance or resistance to a crop plant while maintaining its enzymatic (HPPD) activity.

Accordingly, in one embodiment, the present invention relates to a nucleic acid molecule that encodes a polypeptide with an herbicide tolerance or resistance-increasing activity which is encoded by a nucleic acid sequence comprising a variant of the sequence of SEQ ID NO: 1, 3, 5, 7, 9, 11, 13, 15, 17, 19, 21, 23, 25, 27, 29, or 31, or a homolog or a functional equivalent thereof, and/or which is a protein comprising or consisting of a polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof.

The increase or generation of said "activity" is for example conferred by the increase of activity or of amount in a cell or a part thereof of one or more expression products of said nucleic acid molecule, e.g. proteins, or by de novo expression, i.e. by the generation of said "activity" in the plant.

In one embodiment, said herbicide tolerance or resistance-increasing activity is increased by increasing the amount and/or the specific activity of a mutated HPPD protein comprising a variant of the sequence of SEQ ID NO: 2, 4, 6, 8, 10, 12, 14, 16, 18, 20, 22, 24, 26, 28, 30, or 32, or a homolog or a functional equivalent thereof.

Accordingly, in one embodiment, an increased herbicide tolerance or resistance as compared to a correspondingly non-modified, e.g. a non-transformed, wild type plant is conferred according to method of the invention, by increasing or generating the activity of a polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof, or encoded by the nucleic acid molecule (or gene) comprising a variant of the sequence of SEQ ID NO: 1, 3, 5, 7, 9, 11, 13, 15, 17, 19, 21, 23, 25, 27, 29, or 31, or a homolog of said nucleic acid molecule or polypeptide.

Thus, in one embodiment, the present invention provides a method for producing a plant showing increased or improved herbicide resistance or tolerance as compared to the corresponding origin or wild type plant, by increasing or generating the activity of a mutated HPPD enzyme, e.g. which is conferred by one or more polynucleotide(s) comprising a variant of the sequence of SEQ ID NO: 1, 3, 5, 7, 9, 11, 13, 15, 17, 19, 21, 23, 25, 27, 29, or 31, or a homolog or a functional equivalent thereof, or by one or more protein(s), each comprising a polypeptide encoded by one or more nucleic acid sequence(s) comprising a variant of the sequence of SEQ ID NO: 1, 3, 5, 7, 9, 11, 13, 15, 17, 19, 21, 23, 25, 27, 29, or 31, or a homolog or a functional equivalent thereof, or by one or more protein(s) each comprising a polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof, and (b) optionally, growing the plant cell, plant or part thereof under conditions which permit the development of the plant cell, the plant or the part thereof, and (c) regenerating a plant with increased herbicide tolerance or resistance, as compared to a corresponding, e.g. non-transformed, wild type plant or a part thereof.

Accordingly, in one further embodiment, the said method for producing a plant or a part thereof for the regeneration of said plant, the plant showing an increased herbicide tolerance or resistance, said method comprises (i) growing the plant or part thereof together with a, e.g. non-transformed, wild type plant under conditions of herbicide treatment; and (ii) selecting a plant with increased herbicide tolerance or resistance as compared to a corresponding, e.g. non-transformed, wild type plant, for example after the, e.g. non-transformed, wild type plant shows visual symptoms of deficiency and/or death.

Further, the present invention relates to a method for producing a plant with increased herbicide tolerance or resistance as compared to a corresponding origin or wild type plant, e.g. a transgenic plant, which comprises: (a) increasing or generating, in a plant cell nucleus, a plant cell, a plant or a part thereof, the activity of a mutated HPPD polypeptide of the present invention, e.g. by the methods mentioned herein; and (b) cultivating or growing the plant cell, the plant or the part thereof under conditions which permit the development of the plant cell, the plant or the part thereof; and (c) recovering a plant from said plant cell nucleus, said plant cell, or said plant part, which shows increased herbicide tolerance or resistance as compared to a corresponding, e.g. non-transformed, origin or wild type plant; and (d) optionally, selecting the plant or a part thereof, showing increased herbicide tolerance or resistance, as compared to a corresponding, e.g. non-transformed, wild type plant cell, e.g. which shows visual symptoms of deficiency and/or death.

Furthermore, the present invention also relates to a method for the identification of a plant with an increased herbicide tolerance or resistance comprising screening a population of one or more plant cell nuclei, plant cells, plant tissues or plants or parts thereof for said "activity", comparing the level of activity with the activity level in a reference; identifying one or more plant cell nuclei, plant cells, plant tissues or plants or parts thereof with the activity increased compared to the reference, optionally producing a plant from the identified plant cell nuclei, cell or tissue.

In one further embodiment, the present invention also relates to a method for the identification of a plant with an increased herbicide tolerance or resistance comprising screening a population of one or more plant cell nuclei, plant cells, plant tissues or plants or parts thereof for the expression level of an nucleic acid coding for an polypeptide conferring said activity, comparing the level of expression with a reference; identifying one or more plant cell nuclei, plant cells, plant tissues or plants or parts thereof with the expression level increased compared to the reference, optionally producing a plant from the identified plant cell nuclei, cell or tissue.

Accordingly, in a preferred embodiment, the present invention provides a method for producing a transgenic cell for the regeneration or production of a plant with increased herbicide tolerance or resistance, as compared to a corresponding, e.g. non-transformed, wild type cell by increasing or generating the activity of an a mutated HPPD polypeptide of the present invention. The cell can be for example a host cell, e.g. a transgenic host cell. A host cell can be for example a microorganism, e.g. derived from fungi or bacteria, or a plant cell particular useful for transformation.

Thus, the present invention fulfills the need to identify new, unique genes capable of conferring increased herbicide tolerance or resistance to plants, upon expression or overexpression of exogenous genes.

Accordingly, the present invention provides novel mutated HPPD enzymes comprising a variant of the sequence of SEQ ID NO: 2, 4, 6, 8, 10, 12, 14, 16, 18, 20, 22, 24, 26, 28, 30, or 32, or a homolog or a functional equivalent thereof.

In one embodiment the increase in activity of the polypeptide amounts in an organelle such as a plastid. In another embodiment the increase in activity of the polypeptide amounts in the cytoplasm.

The specific activity of a polypeptide encoded by a nucleic acid molecule of the present invention or of the polypeptide of the present invention can be tested as described in the examples. In particular, the expression of a protein in question in a cell, e.g. a plant cell in comparison to a control is an easy test and can be performed as described in the state of the art.

Accordingly, in one embodiment, the process of the present invention for producing a plant with increased herbicide tolerance or resistance comprises increasing or generating the activity of a gene product conferring the activity of a mutated HPPD enzyme from a microorganism or its functional equivalent or its homolog, e.g. the increase of
(a) a gene product of a gene comprising the nucleic acid molecule comprising a variant of the sequence of SEQ ID NO: 1, 3, 5, 7, 9, 11, 13, 15, 17, 19, 21, 23, 25, 27, 29, or 31, or a functional equivalent or a homologue or functional equivalent thereof; or
(b) a polypeptide comprising a polypeptide, a consensus sequence or a polypeptide motif comprising a variant of the sequence of SEQ ID NO: 2, 4, 6, 8, 10, 12, 14, 16, 18, 20, 22, 24, 26, 28, 30, or 32 or a functional equivalent or a homologue or functional equivalent thereof.

Accordingly, an activity of a mutated HPPD polypeptide from a microorganism is increased in one or more specific compartment(s) or organelle(s) of a cell or plant and confers said increased herbicide tolerance or resistance. For example, said activity can be increased in plastids or mitochondria of a plant cell, thus conferring increase of herbicide tolerance or resistance in a corresponding plant.

In one embodiment, an activity conferred by an expression of a gene described herein or its expression product; i.e. by a mutated HPPD polypeptide of the present invention is increased or generated in the plastid.

In one embodiment, an activity conferred by the expression of a gene described herein or its expression product; i.e. by a mutated HPPD polypeptide of the present invention is increased or generated in the mitochondria.

In one embodiment, an activity conferred by the expression of a gene described herein or its expression product; i.e. by a mutated HPPD polypeptide of the present invention is increased or generated in the cytoplasm.

In one embodiment, an activity conferred by the expression of a gene described herein or its expression product; i.e. by a mutated HPPD polypeptide of the present invention is increased or generated in the endoplasmic reticulum.

As the terms "cytoplasmic" and "non-targeted" shall not exclude a targeted localisation to any cell compartment for the products of the inventive nucleic acid sequences by their naturally occurring sequence properties within the background of the transgenic organism, in one embodiment, an activity as disclosed herein as being conferred by a polypeptide shown in a variant of SEQ ID NO: 2, 4, 6, 8, 10, 12, 14, 16, 18, 20, 22, 24, 26, 28, 30, or 32, or a homolog or a functional equivalent thereof is increase or generated non-targeted. For the purposes of the description of the present invention, the term "cytoplasmic" shall indicate, that the nucleic acid of the invention is expressed without the addition of a non-natural transit peptide encoding sequence. A non-natural transient peptide encoding sequence is a sequence which is not a natural part of a nucleic acid of the invention but is rather added by molecular manipulation steps which are well-known to the person skilled in the art. Therefore the term "cytoplasmic" shall not exclude a targeted localisation to any cell compartment for the products of the inventive nucleic acid sequences by their naturally occurring sequence properties.

In another embodiment the present invention is related to a method for producing a, e.g. transgenic, plant with increased herbicide tolerance or resistance, or a part thereof, as compared to a corresponding, e.g. non-transformed, wild type plant, which comprises (a1) increasing or generating the activity of a mutated HPPD polypeptide, e.g. the activity of said gene or the gene product gene, in an organelle of a plant cell, or (a2) increasing or generating the activity of a protein comprising a variant of the sequence of SEQ ID NO: 2, 4, 6, 8, 10, 12, 14, 16, 18, 20, 22, 24, 26, 28, 30, or 32, or a homolog or a functional equivalent thereof or as encoded by the nucleic acid sequences comprising a variant of the sequence of SEQ ID NO: 1, 3, 5, 7, 9, 11, 13, 15, 17, 19, 21, 23, 25, 27, 29, or 31, or a homolog or a functional equivalent thereof, and which is joined to a nucleic acid sequence encoding a transit peptide in the plant cell; or (a3) increasing or generating the activity of a protein comprising a variant of the sequence of SEQ ID NO: 2, 4, 6, 8, 10, 12, 14, 16, 18, 20, 22, 24, 26, 28, 30, or 32, or a homolog or a functional equivalent thereof or as encoded by the nucleic acid sequences comprising a variant of the sequence of SEQ ID NO: 1, 3, 5, 7, 9, 11, 13, 15, 17, 19, 21, 23, 25, 27, 29, or 31, or a homolog or a functional equivalent thereof, and which is joined to a nucleic acid sequence encoding an organelle localization sequence, especially a chloroplast localization sequence, in a plant cell, (a4) increasing or generating the activity of a protein comprising a variant of the sequence of SEQ ID NO: 2, 4, 6, 8, 10, 12, 14, 16, 18, 20, 22, 24, 26, 28, 30, or 32, or a homolog or a functional equivalent thereof or as encoded by the nucleic acid sequences comprising a variant of the sequence of SEQ ID NO: 1, 3, 5, 7, 9, 11, 13, 15, 17, 19, 21, 23, 25, 27, 29, or 31, or a homolog or a functional equivalent thereof, and which is joined to a nucleic acid sequence encoding an mitochondrion localization sequence in a plant cell, and
(b) regenerating a plant from said plant cell;
(c) growing the plant under conditions which permit the development of a plant with increased herbicide tolerance or resistance as compared to a corresponding, e.g. non-transformed, wild type plant.

The skilled worker is able to link transit peptide nucleic acid sequences to the nucleic acid sequences comprising a variant of the sequence of SEQ ID NO: 1, 3, 5, 7, 9, 11, 13, 15, 17, 19, 21, 23, 25, 27, 29, or 31, or a homolog or a functional equivalent thereof.

Any transit peptide may be used in accordance with the various embodiments of the present invention. For example, specific nucleic acid sequences are encoding transit peptides are disclosed by von Heijne et al. (Plant Molecular Biology Reporter, 9 (2), 104, (1991)) or other transit peptides are disclosed by Schmidt et al. (J. Biol. Chem. 268 (36), 27447 (1993)), Della-Cioppa et al. (Plant. Physiol. 84, 965 (1987)), de Castro Silva Filho et al. (Plant Mol. Biol. 30, 769 (1996)), Zhao et al. (J. Biol. Chem. 270 (11), 6081(1995)), Römer et al. (Biochem. Biophys. Res. Commun. 196 (3), 1414 (1993)), Keegstra et al. (Annu. Rev. Plant Physiol. Plant Mol. Biol. 40, 471(1989)), Lubben et al. (Photosynthesis Res. 17, 173 (1988)) and Lawrence et al. (J. Biol. Chem. 272 (33), 20357 (1997)), which are hereby incorporated by reference. A general review about targeting is disclosed by Kermode Allison R. in Critical Reviews in Plant Science 15 (4), 285 (1996) under the title "Mechanisms of Intracellular Protein Transport and Targeting in Plant Cells".

Additional nucleic acid sequences encoding a transit peptide can be isolated from any organism such as microorganisms, algae or plants containing plastids, preferably containing chloroplasts. A "transit peptide" is an amino acid sequence, whose encoding nucleic acid sequence is translated together with the corresponding structural gene. That means the transit peptide is an integral part of the translated protein and forms an amino terminal extension of the protein. Both are translated as so called "pre-protein". In general the transit peptide is cleaved off from the pre-protein during or just after import of the protein into the correct cell organelle such as a plastid to yield the mature protein. The transit peptide ensures correct localization of the mature protein by facilitating the transport of proteins through intracellular membranes.

For example, such transit peptides, which are beneficially used in the inventive process, are derived from the nucleic acid sequence encoding a protein selected from the group consisting of ribulose bisphosphate carboxylase/oxygenase, 5-enolpyruvyl-shikimate-3-phosphate synthase, acetolactate synthase, chloroplast ribosomal protein CS17, Cs protein, ferredoxin, plastocyanin, ribulose bisphosphate carboxylase activase, tryptophan synthase, acyl carrier protein, plastid chaperonin-60, cytochrome $c_{552}$, 22-kDA heat shock protein, 33-kDa Oxygen-evolving enhancer protein 1, ATP synthase γ subunit, ATP synthase δ subunit, chlorophyll-a/b-binding proteinII-1, Oxygen-evolving enhancer protein 2, Oxygen-evolving enhancer protein 3, photosystem I: P21, photosystem I: P28, photosystem I: P30, photosystem I: P35, photosystem I: P37, glycerol-3-phosphate acyltransferases, chlorophyll a/b binding protein, CAB2 protein, hydroxymethyl-bilane synthase, pyruvate-orthophosphate dikinase, CAB3 protein, plastid ferritin, ferritin, early light-inducible protein, glutamate-1-semialdehyde aminotransferase, protochlorophyllide reductase, starch-granule-bound amylase synthase, light-harvesting chlorophyll a/b-binding protein of photosystem II, major pollen allergen Lol p 5a, plastid ClpB ATP-dependent protease, superoxide dismutase, ferredoxin NADP oxidoreductase, 28-kDa ribonucleoprotein, 31-kDa ribonucleoprotein, 33-kDa ribonucleoprotein, acetolactate synthase, ATP synthase $CF_0$ subunit 1, ATP synthase $CF_0$ subunit 2, ATP synthase $CF_0$ subunit 3, ATP synthase $CF_0$ subunit 4, cytochrome f, ADPglucose pyrophosphorylase, glutamine synthase, glutamine synthase 2, carbonic anhydrase, GapA protein, heat-shock-protein hsp21, phosphate translocator, plastid ClpA ATP-dependent protease, plastid ribosomal protein CL24, plastid ribosomal protein CL9, plastid ribosomal protein PsCL18, plastid ribosomal protein PsCL25, DAHP synthase, starch phosphorylase, root acyl carrier protein II, betaine-aldehyde dehydrogenase, GapB protein, glutamine synthetase 2, phosphoribulokinase, nitrite reductase, ribosomal protein L12, ribosomal protein L13, ribosomal protein L21, ribosomal protein L35, ribosomal protein L40, triose phosphate-3-phosphoglyerate-phosphate translocator, ferredoxin-dependent glutamate synthase, glyceraldehyde-3-phosphate dehydrogenase, NADP-dependent malic enzyme and NADP-malate dehydrogenase, chloroplast 30S ribosomal protein PSrp-1, and the like.

In a particularly preferred embodiment, the nucleic acid sequences of the present invention are linked to a nucleic acid encoding a so-called "signal sequence peptide". For the purposes of the present invention, "signal sequence peptide" refers to amino acid sequences of about 15 to about 50 amino acids in length which are known in the art to be generally located at the amino terminus of proteins and which are capable of targeting said proteins to the endoplasmic reticulum. The core of the signal peptide contains a long stretch of hydrophobic amino acids that has a tendency to form a single alpha-helix. In addition, many signal peptides begin with a short positively charged stretch of amino acids, which may help to enforce proper topology of the polypeptide during translocation by what is known as the positive-inside rule. At the end of the signal peptide there is typically a stretch of amino acids that is recognized and cleaved by signal peptidase. However this cleavage site is absent from transmembrane-domains that serve as signal peptides, which are sometimes referred to as signal anchor sequences. Signal peptidase may cleave during, or after completion of, translocation to generate a free signal peptide and a mature protein. The free signal peptides are then digested by specific proteases. Those skilled in the art would readily appreciate that many signal sequence peptides are known (van Heijne, G., J. Mol. Biol. 184: 99-105 (1985)) and that these peptide sequences or analogues thereof can be easily substituted as long as they fulfill the requirements for a signal peptide as described above.

The skilled worker will recognize that various other nucleic acid sequences encoding transit or signal sequence peptides can easily isolated from plastid-localized, mitochondria-localized or endoplasmic reticulum-localized proteins, which are expressed from nuclear genes as precursors and are then targeted to plastids, mitochondria or endoplasmic reticulum. Nucleic acid sequences encoding a transit or signal sequence peptide can be isolated from organelle-targeted proteins from any organism. Preferably, the transit or signal sequence peptide is isolated from an organism selected from the group consisting of the genera *Acetabularia, Arabidopsis, Brassica, Capsicum, Chlamydomonas, Cururbita, Dunaliella, Euglena, Flaveria, Glycine, Hellanthus, Hordeum, Lemna, Lolium, Lycopersion, Malus, Medicago, Mesembryanthemum, Nicotlana, Oenotherea, Oryza, Petunia, Phaseolus, Physcomitrella, Pinus, Pisum, Raphanus, Silene, Sinapis, Solanum, Spinacea, Stevia, Synechoccus, Synechocystis, Triticum* and *Zea*. More preferably, the nucleic acid sequence encoding the transit or signal sequence peptide is isolated from an organism selected from the group consisting of the species *Acetabularia mediterranea, Arabidopsis thaliana, Brassica campestris, Brassica napus, Capsicum annuum, Chlamydomonas reinhardtii, Cururbita moschata, Dunaliella sallina, Dunaliella tertiolecta, Euglena gracilis, Flaveria trinervia, Glycine max, Hellanthus annuus, Hordeum vulgare, Lemna gibba, Lolium perenne, Lycoperslon esculentum, Malus domestica, Medicago falcata, Medicago sativa, Mesembryanthemum crystallinum, Nicotlana plumbaginifollia, Nicotlana sylvestris, Nicotlana tabacum, Oenotherea hookeri, Oryza sativa, Petunia hybrida, Phaseolus vulgaris, Physcomitrella patens, Pinus tunbergii, Pisum satlvum, Raphanus sativus, Silene pratensis, Sinapis alba, Solanum tuberosum, Spinacea oleracea, Stevia rebaudiana, Synechococcus, Synechocystis, Triticum aestivum* and *Zea mays*. Alternatively, nucleic acid sequences coding for transit or signal sequence peptides may be chemically synthesized either in part or wholly according to structure of transit peptide sequences disclosed in the prior art.

Such transit or signal sequence peptides encoding sequences can be used for the construction of other expression constructs. The transit or signal sequence peptides advantageously used in the inventive process and which are part of the inventive nucleic acid sequences and proteins are typically 20 to 120 amino acids, preferably 25 to 110, 30 to 100 or 35 to 90 amino acids, more preferably 40 to 85 amino acids and most preferably 45 to 80 amino acids as for transit peptides, or about 15 to about 50 amino acids as for signal sequence peptides in length and functions post-translational to direct the protein to the plastid, preferably to the chloroplast, the mitochondrion or endoplasmic reticulum. The nucleic acid sequences encoding such transit or signal sequence peptides are localized upstream of nucleic acid sequence encoding the mature protein. For the correct molecular joining of the transit or signal sequence peptide encoding nucleic acid and the nucleic acid encoding the protein to be targeted it is sometimes necessary to introduce additional base pairs at the joining position, which forms restriction enzyme recognition sequences useful for the molecular joining of the different nucleic acid molecules. This procedure might lead to very few additional amino acids at the N-terminal of the mature imported protein, which usually and preferably do not interfere with the protein function. In any case, the additional base pairs at the joining position which forms restriction enzyme recognition sequences have to be chosen with care, in order to avoid the formation of stop codons or codons which encode amino acids with a strong influence on protein folding, like e.g. proline. It is preferred that such additional codons encode small structural flexible amino acids such as glycine or alanine.

As mentioned above the nucleic acid sequence coding for a protein comprising a variant of the sequence of SEQ ID NO: 2, 4, 6, 8, 10, 12, 14, 16, 18, 20, 22, 24, 26, 28, 30, or 32, or a homolog or a functional equivalent thereof, can be joined to a nucleic acid sequence encoding a transit or a signal sequence peptide. The nucleic acid sequence of the gene to be expressed and the nucleic acid sequence encoding the transit or signal sequence peptide are operably linked. Therefore the transit or signal sequence peptide is fused in frame to the nucleic acid sequence coding for a protein comprising a variant of the sequence of SEQ ID NO: 2, 4, 6, 8, 10, 12, 14, 16, 18, 20, 22, 24, 26, 28, 30, or 32, or a homolog or a functional equivalent thereof.

The proteins translated from said inventive nucleic acid sequences are a kind of fusion proteins that means the nucleic acid sequences encoding the transit or signal sequence peptide, are joint to a gene, e.g. the nucleic acid sequences comprising a variant of the sequence of SEQ ID NO: 1, 3, 5, 7, 9, 11, 13, 15, 17, 19, 21, 23, 25, 27, 29, or 31, or a homolog or a functional equivalent thereof. The person skilled in the art is able to join said sequences in a functional manner. Advantageously the transit or signal sequence peptide part is cleaved off from the protein part during the transport preferably into the endoplasmic reticulum or plastids. The skilled worker knows that other short sequences are also useful in the expression of the mutated HPPD genes of the present invention. Furthermore the skilled worker is aware of the fact that there is not a need for such short sequences in the expression of the genes.

Alternatively to the targeting of the gene, e.g. proteins having the sequences comprising a variant of the sequence of SEQ ID NO: 2, 4, 6, 8, 10, 12, 14, 16, 18, 20, 22, 24, 26, 28, 30, or 32, or a homolog or a functional equivalent thereof, the nucleic acids of the invention can directly be introduced into the plastidic genome.

By transforming the plastids the intraspecies specific transgene flow is blocked, because a lot of species such as corn, cotton and rice have a strict maternal inheritance of plastids. By placing the gene e.g. the genes comprising a variant of the sequence of SEQ ID NO: 1, 3, 5, 7, 9, 11, 13, 15, 17, 19, 21, 23, 25, 27, 29, or 31, or a homolog or a functional equivalent thereof, or active fragments thereof in the plastids of plants, these genes will not be present in the pollen of said plants.

In another embodiment of the invention the gene, e.g. the nucleic acid molecules comprising a variant of the sequence of SEQ ID NO: 1, 3, 5, 7, 9, 11, 13, 15, 17, 19, 21, 23, 25, 27, 29, or 31, or a homolog or a functional equivalent thereof, used in the inventive process are transformed into mitochondria, which are metabolic active.

For a good expression in the plastids the gene, e.g. the nucleic acid sequences comprising a variant of the sequence of SEQ ID NO: 1, 3, 5, 7, 9, 11, 13, 15, 17, 19, 21, 23, 25, 27, 29, or 31, or a homolog or a functional equivalent thereof, are introduced into an expression cassette using a preferably a promoter and terminator, which are active in plastids, preferably a chloroplast promoter. Examples of such promoters include the psbA promoter from the gene from spinach or pea, the rbcL promoter, and the atpB promoter from corn.

In one embodiment, the process of the present invention comprises one or more of the following steps:
(a) stabilizing a protein conferring the increased expression of a protein encoded by the nucleic acid molecule of the invention or of the polypeptide of the invention having the herein-mentioned activity of an mutated HPPD and conferring increased herbicide tolerance or resistance, as compared to a corresponding, e.g. non-transformed, wild type plant cell, plant or part thereof;
(b) stabilizing an mRNA conferring the increased expression of a polynucleotide encoding a polypeptide as mentioned in (a);
(c) increasing the specific activity of a protein conferring the increased expression of a polypeptide as mentioned in (a);
(d) generating or increasing the expression of an endogenous or artificial transcription factor mediating the expression of a protein conferring the increased expression of a polypeptide as mentioned in (a);

(e) stimulating activity of a protein conferring the increased expression of a polypeptide as mentioned in (a), by adding one or more exogenous inducing factors to the organism or parts thereof;
(f) expressing a transgenic gene encoding a protein conferring the increased expression of a polypeptide as mentioned in (a); and/or
(g) increasing the copy number of a gene conferring the increased expression of a nucleic acid molecule encoding a polypeptide as mentioned in (a);
(h) increasing the expression of the endogenous gene encoding a polypeptide as mentioned in (a) by adding positive expression or removing negative expression elements, e.g. homologous recombination can be used to either introduce positive regulatory elements like for plants the 35S enhancer into the promoter or to remove repressor elements form regulatory regions. Further gene conversion methods can be used to disrupt repressor elements or to enhance to activity of positive elements—positive elements can be randomly introduced in plants by T-DNA or transposon mutagenesis and lines can be identified in which the positive elements have been integrated near to a gene of the invention, the expression of which is thereby enhanced; and/or
(i) modulating growth conditions of the plant in such a manner, that the expression or activity of the gene encoding a polypeptide as mentioned in (a), or the protein itself is enhanced;
(j) selecting of organisms with especially high activity of a polypeptide as mentioned in (a) from natural or from mutagenized resources and breeding them into the target organisms, e.g. the elite crops.

Preferably, said mRNA is encoded by the nucleic acid molecule of the present invention and/or the protein conferring the increased expression of a protein encoded by the nucleic acid molecule of the present invention alone or linked to a transit nucleic acid sequence or transit peptide encoding nucleic acid sequence or the polypeptide having the herein mentioned activity, e.g. conferring with increased herbicide tolerance or resistance, as compared to a corresponding, e.g. non-transformed, wild type plant cell, plant or part thereof after increasing the expression or activity of the encoded polypeptide or having the activity of a polypeptide having an activity as the protein comprising a variant of the sequence of SEQ ID NO: 2, 4, 6, 8, 10, 12, 14, 16, 18, 20, 22, 24, 26, 28, 30, or 32, or a homolog or a functional equivalent thereof In general, the amount of mRNA or polypeptide in a cell or a compartment of an organism correlates with the amount of encoded protein and thus with the overall activity of the encoded protein in said volume. Said correlation is not always linear, the activity in the volume is dependent on the stability of the molecules or the presence of activating or inhibiting cofactors. The activity of the abovementioned proteins and/or polypeptides encoded by the nucleic acid molecule of the present invention can be increased in various ways. For example, the activity in an organism or in a part thereof, like a cell, is increased via increasing the gene product number, e.g. by increasing the expression rate, like introducing a stronger promoter, or by increasing the stability of the mRNA expressed, thus increasing the translation rate, and/or increasing the stability of the gene product, thus reducing the proteins decayed. Further, the activity or turnover of enzymes can be influenced in such a way that a reduction or increase of the reaction rate or a modification (reduction or increase) of the affinity to the substrate results, is reached. A mutation in the catalytic centre of an polypeptide of the invention, e.g. as enzyme, can modulate the turn over rate of the enzyme, e.g. a knock out of an essential amino acid can lead to a reduced or completely knock out activity of the enzyme, or the deletion or mutation of regulator binding sites can reduce a negative regulation like a feedback inhibition (or a substrate inhibition, if the substrate level is also increased). The specific activity of an enzyme of the present invention can be increased such that the turn over rate is increased or the binding of a co-factor is improved. Improving the stability of the encoding mRNA or the protein can also increase the activity of a gene product. The stimulation of the activity is also under the scope of the term "increased activity".

Moreover, the regulation of the abovementioned nucleic acid sequences may be modified so that gene expression is increased. This can be achieved advantageously by means of heterologous regulatory sequences or by modifying, for example mutating, the natural regulatory sequences which are present. The advantageous methods may also be combined with each other.

In general, an activity of a gene product in an organism or part thereof, in particular in a plant cell or organelle of a plant cell, a plant, or a plant tissue or a part thereof or in a microorganism can be increased by increasing the amount of the specific encoding mRNA or the corresponding protein in said organism or part thereof.

A modification, i.e. an increase, can be caused by endogenous or exogenous factors. For example, an increase in activity in an organism or a part thereof can be caused by adding a gene product or a precursor or an activator or an agonist to the media or nutrition or can be caused by introducing said subjects into an organism, transient or stable. Furthermore such an increase can be reached by the introduction of the inventive nucleic acid sequence or the encoded protein in the correct cell compartment for example into the nucleus or cytoplasm respectively or into plastids either by transformation and/or targeting.

In one further embodiment of the process according to the invention, organisms are used in which one of the abovementioned genes, or one of the abovementioned nucleic acids, is mutated in a way that the activity of the encoded gene products is less influenced by cellular factors, or not at all, in comparison with the not mutated proteins. For example, well known regulation mechanisms of enzyme activity are substrate inhibition or feed back regulation mechanisms. Ways and techniques for the introduction of substitution, deletions and additions of one or more bases, nucleotides or amino acids of a corresponding sequence are described herein below in the corresponding paragraphs and the references listed there, e.g. in Sambrook et al., Molecular Cloning, Cold Spring Harbour, N.Y., 1989. The person skilled in the art will be able to identify regulation domains and binding sites of regulators by comparing the sequence of the nucleic acid molecule of the present invention or the expression product thereof with the state of the art by computer software means which comprise algorithms for the identifying of binding sites and regulation domains or by introducing into a nucleic acid molecule or in a protein systematically mutations and assaying for those mutations which will lead to an increased specific activity or an increased activity per volume, in particular per cell.

The mutation is introduced in such a way that increased herbicide tolerance or resistance, is not adversely affected.

It can therefore be advantageous to express in an organism a nucleic acid molecule of the invention or a polypeptide of the invention derived from a evolutionary distantly related organism, as e.g. using a prokaryotic gene in a eukaryotic host, as in these cases the regulation mechanism of the host cell may not weaken the activity (cellular or specific) of the gene or its expression product.

The invention is not limited to specific nucleic acids, specific polypeptides, specific cell types, specific host cells, specific conditions or specific methods etc. as such, but may vary and numerous modifications and variations therein will be apparent to those skilled in the art. It is also to be understood that the terminology used herein is for the purpose of describing specific embodiments only and is not intended to be limiting.

Further, "proteins are generally composed of one or more functional regions, commonly termed domains. Different combinations of domains give rise to the diverse range of proteins found in nature. The identification of domains that occur within proteins can therefore provide insights into their function. Pfam-A entries are high quality, manually curated families. The Pfam database is a large collection of protein families, each represented by multiple sequence alignments and hidden Markov models (HMMs)." (see: The Pfam protein families database: R. D. Finn, et al., Nucleic Acids Research (2010), Database Issue 38:D211-222). The Pfam protein family database is a large collection of more than ten thousand protein families and is available under pfam.sangerac.uk/. Profile Hidden Markov Models (HMMs) are flexible, probabilistic models that can be used to describe the consensus patterns shared by sets of homologous protein/domain sequences. HMMs in the Pfam database are constructed from an alignment of a representative set of sequences for each protein domain, called a seed alignment.

Accordingly, the present invention relates to a nucleic acid molecule encoding a polypeptide which is 50% or more, preferably 60%, 70%, or 75%, more preferably 80%, 85%, 90%, or 95%, even more preferred 96%, 97%, 98%, 99% or more and most preferred 100% identical to the polypeptide of SEQ ID NO: 2, 4, 6, 8, 10, 12, 14, 16, 18, 20, 22, 24, 26, 28, 30, or 32, and conferring the increase of the herbicide tolerance or resistance of a plant as described herein. The invention also relates to the polypeptide encoded by said polynucleotide.

The present invention also relates to isolated, recombinantly produced or chemically synthesized nucleic acids comprising a nucleic acid molecule selected from the group consisting of:
(a) a nucleic acid molecule encoding the polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof;
(b) a nucleic acid molecule comprising a variant of the sequence of SEQ ID NO: 1, 3, 5, 7, 9, 11, 13, 15, 17, 19, 21, 23, 25, 27, 29, or 31, or a homolog or a functional equivalent thereof,
(c) a nucleic acid molecule, which, as a result of the degeneracy of the genetic code, can be derived from a variant of the polypeptide sequence of SEQ ID NO: 2, 4, 6, 8, 10, 12, 14, 16, 18, 20, 22, 24, 26, 28, 30, or 32, or a homolog or a functional equivalent thereof, and confers increased herbicide tolerance or resistance, as compared to a corresponding, e.g. non-transformed, wild type plant cell, a plant or a part thereof;
(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of a variant of SEQ ID NO: 1, 3, 5, 7, 9, 11, 13, 15, 17, 19, 21, 23, 25, 27, 29, or 31, or a homolog or a functional equivalent thereof, and confers increased herbicide tolerance or resistance, as compared to a corresponding, e.g. non-transformed, wild type plant cell, a plant or a part thereof;
(e) a nucleic acid molecule encoding a mutated HPPD polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the HPPD polypeptide sequence of SEQ ID NO: 2, 4, 6, 8, 10, 12, 14, 16, 18, 20, 22, 24, 26, 28, 30, or 32, and confers increased herbicide tolerance or resistance, as compared to a corresponding, e.g. non-transformed, wild type plant cell, a plant or a part thereof;
(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;
(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide as depicted in a variant of SEQ ID NO: 1, 3, 5, 7, 9, 11, 13, 15, 17, 19, 21, 23, 25, 27, 29, or 31, ora homolog or a functional equivalent thereof;
(h) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having 15 nt, preferably 20 nt, 30 nt, 50 nt, 100 nt, 200 nt, 500 nt, 750 nt or 1000 nt or more of a nucleic acid molecule complementary to a nucleic acid molecule sequence characterized in (a) to (e) and encoding a polypeptide having the activity represented by a protein comprising a polypeptide as depicted SEQ ID NO: 2, 4, 6, 8, 10, 12, 14, 16, 18, 20, 22, 24, 26, 28, 30, or 32, or a homolog or a functional equivalent thereof,
wherein the variant of a HPPD polypeptide has a substitution of one or more amino acids corresponding to or at positions 30, 39, 54, 57, 84, 210, 212, 223, 243, 247, 249, 251, 264, 291, 306, 317, 318, 319, 321, 326, 327, 331, 341, 342, 345, 350, 363, 367, 373, 374, 375, 379, 405, 407, 410, 412, 414, 419, 421, or 422 of SEQ ID NO:4.

In one embodiment the invention relates to homologs of the aforementioned sequences, which can be isolated advantageously from yeast, fungi, viruses, algae, bacteria, such as *Acetobacter* (subgen. *Acetobacter*) *aceti Acidithiobacillus ferrooxidans; Acinetobacter* sp.; *Actinobacillus* sp; *Aeromonas salmonicida; Agrobacterium tumefaciens; Aquifex aeollicus; Arcanobacterium pyogenes; Aster yellows phytoplasma; Bacillus* sp.; *Bifidobacterium* sp.; *Borrellia burgdorferi Brevibacterium linens; Brucella melltensis; Buchnera* sp.; *Butyrivibrio fibrisolvens; Campylobacterjejuni; Caulobacter crescentus; Chlamydia* sp.; *Chlamydophila* sp.; *Chlorobium limicola; Citrobacter rodentium; Clostridium* sp.; *Comamonas testosteroni; Corynebacterium* sp.; *Coxiella burnetii Deinococcus radiodurans; Dichelobacter nodosus; Edwardsiella ictaluri; Enterobacter* sp.; *Erysipelothrix rhusiopathiae; E. coli; Flavobacterium* sp.; *Francisella tularensis; Frankia* sp. Cpl1; *Fusobacterium nucleatum; Geobacillus stearothermophillus; Gluconobacter oxydans; Haemophillus* sp.; *Hellicobacter pylori; Klebsiella pneumoniae; Lactobacillus* sp.; *Lactococcuslactis; Listeria* sp.; *Mannheimia haemolytica; Mesorhizobium-* loti; *Methylophaga thalassica; Microcystis aeruginosa; Microscilla* sp. PRE1; *Moraxella* sp. TA 144; *Mycobacterium* sp.; *Mycoplasma* sp.; *Neisseria* sp.; *Nitrosomonas* sp.; *Nostoc* sp. PCC 7120; *Novosphingobium aromaticivorans; Oenococcus oeni Pantoea citrea; Pasteurella multocida; Pediococcus pentosaceus; Phormidium foveolarum; Phytoplasma* sp.; *Plectonema boryanum; Prevotella ruminicola; Propionibacterium* sp.; *Proteus vulgaris; Pseudomonas* sp.; *Ralstonia* sp.; *Rhizobium* sp.; *Rhodococcus equi; Rhodothermus marinus; Rickettsia* sp.; *Riemerella anatipestifer; Ruminococcus flavefaciens; Salmonella* sp.; *Selenomonas ruminantium; Serratia entomophila; Shigella* sp.; *Sinorhizobium melloti; Staphylococcus* sp.; *Streptococcus* sp.; *Streptomyces* sp.; *Synechococcus* sp.; *Synechocystis* sp. PCC 6803; *Thermotoga maritima; Treponema* sp.; *Ureaplasma urealyticum; Vibrio cholerae; Vibrio parahaemolyticus; Xylella fastidiosa; Yersinia* sp.; *Zymomonas mobilis*, preferably *Salmonella* sp. or *E. coli* or plants, preferably from yeasts such as from the genera *Saccharomyces, Pichia, Candida, Hansenula, Torulopsis* or Schizosaccharomyces or plants such as *A. thaliana*, maize, wheat, rye, oat, triticale, rice, barley, soybean, peanut, cotton, borage, sunflower, linseed, primrose, rapeseed, canola and turnip rape, *manihot*, pepper, sunflower, *tagetes*, solanaceous plant such as potato, tobacco, eggplant and tomato, *Vicia* species, pea, alfalfa, bushy plants such as coffee, cacao, tea, *Salix* species, trees such as oil palm, coconut, perennial grass, such as ryegrass and fescue, and forage crops, such as alfalfa and clover and from spruce, pine or fir for example. The proteins of the present invention are preferably produced by recombinant DNA techniques. For example, a nucleic acid molecule encoding the protein is cloned into an expression vector, for example in to a binary vector, the expression vector is introduced into a host cell, for example the *A. thaliana* wild type NASC N906 or any other plant cell as described in the examples see below, and the protein is expressed in said host cell. Examples for binary vectors are pBIN19, pBI101, pBinAR (Hofgen and Willmitzer, Plant Science 66, 221 (1990)), pGPTV, pCAMBIA, pBIB-HYG, pBecks, pGreen or pPZP (Hajukiewicz, P. et al., Plant Mol. Biol. 25, 989 (1994), and Hellens et al, Trends in Plant Science 5, 446 (2000)).

In one embodiment as described in more detail SUPRA, the protein of the present invention is preferably targeted to a compartment of the cell, e.g. to the endoplasmic reticulum or in the plastids. Ways of introducing nucleic acids into the endoplasmic reticulum or plastids and producing proteins in this compartment are known to the person skilled in the art have been also described in this application. In one embodiment, the polypeptide of the invention is a protein localized after expression e.g. non-targeted, mitochondrial or plastidic, for example it is fused to a transit or signal sequence peptide as decribed above for plastidic or endoplasmic reticulum localisation. In another embodiment the protein of the present invention is produced without further targeting signal (e.g. as mentioned herein), e.g. in the cytoplasm of the cell. Ways of producing proteins in the cytoplasm are known to the person skilled in the art. Ways of producing proteins without artificial targeting are known to the person skilled in the art.

Advantageously, the nucleic acid sequences according to the invention or the gene construct together with at least one reporter gene are cloned into an expression cassette, which is introduced into the organism via a vector or directly into the genome. This reporter gene should allow easy detection via a growth, fluorescence, chemical, bioluminescence or tolerance assay or via a photometric measurement.

Examples of reporter genes which may be mentioned are antibiotic- or herbicide-tolerance genes, hydrolase genes, fluorescence protein genes, bioluminescence genes, sugar or nucleotide metabolic genes or biosynthesis genes such as the Ura3 gene, the Ilv2 gene, the luciferase gene, the β-galactosidase gene, the gfp gene, the 2-desoxyglucose-6-phosphate phosphatase gene, the β-glucuronidase gene, β-lactamase gene, the neomycin phosphotransferase gene, the hygromycin phosphotransferase gene, a mutated acetohydroxyacid synthase (AHAS) gene (also known as acetolactate synthase (ALS) gene), a gene for a D-amino acid metabolizing enzmye or the BASTA (=gluphosinate-tolerance) gene. These genes permit easy measurement and quantification of the transcription activity and hence of the expression of the genes. In this way genome positions may be identified which exhibit differing productivity. For expression a person skilled in the art is familiar with different methods to introduce the nucleic acid sequences into different organelles such as the preferred plastids. Such methods are for example disclosed by Maiga P. (Annu. Rev. Plant Biol. 55, 289 (2004)), Evans T. (WO 2004/040973), McBride K. E. et al. (U.S. Pat. No. 5,455,818), Daniell H. et al. (U.S. Pat. Nos. 5,932,479 and 5,693,507) and Straub J. M. et al. (U.S. Pat. No. 6,781,033). A preferred method is the transformation of microspore-derived hypocotyl or cotyledonary tissue (which are green and thus contain numerous plastids) leaf tissue and afterwards the regeneration of shoots from said transformed plant material on selective medium. As methods for the transformation bombarding of the plant material or the use of independently replicating shuttle vectors are well known by the skilled worker. But also a PEG-mediated transformation of the plastids or *Agrobacterium* transformation with binary vectors is possible. Useful markers for the transformation of plastids are positive selection markers for example the chloramphenicol-, streptomycin-, kanamycin-, neomycin-, amikamycin-, spectinomycin-, triazine- and/or lincomycin-tolerance genes. As additional markers named in the literature often as secondary markers, genes coding for the tolerance against herbicides such as phosphinothricin (=glufosinate, BASTA™, Liberty™, encoded by the bar gene), glyphosate (=N-(phosphonomethyl)glycine, Roundup™, encoded by the 5-enolpyruvylshikimate-3-phosphate synthase gene=epsps), sulfonylureas (like Staple™, encoded by the acetolactate synthase (ALS) gene), imidazolinones [=IMI, like imazethapyr, imazamox, Clearfield™, encoded by the acetohydroxyacid synthase (AHAS) gene, also known as acetolactate synthase (ALS) gene] or bromoxynil (=Buctril™, encoded by the oxy gene) or genes coding for antibiotics such as hygromycin or G418 are useful for further selection. Such secondary markers are useful in the case when most genome copies are transformed. In addition negative selection markers such as the bacterial cytosine deaminase (encoded by the codA gene) are also useful for the transformation of plastids.

To increase the possibility of identification of transformants it is also desirable to use reporter genes other then the aforementioned tolerance genes or in addition to said genes. Reporter genes are for example β-galactosidase-, β-glucuronidase-(GUS), alkaline phosphatase- and/or green-fluorescent protein-genes (GFP).

In a preferred embodiment a nucleic acid construct, for example an expression cassette, comprises upstream, i.e. at the 5' end of the encoding sequence, a promoter and downstream, i.e. at the 3' end, a polyadenylation signal and optionally other regulatory elements which are operably linked to the intervening encoding sequence with one of the nucleic acids of a variant of SEQ ID NO: 1, 3, 5, 7, 9, 11, 13, 15, 17, 19, 21, 23, 25, 27, 29, or 31, or a homolog or a functional equivalent thereof. By an operable linkage is meant the sequential arrangement of promoter, encoding sequence, terminator and optionally other regulatory elements in such a way that each of the regulatory elements can fulfill its function in the expression of the encoding sequence in due manner. In one embodiment the sequences preferred for operable linkage are targeting sequences for ensuring subcellular localization in plastids. However, targeting sequences for ensuring subcellular localization in the mitochondrium, in the endoplasmic reticulum (=ER), in the nucleus, in oil corpuscles or other compartments may also be employed as well as translation promoters such as the 5' lead sequence in tobacco mosaic virus (Gallie et al., Nucl. Acids Res. 15 8693 (1987).

A nucleic acid construct, for example an expression cassette may, for example, contain a constitutive promoter or a tissue-specific promoter (preferably the USP or napin promoter) the gene to be expressed and the ER retention signal. For the ER retention signal the KDEL amino acid sequence (lysine, aspartic acid, glutamic acid, leucine) or the KKX amino acid sequence (lysine-lysine-X-stop, wherein X means every other known amino acid) is preferably employed.

For expression in a host organism, for example a plant, the expression cassette is advantageously inserted into a vector such as by way of example a plasmid, a phage or other DNA which allows optimal expression of the genes in the host organism. Examples of suitable plasmids are: in *E. coli* pLG338, pACYC184, pBR series such as e.g. pBR322, pUC series such as pUC18 or pUC19, M113mp series, pKC30, pRep4, pHS1, pHS2, pPLc236, pMBL24, pLG200, pUR290, pIN-III113-B1, λgt11 or pBdCl; in *Streptomyces* pIJ101, pIJ364, pIJ702 or pIJ361; in *Bacillus* pUB110, pC194 or pBD214; in *Corynebacterium* pSA77 or pAJ667; in fungi pALS1, pIL2 or pBB116; other advantageous fungal vectors are described by Romanos M. A. et al., Yeast 8, 423 (1992) and by van den Hondel, C. A. M. J. J. et al. [(1991) "Heterologous gene expression in filamentous fungi" ] as well as in "More Gene Manipulations" in "Fungi" in Bennet J. W. & Lasure L. L., eds., pp. 396-428, Academic Press, San Diego, and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., pp. 1-28, Cambridge University Press: Cambridge]. Examples of advantageous yeast promoters are 2 µM, pAG-1, YEp6, YEp13 or pEMBLYe23. Examples of algal or plant promoters are pLGV23, pGHlac+, pBIN19, pAK2004, pVKH or pDH51 (see Schmidt, R. and Willmitzer, L., Plant Cell Rep. 7, 583 (1988)). The vectors identified above or derivatives of the vectors identified above are a small selection of the possible plasmids. Further plasmids are well known to those skilled in the art and may be found, for example, in "Cloning Vectors" (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press, Ch. 6/7, pp. 71-119). Advantageous vectors are known as shuttle vectors or binary vectors which replicate in *E. coli* and *Agrobacterium*.

In a further embodiment of the vector the expression cassette according to the invention may also advantageously be introduced into the organisms in the form of a linear DNA and be integrated into the genome of the host organism by way of heterologous or homologous recombination. This linear DNA may be composed of a linearized plasmid or only of the expression cassette as vector or the nucleic acid sequences according to the invention.

A nucleic acid sequence can also be introduced into an organism on its own.

If in addition to the nucleic acid sequence according to the invention further genes are to be introduced into the organism, all together with a reporter gene in a single vector or each single gene with a reporter gene in a vector in each case can be introduced into the organism, whereby the different vectors can be introduced simultaneously or successively.

The vector advantageously contains at least one copy of the nucleic acid sequences according to the invention and/or the expression cassette (=gene construct) according to the invention.

The invention further provides an isolated recombinant expression vector comprising a nucleic acid encoding a polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof, wherein expression of the vector in a host cell results in increased herbicide tolerance or resistance, as compared to a wild type variety of the host cell.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein.

The recombinant expression vectors of the invention can be designed for expression of the polypeptide of the invention in plant cells. For example, nucleic acid molecules of the present invention can be expressed in plant cells (see Schmidt R., and Willmitzer L., Plant Cell Rep. 7 (1988); Plant Molecular Biology and Biotechnology, C Press, Boca Raton, Fla., Chapter 6/7, p. 71-119 (1993); White F. F., Jenes B. et al., Techniques for Gene Transfer, in: Transgenic Plants, Vol. 1, Engineering and Utilization, eds. Kung und Wu R., 128-43, Academic Press: 1993; Potrykus, Annu. Rev. Plant Physiol. Plant Molec. Biol. 42, 205 (1991) and references cited therein). Suitable host cells are discussed further in Goeddel, Gene Expression Technology: Methods in Enzymology 185, Academic Press: San Diego, Calif. (1990). By way of example the plant expression cassette can be installed in the pRT transformation vector ((a) Toepfer et al., Methods Enzymol. 217, 66 (1993), (b) Toepfer et al., Nucl. Acids. Res. 15, 5890 (1987)). Alternatively, a recombinant vector (=expression vector) can also be transcribed and translated in vitro, e.g. by using the T7 promoter and the T7 RNA polymerase.

In an further embodiment of the present invention, the nucleic acid molecules of the invention are expressed in plants and plants cells such as unicellular plant cells (e.g. algae) (see Falciatore et al., Marine Biotechnology 1 (3), 239 (1999) and references therein) and plant cells from higher plants (e.g., the spermatophytes, such as crop plants), for example to regenerate plants from the plant cells. A nucleic acid molecule depicted in a variant of SEQ ID NO: 1, 3, 5, 7, 9, 11, 13, 15, 17, 19, 21, 23, 25, 27, 29, or 31, or a homolog or a functional equivalent thereof may be "introduced" into a plant cell by any means, including transfection, transformation or transduction, electroporation, particle bombardment, agroinfection, and the like. One transformation method known to those of skill in the art is the dipping of a flowering plant into an Agrobacteria solution, wherein the Agrobacteria contains the nucleic acid of the invention, followed by breeding of the transformed gametes. Other suitable methods for transforming or transfecting host cells including plant cells can be found in Sambrook et al., supra, and other laboratory manuals such as Methods in Molecular Biology, 1995, Vol. 44, *Agrobacterium* protocols, ed: Gartland and Davey, Humana Press, Totowa, N.J.

In one embodiment of the present invention, transfection of a nucleic acid molecule coding for a polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof into a plant is achieved by *Agrobacterium* mediated gene transfer. *Agrobacterium* mediated plant transformation can be performed using for example the GV3101 (pMP90) (Koncz and Schell, Mol. Gen. Genet. 204, 383 (1986)) or LBA4404 (Clontech) *Agrobacterium* tumefaciens strain. Transformation can be performed by standard transformation and regeneration techniques (Deblaere et al., Nucl. Acids Res. 13, 4777 (1994), Gelvin, Stanton B. and Schilperoort Robert A, Plant Molecular Biology Manual, 2nd Ed. —Dordrecht: Kluwer Academic Publ., 1995. —in Sect., Ringbuc Zentrale Signatur: BT11-P ISBN 0-7923-2731-4; Glick Bernard R., Thompson John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., Plant Cell Report 8, 238 (1989); De Block et al., Plant Physiol. 91, 694 (1989)). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., Plant Cell Report 13, 282 (1994). Additionally, transformation of soybean can be performed using for example a technique described in European Patent No. 424 047, U.S. Pat. No. 5,322,783, European Patent No. 397 687, U.S. Pat. No. 5,376,543 or 5,169,770. Transformation of maize can be achieved by particle bombardment, polyethylene glycol mediated DNA uptake or via the silicon carbide fiber technique. (see, for example, Freeling and Walbot "The maize handbook" Springer Verlag: New York (1993) ISBN 3-540-97826-7). A specific example of maize transformation is found in U.S. Pat. No. 5,990,387, and a specific example of wheat transformation can be found in PCT Application No. WO 93/07256.

According to the present invention, the introduced nucleic acid molecule coding for a polypeptides depicted in a variant of SEQ ID NO: 2, 4, 6, 8, 10, 12, 14, 16, 18, 20, 22, 24, 26, 28, 30, or 32, or homologs thereof, may be maintained in the plant cell stably if it is incorporated into a non-chromosomal autonomous replicon or integrated into the plant chromosomes or organelle genome. Alternatively, the introduced nucleic acid molecule may be present on an extra-chromosomal non-replicating vector and be transiently expressed or transiently active.

In one embodiment, a homologous recombinant microorganism can be created wherein the nucleic acid molecule is integrated into a chromosome, a vector is prepared which contains at least a portion of a nucleic acid molecule coding for a protein depicted in a variant of SEQ ID NO: 2, 4, 6, 8, 10, 12, 14, 16, 18, 20, 22, 24, 26, 28, 30, or 32, or a homolog or a functional equivalent thereof into which a deletion, addition, or substitution has been introduced to thereby alter, e.g., functionally disrupt, the gene. For example, the gene is a yeast gene, like a gene of *S. cerevisiae*, or of *Synechocystis*, or a bacterial gene, like an *E. coli* gene, but it can be a homolog from a related plant or even from a mammalian or insect source. The vector can be designed such that, upon homologous recombination, the endogenous nucleic acid molecule coding for a protein depicted in a variant of SEQ ID NO: 2, 4, 6, 8, 10, 12, 14, 16, 18, 20, 22, 24, 26, 28, 30, or 32, or a homolog or a functional equivalent thereof is mutated or otherwise altered but still encodes a functional polypeptide (e.g., the upstream regulatory region can be altered to thereby alter the expression of the endogenous nucleic acid molecule). In a preferred embodiment the biological activity of the protein of the invention is increased upon homologous recombination. To create a point mutation via homologous recombination, DNA-RNA hybrids can be used in a technique known as chimeraplasty (Cole-Strauss et al., Nucleic Acids Research 27 (5), 1323 (1999) and Kmiec, Gene Therapy American Scientist. 87 (3), 240 (1999)). Homologous recombination procedures in *Physcomitrella patens* are also well known in the art and are contemplated for use herein.

Whereas in the homologous recombination vector, the altered portion of the nucleic acid molecule coding for a protein depicted in a variant of SEQ ID NO: 2, 4, 6, 8, 10, 12, 14, 16, 18, 20, 22, 24, 26, 28, 30, or 32, or a homolog or a functional equivalent thereof is flanked at its 5' and 3' ends by an additional nucleic acid molecule of the gene to allow for homologous recombination to occur between the exogenous gene carried by the vector and an endogenous gene, in a microorganism or plant. The additional flanking nucleic acid molecule is of sufficient length for successful homologous recombination with the endogenous gene. Typically, several hundreds of base pairs up to kilobases of flanking DNA (both at the 5' and 3' ends) are included in the vector. See, e.g., Thomas K. R., and Capecchi M. R., Cell 51, 503 (1987) for a description of homologous recombination vectors or Strepp et al., PNAS, 95 (8), 4368 (1998) for cDNA based recombination in *Physcomitrella patens*. The vector is introduced into a microorganism or plant cell (e.g. via polyethylene glycol mediated DNA), and cells in which the introduced gene has homologously recombined with the endogenous gene are selected using art-known techniques.

Whether present in an extra-chromosomal non-replicating vector or a vector that is integrated into a chromosome, the nucleic acid molecule coding for amino acid molecules depicted in a variant of SEQ ID NO: 2, 4, 6, 8, 10, 12, 14, 16, 18, 20, 22, 24, 26, 28, 30, or 32, or a homolog or a functional equivalent thereof preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., EMBO J. 3, 835 (1984)) or functional equivalents thereof but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., Nucl. Acids Research 15, 8693 (1987)). Examples of plant expression vectors include those detailed in: Becker D. et al., Plant Mol. Biol. 20, 1195 (1992); and Bevan M. W., Nucl. Acid. Res. 12, 8711 (1984); and "Vectors for Gene Transfer in Higher Plants" in: Transgenic Plants, Vol. 1, Engineering and Utilization, eds. Kung and Wu R., Academic Press, 1993, S. 15-38.

The host organism (=transgenic organism) advantageously contains at least one copy of the nucleic acid according to the invention and/or of the nucleic acid construct according to the invention.

In principle all plants can be used as host organism. Preferred transgenic plants are, for example, selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae. Preferred are crop plants such as plants advantageously selected from the group of the genus peanut, oilseed rape, canola, sunflower, safflower, olive, sesame, hazelnut, almond, avocado, bay, pumpkin/squash, linseed, soya, pistachio, borage, maize, wheat, rye, oats, sorghum and millet, triticale, rice, barley, cassava, potato, sugarbeet, egg plant, alfalfa, and perennial grasses and forage plants, oil palm, vegetables (brassicas, root vegetables, tuber vegetables, pod vegetables, fruiting vegetables, onion vegetables, leafy vegetables and stem vegetables), buckwheat, Jerusalem artichoke, broad bean, vetches, lentil, dwarf bean, lupin, clover and Lucerne for mentioning only some of them.

In one embodiment of the invention transgenic plants are selected from the group comprising cereals, soybean, rapeseed (including oil seed rape, especially canola and winter oil seed rape), cotton, sugarcane, sugar beet, sunflower and potato, especially corn, soy, rapeseed (including oil seed rape, especially canola and winter oil seed rape), cotton, wheat and rice.

In another embodiment of the invention the transgenic plant is a gymnosperm plant, especially a spruce, pine or fir.

In one embodiment, the host plant is selected from the families Aceraceae, Anacardiaceae, Apiaceae, Asteraceae, Brassicaceae, Cactaceae, Cucurbitaceae, Euphorbiaceae, Fabaceae, Malvaceae, Nymphaeaceae, Papaveraceae, Rosaceae, Salicaceae, Solanaceae, Arecaceae, Bromeliaceae, Cyperaceae, Iridaceae, Liliaceae, Orchidaceae, Gentianaceae, Labiaceae, Magnoliaceae, Ranunculaceae, Carifolaceae, Rubiaceae, Scrophulariaceae, Caryophyllaceae, Ericaceae, Polygonaceae, Violaceae, Juncaceae or Poaceae and preferably from a plant selected from the group of the families Apiaceae, Asteraceae, Brassicaceae, Cucurbitaceae, Fabaceae, Papaveraceae, Rosaceae, Solanaceae, Liliaceae or Poaceae.

Preferred are crop plants and in particular plants mentioned herein above as host plants such as the families and genera mentioned above for example preferred the species *Anacardium occidentale, Calendula officinalis, Carthamus tinctorius, Cichorium intybus, Cynara scolymus, Hellanthus annus, Tagetes lucida, Tagetes erecta, Tagetes tenuifolia; Daucus carota; Corylus avellana, Corylus colurna, Borago officinalis; Brassica napus, Brassica rapa ssp., Sinapis arvensis Brasslca juncea, Brasslca juncea* var. *juncea, Brasslca juncea* var. *crispifolia, Brassica juncea* var. *foliosa, Brassica nigra, Brassica sinapioides, Melanosinapis communis, Brassica oleracea, Arabidopsis thaliana, Anana comosus, Ananas ananas, Bromella comosa, Carlca papaya, Cannabis sative, Ipomoea batatus, Ipomoea pandurata, Convolvulus batatas, Convolvulus tillaceus, Ipomoea fastigiata, Ipomoea tillacea, Ipomoea trlloba, Convolvulus panduratus, Beta vulgaris, Beta vulgaris* var. *altlssima, Beta vulgaris* var. *vulgaris, Beta maritima, Beta vulgaris* var. *perennis, Beta vulgaris* var. *conditiva, Beta vulgaris* var. *esculenta, Cucurbita maxima, Cucurbita mixta, Cucurbita pepo, Cucurbita moschata, Olea europaea, Manihot utillssima, Janipha manihot, Jatropha manihot., Manihot aipil, Manihot dulcis, Manihot manihot, Manihot melanobasis, Manihot esculenta, Ricinus communis, Pisum sativum, Pisum arvense, Pisum humile, Medicago sativa, Medicago falcata, Medicago varia, Glycine max Dolichos soja, Glycine gracilis, Glycine hispida, Phaseolus max, Soja hispida, Soja max, Cocos nucifera, Pelargonium grossularioides, Oleum cocoas, Laurus nobilis, Persea americana, Arachis hypogaea, Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii Linum pratense, Linum trigynum, Punica granatum, Gossypium hirsutum, Gossypium arboreum, Gossypium barbadense, Gossypium herbaceum, Gossypium thurberi, Musa nana, Musa acuminata, Musa paradislaca, Musa* spp., *Elaeis guineensis, Papaver orientale, Papaver rhoeas, Papaver dubium, Sesamum indicum, Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata, Hordeum vulgare, Hordeum jubatum, Hordeum murinum, Hordeum secalinum, Hordeum distichon Hordeum aegiceras, Hordeum hexastichon., Hordeum hexastichum, Hordeum irregulare, Hordeum sativum, Hordeum secalinum, Avena sativa, Avena fatua, Avena byzantina, Avena fatua* var. *sativa, Avena hybrida, Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum militaceum, Zea mays, Triticum aestivum, Triticum durum, Triticum turgidum, Triticum hybernum, Triticum macha, Triticum sativum* or *Triticum vulgare, Cofea* spp., *Coffea arabica, Coffea canephora, Coffea liberica, Capsicum annuum, Capsicum annuum* var. *glabriusculum, Capsicum frutescens, Capsicum annuum, Nicotiana tabacum, Solanum tuberosum, Solanum melongena, Lycopersicon esculentum, Lycopersicon lycopersicum., Lycopersicon pyriforme, Solanum integrifolium, Solanum lycopersicum Theobroma cacao* or *Camellia sinensis.*

Anacardiaceae such as the genera *Pistacia, Mangifera, Anacardium* e.g. the species *Pistacia vera* [pistachios, Pistazie], *Mangifer indica* [Mango] or *Anacardium occidentale* [Cashew]; Asteraceae such as the genera *Calendula,*

*Carthamus, Centaurea, Cichorium, Cynara, Helianthus, Lactuca, Locusta, Tagetes, Valeriana* e.g. the species *Calendula officinalis* [Marigold], *Carthamus tinctorius* [safflower], *Centaurea cyanus* [cornflower], *Cilchorium intybus* [blue daisy], *Cynara scolymus* [Artichoke], *Helilanthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [lettuce], *Tagetes lucida, Tagetes erecta* or *Tagetes tenulfolia* [Marigold]; Apiaceae such as the genera *Daucus* e.g. the species *Daucus carota* [carrot]; Betulaceae such as the genera *Corylus* e.g. the species *Corylus avellana* or *Corylus colurna* [hazelnut]; Boraginaceae such as the genera *Borago* e.g. the species *Borago officinalis* [borage]; Brassicaceae such as the genera *Brassica, Melanosinapis, Sinapis, Arabadopsis* e.g. the species *Brassica napus, Brassica rapa* ssp. [canola, oilseed rape, turnip rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana;* Bromeliaceae such as the genera *Anana, Bromelia* e.g. the species *Anana comosus, Ananas ananas* or *Bromelia comosa* [pineapple]; Caricaceae such as the genera *Carica* e.g. the species *Carica papaya* [papaya]; Cannabaceae such as the genera *Cannabis* e.g. the species *Cannabis sative* [hemp], Convolvulaceae such as the genera *Ipomea, Convolvulus* e.g. the species *Ipomoea batatus, Ipomoea pandurata, Convolvulus batatas, Convolvulus tiliaceus, Ipomoea fastigiata, Ipomoea tilacea, Ipomoea trliloba* or *Convolvulus panduratus* [sweet potato, Man of the Earth, wild potato], Chenopodiaceae such as the genera *Beta,* i.e. the species *Beta vulgaris, Beta vulgaris* var. *altlssima, Beta vulgaris* var. *Vulgaris, Beta maritima, Beta vulgaris* var. *perennis, Beta vulgaris* var. *conditiva* or *Beta vulgaris* var. *esculenta* [sugar beet]; Cucurbitaceae such as the genera *Cucubita* e.g. the species *Cucurbita maxima, Cucurbita mixta, Cucurbita pepo* or *Cucurbita moschata* [pumpkin, squash]; Elaeagnaceae such as the genera *Elaeagnus* e.g. the species *Olea europaea* [olive]; Ericaceae such as the genera *Kalmia* e.g. the species *Kalmia latifolia, Kalmia angustifolia, Kalmia microphyllila, Kalmia polifolia, Kalmia occidentalis, Cistus chamaerhodendros* or *Kalmia lucida* [American laurel, broad-leafed laurel, calico bush, spoon wood, sheep laurel, alpine laurel, bog laurel, western bog-laurel, swamp-laurel]; Euphorbiaceae such as the genera *Manihot, Janipha, Jatropha, Ricinus* e.g. the species *Manihot utilissima, Janipha manihot, Jatropha manihot., Manihot aipil, Manihot dulcis, Manihot manihot, Manihot melanobasis, Manihot esculenta*[manihot, arrowroot, tapioca, cassava] or *Ricinus communis* [castor bean, Castor Oil Bush, Castor Oil Plant, Palma Christi, Wonder Tree]; Fabaceae such as the genera *Pisum, Albizia, Cathormion, Feuillea, Inga, Pithecolobium, Acacia, Mimosa, Medicajo, Glycine, Dolichos, Phaseolus, Soja* e.g. the species *Pisum sativum, Pisum arvense, Pisum humile* [pea], *Albizia berteriana, Abizia julibrissin, Albizia lebbeck, Acacia berteriana, Acacia llittoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia jullibrissin, Acacia nemu, Albizia nemu, Feuilleea jullibrissin, Mimosa jullibrissin, Mimosa speciosa, Sericanrda jullibrissin, Acacia lebbeck, Acacia macrophylla, Albizia lebbek, Feuilleea lebbeck, Mimosa lebbeck, Mimosa speciosa* [bastard logwood, silk tree, East Indian Walnut], *Medicago sativa, Medicago falcata, Medicago varia* [alfalfa] *Glycine max Dolichos soja, Glycine gracilis, Glycine hispida, Phaseolus max, Soja hispida* or *Soja max* [soybean]; Geraniaceae such as the genera *Pelargonium, Cocos, Oleum* e.g. the species *Cocos nucifera, Pelargonium grossularioides* or *Oleum cocois* [coconut]; Gramineae such as the genera *Saccharum* e.g. the species *Saccharum officinarum;* Juglandaceae such as the genera *Juglans, Wallia* e.g. the species *Juglans regia, Juglans aillanthifolia, Juglans sieboldiana, Juglans cinerea, Walhia cinerea, Juglans bixbyi, Juglans callifornica, Juglans hindsli Juglans intermedia, Juglans jamaicensis, Juglans major, Juglans microcarpa, Juglans nigra* or *Wallia nigra* [walnut, black walnut, common walnut, persian walnut, white walnut, butternut, black walnut]; Lauraceae such as the genera *Persea, Laurus* e.g. the species laurel *Laurus nobils* [bay, laurel, bay laurel, sweet bay], *Persea americana Persea americana, Persea gratissima* or *Persea persea* [avocado]; Leguminosae such as the genera *Arachis* e.g. the species *Arachis hypogaea* [peanut]; Linaceae such as the genera *Linum, Adenolinum* e.g. the species *Linum usltatissimum, Linum humlle, Linum austriacum, Linum bienne, Linum angustifolium, Linum catharticum, Linum flavum, Linum grandiflorum, Adenolinum grandiflorum, Linum llewisii, Llnum narbonense, Linum perenne, Linum perenne* var. *lewisii, Linum pratense* or *Linum trigynum* [flax, linseed]; Lythrarieae such as the genera *Punica* e.g. the species *Punica granatum* [pomegranate]; Malvaceae such as the genera *Gossypium* e.g. the species *Gossypium hirsutum, Gossypium arboreum, Gossypium barbadense, Gossypium herbaceum* or *Gossypium thurberi*[cotton]; Musaceae such as the genera *Musa* e.g. the species *Musa nana, Musa acuminata, Musa paradisiaca, Musa* spp. [banana]; Onagraceae such as the genera *Camissonia, Oenothera* e.g. the species *Oenothera biennis* or *Camissonia brevipes* [primrose, evening primrose]; Palmae such as the genera *Elacis* e.g. the species *Elaeis guineensis* [oil plam]; Papaveraceae such as the genera *Papaver* e.g. the species *Papaver orientale, Papaver rhoeas, Papaver dubium* [poppy, oriental poppy, corn poppy, field poppy, shirley poppies, field poppy, long-headed poppy, long-pod poppy]; Pedaliaceae such as the genera *Sesamum* e.g. the species *Sesamum indicum* [sesame]; Piperaceae such as the genera *Piper, Artanthe, Peperomia, Steffensia* e.g. the species *Piperaduncum, Piperamalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata.* [Cayenne pepper, wild pepper]; Poaceae such as the genera *Hordeum, Secale, Avena, Sorghum, Andropogon, Holcus, Panicum, Oryza, Zea, Triticum* e.g. the species *Hordeum vulgare, Hordeum jubatum, Hordeum murinum, Hordeum secalinum, Hordeum distichon Hordeum aegiceras, Hordeum hexastlichon, Hordeum hexastlichum, Hordeum irregulare, Hordeum satlivum, Hordeum secalinum* [barley, pearl barley, foxtail barley, wall barley, meadow barley], *Secale cereale* [rye], *Avena sativa, Avena fatua, Avena byzantlina, Avena fatua* var. *sativa, Avena hybrida* [oat], *Sorghum bicolor, Sorghum halepense, Sorghum saccharatum, Sorghum vulgare, Andropogon drummondi, Holcus bicolor, Holcus sorghum, Sorghum aethiopicum, Sorghum arundinaceum, Sorghum caffrorum, Sorghum cernuum, Sorghum dochna, Sorghum drummondi, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum millet, Panicum mililtaceum* [Sorghum, millet],

*Oryza sativa, Oryza latifolia* [rice], *Zea mays* [corn, maize] *Triticum aestivum, Triticum durum, Triticum turgidum, Triticum hybernum, Triltlicum macha, Triltlicum satlivum* or *Triltlicum vulgare* [wheat, bread wheat, common wheat], Proteaceae such as the genera *Macadamia* e.g. the species *Macadamia intergrifolia* [macadamia]; Rubiaceae such as the genera *Coffea* e.g. the species *Cofea* spp., *Coffea arabica, Coffea canephora* or *Coffea iliberica* [coffee]; Scrophulariaceae such as the genera *Verbascum* e.g. the species *Verbascum blattaria, Verbascum chalxi, Verbascum densiflorum, Verbascum lagurus, Verbascum longifolium, Verbascum lychniltlis, Verbascum nigrum, Verbascum olympicum, Verbascum phlomoldes, Verbascum phoenicum, Verbascum pulverulentum* or *Verbascum thapsus* [mullein, white moth mullein, nettle-leaved mullein, dense-flowered mullein, silver mullein, long-leaved mullein, white mullein, dark mullein, greek mullein, orange mullein, purple mullein, hoary mullein, great mullein]; Solanaceae such as the genera *Capsicum, Nicotiana, Solanum, Lycopersicon* e.g. the species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotlana glauca, Nicotlana langsdorffi, Nicotlana obtuslfolia, Nicotlana quadrivalvis, Nicotiana repanda, Nicotiana rustlica, Nicotiana sylvestris* [tobacco], *Solanum tuberosum* [potato], *Solanum melongena* [egg-plant] (*Lycopersicon esculentum, Lycopersicon lycopersicum., Lycopersicon pyriforme, Solanum integrifolium* or *Solanum lycopersicum* [tomato]; Sterculiaceae such as the genera *Theobroma* e.g. the species *Theobroma cacao* [cacao]; Theaceae such as the genera *Camellia* e.g. the species *Camellia sinensis*) [tea].

The introduction of the nucleic acids according to the invention, the expression cassette or the vector into organisms, plants for example, can in principle be done by all of the methods known to those skilled in the art. The introduction of the nucleic acid sequences gives rise to recombinant or transgenic organisms.

The transfer of foreign genes into the genome of a plant is called transformation. In doing this the methods described for the transformation and regeneration of plants from plant tissues or plant cells are utilized for transient or stable transformation. Suitable methods are protoplast transformation by poly(ethylene glycol)-induced DNA uptake, the "biolistic" method using the gene cannon—referred to as the particle bombardment method, electroporation, the incubation of dry embryos in DNA solution, microinjection and gene transfer mediated by *Agrobacterium*. Said methods are described by way of example in Jenes B. et al., Techniques for Gene Transfer, in: Transgenic Plants, Vol. 1, Engineering and Utilization, eds. Kung S. D and Wu R., Academic Press (1993) 128-143 and in Potrykus, Annu. Rev. Plant Physiol. Plant Molec. Biol. 42, 205 (1991). The nucleic acids or the construct to be expressed is preferably cloned into a vector which is suitable for transforming *Agrobacterium tumefaciens*, for example pBin19 (Bevan et al., Nucl. Acids Res. 12, 8711 (1984)). Agrobacteria transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. 16, 9877 (1988) or is known inter alia from White F. F., Vectors for Gene Transfer in Higher Plants; in Transgenic Plants, Vol. 1, Engineering and Utilization, eds. Kung S. D. and Wu R., Academic Press, 1993, pp. 15-38.

Agrobacteria transformed by an expression vector according to the invention may likewise be used in known manner for the transformation of plants such as test plants like *Arabidopsis* or crop plants such as cereal crops, corn, oats, rye, barley, wheat, soybean, rice, cotton, sugar beet, canola, sunflower, flax, hemp, potatoes, tobacco, tomatoes, carrots, paprika, oilseed rape, tapioca, cassava, arrowroot, *tagetes*, alfalfa, lettuce and the various tree, nut and vine species, in particular oil-containing crop plants such as soybean, peanut, castor oil plant, sunflower, corn, cotton, flax, oilseed rape, coconut, oil palm, safflower (*Carthamus tinctorius*) or cocoa bean, or in particular corn, wheat, soybean, rice, cotton and canola, e.g. by bathing bruised leaves or chopped leaves in an agrobacterial solution and then culturing them in suitable media.

The genetically modified plant cells may be regenerated by all of the methods known to those skilled in the art. Appropriate methods can be found in the publications referred to above by Kung S. D. and Wu R., Potrykus or Höfgen and Willmitzer.

Accordingly, a further aspect of the invention relates to transgenic organisms transformed by at least one nucleic acid sequence, expression cassette or vector according to the invention as well as cells, cell cultures, tissue, parts—such as, for example, leaves, roots, etc. in the case of plant organisms—or reproductive material derived from such organisms. In one embodiment of the invention host plants for the nucleic acid, expression cassette or vector according to the invention are selected from the group comprising corn, soy, oil seed rape (including canola and winter oil seed rape), cotton, wheat and rice.

A further embodiment of the invention relates to the use of a nucleic acid construct, e.g. an expression cassette, containing one or more DNA sequences encoding one or more polypeptides shown in a variant of SEQ ID NO: 2, 4, 6, 8, 10, 12, 14, 16, 18, 20, 22, 24, 26, 28, 30, or 32, or a homolog or a functional equivalent thereof or comprising one or more nucleic acid molecules as depicted in a variant of SEQ ID NO: 1, 3, 5, 7, 9, 11, 13, 15, 17, 19, 21, 23, 25, 27, 29, or 31, or a homolog or a functional equivalent thereof or encoding or DNA sequences hybridizing therewith for the transformation of plant cells, tissues or parts of plants.

In doing so, depending on the choice of promoter, the nucleic acid molecules of the present invention can be expressed specifically in the leaves, in the seeds, the nodules, in roots, in the stem or other parts of the plant. Those transgenic plants overproducing sequences, e.g. as depicted in a variant of SEQ ID NO: 1, 3, 5, 7, 9, 11, 13, 15, 17, 19, 21, 23, 25, 27, 29, or 31, or a homolog or a functional equivalent thereof, the reproductive material thereof, together with the plant cells, tissues or parts thereof are a further object of the present invention.

The expression cassette or the nucleic acid sequences or construct according to the invention containing nucleic acid molecules or sequences as depicted in a variant of SEQ ID NO: 1, 3, 5, 7, 9, 11, 13, 15, 17, 19, 21, 23, 25, 27, 29, or 31, or a homolog or a functional equivalent thereof can, moreover, also be employed for the transformation of the organisms identified by way of example above such as bacteria, yeasts, filamentous fungi and plants.

Within the framework of the present invention, increased herbicide tolerance or resistance, relates to, for example, the artificially acquired trait of increased herbicide tolerance or resistance, by comparison with the non-genetically modified initial plants e.g. the trait acquired by genetic modification of the target organism, and due to functional over-expression of one or more polypeptide (sequences) of a variant of SEQ ID NO: 2, 4, 6, 8, 10, 12, 14, 16, 18, 20, 22, 24, 26, 28, 30, or 32, or a homolog or a functional equivalent thereof, e.g. encoded by the corresponding nucleic acid molecules as depicted in a variant of SEQ ID NO: 1, 3, 5, 7, 9, 11, 13, 15, 17, 19, 21, 23, 25, 27, 29, or 31, and/or homologs, in the organisms according to the invention, advantageously in the transgenic plant according to the invention or produced according to the method of the invention, at least for the duration of at least one plant generation.

A constitutive expression of the polypeptide sequences of a variant of SEQ ID NO: 2, 4, 6, 8, 10, 12, 14, 16, 18, 20, 22, 24, 26, 28, 30, or 32, or a homolog or a functional equivalent thereof, encoded by the corresponding nucleic acid molecule as depicted in a variant of SEQ ID NO: 1, 3, 5, 7, 9, 11, 13, 15, 17, 19, 21, 23, 25, 27, 29, or 31, ora homolog ora functional equivalent thereof is, moreover, advantageous. On the other hand, however, an inducible expression may also appear desirable. Expression of the polypeptide sequences of the invention can be either direct to the cytoplasm or the organelles, preferably the plastids of the host cells, preferably the plant cells.

The activity of the protein encoded by variants of the sequences of SEQ ID NO: 2, 4, 6, 8, 10, 12, 14, 16, 18, 20, 22, 24, 26, 28, 30, or 32, or a homolog or a functional equivalent thereof, encoded by the corresponding nucleic acid molecule as depicted in a variant of SEQ ID NO: 1, 3, 5, 7, 9, 11, 13, 15, 17, 19, 21, 23, 25, 27, 29, or 31, ora homolog ora functional equivalent thereof can be determined, for example, in vitro as described in EXAMPLE 5. In addition, a functional expression of variants of the sequences of SEQ ID NO: 2, 4, 6, 8, 10, 12, 14, 16, 18, 20, 22, 24, 26, 28, 30, or 32, or a homolog or a functional equivalent thereof, encoded by the corresponding nucleic acid molecule as depicted in a variant of SEQ ID NO: 1, 3, 5, 7, 9, 11, 13, 15, 17, 19, 21, 23, 25, 27, 29, or 31, and/or homologs modified in nature and level and its effect on herbicide tolerance or resistance, but also on the metabolic pathways performance can be tested on test plants in greenhouse trials (see EXAMPLE 7).

An additional object of the invention comprises transgenic organisms such as transgenic plants transformed by an expression cassette containing sequences of as depicted in a variant of SEQ ID NO: 1, 3, 5, 7, 9, 11, 13, 15, 17, 19, 21, 23, 25, 27, 29, or 31, or a homolog or a functional equivalent thereof according to the invention or DNA sequences hybridizing therewith, as well as transgenic cells, tissue, parts and reproduction material of such plants.

Particular preference is given in this case to transgenic crop plants such as by way of example barley, wheat, rye, oats, corn, soybean, rice, cotton, sugar beet, oilseed rape and canola, sunflower, flax, hemp, thistle, potatoes, tobacco, tomatoes, tapioca, cassava, arrowroot, alfalfa, lettuce and the various tree, nut and vine species.

In one embodiment of the invention transgenic plants transformed by an expression cassette containing or comprising nucleic acid molecules or sequences as depicted in a variant of SEQ ID NO: 1, 3, 5, 7, 9, 11, 13, 15, 17, 19, 21, 23, 25, 27, 29, or 31, or a homolog or a functional equivalent thereof, according to the invention or DNA sequences hybridizing therewith are selected from the group comprising corn, soy, oil seed rape (including canola and winter oil seed rape), cotton, wheat and rice.

For the purposes of the invention plants are mono- and dicotyledonous plants, mosses or algae, especially plants, for example in one embodiment monocotyledonous plants, or for example in another embodiment dicotyledonous plants. A further refinement according to the invention are transgenic plants as described above which contain a nucleic acid sequence or construct according to the invention or a expression cassette according to the invention.

However, transgenic also means that the nucleic acids according to the invention are located at their natural position in the genome of an organism, but that the sequence, e.g. the coding sequence or a regulatory sequence, for example the promoter sequence, has been modified in comparison with the natural sequence. Preferably, transgenic/recombinant is to be understood as meaning the transcription of one or more nucleic acids or molecules of the invention and being shown in a variant of SEQ ID NO: 1, 3, 5, 7, 9, 11, 13, 15, 17, 19, 21, 23, 25, 27, 29, or 31, or a homolog or a functional equivalent thereof, occurs at a non-natural position in the genome. In one embodiment, the expression of the nucleic acids or molecules is homologous. In another embodiment, the expression of the nucleic acids or molecules is heterologous. This expression can be transiently or of a sequence integrated stably into the genome.

Advantageous inducible plant promoters are by way of example the PRP1 promoter (Ward et al., Plant. Mol. Biol. 22361 (1993)), a promoter inducible by benzenesulfonamide (EP 388 186), a promoter inducible by tetracycline (Gatz et al., Plant J. 2, 397 (1992)), a promoter inducible by salicylic acid (WO 95/19443), a promoter inducible by abscisic acid (EP 335 528) and a promoter inducible by ethanol or cyclohexanone (WO 93/21334). Other examples of plant promoters which can advantageously be used are the promoter of cytoplasmic FBPase from potato, the ST-LSI promoter from potato (Stockhaus et al., EMBO J. 8, 2445 (1989)), the promoter of phosphoribosyl pyrophosphate amidotransferase from *Glycine max* (see also gene bank accession number U87999) or a nodiene-specific promoter as described in EP 249 676.

Such promoters are known to the person skilled in the art or can be isolated from genes which are induced under the conditions mentioned above. In one embodiment, seed-specific promoters may be used for monocotylodonous or dicotylodonous plants.

In principle all natural promoters with their regulation sequences can be used like those named above for the expression cassette according to the invention and the method according to the invention. Over and above this, synthetic promoters may also advantageously be used. In the preparation of an expression cassette various DNA fragments can be manipulated in order to obtain a nucleotide sequence, which usefully reads in the correct direction and is equipped with a correct reading frame. To connect the DNA fragments (=nucleic acids according to the invention) to one another adaptors or linkers may be attached to the fragments. The promoter and the terminator regions can usefully be provided in the transcription direction with a linker or polylinker containing one or more restriction points for the insertion of this sequence. Generally, the linker has 1 to 10, mostly 1 to 8, preferably 2 to 6, restriction points. In general the size of the linker inside the regulatory region is less than 100 bp, frequently less than 60 bp, but at least 5 bp. The promoter may be both native or homologous as well as foreign or heterologous to the host organism, for example to the host plant. In the 5'-3' transcription direction the expression cassette contains the promoter, a DNA sequence which shown in SEQ ID NO: 1, 3, 5, 7, 9, 11, 13, 15, 17, 19, 21, 23, 25, 27, 29, or 31, or a homolog or a functional equivalent thereof and a region for transcription termination. Different termination regions can be exchanged for one another in any desired fashion.

A nucleic acid molecule of the present invention, e.g., a nucleic acid molecule encoding a mutated HPPD polypeptide which confers increased herbicide tolerance or resistance, in plants, can be isolated using standard molecular biological techniques and the sequence information provided herein. For example, a microbial polypeptide encoding cDNA according to present invention can be isolated from a microbial c-DNA library using all or portion of one of the sequences shown in SEQ ID NO: 1, 3, 5, 7, 9, 11, 13, 15, 17, 19, 21, 23, 25, 27, 29, or 31, or a homolog or a functional equivalent thereof. Moreover, a nucleic acid molecule encompassing all or a portion of one of the sequences of SEQ ID NO: 1, 3, 5, 7, 9, 11, 13, 15, 17, 19, 21, 23, 25, 27, 29, or 31, or a homolog or a functional equivalent thereof can be isolated by the polymerase chain reaction using oligonucleotide primers designed based upon this sequence. For example, mRNA can be isolated from plant cells (e.g., by the guanidinium-thiocyanate extraction procedure of Chirgwin et al., Biochemistry 18, 5294 (1979)) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO: 1, 3, 5, 7, 9, 11, 13, 15, 17, 19, 21, 23, 25, 27, 29, or 31, or a homolog or a functional equivalent thereof. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, the genes employed in the present invention can be prepared by standard synthetic techniques, e.g., using a commercially available automated DNA synthesizer.

In an embodiment, the nucleic acid molecule of the invention comprises a variant of one of the nucleotide sequences or molecules as shown in SEQ ID NO: 1, 3, 5, 7, 9, 11, 13, 15, 17, 19, 21, 23, 25, 27, 29, or 31, or a homolog or a functional equivalent thereof. Moreover, the nucleic acid molecule of the invention can comprise only a portion of the coding region of a variant of one of the sequences or molecules of a nucleic acid as shown in SEQ ID NO: 1, 3, 5, 7, 9, 11, 13, 15, 17, 19, 21, 23, 25, 27, 29, or 31, or a homolog or a functional equivalent thereof, for example, a fragment which can be used as a probe or primer or a fragment encoding a biologically active portion of a polypeptide-according to invention.

Portions of proteins encoded by the polynucleotide according to the invention or a polypeptide encoding nucleic acid molecule of the invention are preferably biologically active portions described herein. As used herein, the term "biologically active portion of" a polypeptide is intended to include a portion, e.g. a domain/motif, conferring increased herbicide tolerance or resistance to a plant. To determine whether a polypeptide according to the invention, or a biologically active portion thereof, results in an increased herbicide tolerance or resistance in a plant, an analysis of a plant comprising the mutated HPPD polypeptide may be performed. Such analysis methods are well known to those skilled in the art, as detailed in the Examples. More specifically, nucleic acid fragments encoding biologically active portions of a polypeptide can be prepared by isolating a portion of one of the sequences of the nucleic acid molecules listed in SEQ ID NO: 1, 3, 5, 7, 9, 11, 13, 15, 17, 19, 21, 23, 25, 27, 29, or 31, or a homolog or a functional equivalent thereof expressing the encoded portion of the polypeptide or peptide thereof (e.g., by recombinant expression in vitro) and assessing the activity of the encoded portion.

Biologically active portions of the polypeptide according to the invention are encompassed by the present invention and include peptides comprising amino acid sequences derived from the amino acid sequence of the polypeptide encoding gene, or the amino acid sequence of a protein homologous to the polypeptide according to the invention, which include fewer amino acids than a full length polypeptide according to the invention or the full length protein which is homologous to the polypeptide according to the invention, and exhibits at least some enzymatic or biological activity of the polypeptide according to the invention. Typically, biologically active portions (e.g., peptides which are, for example, 5, 10, 15, 20, 30, 35, 36, 37, 38, 39, 40, 50, 100 or more amino acids in length) comprise a domain or motif with at least one activity of the polypeptide according to the invention. Moreover, other biologically active portions in which other regions of the protein are deleted can be prepared by recombinant techniques and evaluated for one or more of the activities described herein. Preferably, the biologically active portions of the polypeptide according to the invention include one or more selected domains/motifs or portions thereof having biological activity.

The term "biological active portion" or "biological activity" means a polypeptide as depicted in SEQ ID NO: 2, 4, 6, 8, 10, 12, 14, 16, 18, 20, 22, 24, 26, 28, 30, or 32, or a homolog or a functional equivalent thereof or a portion of said polypeptide which still has at least 10% or 20%, preferably 30%, 40%, 50% or 60%, especially preferably 70%, 75%, 80%, 90% or 95% of the enzymatic or biological activity of the natural or starting enzyme or protein.

In the process according to the invention nucleic acid sequences or molecules can be used, which, if appropriate, contain synthetic, non-natural or modified nucleotide bases, which can be incorporated into DNA or RNA. Said synthetic, non-natural or modified bases can for example increase the stability of the nucleic acid molecule outside or inside a cell. The nucleic acid molecules of the invention can contain the same modifications as aforementioned.

As used in the present context the term "nucleic acid molecule" may also encompass the untranslated sequence or molecule located at the 3' and at the 5' end of the coding gene region, for example at least 500, preferably 200, especially preferably 100, nucleotides of the sequence upstream of the 5' end of the coding region and at least 100, preferably 50, especially preferably 20, nucleotides of the sequence downstream of the 3' end of the coding gene region. It is often advantageous only to choose the coding region for cloning and expression purposes.

Preferably, the nucleic acid molecule used in the process according to the invention or the nucleic acid molecule of the invention is an isolated nucleic acid molecule. In one embodiment, the nucleic acid molecule of the invention is the nucleic acid molecule used in the process of the invention.

In various embodiments, the isolated nucleic acid molecule used in the process according to the invention may, for example comprise less than approximately 5 kb, 4 kb, 3 kb, 2 kb, 1 kb, 0.5 kb or 0.1 kb nucleotide sequences which naturally flank the nucleic acid molecule in the genomic DNA of the cell from which the nucleic acid molecule originates.

The nucleic acid molecules used in the process, for example the polynucleotide of the invention or of a part thereof can be isolated using molecular-biological standard techniques and the sequence information provided herein. Also, for example a homologous sequence or homologous, conserved sequence regions at the DNA or amino acid level can be identified with the aid of comparison algorithms. The former can be used as hybridization probes under standard hybridization techniques (for example those described in Sambrook et al., supra) for isolating further nucleic acid sequences useful in this process.

A nucleic acid molecule encompassing a complete sequence of the nucleic acid molecules used in the process, for example the polynucleotide of the invention, or a part thereof may additionally be isolated by polymerase chain reaction, oligonucleotide primers based on this sequence or on parts thereof being used. For example, a nucleic acid molecule comprising the complete sequence or part thereof can be isolated by polymerase chain reaction using oligonucleotide primers which have been generated on the basis of this very sequence. For example, mRNA can be isolated from cells (for example by means of the guanidinium thiocyanate extraction method of Chirgwin et al., Biochemistry 18, 5294(1979)) and cDNA can be generated by means of reverse transcriptase (for example Moloney, MLV reverse transcriptase, available from Gibco/BRL, Bethesda, Md., or AMV reverse transcriptase, obtainable from Seikagaku America, Inc., St. Petersburg, Fla.).

Synthetic oligonucleotide primers for the amplification by means of polymerase chain reaction can be generated on the basis of a sequence shown herein, using known methods. Moreover, it is possible to identify a conserved protein by carrying out protein sequence alignments with the polypeptide encoded by the nucleic acid molecules of the present invention, in particular with the sequences encoded by the nucleic acid molecule shown in SEQ ID NO: 1, 3, 5, 7, 9, 11, 13, 15, 17, 19, 21, 23, 25, 27, 29, or 31, ora homolog ora functional equivalent thereof, from which conserved regions, and in turn, degenerate primers can be derived. Conserved regions are those, which show a very little variation in the amino acid in one particular position of several homologs from different origin. Moreover, it is possible to identify conserved regions from various organisms by carrying out protein sequence alignments with the polypeptide encoded by the nucleic acid of the present invention, in particular with the sequences of the polypeptide molecule shown in SEQ ID NO: 2, 4, 6, 8, 10, 12, 14, 16, 18, 20, 22, 24, 26, 28, 30, or 32, or a homolog or a functional equivalent thereof, from which conserved regions, and in turn, degenerate primers can be derived.

Conserved domains can be identified from all sequences and are described using a subset of the standard Prosite notation, e.g. the pattern Y-x(21,23)-[FW] means that a conserved tyrosine is separated by minimum 21 and maximum 23 amino acid residues from either a phenylalanine or tryptophane. Patterns can match at least 80% of the investigated proteins. Conserved patterns can be identified with the software tool MEME version 3.5.1 or manually. MEME is described by Timothy L. Bailey and Charles Elkan (Proceedings of the Second International Conference on Intelligent Systems for Molecular Biology, pp. 28-36, AAAI Press, Menlo Park, Calif., 1994). The source code for the stand-alone program is publicly available from the San Diego Supercomputer centre. The Prosite patterns of the conserved domains can be used to search for protein sequences matching this pattern.

Various established Bioinformatic centres provide public internet portals for using those patterns in database searches (e.g. PIR (Protein Information Resource, located at Georgetown University Medical Center) or ExPASy (Expert Protein Analysis System)). Alternatively, stand-alone software is available, like the program Fuzzpro, which is part of the EMBOSS software package. For example, the program Fuzzpro not only allows searching for an exact pattern-protein match but also allows setting various ambiguities in the performed search.

Degenerate primers can then be utilized by PCR for the amplification of fragments of novel proteins having above-mentioned activity, e.g. conferring increased herbicide tolerance or resistance, as compared to a corresponding, e.g. non-transformed, wild type plant cell, plant or part thereof after increasing the expression or activity or having the activity of a protein as shown in SEQ ID NO: 2, 4, 6, 8, 10, 12, 14, 16, 18, 20, 22, 24, 26, 28, 30, or 32, ora homolog or a functional equivalent thereof or further functional homologs of the polypeptide of the invention from other organisms.

These fragments can then be utilized as hybridization probe for isolating the complete gene sequence. As an alternative, the missing 5' and 3' sequences can be isolated by means of RACE-PCR. A nucleic acid molecule according to the invention can be amplified using cDNA or, as an alternative, genomic DNA as template and suitable oligonucleotide primers, following standard PCR amplification techniques. The nucleic acid molecule amplified thus can be cloned into a suitable vector and characterized by means of DNA sequence analysis. Oligonucleotides, which correspond to one of the nucleic acid molecules used in the process can be generated by standard synthesis methods, for example using an automatic DNA synthesizer.

Nucleic acid molecules which are advantageously for the process according to the invention can be isolated based on their homology to the nucleic acid molecules disclosed herein using the sequences or part thereof as or for the generation of a hybridization probe and following standard hybridization techniques under stringent hybridization conditions. In this context, it is possible to use, for example, isolated one or more nucleic acid molecules of at least 15, 20, 25, 30, 35, 40, 50, 60 or more nucleotides, preferably of at least 15, 20 or 25 nucleotides in length which hybridize under stringent conditions with the above-described nucleic acid molecules, in particular with those which encompass a nucleotide sequence of the nucleic acid molecule used in the process of the invention or encoding a protein used in the invention or of the nucleic acid molecule of the invention. Nucleic acid molecules with 30, 50, 100, 250 or more nucleotides may also be used.

By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)) or in Current Protocols in Molecular Biology, John Wiley & Sons, N.Y. (1989), 6.3.1-6.3.6.

According to the invention, DNA as well as RNA molecules of the nucleic acid of the invention can be used as probes. Further, as template for the identification of functional homologues Northern blot assays as well as Southern blot assays can be performed. The Northern blot assay advantageously provides further information about the expressed gene product: e.g. expression pattern, occurrence of processing steps, like splicing and capping, etc. The Southern blot assay provides additional information about the chromosomal localization and organization of the gene encoding the nucleic acid molecule of the invention.

A preferred, non-limiting example of stringent hybridization conditions are hybridizations in 6× sodium chloride/sodium citrate (=SSC) at approximately 45° C., followed by one or more wash steps in 0.2×SSC, 0.1% SDS at 50 to 65° C., for example at 50° C., 55° C. or 60° C. The skilled worker knows that these hybridization conditions differ as a function of the type of the nucleic acid and, for example when organic solvents are present, with regard to the temperature and concentration of the buffer. The temperature under "standard hybridization conditions" differs for example as a function of the type of the nucleic acid between 42° C. and 58° C., preferably between 45° C. and 50° C. in an aqueous buffer with a concentration of 0.1×, 0.5×, 1×, 2×, 3×, 4× or 5×SSC (pH 7.2). If organic solvent(s) is/are present in the abovementioned buffer, for example 50% formamide, the temperature under standard conditions is approximately 40° C., 42° C. or 45° C. The hybridization conditions for DNA:DNA hybrids are preferably for example 0.1×SSC and 20° C., 25° C., 30° C., 35° C., 40° C. or 45° C., preferably between 30° C. and 45° C. The hybridization conditions for DNA:RNA hybrids are preferably for example 0.1×SSC and 30° C., 35° C., 40° C., 45° C., 50° C. or 55° C., preferably between 45° C. and 55° C. The abovementioned hybridization temperatures are determined for example for a nucleic acid approximately 100 bp (=base pairs) in length and a G+C content of 50% in the absence of formamide. The skilled worker knows to determine the hybridization conditions required with the aid of textbooks, for example the ones mentioned above, or from the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford.

A further example of one such stringent hybridization condition is hybridization at 4×SSC at 65° C., followed by a washing in 0.1×SSC at 65° C. for one hour. Alternatively, an exemplary stringent hybridization condition is in 50% formamide, 4×SSC at 42° C. Further, the conditions during the wash step can be selected from the range of conditions delimited by low-stringency conditions (approximately 2×SSC at 50° C.) and high-stringency conditions (approximately 0.2×SSC at 50° C., preferably at 65° C.) (20×SSC: 0.3 M sodium citrate, 3 M NaCl, pH 7.0). In addition, the temperature during the wash step can be raised from low-stringency conditions at room temperature, approximately 22° C., to higher-stringency conditions at approximately 65° C. Both of the parameters salt concentration and temperature can be varied simultaneously, or else one of the two parameters can be kept constant while only the other is varied. Denaturants, for example formamide or SDS, may also be employed during the hybridization. In the presence of 50% formamide, hybridization is preferably effected at 42° C. Relevant factors like 1) length of treatment, 2) salt conditions, 3) detergent conditions, 4) competitor DNAs, 5) temperature and 6) probe selection can be combined case by case so that not all possibilities can be mentioned herein.

Thus, in a preferred embodiment, Northern blots are prehybridized with Rothi-Hybri-Quick buffer (Roth, Karlsruhe) at 68° C. for 2 h. Hybridization with radioactive labelled probe is done overnight at 68° C. Subsequent washing steps are performed at 68° C. with 1×SSC. For Southern blot assays the membrane is prehybridized with Rothi-Hybri-Quick buffer (Roth, Karlsruhe) at 68° C. for 2 h. The hybridzation with radioactive labelled probe is conducted over night at 68° C. Subsequently the hybridization buffer is discarded and the filter shortly washed using 2×SSC; 0.1% SDS. After discarding the washing buffer new 2×SSC; 0.1% SDS buffer is added and incubated at 68° C. for 15 minutes. This washing step is performed twice followed by an additional washing step using 1×SSC; 0.1% SDS at 68° C. for 10 min. Some examples of conditions for DNA hybridization (Southern blot assays) and wash step are shown herein below:

(1) Hybridization conditions can be selected, for example, from the following conditions:
  (a) 4×SSC at 65° C.,
  (b) 6×SSC at 45° C.,
  (c) 6×SSC, 100 mg/ml denatured fragmented fish sperm DNA at 68° C.,
  (d) 6×SSC, 0.5% SDS, 100 mg/ml denatured salmon sperm DNA at 68° C.,
  (e) 6×SSC, 0.5% SDS, 100 mg/ml denatured fragmented salmon sperm DNA, 50% formamide at 42° C.,
  (f) 50% formamide, 4×SSC at 42° C.,
  (g) 50% (v/v) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
  (h) 2× or 4×SSC at 50° C. (low-stringency condition), or
  (i) 30 to 40% formamide, 2× or 4×SSC at 42° C. (low-stringency condition).

(2) Wash steps can be selected, for example, from the following conditions:
  (a) 0.015 M NaCl/0.0015 M sodium citrate/0.1% SDS at 50° C.
  (b) 0.1×SSC at 65° C.
  (c) 0.1×SSC, 0.5% SDS at 68° C.
  (d) 0.1×SSC, 0.5% SDS, 50% formamide at 42° C.
  (e) 0.2×SSC, 0.1% SDS at 42° C.
  (f) 2×SSC at 65° C. (low-stringency condition).

Polypeptides having above-mentioned activity, i.e. conferring increased herbicide tolerance or resistance, as compared to a corresponding, e.g. non-transformed, wild type plant cell, plant or part thereof, derived from other organisms, can be encoded by other DNA sequences which hybridize to the sequences shown in SEQ ID NO: 1, 3, 5, 7, 9, 11, 13, 15, 17, 19, 21, 23, 25, 27, 29, or 31, or a homolog or a functional equivalent thereof, under relaxed hybridization conditions and which code on expression for peptides conferring the increased herbicide tolerance or resistance, as compared to a corresponding, e.g. non-transformed, wild type plant cell, plant or part thereof.

Further, some applications have to be performed at low stringency hybridization conditions, without any consequences for the specificity of the hybridization. For example, a Southern blot analysis of total DNA could be probed with a nucleic acid molecule of the present invention and washed at low stringency (55° C. in 2×SSPE, 0.1% SDS). The hybridization analysis could reveal a simple pattern of only genes encoding polypeptides of the present invention or used in the process of the invention, e.g. having the hereinmentioned activity of enhancing the increased herbicide tolerance or resistance, as compared to a corresponding, e.g. non-transformed, wild type plant cell, plant or part thereof. A further example of such low-stringent hybridization conditions is 4×SSC at 50° C. or hybridization with 30 to 40% formamide at 42° C. Such molecules comprise those which are fragments, analogues or derivatives of the polypeptide of the invention or used in the process of the invention and differ, for example, by way of amino acid and/or nucleotide deletion(s), insertion(s), substitution (s), addition(s) and/or recombination (s) or any other modification(s) known in the art either alone or in combination from the above-described amino acid sequences or their underlying nucleotide sequence(s). However, it is preferred to use high stringency hybridization conditions.

Hybridization should advantageously be carried out with fragments of at least 5, 10, 15, 20, 25, 30, 35 or 40 bp, advantageously at least 50, 60, 70 or 80 bp, preferably at least 90, 100 or 110 bp. Most preferably are fragments of at least 15, 20, 25 or 30 bp. Preferably are also hybridizations with at least 100 bp or 200, very especially preferably at least 400 bp in length. In an especially preferred embodiment, the hybridization should be carried out with the entire nucleic acid sequence with conditions described above.

The terms "fragment", "fragment of a sequence" or "part of a sequence" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence or molecule referred to or hybridizing with the nucleic acid molecule of the invention or used in the process of the invention under stringent conditions, while the maximum size is not critical. In some applications, the maximum size usually is not substantially greater than that required to provide the desired activity and/or function(s) of the original sequence.

Typically, the truncated amino acid sequence or molecule will range from about 5 to about 310 amino acids in length. More typically, however, the sequence will be a maximum of about 250 amino acids in length, preferably a maximum of about 200 or 100 amino acids. It is usually desirable to select sequences of at least about 10, 12 or 15 amino acids, up to a maximum of about 20 or 25 amino acids.

The term "epitope" relates to specific immunoreactive sites within an antigen, also known as antigenic determinates. These epitopes can be a linear array of monomers in a polymeric composition—such as amino acids in a protein—or consist of or comprise a more complex secondary or tertiary structure. Those of skill will recognize that immunogens (i.e., substances capable of eliciting an immune response) are antigens; however, some antigen, such as haptens, are not immunogens but may be made immunogenic by coupling to a carrier molecule. The term "antigen" includes references to a substance to which an antibody can be generated and/or to which the antibody is specifically immunoreactive.

In one embodiment the present invention relates to a epitope of the polypeptide of the present invention or used in the process of the present invention and confers an increased herbicide tolerance or resistance as compared to a corresponding, e.g. non-transformed, wild type plant cell, plant or part thereof.

The term "one or several amino acids" relates to at least one amino acid but not more than that number of amino acids, which would result in a homology of below 50% identity. Preferably, the identity is more than 70% or 80%, more preferred are 85%, 90%, 91%, 92%, 93%, 94% or 95%, even more preferred are 96%, 97%, 98%, or 99% identity.

Further, the nucleic acid molecule of the invention comprises a nucleic acid molecule, which is a complement of one of the nucleotide sequences of above mentioned nucleic acid molecules or a portion thereof. A nucleic acid molecule or its sequence which is complementary to one of the nucleotide molecules or sequences shown in a variant of SEQ ID NO: 1, 3, 5, 7, 9, 11, 13, 15, 17, 19, 21, 23, 25, 27, 29, or 31, or a homolog or a functional equivalent thereof, is one which is sufficiently complementary to one of the nucleotide molecules or sequences shown in a variant of SEQ ID NO: 1, 3, 5, 7, 9, 11, 13, 15, 17, 19, 21, 23, 25, 27, 29, or 31, or a homolog or a functional equivalent thereof such that it can hybridize to one of the nucleotide sequences shown in a variant of SEQ ID NO: 1, 3, 5, 7, 9, 11, 13, 15, 17, 19, 21, 23, 25, 27, 29, or 31, or a homolog or a functional equivalent thereof, thereby forming a stable duplex. Preferably, the hybridization is performed under stringent hybrization conditions. However, a complement of one of the herein disclosed sequences is preferably a sequence complement thereto according to the base pairing of nucleic acid molecules well known to the skilled person. For example, the bases A and G undergo base pairing with the bases T and U or C, resp. and visa versa. Modifications of the bases can influence the base-pairing partner.

The nucleic acid molecule of the invention comprises a nucleotide sequence which is at least about 30%, 35%, 40% or 45%, preferably at least about 50%, 55%, 60% or 65%, more preferably at least about 70%, 80%, or 90%, and even more preferably at least about 95%, 97%, 98%, 99% or more homologous to a nucleotide sequence shown in SEQ ID NO: 1, 3, 5, 7, 9, 11, 13, 15, 17, 19, 21, 23, 25, 27, 29, or 31, or a homolog or a functional equivalent thereof, or a portion thereof and preferably has above mentioned activity, in particular having a herbicide tolerance or resistance increasing activity after increasing the activity or an activity of a gene as shown in SEQ ID NO: 1, 3, 5, 7, 9, 11, 13, 15, 17, 19, 21, 23, 25, 27, 29, or 31, or a homolog or a functional equivalent thereof or of a gene product, by for example expression either in the cytosol or cytoplasm or in an organelle such as a plastid or mitochondria or both, preferably in plastids.

In one embodiment, the nucleic acid molecules comprising a variant of the sequence of SEQ ID NO: 1, 3, 5, 7, 9, 11, 13, 15, 17, 19, 21, 23, 25, 27, 29, or 31, ora homolog ora functional equivalent thereof or gene products encoded by said nucleic acid molecules are expressed in combination with a targeting signal as described herein.

The nucleic acid molecule of the invention comprises a nucleotide sequence or molecule which hybridizes, preferably hybridizes under stringent conditions as defined herein, to one of the nucleotide sequences or molecule shown in a variant of SEQ ID NO: 1, 3, 5, 7, 9, 11, 13, 15, 17, 19, 21, 23, 25, 27, 29, or 31, or a homolog or a functional equivalent thereof, or a portion thereof and encodes a protein having above-mentioned activity, e.g. conferring an increased herbicide tolerance or resistance, as compared to a corresponding, e.g. non-transformed, wild type plant cell, plant or part thereof by for example expression either in the cytosol or in an organelle such as a plastid or mitochondria or both, preferably in plastids, and optionally, having the activity of an mutated HPPD enzyme.

Moreover, the nucleic acid molecule of the invention can comprise only a portion of the coding region of one of the sequences shown in SEQ ID NO: 1, 3, 5, 7, 9, 11, 13, 15, 17, 19, 21, 23, 25, 27, 29, or 31, or a homolog or a functional equivalent thereof, for example a fragment which can be used as a probe or primer or a fragment encoding a biologically active portion of the polypeptide of the present invention or of a polypeptide used in the process of the present invention, i.e. having above-mentioned activity, e.g. conferring an increased herbicide tolerance or resistance, as compared to a corresponding, e.g. non-transformed, wild type plant cell, plant or part thereof f its activity is increased by for example expression either in the cytosol or in an organelle such as a plastid or mitochondria or both, preferably in plastids. The nucleotide sequences determined from the cloning of the present protein-according-to-the-invention-encoding gene allows for the generation of probes and primers designed for use in identifying and/or cloning its homologues in other cell types and organisms. The probe/primer typically comprises substantially purified oligonucleotide. The oligonucleotide typically comprises a region of nucleotide sequence that hybridizes under stringent conditions to at least about 12, 15 preferably about 20 or 25, more preferably about 40, 50 or 75 consecutive nucleotides of a sense strand of one of the sequences set forth, e.g., in SEQ ID NO: 1, 3, 5, 7, 9, 11, 13, 15, 17, 19, 21, 23, 25, 27, 29, or 31, or a homolog or a functional equivalent thereof, an anti-sense sequence of one of the sequences, e.g., set forth in SEQ ID NO: 1, 3, 5, 7, 9, 11, 13, 15, 17, 19, 21, 23, 25, 27, 29, or 31, or a homolog or a functional equivalent thereof, or naturally occurring mutants thereof.

Primers based on a nucleotide of invention can be used in PCR reactions to clone homologues of the polypeptide of the invention or of the polypeptide used in the process of the invention, e.g. as the primers described in the examples of the present invention, e.g. as shown in the examples. A PCR with primers based on SEQ ID NO: 1, 3, 5, 7, 9, 11, 13, 15, 17, 19, 21, 23, 25, 27, 29, or 31 will result in a fragment of the gene product as shown SEQ ID NO: 2, 4, 6, 8, 10, 12, 14, 16, 18, 20, 22, 24, 26, 28, 30, or 32, or a homolog or a functional equivalent thereof.

Primer sets are interchangeable. The person skilled in the art knows to combine said primers to result in the desired product, e.g. in a full length clone or a partial sequence. Probes based on the sequences of the nucleic acid molecule of the invention or used in the process of the present invention can be used to detect transcripts or genomic sequences encoding the same or homologous proteins. The probe can further comprise a label group attached thereto, e.g. the label group can be a radioisotope, a fluorescent compound, an enzyme, or an enzyme co-factor. Such probes can be used as a part of a genomic marker test kit for identifying cells which express an polypeptide of the invention or used in the process of the present invention, such as by measuring a level of an encoding nucleic acid molecule in a sample of cells, e.g., detecting mRNA levels or determining, whether a genomic gene comprising the sequence of the polynucleotide of the invention or used in the processes of the present invention has been mutated or deleted.

The nucleic acid molecule of the invention encodes a polypeptide or portion thereof which includes an amino acid sequence which is sufficiently homologous to the amino acid sequence shown in SEQ ID NO: 2, 4, 6, 8, 10, 12, 14, 16, 18, 20, 22, 24, 26, 28, 30, or 32, or a homolog or a functional equivalent thereof such that the protein or portion thereof maintains the ability to participate in increasing herbicide tolerance or resistance, as compared to a corresponding, e.g. non-transformed, wild type plant cell, plant or part thereof, in particular increasing the activity as mentioned above or as described in the examples in plants is comprised.

As used herein, the language "sufficiently homologous" refers to proteins or portions thereof which have amino acid sequences which include a minimum number of identical or equivalent amino acid residues (e.g., an amino acid residue which has a similar side chain as an amino acid residue in one of the sequences of the polypeptide of the present invention) to an amino acid sequence shown in SEQ ID NO: 2, 4, 6, 8, 10, 12, 14, 16, 18, 20, 22, 24, 26, 28, 30, or 32, or a homolog or a functional equivalent thereof such that the protein or portion thereof is able to participate in increasing herbicide tolerance or resistance, as compared to a corresponding, e.g. non-transformed, wild type plant cell, plant or part thereof.

In one embodiment, the nucleic acid molecule of the present invention comprises a nucleic acid that encodes a portion of the protein of the present invention. The protein is at least about 30%, 35%, 40%, 45% or 50%, preferably at least about 55%, 60%, 65% or 70%, and more preferably at least about 75%, 80%, 85%, 90%, 91%, 92%, 93% or 94% and most preferably at least about 95%, 97%, 98%, 99% or more homologous to an entire variant of amino acid sequence SEQ ID NO: 2, 4, 6, 8, 10, 12, 14, 16, 18, 20, 22, 24, 26, 28, 30, or 32, and having above-mentioned activity, e.g. conferring an increased herbicide tolerance or resistance, as compared to a corresponding, e.g. non-transformed, wild type plant cell, plant or part thereof by for example expression either in the cytosol or in an organelle such as a plastid or mitochondria or both, preferably in plastids.

Portions of proteins encoded by the nucleic acid molecule of the invention are preferably biologically active, preferably having above-mentioned annotated activity, e.g. conferring an increased herbicide tolerance or resistance, as compared to a corresponding, e.g. non-transformed, wild type plant cell, plant or part thereof after increase of activity.

As mentioned herein, the term "biologically active portion" is intended to include a portion, e.g., a domain/motif, that confers an increased herbicide tolerance or resistance, e.g. an increased herbicide tolerance or resistance-related trait, as compared to a corresponding, e.g. non-transformed, wild type plant cell, plant or part thereof or has an immunological activity such that it is binds to an antibody binding specifically to the polypeptide of the present invention or a polypeptide used in the process of the present invention for increasing herbicide tolerance or resistance, as compared to a corresponding, e.g. non-transformed, wild type plant cell, plant or part thereof.

The invention further relates to nucleic acid molecules that differ from one of the nucleotide sequences shown in SEQ ID NO: 1, 3, 5, 7, 9, 11, 13, 15, 17, 19, 21, 23, 25, 27, 29, or 31, or a homolog or a functional equivalent thereof (and portions thereof) due to degeneracy of the genetic code and thus encode a polypeptide of the present invention, in particular a polypeptide having above mentioned activity, e.g. as that polypeptides depicted by the sequence shown in SEQ ID NO: 2, 4, 6, 8, 10, 12, 14, 16, 18, 20, 22, 24, 26, 28, 30, or 32, or the functional homologues. Advantageously, the nucleic acid molecule of the invention comprises, or in an other embodiment has, a nucleotide sequence encoding a protein comprising, or in an other embodiment having, a variant of an amino acid sequence shown in SEQ ID NO: 2, 4, 6, 8, 10, 12, 14, 16, 18, 20, 22, 24, 26, 28, 30, or 32, or the functional homologues. In a still further embodiment, the nucleic acid molecule of the invention encodes a full length protein which is substantially homologous to a variant of an amino acid sequence shown in SEQ ID NO: 2, 4, 6, 8, 10, 12, 14, 16, 18, 20, 22, 24, 26, 28, 30, or 32, or the functional homologues.

In addition, it will be appreciated by those skilled in the art that DNA sequence polymorphisms that lead to changes in the amino acid sequences may exist within a population. Such genetic polymorphism in the gene encoding the polypeptide of the invention or comprising the nucleic acid molecule of the invention may exist among individuals within a population due to natural variation.

Nucleic acid molecules corresponding to natural variants homologues of a nucleic acid molecule of the invention, which can also be a cDNA, can be isolated based on their homology to the nucleic acid molecules disclosed herein using the nucleic acid molecule of the invention, or a portion thereof, as a hybridization probe according to standard hybridization techniques under stringent hybridization conditions.

Accordingly, in another embodiment, a nucleic acid molecule of the invention is at least 15, 20, 25 or 30 nucleotides in length. Preferably, it hybridizes under stringent conditions to a nucleic acid molecule comprising a nucleotide sequence of the nucleic acid molecule of the present invention or used in the process of the present invention, e.g. comprising the sequence shown in SEQ ID NO: 1, 3, 5, 7, 9, 11, 13, 15, 17, 19, 21, 23, 25, 27, 29, or 31, ora homolog or a functional equivalent thereof. The nucleic acid molecule is preferably at least 20, 30, 50, 100, 250 or more nucleotides in length.

The term "hybridizes under stringent conditions" is defined above. In one embodiment, the term "hybridizes under stringent conditions" is intended to describe conditions for hybridization and washing under which nucleotide sequences at least 30%, 40%, 50% or 65% identical to each other typically remain hybridized to each other. Preferably, the conditions are such that sequences at least about 70%, more preferably at least about 75% or 80%, and even more preferably at least about 85%, 90% or 95% or more identical to each other typically remain hybridized to each other.

Preferably, nucleic acid molecule of the invention that hybridizes under stringent conditions to a sequence shown in SEQ ID NO: 1, 3, 5, 7, 9, 11, 13, 15, 17, 19, 21, 23, 25, 27, 29, or 31, or a homolog or a functional equivalent thereof corresponds to a naturally-occurring nucleic acid molecule of the invention. As used herein, a "naturally-occurring" nucleic acid molecule refers to an RNA or DNA molecule having a nucleotide sequence that occurs in nature (e.g., encodes a natural protein). Preferably, the nucleic acid molecule encodes a natural protein having above-mentioned activity, e.g. conferring increasing herbicide tolerance or resistance, after increasing the expression or activity thereof or the activity of a protein of the invention or used in the process of the invention by for example expression the nucleic acid sequence of the gene product in the cytosol and/or in an organelle such as a plastid or mitochondria, preferably in plastids.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques.

In addition to naturally-occurring variants of the sequences of the polypeptide or nucleic acid molecule of the invention as well as of the polypeptide or nucleic acid molecule used in the process of the invention that may exist in the population, the skilled artisan will further appreciate that changes can be introduced by mutation into a nucleotide sequence of the nucleic acid molecule encoding the polypeptide of the invention or used in the process of the present invention, thereby leading to changes in the amino acid sequence of the encoded said polypeptide, without altering the functional ability of the polypeptide, preferably not decreasing said activity.

Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein, e.g. the mutated HPPD according to the present invention as disclosed hereinafter. Generally, nucleotide sequence variants of the invention will have at least 30, 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide "sequence identity" to the nucleotide sequence encoding a polypeptide of SEQ ID NO: 2, 4, 6, 8, 10, 12, 14, 16, 18, 20, 22, 24, 26, 28, 30, or 32.

By "variant" polypeptide is intended a polypeptide derived from the protein of SEQ ID NO: 2, 4, 6, 8, 10, 12, 14, 16, 18, 20, 22, 24, 26, 28, 30, or 32, by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein.

Such variants may result from, for example, genetic polymorphism or from human manipulation. Methods for such manipulations are generally known in the art. In a particularly preferred embodiment, the mutant variant of a HPPD polypeptide refers to a substitution of one or more amino acids at one or more sites in the native protein of SEQ ID NO: 2, 4, 6, 8, 10, 12, 14, 16, 18, 20, 22, 24, 26, 28, 30, or 32.

A substitution refers to replacement of amino acids of the protein with other amino acids, e.g. with other amino acids having similar properties (such as similar hydrophobicity, hydrophilicity, antigenicity, propensity to form or break α-helical structures or 1-sheet structures).

Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions can be conservative amino acid substitutions. Conservative substitution tables are well known in the art (see for example Creighton (1984) Proteins. W.H. Freeman and Company (Eds). Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols More specifically, the term "variant" refers to a HPPD nucleic acid having a sequence that is mutated from a wild-type HPPD nucleic acid such as SEQ ID NO: 1, 3, 5, 7, 9, 11, 13, 15, 17, 19, 21, 23, 25, 27, 29, or 31, or refers to a polypeptide having a sequence that is mutated from a wild-type HPPD polypeptide, such as SEQ ID NO: 2, 4, 6, 8, 10, 12, 14, 16, 18, 20, 22, 24, 26, 28, 30, or 32, or homologues thereof; and that confers increased HPPD-inhibiting herbicide tolerance to a plant in which it is expressed. Furthermore, the term "mutated HPPD" refers to the replacement of an amino acid of the wild-type primary sequences SEQ ID NO: 2, 4, 6, 8, 10, 12, 14, 16, 18, 20, 22, 24, 26, 28, 30, or 32.

For example, nucleotide substitutions leading to amino acid substitutions can be made in a sequence of the nucleic acid molecule of the invention or used in the process of the invention, e.g. shown in SEQ ID NO: 1, 3, 5, 7, 9, 11, 13, 15, 17, 19, 21, 23, 25, 27, 29, or 31, or a homolog or a functional equivalent thereof.

A "non-essential" amino acid residue is a residue that can be altered from the wild-type sequence of one without altering the activity of said polypeptide, whereas an "essential" amino acid residue is required for an activity as mentioned above, e.g. leading to increasing herbicide tolerance or resistance, as compared to a corresponding, e.g. non-transformed, wild type plant cell, plant or part thereof in an organism after an increase of activity of the polypeptide. Other amino acid residues, however, (e.g., those that are not conserved or only semi-conserved in the domain having said activity) may not be essential for activity and thus are likely to be amenable to alteration without altering said activity.

Further, a person skilled in the art knows that the codon usage between organisms can differ. Therefore, he may adapt the codon usage in the nucleic acid molecule of the present invention to the usage of the organism or the cell compartment for example of the plastid or mitochondria in which the polynucleotide or polypeptide is expressed. Examples of codon-adapted nucleic acids are show in SEQ ID NO: 33, 34, 35, 36, 37, and 38. In a particular preferred embodiment, codon-adapted nucleic acid molecules of the present invention comprise the sequence of SEQ ID NO: 33, 34, or 35, which represent codon-adapted nucleic acid molecules corresponding to SEQ ID NO: 1, 3 or 9.

Accordingly, the invention relates to nucleic acid molecules encoding a polypeptide having above-mentioned activity, in an organism or parts thereof by for example expression either in the cytosol or in an organelle such as a plastid or mitochondria or both, that contain changes in amino acid residues that are not essential for said activity.

Such polypeptides differ in amino acid sequence from a sequence contained in the sequences shown in SEQ ID NO: 2, 4, 6, 8, 10, 12, 14, 16, 18, 20, 22, 24, 26, 28, 30, or 32, or a homolog thereof yet retain said activity described herein. The nucleic acid molecule can comprise a nucleotide sequence encoding a polypeptide, wherein the polypeptide comprises an amino acid sequence at least about 50% identical to an amino acid sequence shown SEQ ID NO: 2, 4, 6, 8, 10, 12, 14, 16, 18, 20, 22, 24, 26, 28, 30, or 32, or a homolog thereof and is capable of participation in increasing herbicide tolerance or resistance, as compared to a corresponding, e.g. non-transformed, wild type plant cell, plant or part thereof after increasing its activity, e.g. its expression by for example expression either in the cytosol or in an organelle such as a plastid or mitochondria or both, preferably in plastids. Preferably, the protein encoded by the nucleic acid molecule is at least about 60% identical to the sequence shown in SEQ ID NO: 2, 4, 6, 8, 10, 12, 14, 16, 18, 20, 22, 24, 26, 28, 30, or 32, or a homolog thereof, more preferably at least about 70% identical to one of the sequences shown in SEQ ID NO: 2, 4, 6, 8, 10, 12, 14, 16, 18, 20, 22, 24, 26, 28, 30, or 32, or a homolog thereof, even more preferably at least about 80%, 90%, 95% homologous to the sequence shown in SEQ ID NO: 2, 4, 6, 8, 10, 12, 14, 16, 18, 20, 22, 24, 26, 28, 30, or 32, or a homolog thereof, and most preferably at least about 96%, 97%, 98%, or 99% identical to the sequence shown in SEQ ID NO: 2, 4, 6, 8, 10, 12, 14, 16, 18, 20, 22, 24, 26, 28, 30, or 32, or a homolog thereof.

In a specifically preferred embodiment of the present invention, the variant of a HPPD polypeptide differs in the amino acid sequence at one or more positions corresponding to or at positions 30, 39, 54, 57, 84, 210, 212, 223, 243, 247, 249, 251, 264, 291, 306, 317, 318, 319, 321, 326, 327, 331, 341, 342, 345, 350, 363, 367, 373, 374, 375, 379, 405, 407, 410, 412, 414, 419, 421, or 422 of the sequence comprising SEQ ID NO:4. More specifically, the variant of a HPPD polypeptide has a substitution of one or more amino acids corresponding to or at positions 30, 39, 54, 57, 84, 210, 212, 223, 243, 247, 249, 251, 264, 291, 306, 317, 318, 319, 321, 326, 327, 331, 341, 342, 345, 350, 363, 367, 373, 374, 375, 379, 405, 407, 410, 412, 414, 419, 421, or 422 of SEQ ID NO:4.

To determine the percentage homology (=identity, herein used interchangeably) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are homologous at this position (i.e. amino acid or nucleic acid "homology" as used in the present context corresponds to amino acid or nucleic acid "identity". The percentage homology between the two sequences is a function of the number of identical positions shared by the sequences (i.e. % homology=number of identical positions/total number of positions×100). The terms "homology" and "identity" are thus to be considered as synonyms.

For the determination of the percentage homology (=identity) of two or more amino acids or of two or more nucleotide sequences several computer software programs have been developed. The homology of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of homologies of different sequences is the standard blast program, which is included in the Biomax pedant software (Biomax, Munich, Federal Republic of Germany). This leads unfortunately sometimes to suboptimal results since blast does not always include complete sequences of the subject and the querry. Nevertheless as this program is very efficient it can be used for the comparison of a huge number of sequences. The following settings are typically used for such a comparisons of sequences: -p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution, 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence homology are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which has 80% homology with sequence SEQ ID NO: 1 at the nucleic acid level is understood as meaning a sequence which, upon comparison with the sequence SEQ ID NO: 1 by the above program "Needle" with the above parameter set, has a 80% homology.

Homology between two polypeptides is understood as meaning the identity of the amino acid sequence over in each case the entire sequence length which is calculated by comparison with the aid of the above program "Needle" using Matrix: EBLOSUM62, Gap_penalty: 8.0, Extend_penalty: 2.0.

For example a sequence which has a 80% homology with sequence SEQ ID NO: 2 at the protein level is understood as meaning a sequence which, upon comparison with the sequence SEQ ID NO: 2 by the above program "Needle" with the above parameter set, has a 80% homology.

Functional equivalents or variants derived from the nucleic acid sequence as shown in SEQ ID NO: 1, 3, 5, 7, 9, 11, 13, 15, 17, 19, 21, 23, 25, 27, 29, or 31, or a homolog thereof according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the nucleic acids as shown in SEQ ID NO: 1, 3, 5, 7, 9, 11, 13, 15, 17, 19, 21, 23, 25, 27, 29, or 31, or a homolog thereof according to the invention and encode polypeptides having essentially the same properties as the polypeptide as shown in SEQ ID NO: 2, 4, 6, 8, 10, 12, 14, 16, 18, 20, 22, 24, 26, 28, 30, or 32, or a homolog thereof.

Functional equivalents or variants derived from one of the polypeptides as shown in SEQ ID NO: 2, 4, 6, 8, 10, 12, 14, 16, 18, 20, 22, 24, 26, 28, 30, or 32, or a homolog thereof according to the invention by substitution, insertion or deletion have at least 30%, 35%, 40%, 45% or 50%, preferably at least 55%, 60%, 65% or 70% by preference at least 80%, especially preferably at least 85% or 90%, 91%, 92%, 93% or 94%, very especially preferably at least 95%, 97%, 98% or 99% homology with one of the polypeptides as shown in SEQ ID NO: 2, 4, 6, 8, 10, 12, 14, 16, 18, 20, 22, 24, 26, 28, 30, or 32, or a homolog thereof according to the invention and having essentially the same properties as the polypeptide as shown in SEQ ID NO: 2, 4, 6, 8, 10, 12, 14, 16, 18, 20, 22, 24, 26, 28, 30, or 32, or a homolog thereof.

"Essentially the same properties" of a functional equivalent or variant is above all understood as meaning that the functional equivalent has above mentioned activity, by for example expression either in the cytosol or in an organelle such as a plastid or mitochondria or both, preferably in plastids while increasing the amount of protein, activity or function of said functional equivalent in an organism, e.g. a microorgansim, a plant or plant tissue or animal tissue, plant or animal cells or a part of the same.

A nucleic acid molecule encoding an homologous to a protein sequence of SEQ ID NO: 2, 4, 6, 8, 10, 12, 14, 16, 18, 20, 22, 24, 26, 28, 30, or 32, or a homolog or a functional equivalent thereof can be created by introducing one or more nucleotide substitutions, additions or deletions into a nucleotide sequence of the nucleic acid molecule of the present invention, in particular of SEQ ID NO: 1, 3, 5, 7, 9, 11, 13, 15, 17, 19, 21, 23, 25, 27, 29, or 31, or a homolog or a functional equivalent thereof such that one or more amino acid substitutions, additions or deletions are introduced into the encoded protein. Mutations can be introduced into the encoding sequences of SEQ ID NO: 1, 3, 5, 7, 9, 11, 13, 15, 17, 19, 21, 23, 25, 27, 29, or 31, or a homolog or a functional equivalent thereof by standard techniques, such as site-directed mutagenesis and PCR-mediated mutagenesis.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophane), beta-branched side chains (e.g., threonine, valine, isoleucine) and aromatic side chains (e.g., tyrosine, phenylalanine, tryptophane, histidine).

Thus, a predicted nonessential amino acid residue in a polypeptide of the invention or a polypeptide used in the process of the invention is preferably replaced with another amino acid residue from the same family.

According to the present invention, mutations are introduced randomly along all or part of a coding sequence of a nucleic acid molecule of the invention or used in the process of the invention, such as by saturation mutagenesis, and the resultant mutants can be screened for activity described herein to identify mutants that retain or even have increased above mentioned activity, e.g. conferring increased herbicide tolerance or resistance, as compared to a corresponding, e.g. non-transformed, wild type plant cell, plant or part thereof.

The inventors of the present invention have found out that by substituting the amino acids at some positions in the HPPD polypeptide sequences as disclosed herein, the capability of said HPPD polypeptides could e increased.

Thus, in a preferred embodiment, the mutated HPPD of the present invention comprises a variant of the sequence of SEQ ID NO: 4, or a homologue or functional equivalent thereof, which comprises one or more of the following:

the amino acid corresponding to or at position 30 is other than proline, the amino acid corresponding to or at position 39 is other than Phe, the amino acid corresponding to or at position 54 is other than Gly, the amino acid corresponding to or at position 57 is other than Met, the amino acid corresponding to or at position 84 is other than Phe, the amino acid corresponding to or at position 210 is other than Val, the amino acid corresponding to or at position 212 is other than Asn, the amino acid corresponding to or at position 223 is other than Val, the amino acid corresponding to or at position 243 is other than Val, the amino acid corresponding to or at position 247 is other than Leu, the amino acid corresponding to or at position 249 is other than Ser, the amino acid corresponding to or at position 251 is other than Val, the amino acid corresponding to or at position 264 is other than Asn, the amino acid corresponding to or at position 291 is other than Leu, the amino acid corresponding to or at position 306 is other than His, the amino acid corresponding to or at position 317 is other than Gln, the amino acid corresponding to or at position 318 is other than Ala, the amino acid corresponding to or at position 319 is other than Ala, the amino acid corresponding to or at position 321 is other than Gly, the amino acid corresponding to or at position 326 is other than Lys, the amino acid corresponding to or at position 327 is other than Arg, the amino acid corresponding to or at position 331 is other than Lys, the amino acid corresponding to or at position 341 is other than Trp, the amino acid corresponding to or at position 342 is other than Ala, the amino acid corresponding to or at position 345 is other than Glu, the amino acid corresponding to or at position 350 is other than Leu, the amino acid corresponding to or at position 363 is other than Phe, the amino acid corresponding to or at position 367 is other than Leu, the amino acid corresponding to or at position 373 is other than Ile, the amino acid corresponding to or at position 374 is other than Phe, the amino acid corresponding to or at position 375 is other than Ile, the amino acid corresponding to or at position 379 is other than Glu, the amino acid corresponding to or at position 405 is other than Gly, the amino acid corresponding to or at position 407 is other than Phe, the amino acid corresponding to or at position 410 is other than Gly, the amino acid corresponding to or at position 412 is other than Phe, the amino acid corresponding to or at position 414 is other than Glu, the amino acid corresponding to or at position 419 is other than Ile, the amino acid corresponding to or at position 421 is other than Glu, the amino acid corresponding to or at position 422 is other than Tyr.

In another preferred embodiment, the mutated HPPD comprises a variant of the sequence of SEQ ID NO: 4, or a homologue or functional equivalent thereof, in which:

the amino acid corresponding to or at position 367 is Val, and the amino acid corresponding to or at position 375 is Leu.

In another preferred embodiment, the mutated HPPD comprises a variant of the sequence of SEQ ID NO: 4, or a homologue or functional equivalent thereof, in which:

the amino acid corresponding to or at position 367 is Val, and the amino acid corresponding to or at position 375 is Leu, and the amino acid corresponding to or at position 39 is Leu.

In another preferred embodiment, the mutated HPPD comprises a variant of the sequence of SEQ ID NO: 4, or a homologue or functional equivalent thereof, in which:

the amino acid corresponding to or at position 367 is Val, and the amino acid corresponding to or at position 375 is Leu, and the amino acid corresponding to or at position 39 is Trp.

In another preferred embodiment, the mutated HPPD comprises a variant of the sequence of SEQ ID NO: 4, or a homologue or functional equivalent thereof, in which:

the amino acid corresponding to or at position 345 is Ala, Arg, Asn, Asp, Cys, Gln, Gly, His, Ile, Leu, Lys, Met, Phe, Pro, Ser, Thr, Trp, Tyr, or Val, particularly preferred Gln In another preferred embodiment, the mutated HPPD comprises a variant of the sequence of SEQ ID NO: 4, or a homologue or functional equivalent thereof, in which:

the amino acid corresponding to or at position 345 is Gln, and the amino acid corresponding to or at position 341 is Ile.

In another preferred embodiment, the mutated HPPD comprises a variant of the sequence of SEQ ID NO: 4, or a homologue or functional equivalent thereof, in which:

the amino acid corresponding to or at position 345 is Gln, and the amino acid corresponding to or at position 326 is Glu.

In another preferred embodiment, the mutated HPPD comprises a variant of the sequence of SEQ ID NO: 4, or a homologue or functional equivalent thereof, in which:

the amino acid corresponding to or at position 345 is Gln, and the amino acid corresponding to or at position 326 is Asp.

In another preferred embodiment, the mutated HPPD comprises a variant of the sequence of SEQ ID NO: 4, or a homologue or functional equivalent thereof, in which:

the amino acid corresponding to or at position 345 is Gln, and the amino acid corresponding to or at position 326 is Gln.

In another preferred embodiment, the mutated HPPD comprises a variant of the sequence of SEQ ID NO: 4, or a homologue or functional equivalent thereof, in which:

the amino acid corresponding to or at position 318 is Arg, Asn, Asp, Cys, Gln, Glu, Gly, His, Ile, Leu, Lys, Met, Phe, Pro, Ser, Thr, Trp, Tyr, or Val, particularly preferred Pro.

In another preferred embodiment, the mutated HPPD comprises a variant of the sequence of SEQ ID NO: 4, or a homologue or functional equivalent thereof, in which:

the amino acid corresponding to or at position 319 is Arg, Asn, Asp, Cys, Gln, Glu, Gly, His, Ile, Leu, Lys, Met, Phe, Pro, Ser, Thr, Trp, Tyr, Val, particularly preferred Pro.

In another preferred embodiment, the mutated HPPD comprises a variant of the sequence of SEQ ID NO: 4, or a homologue or functional equivalent thereof, in which:

the amino acid corresponding to or at position 318 is Pro, and the amino acid corresponding to or at position 319 is Pro.

In another preferred embodiment, the mutated HPPD comprises a variant of the sequence of SEQ ID NO: 4, or a homologue or functional equivalent thereof, in which:

the amino acid corresponding to or at position 321 is Ala, Arg, Asn, Asp, Cys, Gln, Glu, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 350 is Ala, Arg, Asn, Asp, Cys, Gln, Glu, Gly, His, Ile, Lys, Met, Phe, Pro, Ser, Thr, Trp, Tyr, or Val, particularly preferred Met.

In another preferred embodiment, the mutated HPPD comprises a variant of the sequence of SEQ ID NO: 4, or a homologue or functional equivalent thereof, in which:

the amino acid corresponding to or at position 405 is Ala, Arg, Asn, Asp, Cys, Gln, Glu, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 251 is Ala, Arg, Asn, Asp, Cys, Gln, Glu, Gly, His, Ile, Leu, Lys, Met, Phe, Pro, Ser, Thr, Trp, or Tyr, particularly preferred Ala.

In another preferred embodiment, the mutated HPPD comprises a variant of the sequence of SEQ ID NO: 4, or a homologue or functional equivalent thereof, in which:

the amino acid corresponding to or at position 317 is Ala, Arg, Asn, Asp, Cys, Glu, Gly, His, Ile, Leu, Lys, Met, Phe, Pro, Ser, Thr, Trp, Tyr, or Val, particularly preferred His or Met.

In another preferred embodiment, the mutated HPPD comprises a variant of the sequence of SEQ ID NO: 4, or a homologue or functional equivalent thereof, in which:

the amino acid corresponding to or at position 379 is Ala, Arg, Asn, Asp, Cys, Gln, Gly, His, Ile, Leu, Lys, Met, Phe, Pro, Ser, Thr, Trp, Tyr, or Val, particularly preferred Gln.

In another preferred embodiment, the mutated HPPD comprises a variant of the sequence of SEQ ID NO: 4, or a homologue or functional equivalent thereof, in which:

the amino acid corresponding to or at position 350 is Met, and the amino acid corresponding to or at position 318 is Arg.

In another preferred embodiment, the mutated HPPD comprises a variant of the sequence of SEQ ID NO: 4, or a homologue or functional equivalent thereof, in which:

the amino acid corresponding to or at position 350 is Met, and the amino acid corresponding to or at position 318 is Gly.

In another preferred embodiment, the mutated HPPD comprises a variant of the sequence of SEQ ID NO: 4, or a homologue or functional equivalent thereof, in which:

the amino acid corresponding to or at position 350 is Met, and the amino acid corresponding to or at position 318 is Arg, and the amino acid corresponding to or at position 317 is Asn.

In another preferred embodiment, the mutated HPPD comprises a variant of the sequence of SEQ ID NO: 4, or a homologue or functional equivalent thereof, in which:

the amino acid corresponding to or at position 210 is Ala, Arg, Asn, Asp, Cys, Gln, Glu, Gly, His, Ile, Leu, Lys, Met, Phe, Pro, Ser, Thr, Trp, or Tyr.

In another preferred embodiment, the mutated HPPD comprises a variant of the sequence of SEQ ID NO: 4, or a homologue or functional equivalent thereof, in which:

the amino acid corresponding to or at position 317 is His, and the amino acid corresponding to or at position 318 is Gly, and the amino acid corresponding to or at position 345 is Gln.

In another preferred embodiment, the mutated HPPD comprises a variant of the sequence of SEQ ID NO: 4, or a homologue or functional equivalent thereof, in which:

the amino acid corresponding to or at position 317 is Met, and the amino acid corresponding to or at position 318 is Gly, and the amino acid corresponding to or at position 345 is Gln.

In another preferred embodiment, the mutated HPPD comprises a variant of the sequence of SEQ ID NO: 4, or a homologue or functional equivalent thereof, in which:

the amino acid corresponding to or at position 363 is Ala, Arg, Asn, Asp, Cys, Gln, Glu, Gly, His, Ile, Leu, Lys, Met, Pro, Ser, Thr, Trp, Tyr, or Val, particularly preferred Ile.

In another preferred embodiment, the mutated HPPD comprises a variant of the sequence of SEQ ID NO: 4, or a homologue or functional equivalent thereof, in which:

the amino acid corresponding to or at position 419 is Ala, Arg, Asn, Asp, Cys, Gln, Glu, Gly, His, Leu, Lys, Met, Phe, Pro, Ser, Thr, Trp, Tyr, or Val, particularly preferred Val.

In another preferred embodiment, the mutated HPPD comprises a variant of the sequence of SEQ ID NO: 4, or a homologue or functional equivalent thereof, in which:

the amino acid corresponding to or at position 249 is Ala, Arg, Asn, Asp, Cys, Gln, Glu, Gly, His, Ile, Leu, Lys, Met, Phe, Pro, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 247 is Ala, Arg, Asn, Asp, Cys, Gln, Glu, Gly, His, Ile, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 407 is Ala, Arg, Asn, Asp, Cys, Gln, Glu, Gly, His, Ile, Leu, Lys, Met, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 306 is Ala, Arg, Asn, Asp, Cys, Gln, Glu, Gly, Ile, Leu, Lys, Met, Phe, Pro, Ser, Thr, Trp, Tyr, or Val, particularly preferred Lys.

In another preferred embodiment, the mutated HPPD comprises a variant of the sequence of SEQ ID NO: 4, or a homologue or functional equivalent thereof, in which:

the amino acid corresponding to or at position 30 is Ala, Arg, Asn, Asp, Cys, Gln, Glu, Gly, His, Ile, Leu, Lys, Met, Phe, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 54 is Ala, Arg, Asn, Asp, Cys, Gln, Glu, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 57 is Ala, Arg, Asn, Asp, Cys, Gln, Glu, Gly, His, Ile, Leu, Lys, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 84 is Ala, Arg, Asn, Asp, Cys, Gln, Glu, Gly, His, Ile, Leu, Lys, Met, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 212 is Ala, Arg, Asp, Cys, Gln, Glu, Gly, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 223 is Ala, Arg, Asn, Asp, Cys, Gln, Glu, Gly, His, Ile, Leu, Lys, Met, Phe, Pro, Ser, Thr, Trp, or Tyr.

In another preferred embodiment, the mutated HPPD comprises a variant of the sequence of SEQ ID NO: 4, or a homologue or functional equivalent thereof, in which:

the amino acid corresponding to or at position 243 is Ala, Arg, Asn, Asp, Cys, Gln, Glu, Gly, His, Ile, Leu, Lys, Met, Phe, Pro, Ser, Thr, Trp, or Tyr.

In another preferred embodiment, the mutated HPPD comprises a variant of the sequence of SEQ ID NO: 4, or a homologue or functional equivalent thereof, in which:

the amino acid corresponding to or at position 264 is Ala, Arg, Asp, Cys, Gln, Glu, Gly, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 291 is Ala, Arg, Asn, Asp, Cys, Gln, Glu, Gly, His, Ile, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 327 is Ala, Asn, Asp, Cys, Gln, Glu, Gly, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 331 is Ala, Arg, Asn, Asp, Cys, Gln, Glu, Gly, His, Ile, Leu, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 342 is Arg, Asn, Asp, Cys, Gln, Glu, Gly, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 373 is Ala, Arg, Asn, Asp, Cys, Gln, Glu, Gly, His, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 374 is Ala, Arg, Asn, Asp, Cys, Gln, Glu, Gly, His, Ile, Leu, Lys, Met, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 410 is Ala, Arg, Asn, Asp, Cys, Gln, Glu, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 412 is Ala, Arg, Asn, Asp, Cys, Gln, Glu, Gly, His, Ile, Leu, Lys, Met, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 414 is Ala, Arg, Asn, Asp, Cys, Gln, Gly, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 421 is Ala, Arg, Asn, Asp, Cys, Gln, Gly, His, Ile, Leu, Lys, Met, Phe, Pro, Ser, Thr, Trp, Tyr, or Val.

In another preferred embodiment, the mutated HPPD comprises a variant of the sequence of SEQ ID NO: 4, or a homologue or functional equivalent thereof, in which:

the amino acid corresponding to or at position 422 is Ala, Arg, Asn, Asp, Cys, Gln, Glu, Gly, His, Ile, Leu, Lys, Met, Phe, Pro, Ser, Thr, Trp, or Val.

In another preferred embodiment, the mutated HPPD comprises a variant of the sequence of SEQ ID NO: 4, or a homologue or functional equivalent thereof, in which:

the amino acid corresponding to or at position 251 is Ala, and the amino acid corresponding to or at position 405 is Asp.

In another preferred embodiment, the mutated HPPD comprises a variant of the sequence of SEQ ID NO: 4, or a homologue or functional equivalent thereof, in which:

the amino acid corresponding to or at position 327 is Gly, and the amino acid corresponding to or at position 421 is Asp.

In another preferred embodiment, the mutated HPPD comprises a variant of the sequence of SEQ ID NO: 4, or a homologue or functional equivalent thereof, in which:

the amino acid corresponding to or at position 251 is Ala, and the amino acid corresponding to or at position 306 is Arg, and the amino acid corresponding to or at position 317 is Leu, and the amino acid corresponding to or at position 318 is Pro, and the amino acid corresponding to or at position 321 is Pro, and the amino acid corresponding to or at position 331 is Glu, and the amino acid corresponding to or at position 350 is Met.

Following mutagenesis of one of the sequences as shown herein, the encoded protein can be expressed recombinantly and the activity of the protein can be determined using, for example, assays described herein.

Preferred mutational sites in the HPPD sequences as disclosed herein are depicted in Table 2

TABLE 2

| ID | Pos 1 | Pos 2 | Pos 3 | Pos 4 | Pos 5 | Pos 6 | Pos 7 | Pos 8 | Pos 9 | Pos 10 | Pos 11 | Pos 12 | Pos 13 |
|---|---|---|---|---|---|---|---|---|---|---|---|---|---|
| 2 | P30 | F39 | G54 | M57 | F84 | V210 | N212 | V223 | V243 | L247 | S249 | V251 | N264 |
| 4 | P30 | F39 | G54 | M57 | F84 | V210 | N212 | V223 | V243 | L247 | S249 | V251 | N264 |
| 6 | T42 | F51 | G66 | M69 | F96 | V232 | N234 | V245 | S265 | L269 | S271 | V273 | N286 |
| 8 | T42 | F51 | G66 | M69 | F96 | V231 | N233 | V244 | S264 | L268 | S270 | V272 | N285 |
| 10 | H46 | F55 | G70 | M73 | F100 | V221 | N223 | V234 | A254 | L258 | S260 | V262 | N275 |
| 12 | P7 | L16 | A31 | Y34 | L61 | V172 | N174 | Y187 | E207 | L211 | S213 | V215 | N228 |
| 14 | P7 | F16 | A31 | Y34 | L61 | V172 | N174 | Y187 | D207 | L211 | S213 | V215 | N228 |
| 16 | P7 | F16 | A31 | F34 | L61 | V172 | N174 | Y187 | E207 | L211 | S213 | V215 | N228 |
| 18 | L7 | F16 | G31 | L34 | L61 | V168 | N170 | Y183 | D203 | L207 | S209 | V211 | N223 |
| 20 | P9 | F18 | A33 | Y36 | L63 | V173 | N175 | Y188 | E208 | L212 | S214 | V216 | N229 |
| 22 | P7 | L16 | A31 | F34 | I61 | V172 | N174 | Y187 | E207 | L211 | S213 | V215 | N228 |
| 24 | P38 | W47 | A62 | M65 | F92 | V207 | N209 | Y222 | R242 | L246 | S248 | V250 | N263 |
| 26 | A16 | M25 | A40 | F43 | L70 | V181 | N183 | Y196 | E216 | L220 | S222 | V224 | N237 |
| 28 | P54 | F63 | A78 | F81 | L108 | V219 | N221 | Y234 | E254 | L258 | S260 | V262 | N275 |
| 30 | P17 | F26 | A41 | F44 | F71 | V182 | N184 | Y197 | D217 | L221 | S223 | V225 | N238 |
| 32 | P38 | W47 | A62 | M65 | F92 | V207 | N209 | Y222 | D242 | L246 | S248 | V250 | N263 |
| 40 | H38 | F47 | A62 | A65 | F92 | V213 | N215 | I226 | T246 | L250 | S252 | V254 | N267 |
| 42 | K43 | F52 | G67 | M70 | F97 | V228 | N230 | V241 | A261 | L265 | S267 | V269 | N282 |

| ID | Pos 14 | Pos 15 | Pos 16 | Pos 17 | Pos 18 | Pos 19 | Pos 20 | Pos 21 | Pos 22 |
|---|---|---|---|---|---|---|---|---|---|
| 2 | L291 | H306 | Q317 | A318 | A319 | G321 | K326 | R327 | K331 |
| 4 | L291 | H306 | Q317 | A318 | A319 | G321 | K326 | R327 | K331 |
| 6 | L313 | R328 | M339 | P340 | S341 | P343 | R348 | N349 | R353 |
| 8 | L312 | R327 | M338 | P339 | S340 | P342 | R347 | N348 | R352 |
| 10 | L302 | R317 | M328 | P329 | P330 | P332 | R337 | N338 | R342 |
| 12 | M254 | R269 | L276 | E277 | V278 | — | D284 | D285 | L287 |
| 14 | L254 | R269 | L276 | E277 | V278 | — | D284 | D285 | L287 |
| 16 | I254 | R269 | L276 | Y277 | V278 | — | E284 | D285 | I287 |
| 18 | I249 | K264 | L271 | Q272 | T273 | — | D279 | T280 | T282 |
| 20 | I255 | R270 | L277 | H278 | V279 | — | E285 | D286 | E288 |
| 22 | M254 | R269 | L276 | E277 | V278 | — | D284 | D285 | L287 |
| 24 | L289 | R304 | L311 | D312 | T313 | — | D319 | D320 | W324 |
| 26 | I263 | R278 | L285 | R286 | T287 | — | S293 | A294 | A296 |
| 28 | L301 | Q316 | L323 | T324 | V325 | — | D331 | T332 | T334 |
| 30 | V264 | Q279 | L286 | K287 | V288 | — | T294 | E295 | E297 |
| 32 | V289 | R304 | L311 | A312 | T313 | — | E319 | D320 | R324 |
| 40 | I294 | R309 | L320 | P321 | P322 | L324 | E329 | G330 | L334 |
| 42 | L309 | R324 | M335 | P336 | S337 | P339 | Q344 | N345 | R349 |

| ID | Pos 23 | Pos 24 | Pos 25 | Pos 26 | Pos 27 | Pos 28 | Pos 29 | Pos 30 | Pos 31 |
|---|---|---|---|---|---|---|---|---|---|
| 2 | W341 | A342 | E345 | L350 | F363 | L367 | I373 | F374 | I375 |
| 4 | W341 | A342 | E345 | L350 | F363 | L367 | I373 | F374 | I375 |
| 6 | I363 | K364 | E367 | L372 | F385 | V389 | I395 | F396 | I397 |
| 8 | I362 | K363 | E366 | L371 | F384 | V388 | I394 | F395 | I396 |
| 10 | M352 | V353 | E356 | L361 | F374 | V378 | I384 | F385 | L386 |
| 12 | L297 | Q298 | K301 | L306 | F319 | I323 | L329 | F330 | F331 |
| 14 | L297 | Q298 | K301 | L306 | F319 | V323 | V329 | F330 | Y331 |
| 16 | M297 | E298 | R301 | L306 | F319 | V323 | V329 | F330 | Y331 |
| 18 | I292 | E293 | K296 | L301 | F314 | L318 | V324 | F325 | F326 |
| 20 | M298 | D299 | R302 | L307 | F320 | V324 | V330 | F331 | Y332 |
| 22 | L297 | Q298 | K301 | L306 | F319 | V323 | L329 | F330 | F331 |
| 24 | V334 | E335 | R338 | L343 | F356 | L360 | V366 | F367 | F368 |
| 26 | Y306 | N307 | Q310 | L315 | F328 | V332 | V338 | F339 | Y340 |
| 28 | L344 | E345 | K348 | L353 | F366 | V370 | V376 | F377 | F378 |
| 30 | I307 | E308 | E311 | L316 | F329 | V333 | L339 | F340 | Y341 |
| 32 | I334 | E335 | Q338 | L343 | F356 | L360 | V366 | F367 | F368 |
| 40 | I344 | K345 | Q348 | L353 | F366 | V370 | L376 | F377 | L378 |
| 42 | I359 | K360 | E363 | L368 | F381 | L385 | I391 | F392 | I393 |

| ID | Pos 32 | Pos 33 | Pos 34 | Pos 35 | Pos 36 | Pos 37 | Pos 38 | Pos 39 | Pos 40 |
|---|---|---|---|---|---|---|---|---|---|
| 2 | E379 | G441 | F443 | G446 | F448 | E450 | I455 | E457 | Y458 |
| 4 | E379 | G405 | F407 | G410 | F412 | E414 | I419 | E421 | Y422 |

TABLE 2-continued

|    |      |      |      |      |      |      |      |      |      |
|----|------|------|------|------|------|------|------|------|------|
| 6  | Q401 | G421 | F423 | G426 | F428 | E430 | I435 | E437 | Y438 |
| 8  | Q400 | G420 | F422 | G425 | F427 | E429 | I434 | E436 | Y437 |
| 10 | Q390 | G410 | F412 | G415 | F417 | E419 | I424 | D426 | Y427 |
| 12 | Q335 | —    | F342 | G345 | F347 | A349 | I354 | R356 | E357 |
| 14 | Q335 | —    | F342 | G345 | F347 | A349 | I354 | R356 | E357 |
| 16 | Q335 | —    | F342 | G345 | F347 | A349 | I354 | R356 | E357 |
| 18 | E330 | —    | F337 | G340 | F342 | A344 | I349 | R351 | D352 |
| 20 | Q336 | —    | F343 | G346 | F348 | A350 | I355 | R357 | E358 |
| 22 | Q335 | —    | F342 | G345 | F347 | A349 | I354 | R356 | E357 |
| 24 | E372 | —    | F379 | G382 | F384 | A386 | I391 | R393 | E394 |
| 26 | Q344 | —    | F351 | G354 | F356 | A358 | I363 | R365 | E366 |
| 28 | Q382 | —    | F389 | G392 | F394 | A396 | I401 | R403 | E404 |
| 30 | Q345 | —    | F352 | G355 | F357 | A359 | I364 | R366 | E367 |
| 32 | E372 | —    | F379 | G382 | F384 | A386 | I391 | R393 | E394 |
| 40 | Q382 | G402 | F404 | G407 | F409 | E411 | I416 | D418 | Y419 |
| 42 | Q397 | G417 | F419 | G422 | F424 | E426 | I431 | E433 | Y434 |

The highest homology of the nucleic acid molecule used in the process according to the invention was found for the following database entries by Gap search.

Homologues of the nucleic acid sequences used, with a variant of the sequence shown in SEQ ID NO: 1, 3, 5, 7, 9, 11, 13, 15, 17, 19, 21, 23, 25, 27, 29, or 31, or a homolog or a functional equivalent thereof, comprise also allelic variants with at least approximately 30%, 35%, 40% or 45% homology, by preference at least approximately 50%, 60% or 70%, more preferably at least approximately 90%, 91%, 92%, 93%, 94% or 95% and even more preferably at least approximately 96%, 97%, 98%, 99% or more homology with one of the nucleotide sequences shown or the above-mentioned derived nucleic acid sequences or their homologues, derivatives or analogues or parts of these. As described above, allelic variants encompass in particular functional variants which can be obtained by deletion, insertion or substitution of nucleotides from the sequences shown, preferably from SEQ ID NO: 1, 3, 5, 7, 9, 11, 13, 15, 17, 19, 21, 23, 25, 27, 29, or 31, or a homolog or a functional equivalent thereof, or from the derived nucleic acid sequences, the intention being, however, that the enzyme activity or the biological activity of the resulting proteins synthesized is advantageously retained or increased.

In one embodiment of the present invention, the nucleic acid molecule of the invention or used in the process of the invention comprises variants of the sequences shown in any of the SEQ ID NO: 1, 3, 5, 7, 9, 11, 13, 15, 17, 19, 21, 23, 25, 27, 29, or 31, or a homolog or a functional equivalent thereof. It is preferred that the nucleic acid molecule comprises as little as possible other nucleotides not shown in any one of SEQ ID NO: 1, 3, 5, 7, 9, 11, 13, 15, 17, 19, 21, 23, 25, 27, 29, or 31, or a homolog or a functional equivalent thereof. In one embodiment, the nucleic acid molecule comprises less than 500, 400, 300, 200, 100, 90, 80, 70, 60, 50 or 40 further nucleotides. In a further embodiment, the nucleic acid molecule comprises less than 30, 20 or 10 further nucleotides.

Also preferred is that the nucleic acid molecule used in the process of the invention encodes a polypeptide comprising a variant of the sequence shown in SEQ ID NO: 2, 4, 6, 8, 10, 12, 14, 16, 18, 20, 22, 24, 26, 28, 30, or 32, or a homolog or a functional equivalent thereof. In one embodiment, the nucleic acid molecule encodes less than 150, 130, 100, 80, 60, 50, 40 or 30 further amino acids. In a further embodiment, the encoded polypeptide comprises less than 20, 15, 10, 9, 8, 7, 6 or 5 further amino acids.

In one embodiment, the nucleic acid molecule of the invention or used in the process encodes a polypeptide comprising a variant of the sequence shown in SEQ ID NO: 2, 4, 6, 8, 10, 12, 14, 16, 18, 20, 22, 24, 26, 28, 30, or 32, or a homolog or a functional equivalent thereof comprises less than 100 further nucleotides. In a further embodiment, said nucleic acid molecule comprises less than 30 further nucleotides.

Polypeptides (=proteins), which still have the essential biological or enzymatic activity of the polypeptide of the present invention conferring increased herbicide tolerance or resistance, as compared to a corresponding, e.g. non-transformed, wild type plant cell, plant or part thereof i.e. whose activity is essentially not reduced, are polypeptides with at least 10% or 20%, by preference 30% or 40%, especially preferably 50% or 60%, very especially preferably 80% or 90 or more of the wild type biological activity or enzyme activity, advantageously, the activity is essentially not reduced in comparison with the activity of a polypeptide shown in SEQ ID NO: 2, 4, 6, 8, 10, 12, 14, 16, 18, 20, 22, 24, 26, 28, 30, or 32, or a homolog or a functional equivalent thereof expressed under identical conditions.

Homologues of SEQ ID NO: 1, 3, 5, 7, 9, 11, 13, 15, 17, 19, 21, 23, 25, 27, 29, or 31, or of the encoded sequences of SEQ ID NO: 2, 4, 6, 8, 10, 12, 14, 16, 18, 20, 22, 24, 26, 28, 30, or 32, or a homolog or a functional equivalent thereof also mean truncated sequences, cDNA, single-stranded DNA or RNA of the coding and noncoding DNA sequence. Homologues of said sequences are also understood as meaning derivatives, which comprise noncoding regions such as, for example, UTRs, terminators, enhancers or promoter variants. The promoters upstream of the nucleotide sequences stated can be modified by one or more nucleotide substitution(s), insertion(s) and/or deletion(s) without, however, interfering with the functionality or activity either of the promoters, the open reading frame (=ORF) or with the 3'-regulatory region such as terminators or other 3'-regulatory regions, which are far away from the ORF. It is furthermore possible that the activity of the promoters is increased by modification of their sequence, or that they are replaced completely by more active promoters, even promoters from heterologous organisms. Appropriate promoters are known to the person skilled in the art and are mentioned herein below.

Further, an embodiment of the invention is an expression vector comprising a nucleic acid molecule comprising a nucleic acid molecule selected from the group consisting of:
(a) a nucleic acid molecule encoding the polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof;

(b) a nucleic acid molecule comprising a variant of the sequence of SEQ ID NO: 1, 3, 5, 7, 9, 11, 13, 15, 17, 19, 21, 23, 25, 27, 29, or 31, or a homolog or a functional equivalent thereof, (c) a nucleic acid molecule, which, as a result of the degeneracy of the genetic code, can be derived from a variant of the polypeptide sequence of SEQ ID NO: 2, 4, 6, 8, 10, 12, 14, 16, 18, 20, 22, 24, 26, 28, 30, or 32, or a homolog or a functional equivalent thereof, and confers increased herbicide tolerance or resistance, as compared to a corresponding, e.g. non-transformed, wild type plant cell, a plant or a part thereof;

(d) a nucleic acid molecule having 30% or more identity, preferably 40%, 50%, 60%, 70%, 75%, 80%, 85%, 90%, 95%, 96%, 97%, 98%, 99%, 99.5%, or more with the nucleic acid molecule sequence of a polynucleotide comprising the nucleic acid molecule of SEQ ID NO: 1, 3, 5, 7, 9, 11, 13, 15, 17, 19, 21, 23, 25, 27, 29, or 31, or a homolog or a functional equivalent thereof, and confers increased herbicide tolerance or resistance, as compared to a corresponding, e.g. non-transformed, wild type plant cell, a plant or a part thereof;

(e) a nucleic acid molecule encoding a polypeptide having 30% or more identity, preferably at least 40%, 50%, 60%, 70%, 75%, 80%, 85%, 90%, 95%, 96%, 97%, 98%, 99%, 99.5% or more, with the amino acid sequence of the polypeptide encoded by the nucleic acid molecule of (a), (b), (c) or (d) and having the activity represented by a nucleic acid molecule comprising a polynucleotide of SEQ ID NO: 1, 3, 5, 7, 9, 11, 13, 15, 17, 19, 21, 23, 25, 27, 29, or 31, or a homolog or a functional equivalent thereof, and confers increased herbicide tolerance or resistance as compared to a corresponding, e.g. non-transformed, wild type plant cell, a plant or a part thereof;

(f) nucleic acid molecule which hybridizes with a nucleic acid molecule of (a), (b), (c), (d) or (e) under stringent hybridization conditions and confers increased herbicide tolerance or resistance, as compared to a corresponding, e.g. non-transformed, wild type plant cell, a plant or a part thereof;

(g) a nucleic acid molecule encoding a polypeptide which can be isolated with the aid of monoclonal or polyclonal antibodies made against a polypeptide encoded by one of the nucleic acid molecules of (a), (b), (c), (d), (e) or (f) and having the activity represented by the nucleic acid molecule comprising a polynucleotide as depicted in SEQ ID NO: 1, 3, 5, 7, 9, 11, 13, 15, 17, 19, 21, 23, 25, 27, 29, or 31, or a homolog or a functional equivalent thereof;

(h) a nucleic acid molecule which is obtainable by screening a suitable nucleic acid library, especially a cDNA library and/or a genomic library, under stringent hybridization conditions with a probe comprising a complementary sequence of a nucleic acid molecule of (a) or (b) or with a fragment thereof, having 15 nt, preferably 20 nt, 30 nt, 50 nt, 100 nt, 200 nt, 500 nt, 750 nt or 1000 nt or more of a nucleic acid molecule complementary to a nucleic acid molecule sequence characterized in (a) to (e) and encoding a polypeptide having the activity represented by a protein comprising a polypeptide as depicted SEQ ID NO: 2, 4, 6, 8, 10, 12, 14, 16, 18, 20, 22, 24, 26, 28, 30, or 32, or a homolog or a functional equivalent thereof.

The invention further provides an isolated recombinant expression vector comprising the nucleic acid molecule of the invention, wherein expression of the vector or nucleic acid molecule, respectively in a host cell results in an increased herbicide tolerance or resistance, as compared to the corresponding, e.g. non-transformed, wild type of the host cell.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* T-DNA such as the gene 3 known as octopine synthase of the Ti-plasmid pTiACH5 (Gielen et al., EMBO J. 3, 835 1(984)) or functional equivalents thereof but also all other terminators functionally active in plants are suitable. As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., Nucl. Acids Research 15, 8693 (1987)).

Plant gene expression has to be operably linked to an appropriate promoter conferring gene expression in a timely, cell or tissue specific manner. Preferred are promoters driving constitutive expression (Benfey et al., EMBO J. 8, 2195 (1989)) like those derived from plant viruses like the 35S CaMV (Franck et al., Cell 21, 285 (1980)), the 19S CaMV (see also U.S. Pat. No. 5,352,605 and PCT Application No. WO 84/02913) or plant promoters like those from Rubisco small subunit described in U.S. Pat. No. 4,962,028. Other promoters, e.g. super-promoter (Ni et al., Plant Journal 7, 661 (1995)), Ubiquitin promoter (Callis et al., J. Biol. Chem., 265, 12486 (1990); U.S. Pat. Nos. 5,510,474; 6,020,190; Kawalleck et al., Plant. Molecular Biology, 21, 673 (1993)) or 34S promoter (GenBank Accession numbers M59930 and X16673) were similar useful for the present invention and are known to a person skilled in the art. Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed preferred promoters are preferentially expressed during seed development and/or germination. For example, seed preferred promoters can be embryo-preferred, endosperm preferred, and seed coat-preferred. See Thompson et al., BioEssays 10, 108 (1989). Examples of seed preferred promoters include, but are not limited to, cellulose synthase (celA), Ciml, gamma-zein, globulin-1, maize 19 kD zein (cZ19B1), and the like.

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat.

Nos. 5,412,085 and 5,545,546), and the SGB6 promoter (U.S. Pat. No. 5,470,359), as well as synthetic or other natural promoters.

Additional advantageous regulatory sequences are, for example, included in the plant promoters such as CaMV/35S (Franck et al., Cell 21 285 (1980)), PRP1 (Ward et al., Plant. Mol. Biol. 22, 361 (1993)), SSU, OCS, lib4, usp, STLS1, B33, LEB4, nos, ubiquitin, napin or phaseolin promoter. Also advantageous in this connection are inducible promoters such as the promoters described in EP 388 186 (benzyl sulfonamide inducible), Gatz et al., Plant J. 2, 397 (1992) (tetracyclin inducible), EP-A-0 335 528 (abscisic acid inducible) or WO 93/21334 (ethanol or cyclohexenol inducible). Additional useful plant promoters are the cytoplasmic FBPase promoter or ST-LSI promoter of potato (Stockhaus et al., EMBO J. 8, 2445 (1989)), the phosphorybosyl phyrophoshate amido transferase promoter of *Glycine max* (gene bank accession No. U87999) or the noden specific promoter described in EP-A0 249 676. Additional particularly advantageous promoters are seed specific promoters which can be used for monocotyledones or dicotyledones and are described in U.S. Pat. No. 5,608,152 (napin promoter from rapeseed), WO 98/45461 (phaseolin promoter from *Arabidopsis*), U.S. Pat. No. 5,504,200 (phaseolin promoter from *Phaseolus vulgaris*), WO 91/13980 (Bce4 promoter from *Brassica*) and Baeumlein et al., Plant J., 2 (2), 233 (1992) (LEB4 promoter from leguminosa). Said promoters are useful in dicotyledones. The following promoters are useful for example in monocotyledones Ipt-2- or Ipt-1- promoter from barley (WO 95/15389 and WO 95/23230) or hordein promoter from barley. Other useful promoters are described in WO 99/16890. It is possible in principle to use all natural promoters with their regulatory sequences like those mentioned above for the novel process. It is also possible and advantageous in addition to use synthetic promoters.

The gene construct may also comprise further genes which are to be inserted into the organisms and which are for example involved in herbicide tolerance or resistance increase. It is possible and advantageous to insert and express in host organisms regulatory genes such as genes for inducers, repressors or enzymes which intervene by their enzymatic activity in the regulation, or one or more or all genes of a biosynthetic pathway. These genes can be heterologous or homologous in origin. The inserted genes may have their own promoter or else be under the control of same promoter as the sequences of the nucleic acid of SEQ ID NO: 1, 3, 5, 7, 9, 11, 13, 15, 17, 19, 21, 23, 25, 27, 29, or 31, or their homologs or functional equivalents thereof.

The gene construct advantageously comprises, for expression of the other genes present, additionally 3' and/or 5' terminal regulatory sequences to enhance expression, which are selected for optimal expression depending on the selected host organism and gene or genes.

These regulatory sequences are intended to make specific expression of the genes and protein expression possible as mentioned above. This may mean, depending on the host organism, for example that the gene is expressed or over-expressed only after induction, or that it is immediately expressed and/or over-expressed.

The regulatory sequences or factors may moreover preferably have a beneficial effect on expression of the introduced genes, and thus increase it. It is possible in this way for the regulatory elements to be enhanced advantageously at the transcription level by using strong transcription signals such as promoters and/or enhancers. However, in addition, it is also possible to enhance translation by, for example, improving the stability of the mRNA.

Other preferred sequences for use in plant gene expression cassettes are targeting-sequences necessary to direct the gene product in its appropriate cell compartment (for review see Kermode, Crit. Rev. Plant Sci. 15 (4), 285 (1996) and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, Annu. Rev. Plant Physiol. Plant Mol. Biol. 48, 89 (1997)). Chemically inducible promoters are especially suitable if gene expression is wanted to occur in a time specific manner.

Table 3 lists several examples of promoters that may be used to regulate transcription of the nucleic acid coding sequences of the present invention.

TABLE 3

Examples of tissue-specific and inducible promoters in plants

| Expression | Reference |
|---|---|
| Cor78 - Cold, drought, salt, ABA, wounding-inducible | Ishitani, et al., Plant Cell 9, 1935 (1997), Yamaguchi-Shinozaki and Shinozaki, Plant Cell 6, 251 (1994) |
| Rci2A - Cold, dehydration-inducible | Capel et al., Plant Physiol 115, 569 (1997) |
| Rd22 - Drought, salt | Yamaguchi-Shinozaki and Shinozaki, Mol. Gen. Genet. 238, 17 (1993) |
| Cor15A - Cold, dehydration, ABA | Baker et al., Plant Mol. Biol. 24, 701 (1994) |
| GH3- Auxin inducible | Liu et al., Plant Cell 6, 645 (1994) |
| ARSK1-Root, salt inducible | Hwang and Goodman, Plant J. 8, 37 (1995) |
| PtxA - Root, salt inducible | GenBank accession X67427 |
| SbHRGP3 - Root specific | Ahn et al., Plant Cell 8, 1477 (1998). |
| KST1 - Guard cell specific | Plesch et al., Plant Journal. 28(4), 455- (2001) |
| KAT1 - Guard cell specific | Plesch et al., Gene 249, 83 (2000), Nakamura et al., Plant Physiol. 109, 371 (1995) |
| salicylic acid inducible | PCT Application No. WO 95/19443 |
| tetracycline inducible | Gatz et al., Plant J. 2, 397 (1992) |
| Ethanol inducible | PCT Application No. WO 93/21334 |
| Pathogen inducible PRP1 | Ward et al., Plant. Mol. Biol. 22, 361 -(1993) |
| Heat inducible hsp80 | U.S. Pat. No. 5,187,267 |
| Cold inducible alpha-amylase | PCT Application No. WO 96/12814 |
| Wound-inducible pinII | European Patent No. 375 091 |
| RD29A - salt-inducible | Yamaguchi-Shinozalei et al. Mol. Gen. Genet. 236, 331 (1993) |
| Plastid-specific viral RNA-polymerase | PCT Application No. WO 95/16783, PCT Application WO 97/06250 |

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, Cell 43, 729 (1985)).

In one embodiment, the language "substantially free of cellular material" includes preparations of a protein having less than about 30% (by dry weight) of contaminating material (also referred to herein as a "contaminating polypeptide"), more preferably less than about 20% of contaminating material, still more preferably less than about 10% of contaminating material, and most preferably less than about 5% contaminating material.

The nucleic acid molecules, polypeptides, polypeptide homologs, fusion polypeptides, primers, vectors, and host cells described herein can be used in one or more of the following methods: identification of *S. cerevisiae, E. coli* or *Brassica napus, Glycine max, Zea mays* or *Oryza sativa* and related organisms; mapping of genomes of organisms related to *S. cerevisiae, E. coli*; identification and localization of *S. cerevisiae, E. coli* or *Brassica napus, Glycine max, Zea mays* or *Oryza sativa* sequences of interest; evolutionary studies; determination of polypeptide regions required for function; modulation of a polypeptide activity; modulation of the metabolism of one or more cell functions; modulation of the transmembrane transport of one or more compounds; modulation of herbicide tolerance or resistance, and modulation of expression of polypeptide nucleic acids.

The nucleic acid molecules of the invention are also useful for evolutionary and polypeptide structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the polypeptide that are essential for the functioning of the enzyme. This type of determination is of value for polypeptide engineering studies and may give an indication of what the polypeptide can tolerate in terms of mutagenesis without losing function.

There are a number of mechanisms by which the alteration of the polypeptide of the invention may directly affect herbicide tolerance or resistance.

The effect of the genetic modification in plants regarding herbicide tolerance or resistance can be assessed by treating the modified plant with respective herbicides as, e.g., described in EXAMPLE 7, and then analyzing the growth characteristics and/or metabolism of the plant in comparison to non-modified plants. Such analysis techniques are well known to one skilled in the art, and include evaluation of the plant phenotype, dry weight, fresh weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, Vol. 17; Rehm et al., 1993 Biotechnology, Vol. 3, Chapter III: Product recovery and purification, page 469-714, VCH: Weinheim; Belter P. A. et al., 1988, Bioseparations: downstream processing for biotechnology, John Wiley and Sons; Kennedy J. F., and Cabral J. M. S., 1992, Recovery processes for biological materials, John Wiley and Sons; Shaeiwitz J. A. and Henry J. D., 1988, Biochemical separations, in Ulmann's Encyclopedia of Industrial Chemistry, Vol. B3, Chapter 11, page 1-27, VCH: Weinheim; and Dechow F. J., 1989, Separation and purification techniques in biotechnology, Noyes Publications).

For example, plant expression vectors comprising the nucleic acids disclosed herein, or fragments thereof, can be constructed and transformed into an appropriate plant cell such as rape, maize, cotton, rice, wheat, sugar cane, sugar beet, soy bean, *Arabidopsis thaliana*, potato, *Medicago truncatula*, etc., using standard protocols. The resulting transgenic cells and/or plants derived therefrom can then be assayed for generation or alteration of their herbicide tolerance or resistance.

The present invention also provides antibodies that specifically bind to the polypeptide according to the invention, or a portion thereof, as encoded by a nucleic acid described herein. Antibodies can be made by many well-known methods (see, e.g. Harlow and Lane, "Antibodies; A Laboratory Manual", Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. See, for example, Kelly et al., Bio/Technology 10, 163 (1992); Bebbington et al., Bio/Technology 10, 169 (1992).

Gene expression in plants is regulated by the interaction of protein transcription factors with specific nucleotide sequences within the regulatory region of a gene. One example of transcription factors are polypeptides that contain zinc finger (ZF) motifs. Each ZF module is approximately 30 amino acids long folded around a zinc ion. The DNA recognition domain of a ZF protein is a α-helical structure that inserts into the major grove of the DNA double helix.

The module contains three amino acids that bind to the DNA with each amino acid contacting a single base pair in the target DNA sequence. ZF motifs are arranged in a modular repeating fashion to form a set of fingers that recognize a contiguous DNA sequence. For example, a three-fingered ZF motif will recognize 9 bp of DNA. Hundreds of proteins have been shown to contain ZF motifs with between 2 and 37 ZF modules in each protein (Isalan M. et al., Biochemistry 37 (35), 12026 (1998); Moore M. et al., Proc. Natl. Acad. Sci. USA 98 (4), 1432 (2001) and Moore M. et al., Proc. Natl. Acad. Sci. USA 98 (4), 1437 (2001); U.S. Pat. Nos. 6,007,988 and 6,013,453).

The regulatory region of a plant gene contains many short DNA sequences (cis-acting elements) that serve as recognition domains for transcription factors, including ZF proteins. Similar recognition domains in different genes allow the coordinate expression of several genes encoding enzymes in a metabolic pathway by common transcription factors. Variation in the recognition domains among members of a gene family facilitates differences in gene expression within the same gene family, for example, among tissues and stages of development and in response to environmental conditions.

Typical ZF proteins contain not only a DNA recognition domain but also a functional domain that enables the ZF protein to activate or repress transcription of a specific gene. Experimentally, an activation domain has been used to activate transcription of the target gene (U.S. Pat. No. 5,789,538 and patent application WO 95/19431), but it is also possible to link a transcription repressor domain to the ZF and thereby inhibit transcription (patent applications WO 00/47754 and WO 01/002019). It has been reported that an enzymatic function such as nucleic acid cleavage can be linked to the ZF (patent application WO 00/20622). The invention provides a method that allows one skilled in the art to isolate the regulatory region of one or more polypeptide according to the invention-encoding genes from the genome of a plant cell and to design zinc finger transcription factors linked to a functional domain that will interact with the regulatory region of the gene. The interaction of the zinc finger protein with the plant gene can be designed in such a manner as to alter expression of the gene and preferably thereby to confer increasing herbicide tolerance or resistance.

In particular, the invention provides a method of producing a transgenic plant with a coding nucleic acid, wherein expression of the nucleic acid(s) in the plant results in in increasing herbicide tolerance or resistance, as compared to a wild type plant comprising: (a) transforming a plant cell with an expression vector comprising a encoding nucleic acid, and (b) generating from the plant cell a transgenic plant with enhanced increased herbicide tolerance or resistance as compared to a wild type plant. For such plant transformation, binary vectors such as pBinAR can be used (Hofgen and Willmitzer, Plant Science 66, 221 (1990)). Moreover suitable binary vectors are for example pBIN19, pBI101, pGPTV or pPZP (Hajukiewicz P. et al., Plant Mol. Biol., 25, 989 (1994)).

Alternate methods of transfection include the direct transfer of DNA into developing flowers via electroporation or *Agrobacterium* mediated gene transfer. *Agrobacterium* mediated plant transformation can be performed using for example the GV3101 (pMP90) (Koncz and Schell, Mol. Gen. Genet. 204, 383 (1986)) or LBA4404 (Ooms et al., Plasmid, 7, 15 (1982); Hoekema et al., Nature, 303, 179 (1983)) *Agrobacterium tumefaciens* strain. Transformation can be performed by standard transformation and regeneration techniques (Deblaere et al., Nucl. Acids. Res. 13, 4777 (1994); Gelvin and Schilperoort, Plant Molecular Biology Manual, 2nd Ed. —Dordrecht: Kluwer Academic Publ., 1995. —in Sect., Ringbuc Zentrale Signatur: BT11-P ISBN 0-7923-2731-4; Glick B. R. and Thompson J. E., Methods in Plant Molecular Biology and Biotechnology, Boca Raton: CRC Press, 1993. —360 S., ISBN 0-8493-5164-2). For example, rapeseed can be transformed via cotyledon or hypocotyl transformation (Moloney et al., Plant Cell Reports 8, 238 (1989); De Block et al., Plant Physiol. 91, 694 (1989)). Use of antibiotics for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., Plant Cell Report 13, 282 (1994)). Additionally, transformation of soybean can be performed using for example a technique described in European Patent No. 424 047, U.S. Pat. No. 5,322,783, European Patent No. 397 687, U.S. Pat. No. 5,376,543 or 5,169,770. Transformation of maize can be achieved by particle bombardment, polyethylene glycol mediated DNA uptake or via the silicon carbide fiber technique (see, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

In one embodiment, the present invention relates to a method for the identification of a gene product conferring in increasing herbicide tolerance or resistance, as compared to a corresponding, e.g. non-transformed, wild type cell in a cell of an organism for example plant, comprising the following steps:

(a) contacting, e.g. hybridizing, some or all nucleic acid molecules of a sample, e.g. cells, tissues, plants or microorganisms or a nucleic acid library, which can contain a candidate gene encoding a gene product conferring increased herbicide tolerance or resistance with a nucleic acid molecule as shown in a variant of SEQ ID NO: 1, 3, 5, 7, 9, 11, 13, 15, 17, 19, 21, 23, 25, 27, 29, or 31, or a functional homologue thereof;

(b) identifying the nucleic acid molecules, which hybridize under relaxed or stringent conditions with said nucleic acid molecule, in particular to the nucleic acid molecule sequence shown in a variant of SEQ ID NO: 1, 3, 5, 7, 9, 11, 13, 15, 17, 19, 21, 23, 25, 27, 29, or 31, or a homolog or a functional equivalent thereof, and, optionally, isolating the full length cDNA clone or complete genomic clone;

(c) identifying the candidate nucleic acid molecules or a fragment thereof in host cells, preferably in a plant cell;

(d) increasing the expression of the identified nucleic acid molecules in the host cells for which increased herbicide tolerance or resistance are desired;

(e) assaying the level of increased herbicide tolerance or resistance of the host cells; and (f) identifying the nucleic acid molecule and its gene product which confers increased herbicide tolerance or resistance, in the host cell compared to the wild type.

Relaxed hybridization conditions are: After standard hybridization procedures washing steps can be performed at low to medium stringency conditions usually with washing conditions of 40°-55° C. and salt conditions between 2×SSC and 0.2×SSC with 0.1% SDS in comparison to stringent washing conditions as e.g. 60° to 68° C. with 0.1% SDS. Further examples can be found in the references listed above for the stringend hybridization conditions. Usually washing steps are repeated with increasing stringency and length until a useful signal to noise ratio is detected and depend on many factors as the target, e.g. its purity, GC-content, size etc, the probe, e.g.its length, is it a RNA or a DNA probe, salt conditions, washing or hybridization temperature, washing or hybridization time etc.

In another embodiment, the present invention relates to a method for the identification of a gene product the expression of which confers increased herbicide tolerance or resistance, in a cell, comprising the following steps:

(a) identifying a nucleic acid molecule in an organism, which is at least 20%, preferably 25%, more preferably 30%, even more preferred are 35%. 40% or 50%, even more preferred are 60%, 70% or 80%, most preferred are 90% or 95% or more homolog to the nucleic acid molecule encoding a protein comprising the polypeptide molecule as shown in SEQ ID NO: 2, 4, 6, 8, 10, 12, 14, 16, 18, 20, 22, 24, 26, 28, 30, or 32, or a homolog or a functional equivalent thereof or being encoded by a nucleic acid molecule comprising a polynucleotide as shown in SEQ ID NO: 1, 3, 5, 7, 9, 11, 13, 15, 17, 19, 21, 23, 25, 27, 29, or 31, or a homologue or functional equivalent thereof or a functional equivalent thereof as described herein, for example via homology search in a data bank;

(b) enhancing the expression of the identified nucleic acid molecules in the host cells;

(c) assaying the level of enhancement in increasing herbicide tolerance or resistance, in the host cells; and (d) identifying the host cell, in which the enhanced expression confers the increasing herbicide tolerance or resistance in the host cell compared to a wild type.

Further, the nucleic acid molecule disclosed herein, in particular the nucleic acid molecule shown in a variant of SEQ ID NO: 1, 3, 5, 7, 9, 11, 13, 15, 17, 19, 21, 23, 25, 27, 29, or 31, may be sufficiently homologous to the sequences of related species such that these nucleic acid molecules may serve as markers for the construction of a genomic map in related organism or for association mapping. Furthermore natural variation in the genomic regions corresponding to nucleic acids disclosed herein, in particular the nucleic acid molecule shown in a variant of SEQ ID NO: 1, 3, 5, 7, 9, 11, 13, 15, 17, 19, 21, 23, 25, 27, 29, or 31, or homologous thereof may lead to variation in the activity of the proteins disclosed herein, in particular the proteins comprising polypeptides as shown in a variant of SEQ ID NO: 2, 4, 6, 8, 10, 12, 14, 16, 18, 20, 22, 24, 26, 28, 30, or 32, and their homolgous and in consequence in a natural variation of an increased herbicide tolerance or resistance.

In consequence natural variation eventually also exists in form of more active allelic variants leading already to a relative increase in herbicide tolerance or resistance. Different variants of the nucleic acids molecule disclosed herein, in particular the nucleic acid comprising the nucleic acid molecule as shown a variant of SEQ ID NO: 1, 3, 5, 7, 9, 11, 13, 15, 17, 19, 21, 23, 25, 27, 29, or 31, or a homolog or a functional equivalent thereof, which corresponds to different levels of increased herbicide tolerance or resistance can be identified and used for marker assisted breeding for an increased herbicide tolerance or resistance, Accordingly, the present invention relates to a method for breeding plants with an increased herbicide tolerance or resistance comprising (a) selecting a first plant variety with an increased herbicide tolerance or resistance, based on increased expression of a nucleic acid of the invention as disclosed herein, in particular of a nucleic acid molecule comprising a nucleic acid molecule as shown in a variant of SEQ ID NO: 1, 3, 5, 7, 9, 11, 13, 15, 17, 19, 21, 23, 25, 27, 29, or 31, or a homolog or a functional equivalent thereof, or a polypeptide comprising a polypeptide as shown in a variant of SEQ ID NO: 2, 4, 6, 8, 10, 12, 14, 16, 18, 20, 22, 24, 26, 28, 30, or 32, or a homolog or a functional equivalent thereof, as described herein;

(b) associating the level of increased herbicide tolerance or resistance with the expression level or the genomic structure of a gene encoding said polypeptide or said nucleic acid molecule;

(c) crossing the first plant variety with a second plant variety, which significantly differs in its level of increased herbicide tolerance or resistance; and (d) identifying, which of the offspring varieties has got increased levels of herbicide tolerance or resistance, As described SUPRA, the present invention provides plants, plant tissues, plant cells, and host cells that are resistant or tolerant of at least one herbicide, preferably a HPPD-inhibiting herbicide. In some embodiments, the plants, plant tissues, plant cells, and host cells demonstrate enhanced resistance or enhanced tolerance to at least one herbicide, preferably a HPPD-inhibiting herbicide. The term 'enhanced' refers to an increase in the amount of resistance or tolerance above that which is expected.

The herbicide-resistant plants of the invention that comprise polynucleotides encoding a polypeptide as shown in a variant of SEQ ID NO: 2, 4, 6, 8, 10, 12, 14, 16, 18, 20, 22, 24, 26, 28, 30, or 32, or a homolog or a functional equivalent thereof, also find use in methods for increasing the herbicide-resistance of a plant through conventional plant breeding involving sexual reproduction. The methods comprise crossing a first plant that is a herbicide-resistant plant of the invention to a second plant that may or may not be resistant to the same herbicide or herbicides as the first plant or may be resistant to different herbicide or herbicides than the first plant. The second plant can be any plant that is capable of producing viable progeny plants (i.e., seeds) when crossed with the first plant. Typically, but not necessarily, the first and second plants are of the same species. The methods can optionally involve selecting for progeny plants that comprise the polypeptide as shown in a variant of SEQ ID NO: 2, 4, 6, 8, 10, 12, 14, 16, 18, 20, 22, 24, 26, 28, 30, or 32, or a homolog or a functional equivalent thereof, of the first plant and the herbicide resistance characteristics of the second plant. The progeny plants produced by this method of the present invention have increased resistance to a herbicide when compared to either the first or second plant or both. When the first and second plants are resistant to different herbicides, the progeny plants will have the combined herbicide tolerance characteristics of the first and second plants. The methods of the invention can further involve one or more generations of backcrossing the progeny plants of the first cross to a plant of the same line or genotype as either the first or second plant. Alternatively, the progeny of the first cross or any subsequent cross can be crossed to a third plant that is of a different line or genotype than either the first or second plant. The present invention also provides plants, plant organs, plant tissues, plant cells, seeds, and non-human host cells that are transformed with the at least one polynucleotide molecule, expression cassette, or transformation vector of the invention. Such transformed plants, plant organs, plant tissues, plant cells, seeds, and non-human host cells have enhanced tolerance or resistance to at least one herbicide, at levels of the herbicide that kill or inhibit the growth of an untransformed plant, plant tissue, plant cell, or non-human host cell, respectively. Preferably, the transformed plants, plant tissues, plant cells, and seeds of the invention are *Arabidopsis thaliana* and crop plants.

In other aspects, plants of the invention include those plants which, in addition to being HPPD-inhibiting herbicides-tolerant, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; lipid biosynthesis inhibitors such as acetyl CoA carboxylase (ACCase) inhibitors; or oxynil {i.e. bromoxynil or ioxynil) herbicides as a result of conventional methods of breeding or genetic engineering, Thus, HPPD-inhibiting herbicides-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in Pest Management Science (at volume, year, page): 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. For example, HPPD-inhibiting herbicides-tolerant plants of the invention, in some embodiments, may be tolerant to ACCase inhibitors, such as "dims" {e.g., cycloxydim, sethoxydim, clethodim, or tepraloxydim), "fops" {e.g., clodinafop, diclofop, fluazifop, haloxyfop, or quizalofop), and "dens" (such as pinoxaden); to auxinic herbicides, such as dicamba; to EPSPS inhibitors, such as glyphosate; to other HPPD inhibitors; and to GS inhibitors, such as glufosinate.

In addition to these classes of inhibitors, HPPD-inhibiting herbicides-tolerant plants of the invention may also be tolerant to herbicides having other modes of action, for example, chlorophyll/carotenoid pigment inhibitors, cell membrane disrupters, photosynthesis inhibitors, cell division inhibitors, root inhibitors, shoot inhibitors, and combinations thereof.

Such tolerance traits may be expressed, e.g.: as mutant or wildtype HPPD proteins, as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-S-transferase (GST), phosphinothricin acetyltransferase (PAT or bar), or CYP450s proteins having an herbicidedegrading activity. HPPD-inhibiting herbicides—tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, HPPD-inhibiting herbicides-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as [delta]-endotoxins, e.g. CryIA(b), CryIA(c), CryIF, CryIF(a2), CryIIA (b), CryIIIA, CryIIIB(bI) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMGCoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pretoxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda).

In some embodiments, expression of one or more protein toxins (e.g., insecticidal proteins) in the HPPD-inhibiting herbicides-tolerant plants is effective for controlling organisms that include, for example, members of the classes and orders: Coleoptera such as the American bean weevil *Acanthoscelides obtectus*; the leaf beetle *Agelastica alni*; click beetles (*Agriotes lineatus, Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles {*Lyctus* spp., the pollen beetle *Meligethes aeneus*; the common cockshafer *Melolontha melolontha*; the American spider beetle *Mezium americanum*; the golden spider beetle *Niptus hololeucs*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*, the flour beetles *Tribolium castaneum* and *Tribolium confusum*; warehouse and cabinet beetles {*Trogoderma* spp.); the sunflower beetle *Zygogramma exclamationis*; Dermaptera (earwigs) such as the European earwig *Forficula auricularia* and the striped earwig *Labidura riparia*; Dictyoptera such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the citrus spiny whitefly *Aleurocanthus spiniferus*; the sweet potato whitefly *Bemesia tabaci*; the cabbage aphid *Brevicoryne brassicae*; the pear psylla *Cacopsylla pyricola*; the currant aphid *Cryptomyzus ribis*; the grape *phylloxera* Daktulosphaira vitifoliae; the citrus psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum*

*padi*; the grain aphid *Sitobion avenae*; Lepidoptera such as *Adoxophyes orana* (summer fruit *tortrix* moth); *Archips podana* (fruit tree *tortrix* moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis virescens* (tobacco budworm), *Homeosoma electellum* (sunflower moth); *Homona magnanima* (oriental tea tree *tortrix* moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (citrus leafminer); *Pieris brassicae* (cabbage white butterfly); *Rachiplusia ni* (soybean looper); *Spodoptera exigua* (beet armyworm); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differentialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculata*; Thysanoptera such as the tobacco thrips *Frankliniella fusca*, the flower thrips *Frankliniella intonsa*, the western flower thrips *Frankliniella occidentalism* the cotton bud thrips *Frankliniella schultzei*, the banded greenhouse thrips *Hercinothrips femoralis*, the soybean thrips *Neohydatothrips variabilis*, Kelly's citrus thrips *Pezothrips kellyanus*, the avocado thrips *Scirtothrips perseae*, the melon thrips *Thrips palmi*, and the onion thrips *Thrips tabaci*; and the like, and combinations comprising one or more of the foregoing organisms.

In another embodiment, the mutated HPPD enzymes of the present invention and herbicide, in particular HPPD-inhibiting herbicide, resistant plants of the invention find use in methods for controlling weeds.

Thus, the present invention further provides a method for controlling undesired vegetation at a plant cultivation site in the vicinity of an herbicide-resistant plant, such as a plant comprising an mutated HPPD nucleic acid molecule of the invention, i.e. a nucleotide sequence encoding a polypeptide comprising a variant of the sequence of SEQ ID NO: 2, 4, 6, 8, 10, 12, 14, 16, 18, 20, 22, 24, 26, 28, 30, or 32, or a homolog or a functional equivalent thereof.

The method comprises applying an effective amount of a herbicide, preferably a HPPD-inhibiting herbicide to the weeds and to the herbicide-resistant plant, wherein the plant has resistance to at least one herbicide, preferably a HPPD-inhibiting herbicide, when compared to a wild-type plant.

Furthermore, the present invention provides method for growing the plant according to the present invention while controlling weeds in the vicinity of said plant, said method comprising the steps of:

a) growing said plant; and
b) applying a herbicide composition comprising a HPPD-inhibiting herbicide to the plant and weeds, wherein the herbicide normally inhibits hydroxyphenylpyruvate dioxygenase, at a level of the herbicide that would inhibit the growth of a corresponding wild-type plant.

In another embodiment, the invention relates to a combination useful for weed control, comprising (a) a polynucleotide encoding mutated HPPD polypeptide according to the present invention, which polynucleotide is capable of being expressed in a plant to thereby provide to that plant tolerance to a HPPD inhibiting herbicide; and (b) a HPPD inhibiting herbicide.

In another embodiment, the invention relates to a process for preparing a combination useful for weed control comprising (a) providing a polynucleotide encoding a wildtype or mutated mutated HPPD polypeptide according to the present invention, which polynucleotide is capable of being expressed in a plant to thereby provide to that plant tolerance to a HPPD inhibiting herbicide; and (b) providing a HPPD inhibiting herbicide.

In a preferred embodiment, said step of providing a polynucleotide comprises providing a plant containing the polynucleotide.

In another preferred embodiment, said step of providing a polynucleotide comprises providing a seed containing the polynucleotide.

In another preferred embodiment, said process further comprises a step of applying the HPPD inhibiting herbicide to the seed.

In another embodiment, the invention relates to the use of a combination useful for weed control, comprising (a) a polynucleotide encoding a wildtype or mutated mutated HPPD polypeptide according to the present invention, which polynucleotide is capable of being expressed in a plant to thereby provide to that plant tolerance to a HPPD inhibiting herbicide; and (b) a HPPD inhibiting herbicide, to control weeds at a plant cultivation site.

The term "control of undesired vegetation" is to be understood as meaning the controlling, particularly killing of weeds and/or otherwise retarding or inhibiting the normal growth of the weeds. Weeds, in the broadest sense, are understood as meaning all those plants which grow in locations where they are undesired, e.g. at a plant cultivation site. The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus*, and *Taraxacum*. Monocotyledonous weeds include, but are not limited to, weeds of of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus*, and *Apera*. In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

Generally, the term "herbicide" is used herein to mean an active ingredient that kills, controls or otherwise adversely modifies the growth of plants. The preferred amount or concentration of the herbicide is an "effective amount" or "effective concentration." By "effective amount" and "effective concentration" is intended an amount and concentration, respectively, that is sufficient to kill or inhibit the growth of a similar, wild-type, plant, plant tissue, plant cell, microspore, or host cell, but that said amount does not kill or inhibit as severely the growth of the herbicide-resistant plants, plant tissues, plant cells, microspores, and host cells of the present invention. Typically, the effective amount of a herbicide is an amount that is routinely used in agricultural production systems to kill weeds of interest. Such an amount is known to those of ordinary skill in the art, or can be easily determined using methods known in the art. Furthermore, it is recognized that the effective amount of an herbicide in an agricultural production system might be substantially different than an effective amount of an herbicide for a plant culture system such as, for example, the microspore culture system. Herbicidal activity is exhibited by herbicides useful for the the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the herbicide postemergence to relatively immature undesirable vegetation to achieve the maximum control of weeds.

The herbicides useful for the present invention are those that interfere with the activity of the HPPD enzyme such that HPPD activity is reduced in the presence of the herbicide. Such herbicides may also be referred to herein as "HPPD-inhibiting herbicides" or simply "mutated HPPD inhibitors." As used herein, an "HPPD-inhibiting herbicide" or an "HPPD inhibitor" is not meant to be limited to single herbicide that interferes with the activity of the HPPD enzyme. Thus, unless otherwise stated or evident from the context, an "HPPD-inhibiting herbicide" or an "HPPD inhibitor" can be a one herbicide or a mixture of two, three, four, or more herbicides, each of which interferes with the activity of the HPPD enzyme. The HPPD-inhibiting herbicide for use in the methods provided herein can be applied by any method known in the art including, but not limited to, seed treatment, soil treatment, and foliar treatment.

By a "herbicide-tolerant" or "herbicide-resistant" plant, it is intended that a plant that is tolerant or resistant to at least one herbicide at a level that would normally kill, or inhibit the growth of, a normal or wild-type plant. By "herbicide-tolerant mutated HPPD protein" or "herbicide-resistant mutated HPPD protein", it is intended that such a mutated HPPD protein displays higher mutated HPPD activity, relative to the HPPD activity of a wild-type HPPD protein, when in the presence of at least one herbicide that is known to interfere with HPPD activity and at a concentration or level of the herbicide that is known to inhibit the HPPD activity of the HPPD protein. Furthermore, the HPPD activity of such a herbicide-tolerant or herbicide-resistant mutated HPPD protein may be referred to herein as "herbicide-tolerant" or "herbicide-resistant" mutated HPPD activity.

In a preferred embodiment, the HPPD-inhibiting herbicide refers to the class of anellated heterocyclic compounds.

In one embodiment of the present invention, the HPPD-inhibiting herbicide, preferably the anellated heterocycle, useful for the present invention refers to a substituted pyridine compound of formula I:

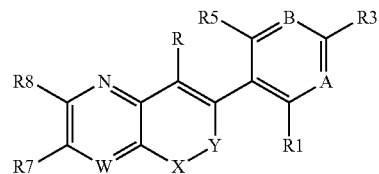

wherein

R is hydroxy or O—$R^A$, where $R^A$ is $C_1$-$C_8$-alkyl, $C_2$-$C_8$-alkenyl, $C_2$-$C_8$-alkynyl, aryl-$C_1$-$C_4$-alkyl, $C_1$-$C_8$-alkylcarbonyl, $C_1$-$C_8$-alkoxycarbonyl, $C_1$-$C_8$-alkylthiocarbonyl or $C_1$-$C_8$-alkylsulfonyl, where the aryl moiety is unsubstituted or substituted by one to five $R^a$ and each $R^a$ is independently halogen, cyano, nitro, $C_1$-$C_8$-alkyl, $C_1$-$C_8$-haloalkyl, $C_1$-$C_8$-alkoxy or $C_1$-$C_8$-haloalkoxy;

$R^1$ is cyano, halogen, nitro, $C_1$-$C_6$-alkyl, $C_2$-$C_6$-alkenyl, $C_2$-$C_6$-alkynyl, $C_1$-$C_6$-haloalkyl, Z—$C_1$-$C_6$-alkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, $S(O)_nR^b$, Z-phenoxy or Z-heterocyclyloxy, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^c$;

Z is independently a covalent bond or $C_1$-$C_4$-alkylene;

n is independently 0, 1 or 2;

$R^b$ is independently $C_1$-$C_8$-alkyl, $C_2$-$C_6$-alkenyl, $C_2$-$C_6$-alkynyl, $C_2$-$C_6$-haloalkenyl, $C_2$-$C_6$-haloalkynyl or $C_1$-$C_6$-haloalkyl;

$R^c$ is independently Z—CN, Z—OH, Z—$NO_2$, Z-halogen, oxo (=O), =N—$R^d$, $C_1$-$C_8$-alkyl, $C_1$-$C_4$-haloalkyl, $C_2$-$C_8$-alkenyl, $C_2$-$C_8$-alkynyl, Z—$C_1$-$C_8$-alkoxy, Z—$C_1$-$C_8$-haloalkoxy, Z—$C_3$-$C_{10}$-cycloalkyl, O—Z—$C_3$-$C_{10}$-cycloalkyl, Z—C(=O)—$R^d$, $NR^iR^{ii}$, Z-(tri-$C_1$-$C_4$-alkyl)silyl, Z-phenyl or $S(O)_nR^b$; or two groups $R^c$ may together form a ring which has 3 to 6 ring members and, in addition to carbon atoms, may contain heteroatoms selected from the group consisting of O, N and S and may be unsubstituted or substituted by further groups $R^c$;

$R^d$ is independently hydrogen, OH, $C_1$-$C_8$-alkyl, $C_1$-$C_4$-haloalkyl, Z—$C_3$-$C_6$-cycloalkyl, $C_2$-$C_8$-alkenyl, Z—$C_5$-$C_6$-cycloalkenyl, $C_2$-$C_8$-alkynyl, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy, $NR^iR^{ii}$, $C_1$-$C_6$-alkylsulfonyl, Z-(tri-$C_1$-$C_4$-alkyl)silyl, Z-phenyl, Z-phenoxy, Z-phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^c$;

$R^i$, $R^{ii}$ independently of one another are hydrogen, $C_1$-$C_8$-alkyl, $C_1$-$C_4$-haloalkyl, $C_3$-$C_8$-alkenyl, $C_3$-$C_8$-alkynyl, Z—$C_3$-$C_6$-cycloalkyl, Z—$C_1$-$C_8$-alkoxy, Z—$C_1$-$C_8$-haloalkoxy, Z—C(=O)—$R^d$, Z-phenyl, a 3- to 7-membered monocyclic or 9- or 10-membered bicyclic saturated, unsaturated or aromatic heterocycle which contains 1, 2, 3 or 4 heteroatoms selected from the group consisting of O, N and S and which is attached via Z;

$R^i$ and $R^{ii}$ together with the nitrogen atom to which they are attached may also form a 5- or 6-membered monocyclic or 9- or 10-membered bicyclic heterocycle which contains 1, 2, 3 or 4 heteroatoms selected from the group consisting of O, N and S;

A is N or C—$R^2$;

B is N or C—$R^4$;

$R^2$, $R^3$ independently of one another are hydrogen, Z-halogen, Z—CN, Z—OH, Z—$NO_2$, $C_1$-$C_8$-alkyl, $C_1$-$C_4$-haloalkyl, $C_2$-$C_8$-alkenyl, $C_2$-$C_8$-alkynyl, $C_2$-$C_8$-haloalkenyl, $C_2$-$C_8$-haloalkynyl, Z—$C_1$-$C_8$-alkoxy, Z—$C_1$-$C_8$-haloalkoxy, Z—$C_1$-$C_4$-alkoxy-$C_1$-$C_4$-alkoxy, Z—$C_1$-$C_4$-alkythio, Z—$C_1$-$C_4$-alkylthio-$C_1$-$C_4$-alkylthio, Z—$C_1$-$C_6$-haloalkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, Z—$C_3$-$C_{10}$-cycloalkyl, O—Z—$C_3$-$C_{10}$-cycloalkyl, Z—C(=O)—$R^d$, $NR^iR^{ii}$, Z-(tri-$C_1$-$C_4$-alkyl)silyl, S(O)$_n R^b$, Z-phenyl, $Z^1$-phenyl, Z-heterocyclyl or $Z^1$-heterocyclyl, where heterocyclyl is a 5- or 6-membered monocyclic or 9- or 10-membered bicyclic saturated, partially unsaturated or aromatic heterocycle which contains 1, 2, 3 or 4 heteroatoms selected from the group consisting of O, N and S, where cyclic groups are unsubstituted or partially or fully substituted by $R^c$; $R^2$ together with the group attached to the adjacent carbon atom may also form a 5- to 10-membered saturated or partially or fully unsaturated mono- or bicyclic ring which, in addition to carbon atoms, may contain 1, 2 or 3 heteroatoms selected from the group consisting of O, N and S and may be substituted by further groups $R^c$;

$Z^1$ is independently a covalent bond, $C_1$-$C_4$-alkyleneoxy, $C_1$-$C_4$-oxyalkylene or $C_1$-$C_4$-alkyleneoxy-$C_1$-$C_4$-alkylene;

$R^4$, $R^5$ independently of one another are hydrogen, halogen or $C_1$-$C_4$-alkyl;

W is N or C—$R^6$;

$R^6$ is hydrogen, $C_1$-$C_4$-alkyl, $C_1$-$C_4$-haloalkyl, $C_1$-$C_4$-alkoxy, $C_1$-$C_4$-alkylthio, $C_1$-$C_4$-haloalkoxy or $C_1$-$C_4$-haloalkylthio;

$R^7$, $R^8$ independently of one another are hydrogen, halogen or $C_1$-$C_4$-alkyl;

X is O, $NR^z$ or $CR^xR^y$;

$R^x$, $R^y$ independently of one another are hydrogen, $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl or halogen; or $R^x$ and $R^y$ are together a $C_2$-$C_5$-alkylene or $C_2$-$C_5$-alkenylene chain and form a 3-, 4-, 5- or 6-membered saturated, partially unsaturated or fully unsaturated monocyclic ring together with the carbon atom they are bonded to, wherein 1 or 2 of any of the $CH_2$ or CH groups in the $C_2$-$C_5$-alkylene or $C_2$-$C_5$-alkenylene chain may be replaced by 1 or 2 heteroatoms independently selected from O or S;

$R^z$ is $C_1$-$C_5$-alkyl, $C_2$-$C_5$-alkenyl, $C_2$-$C_5$-alkynyl, $C_1$-$C_5$-haloalkyl, $C_1$-$C_2$-alkoxy-$C_1$-$C_2$-alkyl Y is CO or $SO_2$.

where in the groups $R^1$, $R^2$ and $R^3$ and their subsubstituents, the carbon chains and/or the cyclic groups may be partially or fully substituted by groups $R^c$, or an agriculturally suitable salt or N-oxide thereof.

According to a preferred embodiment of the invention preference is also given to those compounds of formula I, wherein the variables, either independently of one another or in combination with one another, have the following meanings:

Preferably, R is hydroxy or O—$R^A$, where $R^A$ is $C_1$-$C_8$-alkyl, $C_2$-$C_8$-alkenyl, $C_2$-$C_8$-alkynyl, aryl-$C_1$-$C_4$-alkyl, $C_1$-$C_8$-alkylcarbonyl, $C_1$-$C_8$-alkoxycarbonyl, $C_1$-$C_8$-alkylthiocarbonyl or $C_1$-$C_8$-alkylsulfonyl, where the aryl moiety is unsubstituted.

More preferably, R is hydroxy or O—$R^A$, where $R^A$ is $C_1$-$C_8$-alkylcarbonyl.

In one embodiment, R is hydroxy.

In one embodiment, R is O—$R^A$, where $R^A$ is $C_1$-$C_8$-alkylcarbonyl.

In another embodiment, R is selected from the group consisting of hydroxy, methoxy, allyloxy, propargyloxy, cyclopropylcarbonyloxy, benzyloxy, prop-2-ylcarbonyloxy, 2-methyl-prop-2-ylcarbonyloxy, methoxycarbonyloxy, ethoxycarbonyloxy, methylthiocarbonyloxy, ethylthiocarbonyloxy, ethylthiocarbonyloxy and methylsulfonyloxy.

Preferably, R is selected from the group consisting of hydroxy, cyclopropylcarbonyloxy, and 2-methyl-prop-2-ylcarbonyloxy, In particular, R is hydroxy or 2-methyl-prop-2-ylcarbonyloxy In one embodiment, R is hydroxy.

In one embodiment, R is 2-methyl-prop-2-ylcarbonyloxy $R^i$ and $R^{ii}$ are preferably $C_1$-$C_8$-alkyl, $C_1$-$C_4$-haloalkyl, Z—$C_3$-$C_6$-cycloalkyl, Z—$C_1$-$C_8$-alkoxy, Z—$C_1$-$C_8$-haloalkoxy, Z-phenyl, Z—C(=O)—$R^d$ or Z-hetaryl. Preference is given here to $CH_3$, $C_2H_5$, n-propyl, $CH(CH_3)_2$, butyl, 2-chloroethyl, cyclopentyl, cyclohexyl, 2-ethoxymethyl, 2-chloroethoxy, phenyl, pyrimidines or triazines, which rings are unsubstituted or substituted. Preferred substituents are $C_1$-$C_4$-alkylcarbonyl or $C_1$-$C_4$-haloalkylcarbonyl, in particular C(=O)$CH_3$, C(=O)—$C_2H_5$, C(=O)—$C_3H_7$, C(=O)—$CH(CH_3)_2$, butylcarbonyl and C(=O)—$CH_2Cl$. Particularly preferred aspects of group $NR^iR^{ii}$ are N(di-$C_1$-$C_4$-alkyl), in particular N($CH_3$)—$C_1$-$C_4$-alkyl, such as N($CH_3$)$_2$, N($CH_3$)$CH_2CH_3$, N($CH_3$)$C_3H_7$ and N($CH_3$)CH($CH_3$)$_2$.

Further particularly preferred aspects of $NR^iR^{ii}$ are NH-aryl, where aryl is preferably phenyl which is substituted—in particular in the 2- and 6-position—by one to three identical or different groups selected from the group consisting of halogen, $CH_3$, halo-$C_1$-$C_2$-alkyl, halo-$C_1$-$C_2$-alkoxy and carboxyl, such as 2-Cl, 6-COOH-$C_6H_3$, 2,6-$Cl_2$-$C_6H_3$, 2,6-$F_2$—$C_6H_3$, 2,6-$C_2$ 3-$C_6H_2$, 2-$CF_3$,6-$CH_2CHF_2$—$C_6H_3$, 2-$CF_3$,6-$OCF_3$—$C_6H_3$ and 2-$CF_3$,6-$CH_2CHF_2$—$C_6H_3$.

For the compounds of the formula I, the groups $R^c$ are preferably selected from the group consisting of halogen, oxo (=O), =N—$R^d$, $C_1$-$C_4$-alkyl, $C_1$-$C_4$-haloalkyl, $C_2$-$C_6$-alkenyl, $C_2$-$C_6$-alkynyl, Z—$C_1$-$C_4$-haloalkoxy, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkylthio-$C_1$-$C_4$-alkyl, Z—C(=O)—$R^d$ and S(O)$_n R^b$, where $R^b$ is preferably $C_1$-$C_4$-alkyl or $C_1$-$C_4$-haloalkyl and n is 0, 1 or 2.

Particularly preferably, $R^c$ is a group selected from the group consisting of halogen, $C_1$-$C_4$-alkyl, $C_3$-$C_6$-acycloalkyl, $C_1$-$C_4$-haloalkyl, $C_1$-$C_4$-alkoxy, $C_1$-$C_4$-alkylthio, $C_1$-$C_4$-alkoxy-$C_1$-$C_4$-alkyl, $C_1$-$C_4$-alkylthio-$C_1$-$C_4$-alkyl, $C_1$-$C_4$-alkoxy-$C_1$-$C_4$-alkoxy-$C_1$-$C_4$-alkyl, $C_1$-$C_4$-haloalkoxy, $C_1$-$C_4$-haloalkylthio, $C_3$-$C_4$-alkenyl, $C_3$-$C_4$-alkynyl and =N—$C_1$-$C_4$-alkoxy.

Two groups $R^c$ together may form a ring which preferably has three to seven ring members and, in addition to carbon atoms, may also contain heteroatoms from the group consisting of O, N and S and which may be unsubstituted or substituted by further groups $R^c$. These substituents $R^c$ are preferably selected from the group consisting of halogen, $C_1$-$C_4$-alkyl, $C_1$-$C_4$-alkoxy and $C_1$-$C_4$-haloalkyl.

Groups $R^d$ preferred for the compounds of the formula I are selected from the group consisting of OH, Z—$C_1$-$C_6$-alkoxy, Z—$C_1$-$C_4$-haloalkoxy, Z—$C_3$-$C_8$-alkenyloxy, Z—$C_3$-$C_8$-alkynyloxy and $NR^iR^{ii}$.

Groups $R^c$ and $R^d$ are selected independently of one another if a plurality of such groups is present.

In a preferred embodiment of the compounds of the formula I, $R^1$ is cyano, halogen, nitro, $C_1$-$C_6$-alkyl, $C_2$-$C_6$-alkenyl, $C_2$-$C_6$-alkynyl, $C_1$-$C_6$-haloalkyl, Z—$C_1$-$C_6$-alkoxy, Z—$C_1$-$C_4$-alkoxy-$C_1$-$C_4$-alkoxy, Z—$C_1$-$C_4$-alkylthio, Z—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkoxy, $S(O)_nR^b$.

In a particularly preferred embodiment of the compounds of the formula I, $R^1$ is halogen, CN, $NO_2$, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkylthio-$C_1$-$C_4$-alkyl, $C_1$-$C_4$-alkylthio-$C_1$-$C_4$-alkylthio-$C_1$-$C_4$-alkyl, $C_1$-$C_4$-alkoxy, $C_1$-$C_4$-haloalkoxy, $C_3$-$C_4$-alkenyloxy, $C_3$-$C_4$-alkynyloxy, $C_1$-$C_4$-alkoxy-$C_1$-$C_4$-alkoxy, $C_1$-$C_4$-haloalkoxy-$C_1$-$C_4$-alkoxy, $S(O)_n$—$C_1$-$C_4$-alkyl and $S(O)_n$—$C_1$-$C_4$-haloalkyl. Particularly preferably, $R^1$ is selected from the group consisting of F, Cl, Br, $NO_2$, $CH_3$, $CHF_2$, $CF_3$, $OCH_3$, $OCF_3$, $SCF_3$, $SO_2CH_3$, $SO_2CH_2CH_3$, $OCH_2CH_2OCH_3$, $CH_2OCH_2OCH_3$ and $CH_2OCH_2CF_3$. Particularly preferably, $R^1$ is selected from the group consisting of F, Cl, Br, $NO_2$, $CH_3$, $CF_3$, $OCH_3$, $OCF_3$, $SCF_3$, $SO_2CH_3$, $SO_2CH_2CH_3$, $OCH_2CH_2OCH_3$, $CH_2OCH_2CH_2OCH_3$ and $CH_2OCH_2CF_3$.

In a further preferred embodiment of the HPPD-inhibiting herbicides of the formula I, A is $CR^2$, B is CR4, X is CRxRy, Y is $SO_2$ and W is CR6. These compounds correspond to the formula I.1

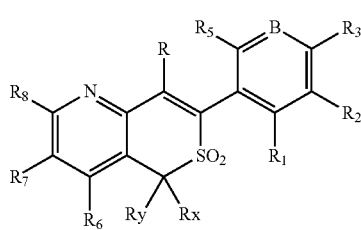

where the variables have the meanings defined at the outset and preferably the meanings mentioned as preferred.

More preferably, in the compounds of the formula I.1, the group
$R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, I, $NO_2$, $CH_3$, $CF_3$, $OCH_3$, $OCF_3$, $OCHF_2$, $SCF_3$, $SCHF_2$, $SO_2CH_3$, or $CH_2OCH_2CH_2OCH_3$; and/or $R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio, or $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.
R4 is H
R5 is H or halogen
R6 is H
R7 is H
R8 is H
Rx, Ry is H or $CH_3$
B is N or CH Particularly preferably, in the compounds of the formula I.1, the group
$R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, $NO_2$, $CH_3$, $CF_3$, $OCH_3$, $OCF_3$, $OCHF_2$, $SCF_3$, $SCHF_2$, $SO_2CH_3$, or $CH_2OCH_2CH_2OCH_3$; and/or
$R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio or $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.

In a preferred embodiment of the compounds of the formula I.1, $R^2$ is $Z^1$-heterocyclyl where heterocyclyl is a 5- or 6-membered monocyclic or 9- or 10-membered bicyclic, saturated, partially unsaturated or aromatic heterocycle which contains 1, 2, 3 or 4 heteroatoms selected from the group consisting of O, N and S, cyclic groups being unsubstituted or partially or fully substituted by $R^b$.

$R^2$ is in this case preferably a 3- to 7-membered monocyclic or 9- or 10-membered bicyclic saturated, partially unsaturated or aromatic heterocycle which is attached via $Z^1$ and contains 1, 2, 3 or 4 heteroatoms selected from the group consisting of O, N and S, where the cyclic groups are unsubstituted or partially or fully substituted by groups $R^c$.

In a further preferred aspect of the compounds of the formula I.1, $R^2$ is a 3- to 7-membered monocyclic or 9- or 10-membered bicyclic saturated, partially unsaturated or aromatic heterocycle which is attached directly or via $C_1$-$C_4$-alkyleneoxy, $C_1$-$C_4$-oxyalkylene or $C_1$-$C_4$-alkyleneoxy-$C_1$-$C_4$-alkylene, which contains 1, 2, 3 or 4 heteroatoms selected from the group consisting of O, N and S and which may be substituted as defined at the outset.

A preferred aspect of group $R^2$ relates to five- or six-membered saturated or partially unsaturated heterocycles, such as, for example, isoxazoline, tetrazolone, 1,2-dihydrotetrazolone, 1,4-dihydrotetrazolone, tetrahydrofuran, dioxolane, piperidine, morpholine and piperazine. Particular preference is given to 3-isoxazoline, 5-isoxazoline, 1-tetrazolone, 2-tetrazolone, [1,3]dioxolane-2 and N-morpholine. Especially preferred are: 4,5-dihydroisoxazole-3, unsubstituted or substituted by 5-$CH_3$, 5-$CH_2F$ or 5-$CHF_2$; 4,5-dihydroisoxazole-5, unsubstituted or substituted by 3-$CH_3$, 3-$OCH_3$, 3-$CH_2OCH_3$, 3-$CH_2SCH_3$; 1-methyl-5-oxo-1,5-dihydrotetrazole-2; 4-methyl-5-oxo-4,5-dihydrotetrazole-1 and N-morpholine.

A further preferred aspect of group $R^2$ relates to five- or six-membered aromatic heterocycles, such as, for example, isoxazole, pyrazole, thiazole, furyl, pyridine, pyrimidine and pyrazine. Particular preference is given to 3-isoxazole, 5-isoxazole, 3-pyrazole, 5-pyrazole, 2-thiazole, 2-oxazole, 2-furyl. Especially preferred are: 3-isoxazole, 5-methyl-3-isoxazole, 5-isoxazole, 3-methyl-5-isoxazole, 1-methyl-1H-pyrazole-3, 2-methyl-2H-pyrazole-3 and thiazole-2.

In a preferred aspect of the compounds of the formula I, the groups $R^c$ independently of one another are Z—CN, Z—OH, Z—$NO_2$, Z-halogen, oxo (=O), =N—$R^d$, $C_1$-$C_8$-alkyl, $C_1$-$C_4$-haloalkyl, $C_2$-$C_8$-alkenyl, $C_2$-$C_8$-alkynyl, Z—$C_1$-$C_8$-alkoxy, Z—$C_1$-$C_8$-haloalkoxy, Z—$C_3$-$C_{10}$-cycloalkyl, O—Z—$C_3$-$C_{10}$-cycloalkyl, Z—C(=O)—$R^d$, $NR^iR^{ii}$, Z-(tri-$C_1$-$C_4$-alkyl)silyl, Z-phenyl or $S(O)_nR^b$.

In a preferred aspect of heterocyclic groups $R^2$, the groups $R^c$ independently of one another are preferably $C_1$-$C_4$-alkyl, $C_1$-$C_4$-haloalkyl, $C_1$-$C_4$-alkoxy, $C_1$-$C_4$-alkoxy-$C_1$-$C_4$-alkyl, $C_1$-$C_4$-alkylthio-$C_1$-$C_4$-alkyl, $C_1$-$C_4$-alkylthio or $C_1$-$C_4$-alkylsulfonyl. Especially preferred are $CH_3$, $C_2H_5$, $CH_2F$, $CF_2H$, $CF_3$, $OCH_3$, $CH_2OCH_3$, $CH_2SCH_3$, $SCH_3$ and $SO_2CH_3$.

The group $R^b$ is preferably $C_1$-$C_8$-alkyl.

In a preferred aspect, the group $Z^1$ is a covalent bond.

In a further preferred aspect, the group $Z^1$ is $C_1$-$C_4$-alkyleneoxy, in particular $OCH_2$ or $OCH_2CH_2$.

In a further preferred aspect, the group $Z^1$ is $C_1$-$C_4$-oxyalkylene, in particular $CH_2O$ or $CH_2CH_2O$.

In a further preferred aspect, the group $Z^1$ is $C_1$-$C_4$-alkyleneoxy-$C_1$-$C_4$-alkylene, in particular $OCH_2OCH_2$ or $OCH_2CH_2OCH_2$.

Particularly preferred aspects of heterocycles attached via $Z^1$ include tetrahydrofuran-2-ylmethoxymethyl and [1,3] dioxolan-2-ylmethoxy.

In another preferred embodiment of the compounds of the formula I.1, $R^2$ is a group selected from the group consisting of halogen, $C_1$-$C_8$-alkyl, $C_2$-$C_6$-haloalkyl, $C_1$-$C_4$-alkoxy-$C_1$-$C_4$-alkyl, $C_2$-$C_8$-alkenyl, $C_2$-$C_8$-alkynyl, $C_2$-$C_8$-haloalkenyl, $C_2$-$C_8$-haloalkynyl, $C_1$-$C_6$-alkoxy, Z—$C_1$-$C_4$-alkoxy-$C_1$-$C_4$-alkoxy, Z—$C_1$-$C_4$-haloalkoxy-$C_1$-$C_4$-alkoxy, Z—$C_1$-$C_6$-haloalkoxy, $C_2$-$C_8$-alkenyloxy, $C_2$-$C_8$-alkynyloxy, Z—$C_1$-$C_4$-alkythio, Z—$C_1$-$C_6$-haloalkylthio, Z—C(=O)—$R^d$ or $S(O)_nR^b$, $C_1$-$C_4$-cycloalkyl-$C_1$-$C_4$-alkoxy-$C_1$-$C_4$-alkyl, $C_1$-$C_4$-cycloalkyl-$C_1$-$C_4$-alkoxy.

In yet another preferred embodiment of the compounds of the formula I.1, $R^2$ is a group selected from the group consisting of halogen, $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_2$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_8$-alkyl, $S(O)_2$—$C_1$-$C_8$-haloalkyl and N—($C_1$-$C_4$-alkyl) amino-N-sulfonyl-$C_1$-$C_4$-alkyl.

In a particularly preferred aspect of these compounds of the formula I.1, $R^2$ is a group selected from the group consisting of $C_1$-$C_6$-alkyl, $C_1$-$C_4$-alkoxy-$C_1$-$C_4$-alkyl, $C_1$-$C_4$-haloalkoxy-$C_1$-$C_4$-alkyl, $C_2$-$C_6$-alkenyl, $C_2$-$C_6$-alkynyl, $C_2$-$C_4$-alkoxy, $C_1$-$C_4$-haloalkoxy, $C_3$-$C_6$-alkenyloxy, $C_3$-$C_6$-alkynyloxy, $C_3$-$C_6$-haloalkenyloxy, $C_3$-$C_6$-haloalkynyloxy, $C_1$-$C_4$-alkoxycarbonyl, $S(O)_2$—$C_1$-$C_4$-alkyl and $S(O)_2$—$C_1$-$C_6$-haloalkyl.

Particularly preferred groups $R^2$ include $C_2$-$C_4$-alkenyl, $C_2$-$C_4$-alkynyl, $C_1$-$C_2$-haloalkoxy-$C_1$-$C_2$-alkyl, $C_3$-$C_4$-alkenyloxy, $C_3$-$C_4$-alkynyloxy, $C_1$-$C_4$-alkylsulfonyl, $C_1$-$C_4$-alkoxy, $C_1$-$C_4$-alkoxycarbonyl and $S(O)_2$—$C_1$-$C_4$-alkyl, chlorine, bromine. Special preference is given to $CH=CH_2$, $CH=CHCH_3$, $CH_2OCH_2CF_3$, $OC_2H_5$, $OCH_2CH=CH_2$, $OCH_2C\equiv CH$, $OCH_2CH_2OCH_3$, $COOCH_3$, $COOC_2H_5$ and $SO_2CH_3$, $SO_2C_2H_5$ and $SO_2CH(CH_3)_2$, cyclopropyl-methoxy-methyl (cyPr-$CH_2$—O—$CH_2$—), difluoromethoxy ($CHF_2$—O—); and 1,1,1-triflouroethoxy ($CF_3CH_2$—O—).

In a further preferred aspect, $R^2$ together with the group attached to the adjacent carbon atom forms a five- to ten-membered saturated, partially unsaturated or fully unsaturated mono- or bicyclic ring which, in addition to carbon atoms, may contain 1, 2 or 3 heteroatoms selected from the group consisting of O, N and S and which may be substituted by further groups $R^c$.

In a particularly preferred aspect, $R^2$ together with $R^1$ or $R^3$ forms a five- to ten-membered mono- or bicyclic, saturated, partially unsaturated or fully unsaturated ring which contains 1, 2, 3 or 4 heteroatoms selected from the group consisting of O, N and S and which may be partially or fully substituted by groups $R^c$. Suitable are, for example, the following: 4-dihydro-2H-thiopyrano[2,3-b]pyridine 1,1-dioxide, 3,4-dihydro-2H-thiopyrano[3,2-b]pyridine 1,1-dioxide, 2,3-dihydro-[1,4]dithiino[2,3-b]pyridine 1,1,4,4-tetraoxide, 1H-thiazolo[5,4-b]pyridin-2-one, 2,3-dihydrothieno[2,3-b]pyridine 1,1-dioxide, 1,8-naphthyridine, 1,5-naphthyridine, 1,7-naphthyridine and isothiazolo[5,4-b]pyridine Preferably, $R^2$ together with $R^1$ or $R^3$ forms a five- or six-membered monocyclic, saturated or partially unsaturated ring.

In a further preferred embodiment of the compounds of the formula I (in particular of the formula I.1), $R^3$ is hydrogen, cyano, halogen, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_2$-$C_4$-alkenyloxy, $C_2$-$C_4$-alkynyloxy or $S(O)_nR^b$.

In a particularly preferred embodiment of the compounds of the formula I (in particular of the formula I.1), $R^3$ is hydrogen, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_n$—$C_1$-$C_4$-alkyl and $S(O)_n$—$C_1$-$C_4$-haloalkyl, where n is preferably 0 or 2. Particularly preferably, $R^3$ is selected from the group consisting of H, F, Cl, Br, CN, $NO_2$, $CH_3$, $CF_3$, $CHF_2$, $OCH_3$, $OCF_3$, $OCHF_2$, $SCH_3$, $SCF_3$, $SCHF_2$, $SO_2CH_3$ and $SO_2CH_2CH_3$.

In further preferred aspects of the formula I.1, the groups $R^1$, $R^2$ and $R^3$ together form a substitution pattern selected from the group consisting of:

$R^1$=Cl, $R^2$=H, $R^3$=Cl;
$R^1$=Cl, $R^2$=H, $R^3$=$CF_3$;
$R^1$=Cl, $R^2$=H, $R^3$=$SO_2CH_3$;
$R^1$=Cl, $R^2$=H, $R^3$=$OCH_3$;
$R^1$=Cl, $R^2$=H, $R^3$=$CH_3$;
$R^1$=$CH_3$, $R^2$=H, $R^3$=Cl;
$R^1$=$CH_3$, $R^2$=H, $R^3$=$CF_3$;
$R^1$=$CH_3$, $R^2$=H, $R^3$=$SO_2CH_3$;
$R^1$=$CH_3$, $R^2$=H, $R^3$=$OCH_3$;
$R^1$=$CF_3$, $R^2$=H, $R^3$=$CH_3$;
$R^1$=$CF_3$, $R^2$=H, $R^3$=Cl;
$R^1$=$CF_3$, $R^2$=H, $R^3$=$CF_3$;
$R^1$=$CF_3$, $R^2$=H, $R^3$=$SO_2CH_3$;
$R^1$=$CF_3$, $R^2$=H, $R^3$=$OCH_3$;
$R^1$=$SO_2CH_3$, $R^2$=H, $R^3$=$CH_3$,
$R^1$=$SO_2CH_3$, $R^2$=H, $R^3$=Cl;
$R^1$=$SO_2CH_3$, $R^2$=H, $R^3$=$CF_3$;
$R^1$=$SO_2CH_3$, $R^2$=H, $R^3$=$SO_2CH_3$;
$R^1$=$SO_2CH_3$, $R^2$=H, $R^3$=$OCH_3$; and
$R^1$=$SO_2CH_3$, $R^2$=H, $R^3$=$CH_3$.

In a further preferred embodiment of the HPPD-inhibiting herbicides of the formula I, A is N, B is CR4, X is CRxRy, Y is SO2 and W is CR6. These compounds correspond to the formula I.2

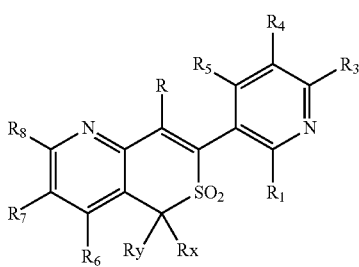

I.2 where the variables have the meanings defined at the outset and preferably the meanings mentioned as preferred.

More preferably, in the compounds of the formula I.2, the group $R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, I, $NO_2$, $CH_3$, $CF_3$, $OCH_3$, $OCF_3$, $OCHF_2$, $SCF_3$, $SCHF_2$, $SO_2CH_3$, or $CH_2OCH_2CH_2OCH_3$; and/or $R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio, or $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.

R4 is H
R5 is H or halogen
R6 is H
R7 is H
R8 is H
Rx, Ry is H or $CH_3$

Particularly preferably, in the compounds of the formula I.1, the group $R^1$ is halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio or $C_1$-$C_4$-alkylsulfonyl, in particular F, Cl, Br, $NO_2$, $CH_3$, $CF_3$, $OCH_3$, $OCF_3$, $OCHF_2$, $SCF_3$, $SCHF_2$, $SO_2CH_3$, or $CH_2OCH_2CH_2OCH_3$; and/or $R^3$ is H, halogen, CN, $NO_2$, $C_1$-$C_4$-alkyl, $C_1$-$C_4$-haloalkyl, $C_1$-$C_4$-alkoxy, $C_1$-$C_4$-alkylthio or $C_1$-$C_4$-alkylsulfonyl, in particular H, F, Cl, Br, CN, $NO_2$, $CH_3$, $CH_2CH_3$, $CF_3$, $CHF_2$, $OCH_3$, $OCF_3$, $OCHF_2$, $SCH_3$, $SO_2CH_3$ or $SO_2CH_2CH_3$.

In a further preferred embodiment of the compounds of the formula I (in particular of the formula I.2), $R^3$ is hydrogen, cyano, halogen, nitro, $C_1$-$C_4$-alkyl, $C_1$-$C_4$-haloalkyl, $C_1$-$C_4$-alkoxy, $C_1$-$C_4$-haloalkoxy, $C_2$-$C_4$-alkenyl, $C_2$-$C_4$-alkynyl, $C_2$-$C_4$-alkenyloxy, $C_2$-$C_4$-alkynyloxy or $S(O)_nR^b$.

In a particularly preferred embodiment of the compounds of the formula I (in particular of the formula I.1), $R^3$ is hydrogen, halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_n$—$C_1$-$C_4$-alkyl and $S(O)_n$—$C_1$-$C_4$-haloalkyl, where n is preferably 0 or 2. Particularly preferably, $R^3$ is selected from the group consisting of H, F, Cl, Br, CN, $NO_2$, $CH_3$, $CF_3$, $CHF_2$, $OCH_3$, $OCF_3$, $OCHF_2$, $SCH_3$, $SCF_3$, $SCHF_2$, $SO_2CH_3$ and $SO_2CH_2CH_3$.

In further preferred aspects of the formula I.1, the groups $R^1$, $R^2$ and $R^3$ together form a substitution pattern selected from the group consisting of:

$R^1$=Cl, $R^3$=Cl;
$R^1$=Cl, $R^3$=$CF_3$;
$R^1$=Cl, $R^3$=$SO_2CH_3$;
$R^1$=Cl, $R^3$=$OCH_3$;
$R^1$=Cl, $R^3$=$CH_3$;
$R^1$=$CH_3$, $R^3$=Cl;
$R^1$=$CH_3$, $R^3$=$CF_3$;
$R^1$=$CH_3$, $R^3$=$SO_2CH_3$;
$R^1$=$CH_3$, $R^3$=$OCH_3$;
$R^1$=$CF_3$, $R^3$=$CH_3$;
$R^1$=$CF_3$, $R^3$=Cl;
$R^1$=$CF_3$, $R^3$=$CF_3$;
$R^1$=$CF_3$, $R^3$=$SO_2CH_3$;
$R^1$=$CF_3$, $R^3$=$OCH_3$;
$R^1$=$SO_2CH_3$, $R^3$=$CH_3$,
$R^1$=$SO_2CH_3$, $R^3$=Cl;
$R^1$=$SO_2CH_3$, $R^3$=$CF_3$;
$R^1$=$SO_2CH_3$, $R^3$=$SO_2CH_3$;
$R^1$=$SO_2CH_3$, $R^3$=$OCH_3$; and
$R^1$=$SO_2CH_3$, $R^3$=$CH_3$.

In another preferred embodiment, the HPPD-inhibiting herbicide refers to a pyrazolone, isoxazole, or a triketone derivative herbicide.

Preferably the herbicide is selected from the group consisting of benzobicyclon, benzofenap, isoxaflutole, mesotrione, pyrasulfotole, pyrazolynate, pyrazoxyfen, sulcotrione, tefuryltrione, tembotrione, topramezone, bicyclopyrone (4-hydroxy-3-[[2-(2-methoxyethoxy)methyl]-6-(trifluoromethyl)-3-pyridinyl]carbonyl]-bicyclo[3.2.1]-oct-3-en-2-one).

In another preferred embodiment, the HPPD-inhibiting herbicide refers to an N-heterocyclylarylcarboxamide. N-heterocyclyl-arylcarboxamides which are particularly useful for the present invention encompasses the compounds as depicted in the following Table A.

TABLE A

| General Structure | Possible substituents as defined in Publication Number | Pages |
|---|---|---|
| I | WO2011/035874 or EP0173657 | 1 to 9 / 1 to 3 |

TABLE A-continued

| General Structure | Possible substituents as defined in | |
|---|---|---|
| | Publication Number | Pages |
| II | WO2012/028579 | 1 to 5 |
| III | EP0173657 | 1 to 3 |

In another preferred embodiment, the HPPD-inhibiting herbicide refers to a bicycloarylcarboxamide. Bicycloarylcarboxamides which which are particularly useful for the present invention encompasses encompasses the compounds as depicted in the following Table B.

TABLE B

| No: | General Structure | Possible Substituents as defined in: | |
|---|---|---|---|
| | | Application number and reference | Publication Number |
| 1 | I | PCT/EP2012/072692 PF72975 | WO2013/072402 |
| 2 | II | US 61/639081 PF73636 | WO2013/076315 |

The above referenced application, in particular the disclosures referring to the compounds of Table B and their possible substitutents are entirely incorporated by reference.

In another preferred embodiment, the HPPD-inhibiting herbicide refers to a benzamide. Benzamides which which are particularly useful for the present invention encompasses encompasses the compounds as depicted in the following Table C.

TABLE C

| No: | General Structure | Possible Substituents as defined in: | |
|---|---|---|---|
| | | Application number and reference | Publication Number |
| 1 | I | PCT/EP2012/072469 PF72974 | WO2013/072300 |

TABLE C-continued

| No: | General Structure | Possible Substituents as defined in: | |
|---|---|---|---|
| | | Application number and reference | Publication Number |
| 2 | II | US 61/639079 PF73635 | WO2013/083859 |

The above referenced application, in particular the disclosures referring to the compounds of Table C and their possible substitutents are entirely incorporated by reference.

In another preferred embodiment, the HPPD-inhibiting herbicide refers to a heteroarylcarboxamide having the formula I:

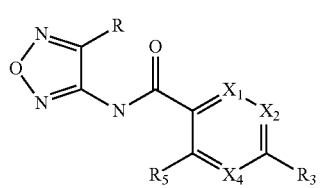

I wherein
$X^1$ is N or $CR^1$;
$X^2$ is N or $CR^2$;
$X^4$ is N or $CR^4$;
provided that a least one of $X^1$, $X^2$ and $X^4$ is N;
R is selected from the group consisting of hydrogen, cyano, nitro, halogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, O—$R^a$, Z—S(O)$_n$—$R^b$, Z—C(=O)—$R^c$, Z—C(=O)—O$R^d$, Z—C(=O)—N$R^e R^f$, Z—N$R^g R^h$, Z-phenyl and Z-heterocyclyl, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

$R^1$ is selected from the group consisting of $Z^1$-cyano, halogen, nitro, $C_1$-$C_8$-alkyl, $C_2$-$C_8$-alkenyl, $C_2$-$C_8$-alkynyl, $C_1$-$C_8$-haloalkyl, $C_1$-$C_8$-alkoxy, $C_1$-$C_4$-alkoxy-$C_1$-$C_4$-alkyl, $Z^1$—$C_1$-$C_4$-alkoxy-$C_1$-$C_4$-alkoxy, $C_1$-$C_4$-alkylthio-$C_1$-$C_4$-alkyl, $Z^1$—$C_1$-$C_4$-alkylthio-$C_1$-$C_4$-alkylthio, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $Z^1$—$C_1$-$C_4$-haloalkoxy-$C_1$-$C_4$-alkoxy, $Z^1$—$S(O)_k$—$R^{1b}$, $Z^1$-phenoxy and $Z^1$-heterocyclyloxy, where heterocyclyloxy is an oxygen bound 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups $R^{11}$, which are identical or different;

$R^2$, $R^3$ are identical or different and independently selected from the group consisting of hydrogen, halogen, $Z^2$—OH, $Z^2$—$NO_2$, $Z^2$-cyano, $C_1$-$C_6$-alkyl, $C_2$-$C_8$-alkenyl, $C_2$-$C_8$-alkynyl, $Z^2$—$C_3$-$C_{10}$-cycloalkyl, $Z^2$—$C_3$-$C_{10}$-cycloalkoxy, where the $C_3$-$C_{10}$-cycloalkyl groups in the two aforementioned radicals are unsubstituted or partially or completely halogenated, $C_1$-$C_8$-haloalkyl, $Z^2$—$C_1$-$C_8$-alkoxy, $Z^2$—$C_1$-$C_8$-haloalkoxy, $Z^2$—$C_1$-$C_4$-alkoxy-$C_1$-$C_4$-alkoxy, $Z^2$—$C_1$-$C_4$-alkylthio-$C_1$-$C_4$-alkylthio, $Z^2$—$C_2$-$C_8$-alkenyloxy, $Z^2$—$C_2$-$C_8$-alkynyloxy, $Z^2$—$C_1$-$C_8$-haloalkoxy, $Z^2$—$C_1$-$C_4$-haloalkoxy-$C_1$-$C_4$-alkoxy, $Z^2$-(tri-$C_1$-$C_4$-alkyl)silyl, $Z^2$—$S(O)_k$—$R^{2b}$,
$Z^2$—$C(=O)$—$R^{2c}$, $Z^2$—$C(=O)$—$OR^{2d}$, $Z^2$—$C(=O)$—$NR^{2e}R^{2f}$, $Z^2$—$NR^{2g}R^{2h}$, $Z^{2a}$-phenyl and $Z^{2a}$ heterocyclyl, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in $Z^{2a}$-phenyl and $Z^{2a}$-heterocyclyl are unsubstituted or substituted by 1, 2, 3 or 4 groups $R^{21}$, which are identical or different;

$R^4$ is selected from the group consisting of hydrogen, halogen, cyano, nitro, $C_1$-$C_4$-alkyl and $C_1$-$C_4$-haloalkyl;

$R^5$ is selected from the group consisting of hydrogen, halogen, cyano, nitro, $C_1$-$C_4$-alkyl and $C_1$-$C_4$-haloalkyl;

where for $X^2$=$CR^2$, $R^2$ together with $R^3$ or together with $R^1$, if present, may also form a fused 5-, 6-, 7-, 8-, 9- or 10-membered carbocycle or a fused 5-, 6-, 7-, 8-, 9- or 10-membered heterocycle, where the fused heterocycle has 1, 2, 3 or 4 heteroatoms selected from O, S and N as ring members, where the fused carbocycle and the fused heterocycle are monocyclic or bicyclic and where the fused carbocycle and the fused heterocycle are unsubstituted or carry 1, 2, 3, 4, 5, 6, 7, 8, 9 or 10 radicals $R^q$;

n is 0, 1 or 2;

k is 0, 1 or 2;

R', $R^{11}$, $R^{21}$ independently of each other are selected from the group consisting of halogen, $NO_2$, CN, $C_1$-$C_6$-alkyl, $C_3$-$C_7$-cycloalkyl, $C_3$-$C_7$-halocycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_1$-$C_4$-alkoxy-$C_1$-$C_4$-alkyl, $C_1$-$C_4$-alkylthio-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy and $C_3$-$C_7$-cycloalkoxy or two vicinal radicals R', $R^{11}$ or $R^{21}$ together may form a group =O (oxo);

Z, $Z^1$, $Z^2$ independently of each other are selected from the group consisting of a covalent bond and $C_1$-$C_4$-alkanediyl;

$Z^{2a}$ is selected from the group consisting of a covalent bond, $C_1$-$C_4$-alkanediyl, O—$C_1$-$C_4$-alkanediyl, $C_1$-$C_4$-alkanediyl-O and $C_1$-$C_4$-alkanediyl-O—$C_1$-$C_4$-alkanediyl;

$R^a$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^b$, $R^{1b}$, $R^{2b}$ independently of each other are selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^c$, $R^{2c}$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl or heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl, benzyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^d$, $R^{2d}$ independently of each other are selected from the group consisting of $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^e$, $R^f$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^e$, $R^f$ together with the nitrogen atom, to which they are bound may form a 5-, 6- or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^{2e}$, $R^{2f}$ independently of each other have the meanings given for $R^e$, $R^f$;

$R^g$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^h$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, a radical C(=O)—$R^k$, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^g$, $R^h$ together with the nitrogen atom, to which they are bound may form a 5-, 6- or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of =O, halogen, $C_1$-$C_4$-alkyl, $C_1$-$C_4$-haloalkyl, $C_1$-$C_4$-alkoxy and $C_1$-$C_4$-haloalkoxy;

$R^{2g}$, $R^{2h}$ independently of each other have the meanings given for $R^g$, $R^h$;

$R^k$ has the meanings given for $R^c$;

$R^q$ is selected from the group consisting of halogen, $Z^q$—OH, $Z^q$—$NO_2$, $Z^q$-cyano, oxo (=O), =N—$R^{q1}$, $C_1$-$C_4$-alkyl, $C_1$-$C_4$-haloalkyl, $C_2$-$C_4$-alkenyl, $C_2$-$C_4$-alkynyl, $Z^q$—$C_1$-$C_4$-alkoxy, $Z^q$—$C_1$-$C_4$-alkoxy-$C_1$-$C_4$-alkoxy, $C_1$-$C_4$-alkylthio, $C_1$-$C_4$-haloalkylthio, $Z^q$—$C_1$-$C_4$-haloalkoxy, $Z^q$—$C_3$-$C_{10}$-cycloalkyl, O—$Z^q$—$C_3$-$C_{10}$-cycloalkyl, $Z^q$-(tri-$C_1$-$C_4$-alkyl)silyl, $Z^q$—S(O)$_k$—$R^{q2}$, $Z^2$—C(=O)—$R^{q3}$, $Z^2$—$NR^{q4}R^{q5}$ and $Z^q$-phenyl, where phenyl in $Z^q$-phenyl is unsubstituted or substituted by 1, 2, 3 or 4 groups $R^{q6}$, which are identical or different; where $Z^q$ has one of the meanings given for Z;

$R^{q1}$ $C_1$-$C_4$-alkoxy, $C_1$-$C_4$-haloalkoxy and $C_3$-$C_7$-cycloalkoxy, which is unsubstituted or partially or completely halogenated;

$R^{q2}$ has one of the meanings given for $R^b$;

$R^{q3}$ has one of the meanings given for $R^c$;

$R^{q4}$, $R^{q5}$ independently of each other have the meanings given for $R^g$, $R^h$;

$R^{q6}$ has one of the meanings given for R';

or an N-oxide or an agriculturally suitable salt thereof.

In another preferred embodiment of the present invention, the HPPD-inhibiting herbicide refers to a heteroarylcarboxamide having the formula I:

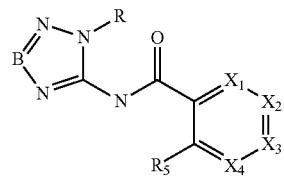

wherein

B is N or CH;

$X^1$ is N or $CR^1$;

$X^2$ is N or $CR^2$;

$X^3$ is N or $CR^3$;

$X^4$ is N or $CR^4$;

provided that a least one of $X^1$, $X^3$ and $X^4$ is N;

R is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^b$—S(O)$_n$—$C_1$-$C_3$-alkyl, $R^c$—C(=O)—$C_1$-$C_3$-alkyl, $R^d$O—C(=O)—$C_1$-$C_3$-alkyl, $R^eR^fN$—C(=O)—$C_1$-$C_3$-alkyl, $R^gR^hN$—$C_1$-$C_3$-alkyl, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

$R^1$ is selected from the group consisting of cyano-$Z^1$, halogen, nitro, $C_1$-$C_8$-alkyl, $C_2$-$C_8$-alkenyl, $C_2$-$C_8$-alkynyl, $C_1$-$C_8$-haloalkyl, $C_1$-$C_8$-alkoxy, $C_1$-$C_4$-alkoxy-$C_1$-$C_4$-alkyl, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $C_1$-$C_4$-haloalkoxy-$C_1$-$C_4$-alkoxy-$Z^1$, $R^{1b}$—S(O)$_k$—$Z^1$, phenoxy-$Z^1$ and heterocyclyloxy-$Z^1$, where heterocyclyoxy is an oxygen bound 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyoxy are unsubstituted or substituted by 1, 2, 3 or 4 groups $R^{11}$, which are identical or different;

$R^2$, $R^3$ are identical or different and independently selected from the group consisting of hydrogen, halogen, OH—$Z^2$, $NO_2$—$Z^2$, cyano-$Z^2$, $C_1$-$C_6$-alkyl, $C_2$-$C_8$-alkenyl, $C_2$-$C_8$-alkynyl, $C_3$-$C_{10}$-cycloalkyl-$Z^2$, $C_3$-$C_{10}$-cycloalkoxy-$Z^2$, where the $C_3$-$C_{10}$-cycloalkyl groups in the two aforementioned radicals are unsubstituted or partially or completely halogenated, $C_1$-$C_8$-haloalkyl, $C_1$-$C_8$-alkoxy-$Z^2$, $C_1$-$C_8$-haloalkoxy-$Z^2$, $C_1$-$C_4$-alkoxy-$C_1$-$C_4$-alkoxy-$Z^2$, $C_1$-$C_4$-alkylthio-$C_1$-$C_4$-alkylthio-$Z^2$, $C_2$-$C_8$-alkenyloxy-$Z^2$, $C_2$-$C_8$-alkynyloxy-$Z^2$, $C_2$-$C_8$-haloalkenyloxy-$Z^2$, $C_2$-$C_8$-haloalkynyloxy-$Z^2$, $C_1$-$C_4$-haloalkoxy-$C_1$-$C_4$-alkoxy-$Z^2$, (tri-$C_1$-$C_4$-alkyl)silyl-$Z^2$, $R^{2b}$—S(O)$_k$—$Z^2$, $R^{2c}$—C(=O)—$Z^2$, $R^{2d}$O—C(=O)—$Z^2$, $R^{2e}R^{2f}$N—C(=O)—$Z^2$, $R^{2g}R^{2h}$N—$Z^2$, phenyl-$Z^{2a}$ and heterocyclyl-$Z^{2a}$, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenyl-$Z^{2a}$ and heterocyclyl-$Z^{2a}$ are unsubstituted or substituted by 1, 2, 3 or 4 groups $R^{21}$, which are identical or different;
- $R^4$ is selected from the group consisting of hydrogen, halogen, cyano, nitro, $C_1$-$C_4$-alkyl and $C_1$-$C_4$-haloalkyl;
- $R^5$ is selected from the group consisting of hydrogen, halogen, cyano, nitro, $C_1$-$C_4$-alkyl and $C_1$-$C_4$-haloalkyl;
- where for $X^2$=$CR^2$, $R^2$ together with $R^3$, if present, or together with $R^1$, if present, may also form a fused 5-, 6-, 7-, 8-, 9- or 10-membered carbocycle or a fused 5-, 6-, 7-, 8-, 9- or 10-membered heterocycle, where the fused heterocycle has 1, 2, 3 or 4 heteroatoms selected from O, S and N as ring members, where the fused carbocycle and the fused heterocycle are monocyclic or bicyclic and where the fused carbocycle and the fused heterocycle are unsubstituted or carry 1, 2, 3, 4, 5, 6, 7, 8, 9 or 10 radicals $R^q$;
- n is 0, 1 or 2;
- k is 0, 1 or 2;
- R', $R^{11}$, $R^{21}$ independently of each other are selected from the group consisting of halogen, $NO_2$, CN, $C_1$-$C_6$-alkyl, $C_3$-$C_7$-cycloalkyl, $C_3$-$C_7$-halocycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkyloxy, $C_1$-$C_4$-alkoxy-$C_1$-$C_4$-alkyl, $C_1$-$C_4$-alkylthio-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy and $C_3$-$C_7$-cycloalkoxy or two vicinal radicals R', $R^{11}$ or $R^{21}$ together may form a group =O (oxo);
- Z, $Z^1$, $Z^2$ independently of each other are selected from the group consisting of a covalent bond and $C_1$-$C_4$-alkanediyl;
- $Z^{2a}$ is selected from the group consisting of a covalent bond, $C_1$-$C_4$-alkanediyl, O—$C_1$-$C_4$-alkanediyl, $C_1$-$C_4$-alkanediyl-O and $C_1$-$C_4$-alkanediyl-O—$C_1$-$C_4$-alkanediyl;
- $R^b$, $R^{1b}$, $R^{2b}$ independently of each other are selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;
- $R^c$, $R^{2c}$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl, benzyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;
- $R^d$, $R^{2d}$ independently of each other are selected from the group consisting of $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;
- $R^e$, $R^f$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or
- $R^e$, $R^f$ together with the nitrogen atom, to which they are bound may form a 5-, 6- or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;
- $R^{2e}$, $R^{2f}$ independently of each other have the meanings given for $R^e$, $R^f$;
- $R^g$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^h$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, a radical $C(=O)$—$R^k$, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^g$, $R^h$ together with the nitrogen atom, to which they are bound may form a 5-, 6- or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of oxo (=O), halogen, $C_1$-$C_4$-alkyl, $C_1$-$C_4$-haloalkyl, $C_1$-$C_4$-alkoxy and $C_1$-$C_4$-haloalkoxy;

$R^{2g}$, $R^{2h}$ independently of each other have the meanings given for $R^g$, $R^h$;

$R^k$ has the meanings given for $R^c$;

$R^q$ is selected from the group consisting of halogen, OH—$Z^q$, $NO_2$—$Z^q$, cyano-$Z^q$, oxo (=O), $R^{q1}N=$, $C_1$-$C_4$-alkyl, $C_1$-$C_4$-haloalkyl, $C_2$-$C_4$-alkenyl, $C_2$-$C_4$-alkynyl, $C_1$-$C_4$-alkoxy-$Z^q$, $C_1$-$C_4$-alkoxy-$C_1$-$C_4$-alkoxy-$Z^q$, $C_1$-$C_4$-alkylthio, $C_1$-$C_4$-haloalkylthio, $C_1$-$C_4$-haloalkoxy-$Z^q$, $C_3$-$C_{10}$-cycloalkyl-$Z^q$, $C_3$-$C_{10}$-cycloalkyl-$Z^q$—O, (tri-$C_1$-$C_4$-alkyl)silyl-$Z^q$, $R^{q2}$—$S(O)_k$—$Z^q$, $R^{q3}$—$C(=O)$—$Z^q$, $R^{q4}R^{q5}N$—$Z^q$ and phenyl-$Z^q$, where phenyl in phenyl-$Z^q$ is unsubstituted or substituted by 1, 2, 3 or 4 groups $R^{q6}$, which are identical or different; where $Z^q$ has one of the meanings given for Z;

$R^{q1}$ $C_1$-$C_4$-alkoxy, $C_1$-$C_4$-haloalkoxy and $C_3$-$C_7$-cycloalkoxy, which is unsubstituted or partially or completely halogenated;

$R^{q2}$ has one of the meanings given for $R^b$;

$R^{q3}$ has one of the meanings given for $R^c$;

$R^{q4}$, $R^{q5}$ independently of each other have the meanings given for $R^g$, $R^h$;

$R^{q6}$ has one of the meanings given for R';

an N-oxide or an agriculturally suitable salt thereof.

In another preferred embodiment of the present invention, the HPPD-inhibiting herbicide refers to a pyridylcarboxamide having the formula I:

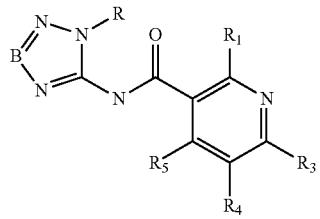

where

B is N or CH;

R is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, $C_1$-$C_4$-haloalkoxy-$C_1$-$C_4$-alkyl, $R^b$—$S(O)_n$—$C_1$-$C_3$-alkyl, $R^c$—$C(=O)$—$C_1$-$C_3$-alkyl, $R^dO$—$C(=O)$—$C_1$-$C_3$-alkyl, $R^eR^fN$—$C(=O)$—$C_1$-$C_3$-alkyl, $R^gR^hN$—$C_1$-$C_3$-alkyl, phenyl-Z and heterocyclyl-Z, where heterocyclyl is a 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups R', which are identical or different;

$R^1$ is selected from the group consisting of cyano-$Z^1$, halogen, nitro, $C_1$-$C_8$-alkyl, $C_2$-$C_8$-alkenyl, $C_2$-$C_8$-alkynyl, $C_1$-$C_8$-haloalkyl, $C_1$-$C_8$-alkoxy, $C_1$-$C_4$-alkoxy-$C_1$-$C_4$-alkyl, $C_1$-$C_4$-alkoxy-$C_1$-$C_4$-alkoxy-$Z^1$, $C_1$-$C_4$-alkylthio-$C_1$-$C_4$-alkyl, $C_1$-$C_4$-alkylthio-$C_1$-$C_4$-alkylthio-$Z^1$, $C_2$-$C_6$-alkenyloxy, $C_2$-$C_6$-alkynyloxy, $C_1$-$C_6$-haloalkoxy, $C_1$-$C_4$-haloalkoxy-$C_1$-$C_4$-alkyl, $C_1$-$C_4$-haloalkoxy-$C_1$-$C_4$-alkoxy-$Z^1$, $R^{1b}$—$S(O)_k$—$Z^1$, phenoxy-$Z^1$, and heterocyclyloxy-$Z^1$, where heterocyclyloxy is an oxygen bound 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenoxy and heterocyclyloxy are unsubstituted or substituted by 1, 2, 3 or 4 groups $R^{11}$, which are identical or different;

$R^3$ is selected from the group consisting of hydrogen, halogen, OH—$Z^2$, $NO_2$—$Z^2$, cyano-$Z^2$, $C_1$-$C_6$-alkyl, $C_2$-$C_8$-alkenyl, $C_2$-$C_8$-alkynyl, $C_3$-$C_{10}$-cycloalkyl-$Z^2$, $C_3$-$C_{10}$cycloalkoxy-$Z^2$, where the $C_3$-$C_{10}$-cycloalkyl groups in the two aforementioned radicals are unsubstituted or partially or completely halogenated, $C_1$-$C_8$-haloalkyl, $C_1$-$C_8$-alkoxy-$Z^2$, $C_1$-$C_8$-haloalkoxy-$Z^2$, $C_1$-$C_4$-alkoxy-$C_1$-$C_4$-alkoxy-$Z^2$, $C_1$-$C_4$-alkylthio-$C_1$-$C_4$-alkylthio-$Z^2$, $C_2$-$C_8$-alkenyloxy-$Z^2$, $C_2$-$C_8$-alkynyloxy-$Z^2$, $C_2$-$C_8$-haloalkenyloxy-$Z^2$, $C_2$-$C_8$-haloalkynyloxy-$Z^2$, $C_1$-$C_4$-haloalkoxy-$C_1$-$C_4$-alkoxy-$Z^2$, (tri-$C_1$-$C_4$-alkyl)silyl-$Z^2$, $R^{2b}$—$S(O)_k$—$Z^2$, $R^{2c}$—$C(=O)$—$Z^2$, $R^{2d}O$—$C(=O)$—$Z^2$, $R^{2e}R^{2f}N$—$C(=O)$—$Z^2$, $R^{2g}R^{2h}N$—$Z^2$, phenyl-$Z^{2a}$ and heterocyclyl-$Z^{2a}$, where heterocyclyl is a 3-, 4-, 5- or 6-membered monocyclic or 8-, 9- or 10-membered bicyclic saturated, partially unsaturated or aromatic heterocycle, which contains 1, 2, 3 or 4 heteroatoms as ring members, which are selected from the group consisting of O, N and S, where the cyclic groups in phenyl-$Z^{2a}$ and heterocyclyl-$Z^{2a}$ are unsubstituted or substituted by 1, 2, 3 or 4 groups $R^{21}$, which are identical or different;

$R^4$ is selected from the group consisting of hydrogen, halogen, cyano, nitro, $C_1$-$C_4$-alkyl and $C_1$-$C_4$-haloalkyl;

$R^5$ is selected from the group consisting of hydrogen, halogen, $C_1$-$C_4$-alkyl and $C_1$-$C_4$-haloalkyl;

provided that at least one of the radicals $R^4$ and $R^5$ is different from hydrogen;

n is 0, 1 or 2;

k is 0, 1 or 2;

R', $R^{11}$, $R^{21}$ independently of each other are selected from the group consisting of halogen, $NO_2$, CN, $C_1$-$C_6$-alkyl, $C_3$-$C_7$-cycloalkyl, $C_3$-$C_7$-halocycloalkyl, $C_1$-$C_6$-haloalkyl, $C_2$-$C_6$-alkenyl, $C_2$-$C_6$-haloalkenyl, $C_2$-$C_6$- alkynyl, $C_2$-$C_6$-haloalkynyl, $C_1$-$C_6$-alkoxy, $C_1$-$C_4$-alkoxy-$C_1$-$C_4$-alkyl, $C_1$-$C_4$-alkylthio-$C_1$-$C_4$-alkyl, $C_1$-$C_4$-haloalkoxy-$C_1$-$C_4$-alkyl, $C_1$-$C_4$-alkoxy-$C_1$-$C_4$-alkoxy, $C_3$-$C_7$-cycloalkoxy and $C_1$-$C_6$-haloalkyloxy, or two vicinal radicals R', $R^{11}$ or $R^{21}$ together may form a group =O;

Z, $Z^1$, $Z^2$ independently of each other are selected from the group consisting of a covalent bond and $C_1$-$C_4$-alkanediyl;

$Z^{2a}$ is selected from the group consisting of a covalent bond, $C_1$-$C_4$-alkanediyl, O—$C_1$-$C_4$-alkanediyl, $C_1$-$C_4$-alkanediyl-O and $C_1$-$C_4$-alkanediyl-O—$C_1$-$C_4$-alkanediyl;

$R^b$, $R^{1b}$, $R^{2b}$ independently of each other are selected from the group consisting of $C_1$-$C_6$-alkyl, $C_3$-$C_7$-cycloalkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, phenyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^c$, $R^{2c}$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl, benzyl and heterocyclyl, where heterocyclyl is a 5- or 6-membered monocyclic saturated, partially unsaturated or aromatic heterocycle, which contains 1, 2, 3 or 4 heteroatoms as ring members, which are selected from the group consisting of O, N and S, where phenyl, benzyl and heterocyclyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^d$, $R^{2d}$ independently of each other are selected from the group consisting of $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^e$, $R^f$ independently of each other are selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^e$, $R^f$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^{2e}$, $R^{2f}$ independently of each other have the meanings given for $R^e$, $R^f$;

$R^g$ is from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy;

$R^h$ is selected from the group consisting of hydrogen, $C_1$-$C_6$-alkyl, $C_3$-$C_7$-cycloalkyl, $C_3$-$C_7$-cycloalkyl-$C_1$-$C_4$-alkyl, where the $C_3$-$C_7$-cycloalkyl groups in the two aforementioned radicals are unsubstituted or partially or completely halogenated, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy-$C_1$-$C_4$-alkyl, a radical C(=O)—$R^k$, phenyl and benzyl, where phenyl and benzyl are unsubstituted or substituted by 1, 2, 3 or 4 groups, which are identical or different and selected from the group consisting of halogen, $C_1$-$C_4$-alkyl, $C_1$-$C_4$-haloalkyl, $C_1$-$C_4$-alkoxy and $C_1$-$C_4$-haloalkoxy, or $R^g$, $R^h$ together with the nitrogen atom, to which they are bound may form a 5-, 6 or 7-membered, saturated or unsaturated N-bound heterocyclic radical, which may carry as a ring member a further heteroatom selected from O, S and N and which is unsubstituted or may carry 1, 2, 3 or 4 groups, which are identical or different and selected from the group consisting of =O, halogen, $C_1$-$C_4$-alkyl, $C_1$-$C_4$-haloalkyl, $C_1$-$C_4$-alkoxy and $C_1$-$C_4$-haloalkoxy;

$R^{2g}$, $R^{2h}$ independently of each other have the meanings given for $R^g$, $R^h$;

$R^k$ has the meanings given for $R^c$;

an N-oxide or an agriculturally suitable salt thereof.

The HPPD-inhibiting herbicides useful for the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides.

Consequently, in certain embodiments, the mutated HPPD nucleic acids of the present invention can be stacked with any combination of polynucleotide sequences of interest in order to create plants with a desired phenotype. For example, the mutated HPPD nucleic acids of the present invention may be stacked with any other polynucleotides encoding polypeptides having pesticidal and/or insecticidal activity, such as, for example, the *Bacillus thuringiensis* toxin proteins (described in U.S. Pat. Nos. 5,366,892; 5,747,450; 5,737,514; 5,723,756; 5,593,881; and Geiser et al (1986) Gene 48: 109). The combinations generated can also include multiple copies of any one of the polynucleotides of interest.

By way of example, polynucleotides that may be stacked with the nucleic acids of the present invention include nucleic acids encoding polypeptides conferring resistance to pests/pathogens such as viruses, nematodes, insects or fungi, and the like. Exemplary polynucleotides that may be stacked with nucleic acids of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al., (1986) Gene 48:109), lectins (Van Damme et al. (1994) Plant Mol. Biol. 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al. (1994) Science 266:789; Martin et al., (1993) Science 262:1432; Mindrinos et al. (1994) Cell 78:1089); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) Science, 304:1151-1154; and in U.S. Patent App. Pub. Nos. 20070004912, 20050246798, and 20050060767)); glufosinate resistance (e.g, phosphinothricin acetyl transferase genes PAT and BAR, described in U.S. Pat. Nos. 5,561,236 and 5,276,268); resistance to herbicides including sulfonyl urea, DHT (2,4D), and PPO herbicides (e.g., glyphosate acetyl transferase, aryloxy alkanoate dioxygenase, acetolactate synthase, and protoporphyrinogen oxidase); a cytochrome P450 or variant thereof that confers herbicide resistance or tolerance to, inter alia, HPPD herbicides (U.S. patent application Ser. No. 12/156,247; U.S. Pat. Nos. 6,380,465; 6,121,512; 5,349,127; 6,649,814; and 6,300,544; and PCT Patent App. Pub. No. WO2007000077); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) J. Bacteriol. 170:5837-5847) facilitate expression of polyhydroxyalkanoates (PHAs)); the disclosures of which are herein incorporated by reference.

In a particularly preferred embodiment, the plant comprises at least one additional heterologous nucleic acid comprising a nucleotide sequence encoding a herbicide tolerance enzyme selected, for example, from the group consisting of 5-enolpyruvylshikimate-3-phosphate synthase (EPSPS), Glyphosate acetyl transferase (GAT), Cytochrome P450, phosphinothricin acetyltransferase (PAT), Acetohydroxyacid synthase (AHAS; EC 4.1.3.18, also known as acetolactate synthase or ALS), Protoporphyrinogen oxidase (PPGO), Phytoene desaturase (PD) and dicamba degrading enzymes as disclosed in WO 02/068607.

Generally, the herbicidal compounds useful for the present invention may be used in conjunction with additional herbicides to which the crop plant is naturally tolerant, or to which it is resistant via expression of one or more additional transgenes, e.g. those mentioned SUPRA, or to which it is resistant via mutagenesis and breeding methods as described above in greater detail.

Preferably, herbicides that can be applied in conjunction with one or more other HPPDherbicides to obtain control of a wider variety of undesirable vegetation include sulfonamides such as metosulam, flumetsulam, cloransulam-methyl, diclosulam, penoxsulam and florasulam, sulfonylureas such as chlorimuron, tribenuron, sulfometuron, nicosulfuron, chlorsulfuron, amidosulfuron, triasulfuron, prosulfuron, tritosulfuron, thifensulfuron, sulfosulfuron and metsulfuron, imidazolinones such as imazaquin, imazapic, ima-zethapyr, imzapyr, imazamethabenz and imazamox, phenoxyalkanoic acids such as 2,4-D, MCPA, dichlorprop and mecoprop, pyridinyloxyacetic acids such as triclopyr and fluroxypyr, carboxylic acids such as clopyralid, picloram, aminopyralid and dicamba, dinitroanilines such as trifluralin, benefin, benfluralin and pendimethalin, chloroacetanilides such as alachlor, acetochlor and metolachlor, semicarbazones (auxin transport inhibitors) such as chlorflurenol and diflufenzopyr, aryloxyphenoxypropionates such as fluazifop, haloxyfop, diclofop, clodinafop and fenoxaprop and other common herbicides including glyphosate, glufosinate, acifluorfen, bentazon, clomazone, fumiclorac, fluometuron, fomesafen, lactofen, linuron, isoproturon, simazine, norflurazon, paraquat, diuron, diflufenican, picolinafen, cinidon, sethoxydim, tralkoxydim, quinmerac, isoxaben, bromoxynil, metribuzin and mesotrione, glyphosate, glufosinate.

Unless already included in the disclosure above, the additional herbicides that can be applied in conjunction with one or more other HPPD—herbicides to obtain control of a wider variety of undesirable vegetation can, further, comprise compounds:

(a) from the group of Lipid Biosynthesis Inhibitors:
Alloxydim, Alloxydim-natrium, Butroxydim, Clethodim, Clodinafop, Clodinafop-propargyl, Cycloxydim, Cyhalofop, Cyhalofop-butyl, Diclofop, Diclofop-methyl, Fenoxaprop, Fenoxaprop-ethyl, Fenoxaprop-P, Fenoxaprop-P-ethyl, Fluazifop, Fluazifop-butyl, Fluazifop-P, Fluazifop-P-butyl, Haloxyfop, Haloxyfop-methyl, Haloxyfop-P, HaloxyfopP-methyl, Metamifop, Pinoxaden, Profoxydim, Propaquizafop, Quizalofop, Quizalofopethyl, Quizalofop-tefuryl, Quizalofop-P, Quizalofop-P-ethyl, Quizalofop-P-tefuryl, Sethoxydim, Tepraloxydim, Tralkoxydim, Benfuresat, Butylat, Cycloat, Dalapon, Dimepiperat, EPTC, Esprocarb, Ethofumesat, Flupropanat, Molinat, Orbencarb, Pebulat, Prosulfocarb, TCA, Thiobencarb, Tiocarbazil, Triallat and Vernolat;

(b) from the group of Acetohydroxyacid synthase (AHAS) Inhibitors:
Amidosulfuron, Azimsulfuron, Bensulfuron, Bensulfuron-methyl, Bispyribac, Bispyribac-natrium, Chlorimuron, Chlorimuron-ethyl, Chlorsulfuron, Cinosulfuron, Cloransulam, Cloransulam-methyl, Cyclosulfamuron, Diclosulam, Ethametsulfuron, Ethametsulfuron-methyl, Ethoxysulfuron, Flazasulfuron, Florasulam, Flucarbazon, Flucarbazon-natrium, Flucetosulfuron, Flumetsulam, Flupyrsulfuron, Flupyrsulfuron-methyl-natrium, Foramsulfuron, Halosulfuron, Halosulfuron-methyl, Imazamethabenz, Imazamethabenz-methyl, Imazamox, Imazapic, Imazapyr, Imazaquin, Ima-zethapyr, Imazosulfuron, Iodosulfuron, Iodosulfuron-methyl-natrium, Mesosulfuron, Metosulam, Metsulfuron, Metsulfuron-methyl, Nicosulfuron, Orthosulfamuron, Oxasulfuron, Penoxsulam, Primisulfuron, Primisulfuron-methyl, Propoxycarbazon, Propoxycarbazon-natrium, Prosulfuron, Pyrazosulfuron, Pyrazosulfuron-ethyl, Pyribenzoxim, Pyrimisulfan, Pyriftalid, Pyriminobac, Pyriminobac-methyl, Pyrithiobac, Pyrithiobac-natrium, Pyroxsulam, Rimsulfuron, Sulfometuron, Sulfometuron-methyl, Sulfosulfuron, Thiencarbazon, Thiencarbazon-methyl, Thifensulfuron, Thifensulfuron-methyl, Triasulfuron, Tribenuron, Tribenuron-methyl, Trifloxysulfuron, Triflusulfuron, Triflusulfuron-methyl and Tritosulfuron;

(c) from the group of Photosynthesis-Inhibitors:

Ametryn, Amicarbazon, Atrazin, Bentazon, Bentazon-natrium, Bromacil, Bromofenoxim, Bromoxynil and its salts and esters, Chlorobromuron, Chloridazon, Chlorotoluron, Chloroxuron, Cyanazin, Desmedipham, Desmetryn, Dimefuron, Dimethametryn, Diquat, Diquat-dibromid, Diuron, Fluometuron, Hexazinon, Ioxynil and its salts and esters, Isoproturon, Isouron, Karbutilat, Lenacil, Linuron, Metamitron, Methabenzthiazuron, Metobenzuron, Metoxuron, Metribuzin, Monolinuron, Neburon, Paraquat, Paraquat-dichlorid, Paraquat-dimetilsulfat, Pentanochlor, Phenmedipham, Phenmedipham-ethyl, Prometon, Prometryn, Propanil, Propazin, Pyridafol, Pyridat, Siduron, Simazin, Simetryn, Tebuthiuron, Terbacil, Terbumeton, Terbuthylazin, Terbutryn, Thidiazuron and Trietazin;

d) from the group of Protoporphyrinogen-IX-Oxidase-Inhibitors:

Acifluorfen, Acifluorfen-natrium, Azafenidin, Bencarbazon, Benzfendizon, Benzoxazinone (as described in WO2010/145992) Bifenox, Butafenacil, Carfentrazon, Carfentrazon-ethyl, Chlomethoxyfen, Cinidon-ethyl, Fluazolat, Flufenpyr, Flufenpyr-ethyl, Flumiclorac, Flumiclorac-pentyl, Flumioxazin, Fluoroglycofen, Fluoroglycofen-ethyl, Fluthiacet, Fluthiacet-methyl, Fomesafen, Halosafen, Lactofen, Oxadiargyl, Oxadiazon, Oxyfluorfen, Pentoxazon, Profluazol, Pyraclonil, Pyraflufen, Pyraflufen-ethyl, Saflufenacil, Sulfentrazon, Thidiazimin, 2-Chlor-5-[3,6-dihydro-3-methyl-2,6-dioxo-4-(trifluormethyl)-1 (2H)-pyrimidinyl]-4-fluor-N-[(isopropyl)methylsulfamoyl]benzamid (H-1; CAS 372137-35-4), [3-[2-Chlor-4-fluor-5-(1-methyl-6-trifluormethyl-2,4-dioxo-1,2,3,4,-tetrahydropyrimidin-3-yl)phenoxy]-2-pyridyloxy]acetic acidethylester (H-2; CAS 353292-31-6), N-Ethyl-3-(2,6-dichlor-4-trifluormethylphenoxy)-5-methyl-1H-pyrazol-1-carboxamid (H-3; CAS 452098-92-9), N-Tetrahydrofurfuryl-3-(2,6-dichlor-4-trifluormethylphenoxy)-5-methyl-1H-pyrazol-1-carboxamid (H-4; CAS 915396-43-9), N-Ethyl-3-(2-chlor-6-fluor-4-trifluormethylphenoxy)-5-methyl-1H-pyrazol-1-carboxamid (H-5; CAS 452099-05-7) and N-Tetrahydrofurfuryl-3-(2-chlor-6-fluor-4-trifluormethylphenoxy)-5-methyl-1H-pyrazol-1-carboxamid (H-6; CAS 45100-03-7);

e) from the group of Bleacher-Herbicides:

Aclonifen, Amitrol, Beflubutamid, Benzobicyclon, Benzofenap, Clomazon, Coumarone-derivative herbicides, Diflufenican, Fluridon, Flurochloridon, Flurtamon, Isoxaflutol, Mesotrion, Norflurazon, Picolinafen, Pyrasulfutol, Pyrazolynat, Pyrazoxyfen, Sulcotrion, Tefuryltrion, Tembotrion, Topramezon, 4-Hydroxy-3-[[2-[(2-methoxyethoxy)methyl]-6-(trifluormethyl)-3-pyridyl]carbonyl]bicyclo[3.2.1]oct-3-en-2-one (H-7; CAS 352010-68-5) and 4-(3-Trifluormethylphenoxy)-2-(4-trifluormethylphenyl)pyrimidin (H-8; CAS 180608-33-7);

f) from the group of 5-enolpyruvylshikimate-3-phosphate-synthase-Inhibitors:

Glyphosat, Glyphosat-isopropylammonium and Glyphosat-trimesium (Sulfosat);

g) from the group of Glutamin-Synthase-Inhibitors:

Bilanaphos (Bialaphos), Bilanaphos-natrium, Glufosinat and Glufosinat-ammonium;

h) from the group of DHP-Synthase-Inhibitors: Asulam;

i) from the group of Mitose-Inhibitors:

Amiprophos, Amiprophos-methyl, Benfluralin, Butamiphos, Butralin, Carbetamid, Chlorpropham, Chlorthal, Chlorthal-dimethyl, Dinitramin, Dithiopyr, Ethalfluralin, Fluchloralin, Oryzalin, Pendimethalin, Prodiamin, Propham, Propyzamid, Tebutam, Thiazopyr and Trifluralin;

j) from the group of VLCFA-Inhibitors:

Acetochlor, Alachlor, Anilofos, Butachlor, Cafenstrol, Dimethachlor, Dimethanamid, Dimethenamid-P, Diphenamid, Fentrazamid, Flufenacet, Mefenacet, Metazachlor, Metolachlor, Metolachlor-S, Naproanilid, Napropamid, Pethoxamid, Piperophos, Pretilachlor, Propachlor, Propisochlor, Pyroxasulfon (KIH-485) and Thenylchlor;

Compounds of the formula 2:

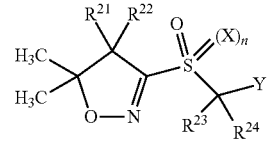

Particularly preferred Compounds of the formula 2 are:
3-[5-(2,2-Difluor-ethoxy)-1-methyl-3-trifluormethyl-1H-pyrazol-4-ylmethansulfonyl]-4-fluor-5,5-dimethyl-4,5-dihydro-isoxazol (2-1); 3-{[5-(2,2-Difluor-ethoxy)-1-methyl-3-trifluormethyl-1H-pyrazol-4-yl]-fluor-methansulfonyl}-5,5-dimethyl-4,5-dihydro-isoxazol (2-2); 4-(4-Fluor-5,5-dimethyl-4,5-dihydro-isoxazol-3-sulfonylmethyl)-2-methyl-5-trifluormethyl-2H-[1,2,3]triazol (2-3); 4-[(5,5-Dimethyl-4,5-dihydro-isoxazol-3-sulfonyl)-fluor-methyl]-2-methyl-5-trifluormethyl-2H-[1,2,3]triazol (2-4); 4-(5,5-Dimethyl-4,5-dihydro-isoxazol-3-sulfonylmethyl)-2-methyl-5-trifluormethyl-2H-[1,2,3]triazol (2-5); 3-{[5-(2,2-Difluor-ethoxy)-1-methyl-3-trifluormethyl-1H-pyrazol-4-yl]-difluor-methansulfonyl}-5,5-dimethyl-4,5-dihydro-isoxazol (2-6); 4-[(5,5-Dimethyl-4,5-dihydro-isoxazol-3-sulfonyl)-difluor-methyl]-2-methyl-5-trifluormethyl-2H[1,2,3]triazol (2-7); 3-{[5-(2,2-Difluor-ethoxy)-1-methyl-3-trifluormethyl-1H-pyrazol-4-yl]-difluor-methansulfonyl}-4-fluor-5,5-dimethyl-4,5-dihydro-isoxazol (2-8); 4-[Difluor-(4-fluor-5,5-dimethyl-4,5-dihydro-isoxazol-3-sulfonyl)-methyl]-2-methyl-5-trifluormethyl-2H-[1,2,3]triazol (2-9);

k) from the group of Cellulose-Biosynthesis-Inhibitors:

Chlorthiamid, Dichlobenil, Flupoxam and Isoxaben;

l) from the group of Uncoupling-Herbicides:

Dinoseb, Dinoterb and DNOC and its salts;

m) from the group of Auxin-Herbicides:

2,4-D and its salts and esters, 2,4-DB and its salts and esters, Aminopyralid and its salts wie Aminopyralid-tris(2-hydroxypropyl)ammonium and its esters, Benazolin, Benazolin-ethyl, Chloramben and its salts and esters, Clomeprop, Clopyralid and its salts and esters, Dicamba and its salts and esters, Dichlorprop and its salts and esters, Dichlorprop-P and its salts and esters, Fluroxypyr, Fluroxypyr-butometyl, Fluroxypyr-meptyl, MCPA and its salts and esters, MCPA-thioethyl, MCPB and its salts and esters, Mecoprop and its salts and esters, Mecoprop-P and its salts and esters, Picloram and its salts and esters, Quinclorac, Quinmerac, TBA (2,3,6) and its salts and esters, Triclopyr and its salts and esters, and 5,6-Dichlor-2-cyclopropyl-4-pyrimidincarbonic acid (H-9; CAS 858956-08-8) and its salts and esters;

n) from the group of Auxin-Transport-Inhibitors: Diflufenzopyr, Diflufenzopyr-natrium, Naptalam and Naptalam-natrium;

o) from the group of other Herbicides: Bromobutid, Chlorflurenol, Chlorflurenol-methyl, Cinmethylin, Cumyluron, Dalapon, Dazomet, Difenzoquat, Difenzoquat-metilsulfate, Dimethipin, DSMA, Dymron, Endothal and its salts, Etobenzanid, Flamprop, Flamprop-isopropyl, Flamprop-methyl Flamprop-M-isopropyl, Flamprop-M-methyl, Flurenol, Flurenol-butyl, Flurprimidol, Fosamin, Fosamine-ammonium, Indanofan, Maleinic acidhydrazid, Mefluidid, Metam, Methylazid, Methylbromid, Methyldymron, Methyljodid. MSMA, oleic acid, Oxaziclomefon, Pelargonic acid, Pyributicarb, Quinoclamin, Triaziflam, Tridiphan and 6-Chlor-3-(2-cyclopropyl-6-methylphenoxy)-4-pyridazinol (H-10; CAS 499223-49-3) and its salts and esters.

Examples for preferred Safeners C are Benoxacor, Cloquintocet, Cyometrinil, Cyprosulfamid, Dichlormid, Dicyclonon, Dietholate, Fenchlorazol, Fenclorim, Flurazol, Fluxofenim, Furilazol, Isoxadifen, Mefenpyr, Mephenat, Naphthalic acid anhydrid, Oxabetrinil, 4-(Dichloracetyl)-1-oxa-4-azaspiro[4.5]decan (H-11; MON4660, CAS 71526-07-3) and 2,2,5-Trimethyl-3-(dichloracetyl)-1,3-oxazolidin (H-12; R-29148, CAS 52836-31-4).

The compounds of groups a) to o) and the Safeners C are known Herbicides and Safeners, see e.g. The Compendium of Pesticide Common Names (www.alanwood.net/pesticides/); B. Hock, C. Fedtke, R. R. Schmidt, Herbicides, Georg Thieme Verlag, Stuttgart 1995. Other herbicidal effectors are known from WO 96/26202, WO 97/41116, WO 97/41117, WO 97/41118, WO 01/83459 and WO 2008/074991 as well as from W. Krämer et al. (ed.) "Modern Crop Protection Compounds", Vol. 1, Wiley VCH, 2007 and the literature cited therein.

Prior to application, the HPPD-inhibiting herbicide can be converted into the customary formulations, for example solutions, emulsions, suspensions, dusts, powders, pastes and granules. The use form depends on the particular intended purpose; in each case, it should ensure a fine and even distribution of the compound according to the invention.

The formulations can be prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

In general, the formulations comprise from 0.01 to 95% by weight, preferably from 0.1 to 90% by weight, of the HPPD-inhibiting herbicide. In this case, the HPPD-inhibiting herbicides are employed in a purity of from 90% to 100% by weight, preferably 95% to 100% by weight (according to NMR spectrum). For seed treatment purposes, respective formulations can be diluted 2-10 fold leading to concentrations in the ready to use preparations of 0.01 to 60% by weight active compound by weight, preferably 0.1 to 40% by weight. The HPPD-inhibiting herbicide can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the HPPD-inhibiting herbicide according to the invention. Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water. The active compound concentrations in the ready-to-use preparations can be varied within relatively wide ranges. In general, they are from 0.0001 to 10%, preferably from 0.01 to 1% per weight. The HPPD-inhibiting herbicide may also be used successfully in the ultra-low-volume process (ULV), it being possible to apply formulations comprising over 95% by weight of active compound, or even to apply the active compound without additives. Suitable formulations are described in detail in PCT/EP2009/063387 and PCT/EP2009/063386, which are incorporated herein by reference.

In other aspects, a method for treating a plant of the present invention is provided. In some embodiments, the method comprises contacting the plant with an agronomically acceptable composition as defined above.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a HPPD-inhibiting herbicides herbicidal composition to the descendent plant.

In another embodiment, the invention refers to harvestable parts of the transgenic plant according to the present invention. Preferably, the harvestable parts comprise the mutated HPPD nucleic acid or mutated HPPD protein of the present invention. The harvestable parts may be seeds, roots, leaves and/or flowers comprising the mutated HPPD nucleic acid or mutated HPPD protein or parts thereof. Preferred parts of soy plants are soy beans comprising the mutated HPPD nucleic acid or mutated HPPD protein.

In another embodiment, the invention refers to products derived from a transgenic plant according to the present invention, parts thereof or harvestable parts thereof. A preferred product is meal or oil, preferably, soybean meal or soybean oil. Preferably, the soybean meal and/or oil comprises the mutated HPPD nucleic acid or mutated HPPD protein.

In another embodiment, the invention refers to a method for the production of a product, which method comprises
a) growing the plants of the invention or obtainable by the methods of invention and
b) producing said product from or by the plants of the invention and/or parts, e.g. seeds, of these plants.

In a further embodiment the method comprises the steps
a) growing the plants of the invention,
b) removing the harvestable parts as defined above from the plants and
c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

In another embodiment, the present invention relates to a kit comprising the nucleic acid molecule, the vector, the host cell, the polypeptide, plant cell, the plant or plant tissue, the harvestable part, the propagation material and/or the compound and/or agonist identified according to the method of the invention.

The compounds of the kit of the present invention may be packaged in containers such as vials, optionally with/in buffers and/or solution. If appropriate, one or more of said components might be packaged in one and the same container. Additionally or alternatively, one or more of said components might be adsorbed to a solid support as, e.g. a nitrocellulose filter, a glas plate, a chip, or a nylon membrane or to the well of a micro titerplate. The kit can be used for any of the herein described methods and embodiments, e.g. for the production of the host cells, transgenic plants, detection of homologous sequences, identification of antagonists or agonists, as food or feed or as a supplement thereof or as supplement for the treating of plants, etc. Further, the kit can comprise instructions for the use of the kit for any of said embodiments. In one embodiment said kit comprises further a nucleic acid molecule encoding one or more of the aforementioned protein, a vector, a host cell, a plant cell or plant tissue or a plant. In another embodiment said kit comprises PCR primers to detect and discrimante the nucleic acid molecule to be reduced in the process of the invention, e.g. of the nucleic acid molecule of the invention.

In a further embodiment, the present invention relates to a method for the production of an agricultural composition providing the nucleic acid molecule for the use according to the process of the invention, the nucleic acid molecule of the invention, the vector of the invention, or the polypeptide of the invention and formulating the nucleic acid molecule, the vector or the polypeptide of the invention in a form applicable as plant agricultural composition.

In another embodiment, the present invention relates to a method for the production of the plant culture composition comprising the steps of the method of the present invention; and formulating the compound identified in a form acceptable as agricultural composition.

Under "acceptable as agricultural composition" is understood, that such a composition is in agreement with the laws regulating the content of fungicides, plant nutrients, herbicides, etc. Preferably such a composition is without any harm for the protected plants and the animals (humans included) fed therewith. Said polypeptide or nucleic acid molecule or the genomic structure of the genes encoding said polypeptide or nucleic acid molecule of the invention.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes and variations may be made therein without departing from the scope of the invention. The invention is further illustrated by the following examples, which are not to be construed in any way as limiting. On the contrary, it is to be clearly understood that various other embodiments, modifications and equivalents thereof, which, after reading the description herein, may suggest themselves to those skilled in the art without departing from the spirit of the present invention and/or the scope of the claims.

EXAMPLES

Example 1: Sequencing and Full Length Assembly of *Scenedesmus, Helianthus* and *Lemna* HPPD Genes Isolation of RNA and cDNA synthesis Leaf tissue of *Scenedesmus obliquus, Helianthus annus* and *Lemna paucicosata* were harvested, frozen and grounded in liquid nitrogen and total RNA was extracted using an Ambion RNAqueous-Midi kit (AM1911, Ambion) with the Plant RNA Isolation Aid (AM9690, Ambion) as per manufacturer's recommendation. The last elution was done with 10 ul of elution solution. To validate the quality of the extracted RNA 1 uL of the final product was run on a Bioanalyzer 2100 using the RNA 6000 Nano kit with the Plant RNA Nano method. The final solution, containing purified RNA, was stored at −80° C. until library preparation.

To identify ortholge HPPD genes of *Scenedesmus obliquus* (Götingen, Germany) degenerated PCR primer are defined from conserved regions of HPPD protein alignment. Forward primers for HPPD are generated from consensus sequence S-G-L-N-S-A/M/V-V-L-A (SEQ ID NO: 43 reverse primers are derived from consensus sequence C-G-G-F-G-K-G-N-F (SEQ ID NO: 44; Table X2). Based on the received HPPD gene sequence tags, protein coding sequence are completed by adapter PCR or TAIL PCR techniques as described by Liu and Whittier (1995, Genomics 25: 674-681) and Yuanxin et al. (2003 Nuc Acids Research 31: 1-7) or Spertini et al. (1999 Biotechniques 27: 308-314) on copy DNA or genomic DNA. This strategy resulted in Scendesmus HPPD full length SEQUENCE No. 1 and derived amino acid SEQUENCE ID No. 2.

TABLE 4

PCR primer for partial amplification of SoHPPD

| Primer name | Primer sequence (5'-3') | SEQ ID NO: |
|---|---|---|
| So_Deg_HPPD_Fw | WSNGGNYTNAAYWSNRYNGTNYTNGC | 45 |
| So_Deg_HPPD_Rv | RAARTTNCCYTTNCCRAANCCNCCRC | 46 |

A similar strategy was used for *Helianthus annuus* HPPD sequence. Based on a EST fragments found in genebank (genebank ID: CD847425, BU029179), HPPD full length gene sequence were amplified by RACE PCR (18373-019 and 18374-058, life technologies) as per manufacturer recommendation.

For assembly of *Lemna paucicostata* HPPD gene, an RNA sequencing experiment was performed. RNA sequencing libraries were produced using TruSeq RNA Sample preparation kits V2 (RS-122-2001) from Illumina according to the instructions of the manufacturer. Briefly, 1 μg of total RNA was first purified twice on a poly-dT column. During the second elution step, RNA was fragmented and primed for cDNA synthesis. The material was reverse transcribed, RNA was removed and the second strand was produced. After rendering the ends of the fragment blunt, 3' ends were adenylated and Illumina sequencing-specific bar-coded adaptors were ligated at both ends of the fragments. The DNA fragments bearing adaptors at both ends were enriched by a 15 cycle PCR amplification. Libraries are pooled prior to sequencing. The pooled libraries were first put on a flowcell using a TruSeq PE Cluster kit V3 (PE-401-3001) on the cBot and clusters are amplified on the device. Afterwards, the flowcell is transferred onto the Illumina Hiseq machine and the material on the flowcell is then sequenced using Illumina TruSeq SBS Kit V3 (FC-401-3001) as per manufacturer's recommendation.

The data produced by the Illumina Hiseq sequencer was first trimmed at both ends using a quality threshold of 15 using the FASTQC Quality Trimmer (www.bioinformatics.babraham.ac.uk/projects/fastqc/). These sequences were further analyzed to remove any Illumina adaptor sequences using CutAdapt (code.google.com/p/cutadapt/). Sequence reads were assembled using CLC bio algorithm (version 4.01). The HPPD full length gene sequence (SEQUENCE ID 7) was identified by performing a BLAST search with *Arabidopsis thaliana* HPPD sequence as query and the Lemna CLC bio assembly as database.

Example 2: Cloning of HPPD Encoding Genes and Mutants

All wild type HPPD encoding genes and mutants thereof were synthesized by an external service provider and subcloned into a modified pET24D (Novagen) expression vector resulting in N-terminally His-tagged expression constructs.

Example 3 Heterologous Expression and Purification of Recombinant Mutated HPPD Enzymes Recombinant mutated HPPD enzymes are produced and overexpressed in *E. coli* Chemically competent BL21 (DE3) cells (Invitrogen, Carlsbad, USA) are transformed with pEXP5-NT/TOPO® (see EXAMPLE 2) or with other expression vectors according to the manufacturer's instructions.

Transformed cells are grown in autoinduction medium (ZYM 5052 supplemented with 100 μg/ml ampicillin) for 6 h at 37° C. followed by 24 h at 25° C.

At an OD600 (optical density at 600 nm) of 8 to 12, cells are harvested by centrifugation (8000×g). The cell pellet is resuspended in a lysis buffer (50 mM sodium phosphate buffer, 0.5 M NaCl, 10 mM Imidazole, pH 7.0) supplemented with complete EDTA free protease inhibitor mix (Roche-Diagnostics) and homogenized using an Avestin Press. The homogenate is cleared by centrifugation (40,000× g). $His_6$-tagged HPPD or mutant variants are purified by affinity chromatography on a Protino Ni-IDA 1000 Packed Column (MachereyNagel) according to the manufacturer's instructions. Purified HPPD or mutant variants are dialyzed against 100 mM sodium phosphate buffer pH 7.0, supplemented with 10% glycerin and stored at −86° C. Protein content is determined according to Bradford using the Bio-Rad protein assay (Bio-Rad Laboratories, Hercules, USA). The purity of the enzyme preparation is estimated by SDS-PAGE.

Example 4: Assay for HPPD Activity

HPPD produces homogentisic acid and $CO_2$ from 4-hydroxyphenylpyruvate (4-HPP) and $O_2$. The activity assay for HPPD is based on the analysis of homogentisic acid by reversed phase HPLC.

The assay mixture can contain 150 mM potassium phosphate buffer pH 7.0, 50 mM L-ascorbic acid, 100 μM Catalase (Sigma-Aldrich), 1 μM $FeSO_4$ and 0.2 units of purified mutated HPPD enzyme in a total volume of 505 μl. 1 unit is defined as the amount of enzyme that is required to produce 1 nmol of HGA per minute at 20° C.

After a preincubation of 30 min the reaction is started by adding 4-HPP to a final concentration of 0.05 mM. The reaction is allowed to proceed for 45 min at room temperature. The reaction is stopped by the addition of 50 μl of 4.5 M phosphoric acid. The sample is filtered using a 0.2 μM pore size PVDF filtration device.

5 μl of the cleared sample is analyzed on an UPLC HSS T3 column (particle size 1.8 μm, dimensions 2.1×50 mm; Waters) by isocratic elution using 90% 20 mM $NaH_2PO_4$ pH 2.2, 10% methanol (v/v).

HGA is detected electrochemically at 750 mV (mode: DC; polarity: positive) and quantified by integrating peak areas (Empower software; Waters).

Inhibitors are dissolved in DMSO (dimethylsulfoxide) to a concentration of 0.5 mM. From this stock solution serial five-fold dilutions are prepared in DMSO, which are used in the assay. The respective inhibitor solution accounts for 1% of the assay volume. Thus, final inhibitor concentrations range from 5 µM to 320 pM, respectively. Activities are normalized by setting the uninhibited enzyme activity to 100%. $IC_{50}$ values are calculated using non-linear regression.

Example 5: In Vitro Characterization of Mutated HPPD Enzymes

Using methods which are described in the above examples or well known in the art, purified, recombinant mutated HPPD enzymes are characterized with respect to their kinetic properties and sensitivity towards HPPD inhibiting herbicides. Apparent michaelis constants ($K_m$) and maximal reaction velocities ($V_{max}$) are calculated by non-linear regression with the software GraphPad Prism 5 (GraphPad Software, La Jolla, USA) using a substrate inhibition model. Apparent $k_{cat}$ values are calculated from $V_{max}$ assuming 100% purity of the enzyme preparation. Weighted means (by standard error) of $K_m$ and $IC_{50}$ values are calculated from at least three independent experiments. The Cheng-Prusoff equation for competitive inhibition (Cheng, Y. C.; Prusoff, W. H. Biochem Pharmacol 1973, 22, 3099-3108) is used to calculate dissociation constants ($K_i$).

Field performance of the HPPD enzyme, which is used as a herbicide tolerance trait may depend not only on its lack of sensitivity towards HPPD inhibiting herbicides but also on its activity. To assess the potential performance of a herbicide tolerance trait a tolerance index (TI) is calculated using the following formula:

$$TI = \frac{k_{cat} \times K_i}{K_m}$$

Easy comparison and ranking of each trait is enabled by normalizing tolerance indexes on *Arabidopsis* wild-type HPPD.

Examples of the data obtained in an in vitro assay are depicted in Table 5 and in Table 6.

TABLE 5

Determination of michaelis constants ($K_m$) for 4-HPP, turnover numbers ($k_{cat}$), catalytic efficiencies ($k_{cat}/K_m$), dissociation constants ($K_i$) and tolerance indexes (TI) for various HPPD enzymes.

| Enzyme | $K_m$ [µM] (4-HPP) | $k_{cat}$ [s$^{-1}$] | $k_{cat}/K_m$ [µM$^{-1}$ s$^{-1}$] | $K_i$ [nM] (Inhibitor 1)* | $K_i$ [nM] (Inhibitor 3)* | TI (Inhibitor 1)* | TI (Inhibitor 3)* |
|---|---|---|---|---|---|---|---|
| *Arabidopsis* | 13 | 12.9 | 1 | 0.95 | 29 | 0.95E−3 | 23.8E−3 |
| *Scenedesmus* | 160 | 6 | 0.038 | 11 | 110 | 0.42E−3 | 4.41E−3 |
| *Scendesmus* Short | 89 | 17 | 0.191 | 46 | 580 | 8.85E−3 | 110E−3 |

*HPPD inhibiting herbicides used in this example are [3-(4,5-dihydroisoxazol-4-yl)-2-methyl-4-methylsulfonyl-phenyl]-(5-hydroxy-1-methyl-pyrazol-4-yl)methanone (Inhibitor 1) and (N-[2,6-dichloro-3-(8-hydroxy-5,5-dimethyl-6,6-dioxo-thiopyrano[4,3-b]pyridin-7-yl)phenyl]-N-methyl-methanesulfonamide) (Inhibitor 3).

TABLE 6

Normalized tolerance indexes of various HPPD enzymes.

| HPPD Enzyme (SEQ ID NO:) | TI Inhibitor 1* | TI Inhibitor 2* | TI Inhibitor 3* | TI Inhibitor 4* | TI Inhibitor 5* | TI Inhibitor 6* | TI Inhibitor 7* | TI Inhibitor 8* | TI Inhibitor 9* |
|---|---|---|---|---|---|---|---|---|---|
| *Arabidopsis* (Seq ID: 42) | 1.0 | 1.0 | 1.0 | 1.0 | 1.0 | 1.0 | 1.0 | 1.0 | 1.0 |
| *Scenedesmus* (Seq ID: 2) | 0.4 | 0.5 | 0.2 | 0.1 | 0.0 | 0.3 | 0.1 | 0.1 | 0.1 |
| *Scenedesmus* Short (Seq ID: 4) | 9.3 | 0.0 | 4.6 | 1.4 | 1.3 | 6.6 | 0.4 | 0.9 | 1.2 |
| SoHPPD L367V, I375L (short) | 3.6 | 0.0 | 1.0 | 0.3 | 0.3 | 2.1 | 0.4 | 0.7 | 0.4 |
| SoHPPD F39W, L367V, I375L (short) | 1.2 | 0.0 | 0.5 | 0.2 | 0.1 | 0.7 | 0.2 | 0.5 | 0.2 |
| SoHPPD E345Q (short) | 0.7 | 0.5 | 0.6 | 0.3 | 0.2 | 1.2 | 0.1 | 0.5 | 0.2 |
| SoHPPD K326E, E345Q (short) | 0.3 | 0.0 | 0.1 | 0.0 | 0.0 | 0.2 | 0.1 | 0.1 | 0.1 |
| SoHPPD A318P, A319P (short) | 4.6 | 0.2 | 2.0 | 0.6 | 0.5 | 3.3 | 0.6 | 0.8 | 0.7 |
| SoHPPD V251A (short) | 0.5 | 0.0 | 0.1 | 0.0 | 0.0 | 0.4 | 0.0 | 0.1 | 0.1 |
| SoHPPD Q317M (short) | 13.8 | 0.6 | 4.1 | 1.3 | 0.9 | 8.7 | 0.9 | 0.8 | 1.1 |
| SoHPPD Q317H (short) | 6.1 | 0.2 | 2.0 | 0.6 | 0.4 | 4.1 | 1.4 | 0.5 | 0.7 |
| SoHPPD E379Q (short) | 0.7 | 0.0 | 0.2 | 0.1 | 0.0 | 0.5 | 0.2 | 0.4 | 0.2 |

TABLE 6-continued

Normalized tolerance indexes of various HPPD enzymes.

| HPPD Enzyme (SEQ ID NO:) | TI Inhibitor 1* | TI Inhibitor 2* | TI Inhibitor 3* | TI Inhibitor 4* | TI Inhibitor 5* | TI Inhibitor 6* | TI Inhibitor 7* | TI Inhibitor 8* | TI Inhibitor 9* |
|---|---|---|---|---|---|---|---|---|---|
| SoHPPD A318R, L350M (short) | 12.9 | 0.8 | 2.5 | 1.0 | 0.7 | 8.6 | 0.7 | 1.2 | 1.2 |
| SoHPPD Q317H, A318G, E345Q (short) | 11.3 | 0.4 | 3.5 | 1.4 | 0.9 | 7.0 | 1.3 | 1.0 | 0.9 |
| SoHPPD F363I (short) | 16.0 | 0.8 | 1.7 | 0.3 | 0.6 | no inhibition | 1.7 | no inhibition | no inhibition |
| SoHPPD I419V (short) | 0.8 | 0.1 | 0.9 | 0.3 | 0.1 | 1.5 | 0.2 | 0.3 | 0.3 |
| SoHPPD I455V | 3.3 | 0.1 | 1.4 | 0.5 | 0.7 | 2.1 | 0.3 | 0.3 | 0.4 |
| SoHPPD H306K (short) | 1.6 | 0.1 | 0.8 | 0.3 | 0.2 | 1.2 | 0.2 | 0.3 | 0.2 |
| SoHPPD F363I | 4.0 | 0.1 | 0.8 | 0.1 | 0.4 | 61.1 | 0.2 | no inhibition | 2.7 |
| SoHPPD A318R, L350M | 3.8 | 0.1 | 1.0 | 0.3 | 0.2 | 1.3 | 0.1 | 0.2 | 0.2 |
| SoHPPD Q317H, A318G, E345Q | 1.9 | 0.1 | 1.0 | 0.4 | 0.2 | 0.8 | 0.1 | 0.1 | 0.1 |
| SoHPPD Q317H | 1.9 | 0.1 | 0.8 | 0.3 | 0.2 | 1.0 | 0.1 | 0.1 | 0.1 |
| SoHPPD L367V, I375L | 1.2 | 0.0 | 0.5 | 0.2 | 0.1 | 0.6 | 0.0 | 0.0 | 0.1 |
| SoHPPD V251A, H306R, Q317L, A318P, G321P, K331E, L350M (short) | 11.5 | 0.7 | 1.1 | 0.0 | 0.3 | 18.3 | 0.1 | 0.2 | n.d. |
| SoHPPD R327G, E421D (short) | 4.0 | 0.2 | 1.2 | 0.0 | 0.3 | 2.7 | 0.5 | 0.5 | n.d. |
| SoHPPD E345Q, K326D (short) | 2.1 | 0.1 | 0.8 | 0.0 | 0.2 | 1.2 | 0.3 | 0.3 | n.d. |
| SoHPPD E345Q, K326Q (short) | 1.8 | 0.1 | 0.5 | 0.0 | 0.2 | 1.1 | 0.2 | 0.3 | n.d. |

*HPPD inhibiting herbicides used in this example are [3-(4,5-dihydroisoxazol-3-yl)-2-methyl-4-methylsulfonyl-phenyl]-(5-hydroxy-1-methyl-pyrazol-4-yl)methanone (Inhibitor 1), 2-(4-methylsulfonyl-2-nitro-benzoyl)cyclohexane-1,3-dione (Inhibitor 2), N-[2,6-dichloro-3-(8-hydroxy-5,5-dimethyl-6,6-dioxo-thiopyrano[4,3-b]pyridin-7-yl)phenyl] -N-methyl-methanesulfonamide (Inhibitor 3), 7-[2-ethylsulfonyl-4-(trifluoromethyl)phenyl]-5,5-dimethyl-6,6-dioxo-thiopyrano[4,3-b]pyridin-8-ol (Inhibitor 4), N-[2,6-dichloro-3-(8-hydroxy-5,5-dimethyl-6,6-dioxo-thiopyrano[4,3-b]pyridin-7-yl)phenyl]-N-methyl-acetamide (Inhibitor 5), 2-methyl-N-(4-methyl-1,2,5-oxadiazol-3-yl)-3,4-bis(methylsulfonyl)benzamide (Inhibitor 6), 2,4-dichloro-6-fluoro-3-methylsulfanyl-N-(1-methyltetrazol-5-yl)benzamide (Inhibitor 7), 2,6-dichloro-3-ethylsulfanyl-N-(1-methyltetrazol-5-yl)benzamide (Inhibitor 8), 2,4-dichloro-3-ethylsulfinyl-6-fluoro-N-(1-methyltetrazol-5-yl)benzamide (Inhibitor 9), n.d. not determined.

A number of conclusions can be derived from the data in Table 6. The reference HPPD enzyme SEQ ID NO:42 was included as a comparative control in a representative number of experiments and the TI values given for various mutant HPPD enzymes based on the amino acid sequence of Scenedesmus obliquus are normalized to the value of the benchmark enzyme (SEQ ID NO:42). The properties of HPPD mutants indicated that certain amino acid substitutions within the coding sequence provided significant improvements relative to HPPD SEQ ID NO: 42 in respect to the tolerance indexes against HPPD-inhibiting herbicides.

It can be seen from the above example that an HPPD enzyme can be selected as one which is tolerant to different classes of HPPD-inhibiting herbicides as it can be observed that the tolerance index of this enzyme exceeded the tolerance index of the benchmark enzyme. For example, the mutant with amino acid glutamine 317 exchanged to methionine is useful as a gene conferring herbicide tolerance in the present invention because the in vitro tolerance index was improved compared to the benchmark enzyme.

In detail, it can be observed that the mutant HPPD enzyme Q317M had a 13.8-fold tolerance to Inhibitor 1, 4.1-fold to Inhibitor 3, and 8.7-fold to Inhibitor 6. In addition, the polynucleotide comprising the sequence of Scenedesmus HPPD with glutamine 317 exchanged to methionine, alanine 318 substituted by glycine and glutamate 345 mutated to glutamin conferred resistance to Inhibitor 1, Inhibitor 3, Inhibitor 4, Inhibitor 6 and Inhibitor 7 and hence is a particularly preferred embodiment of the present invention.

It can be further seen that the polynucleotide that encodes a variant of the Scenedesmus HPPD short (SEQ ID NO:4) with amino acid phenylalanine 363 exchanged to isoleucine is of particular interest because this HPPD enzyme showed an excellent tolerance against HPPD Inhibitor 1 and was not inhibited by Inhibitor 6, Inhibitor 8 and Inhibitor 9 tested in the present invention. Thus, this enzyme is highly tolerant to HPPD-inhibiting substances and is especially preferred to generate plants that are resistant to different classes of HPPD-inhibiting herbicides. In addition to that, a variant of the full-length sequence of Scenedesmus obliquus (SEQ ID NO: 2) in which phenylalanine 363 was exchanged by isoleucine resulted in an increased tolerance to Inhibitor 1 (4-fold), Inhibitor 6 (61.1-fold), Inhibitor 8 (no inhibition), and Inhibitor 9 (2,7.fold) compared to the reference Enzyme SEQ ID NO: 42.

In addition, a variant of the Scenedesmus HPPD short (SEQ ID NO:4) comprising the combined mutation of alanine at position 318 to arginine together with the exchange of leucine at position 350 to methionine resulted in a significant improvement of the HPPD enzyme because the mutated HPPD enzyme had an improved behavior against HPPD-inhibiting herbicides tested in the present invention and its tolerance index increased 12.9-fold for Inhibitor 1 and 8.6-fold for Inhibitor 6 compared to the reference HPPD SEQ ID NO:42.

Furthermore, a polynucleotide which encodes a variant of the *Scenedesmus* HPPD short (SEQ ID NO:4) where glutamine 317 exchanged to histidine, alanine 318 substituted by glycine, and glutamate 345 mutated to glutamine can be selected as a transgene that encodes an inhibitor-resistant HPPD because it is found that the tolerance index of the mutant was significantly improved to Inhibitor 1 (11.3-fold tolerance) and Inhibitor 6 (7-fold tolerance) tested in the present invention.

In addition, it can be seen from the results depicted in Table 8 that the combined substitutions of several amino acids (valine 251 to alanine, histidine 306 to arginine, glutamine 317 to leucine, alanine 318 to proline, glycine 321 to proline, lysin 331 to glutamate and leucine 350 to methionine) in a variant of the *Scenedesmus* HPPD short (SEQ ID NO:4) provided a significant improvement compared to the benchmark enzyme (SEQ ID NO:42). In detail, the combined mutation resulted in a 11.5-fold tolerance to Inhibitor 1 and a 18.2-fold tolerance to Inhibitor 6. Thus, this mutant can be selected as a mutant which encodes an inhibitor-resistant HPPD and is useful for generating herbicide tolerant plants.

Example 6: Engineering Herbicide Tolerant Plants Having Additional HPPD-Encoding Sequences Various methods for the production of stably transformed plants are well known in the art. HPPD-inhibiting herbicide tolerant soybean (*Glycine max*) or corn (*Zea mays*) plants can be produced by a method described by Olhoft et al. (US patent 2009/0049567). Briefly, HPPD encoding polynucleotides are cloned into a binary vector using standard cloning techniques as described by Sambrook et al. (Molecular cloning (2001) Cold Spring Harbor Laboratory Press). The final vector construct contains an HPPD encoding sequence flanked by a promoter sequence (e.g. the ubiquitin promoter (PcUbi) sequence) and a terminator sequence (e.g. the nopaline synthase terminator (NOS) sequence) and a resistance marker gene cassette (e.g. AHAS) (FIG. 2). Optionally, the HPPD gene can provide the means of selection.

*Agrobacterium*-mediated transformation is used to introduce the DNA into soybean's axillary meristem cells at the primary node of seedling explants. After inoculation and co-cultivation with Agrobacteria, the explants are transferred to shoot induction medium without selection for one week. The explants are subsequently transferred to shoot induction medium with 1-3 μM imazapyr (Arsenal) for 3 weeks to select for transformed cells. Explants with healthy callus/shoot pads at the primary node are then transferred to shoot elongation medium containing 1-3 μM imazapyr until a shoot elongates or the explant dies. After regeneration, transformants are transplanted to soil in small pots, placed in growth chambers (16 hr day/8 hr night; 25° C. day/23° C. night; 65% relative humidity; 130-150 mE m−2 s−1) and subsequently tested for the presence of the T-DNA via Taqman analysis. After a few weeks, healthy, transgenic positive, single copy events are transplanted to larger pots and allowed to grow in the growth chamber.

Transformation of corn plants is done by a method described by McElver and Singh (WO 2008/124495). Plant transformation vector constructs containing HPPD sequences are introduced into maize immature embryos via *Agrobacterium*-mediated transformation. Transformed cells are selected in selection media supplemented with 0.5-1.5 μM imazethapyr for 3-4 weeks. Transgenic plantlets are regenerated on plant regeneration media and rooted afterwards. Transgenic plantlets are subjected to TaqMan analysis for the presence of the transgene before being transplanted to potting mixture and grown to maturity in greenhouse.

*Arabidopsis thaliana* is transformed with HPPD sequences by floral dip method as decribed by McElver and Singh (WO 2008/124495). Transgenic *Arabidopsis* plants are subjected to TaqMan analysis for analysis of the number of integration loci.

Transformation of *Oryza sativa* (rice) are done by protoplast transformation as decribed by Peng et al. (U.S. Pat. No. 6,653,529)

T0 or T1 transgenic plant of soybean, corn, rice and *Arabidopsis thaliana* containing HPPD sequences are tested for improved tolerance to "HPPD-inhibiting herbicides" in germination assays or greenhouse studies (EXAMPLE 7).

Example 7: Demonstration of Herbicide Tolerance

Transgenic T1 or T2 plants of soybean, corn, rice or *Arabidopsis* expressing heterologous HPPD enzymes are tested for tolerance against HPPD-inhibiting herbicides, including [3-(4,5-dihydroisoxazol-3-yl)-2-methyl-4-methylsulfonyl-phenyl]-(5-hydroxy-1-methyl-pyrazol-4-yl)methanone, 2-(4-methylsulfonyl-2-nitro-benzoyl)cyclohexane-1, 3-dione, N-[2,6-dichloro-3-(8-hydroxy-5,5-dimethyl-6,6-dioxo-thiopyrano[4,3-b]pyridin-7-yl)phenyl]-N-methyl-methanesulfonamide, 7-[2-ethylsulfonyl-4-(trifluoromethyl) phenyl]-5,5-dimethyl-6,6-dioxo-thiopyrano[4,3-b]pyridin-8-ol, N-[2,6-dichloro-3-(8-hydroxy-5,5-dimethyl-6,6-dioxo-thiopyrano[4,3-b]pyridin-7-yl)phenyl]-N-methyl-acetamide, 2-methyl-N-(4-methyl-1,2,5-oxadiazol-3-yl)-3, 4-bis(methylsulfonyl)benzamide, 2,4-dichloro-6-fluoro-3-methylsulfanyl-N-(1-methyltetrazol-5-yl)benzamide, 2,6-dichloro-3-ethylsulfanyl-N-(1-methyltetrazol-5-yl) benzamide, 2,4-dichloro-3-ethylsulfinyl-6-fluoro-N-(1-methyltetrazol-5-yl)benzamide, (1R,5S)-3-[2-(2-methoxyethoxymethyl)-6-(trifluoromethyl)pyridine-3-carbonyl]bicyclo[3.2.1]oct-2-en-4-one, 2-chloro-3-methylsulfanyl-N-(1-methyltetrazol-5-yl)-4-(trifluoromethyl)benzamide, and 2-[8-chloro-4-(4-methoxyphenyl)-3-oxo-quinoxaline-2-carbonyl] cyclohexane-1,3-dione, in greenhouse experiments.

For the pre-emergence treatment, the herbicides are applied directly after sowing by means of finely distributing nozzles. The containers are irrigated gently to promote germination and growth and subsequently covered with transparent plastic hoods until the plants have rooted. This cover causes uniform germination of the test plants, unless this has been impaired by the herbicides.

For post emergence treatment, the test plants are first grown to a height of 3 to 15 cm, depending on the plant habit, and only then treated with the herbicides. For this purpose, the test plants are either sown directly and grown in the same containers, or they are first grown separately and transplanted into the test containers a few days prior to treatment.

For testing of T0 plants, cuttings can be used. In the case of soybean plants, an optimal shoot for cutting is about 7.5 to 10 cm tall, with at least two nodes present. Each cutting is taken from the original transformant (mother plant) and dipped into rooting hormone powder (indole-3-butyric acid, IBA). The cutting is then placed in oasis wedges inside a bio-dome. Wild type cuttings are also taken simultaneously to serve as controls. The cuttings are kept in the bio-dome for 5-7 days and then transplanted to pots and then acclimated in the growth chamber for two more days. Subsequently, the cuttings are transferred to the greenhouse, acclimated for approximately 4 days, and then subjected to spray tests as indicated. Depending on the species, the plants are kept at 10-25° C. or 20-35° C. The test period extends over 3 weeks. During this time, the plants are tended and their response to the individual treatments is evaluated. Herbicide injury evaluations are taken at 2 and 3 weeks after treatment. Plant injury is rated on a scale of 0 to 9, 0 being no injury and 9 being complete death.

Tolerance to HPPD-inhibiting herbicides can also be assessed in *Arabidopsis*. In this case transgenic *Arabidopsis thaliana* plants are assayed for improved tolerance to HPPD-inhibiting herbicides in 48-well plates (germination assay). Seeds are surface sterilized by stirring for 5 min in ethanol+ water (70+30 by volume), rinsing one time with ethanol+ water (70+30 by volume) and two times with a sterile, deionized water. The seeds are resuspended in 0.1% agar dissolved in water (w/v). Four to five seeds per well are plated on solid nutrient medium consisting of half-strength Murashige Skoog nutrient solution, pH 5.8 (Murashige and Skoog (1962) Physiologia Plantarum 15: 473-497). Compounds are dissolved in dimethylsulfoxid (DMSO) and added to the medium prior solidification (final DMSO concentration 0.1%). Multi well plates are incubated in a growth chamber at 22° C., 75% relative humidity and 110 µmol Phot*m−2*s−1 with 14:10 h light:dark photoperiod. Growth inhibition is evaluated seven to ten days after seeding in comparison to wild type plants. Tolerance factor is calculated by dividing the plant growth $IC_{50}$ value of transgenic plants containing a HPPD sequence by that of wildtype plants.

Additionally, T1 and T2 transgenic *Arabidopsis* plants can be tested for improved tolerance to HPPD-inhibiting herbicides in greenhouse studies. Herbicide injury scoring is done 2-3 weeks after treatment and is rated on a scale of 0 to 100%, 0% being no injury and 100% being complete death.

TABLE 7

Tolerance factor of HPPD overexpressing *Arabidopsis* plants based on germination in the presence of [3-(4,5-dihydroisoxazol-3-yl)-2-methyl-4-methylsulfonyl-phenyl]-(5-hydroxy-1-methyl-pyrazol-4-yl)methanone. The tolerance factor is a mean value from 5 T2 events evaluated in parallel and non-transgenic event is set to 1.

| *Arabidopsis* overexpression line | Tolerance factor Inhibitor 1* |
|---|---|
| SoHPPD (SEQ ID NO: 2) | 92 |
| SoHPPD (SEQ ID NO: 4) | 82 |
| SoHPPD Q317H (short) | 100 |
| SoHPPD_F363I (short) | 1000 |
| SoHPPD Q317H, A318G, E345Q (short) | 50 |
| SoHPPD I419V (short) | 100 |
| SoHPPD I455V | 7 |

Compared to the non-transgenic control, the results demonstrate that all plants comprising a polynucleotide encoding mutated versions of *Scenedesmus* HPPD had an increased tolerance to HPPD-inhibiting herbicide.

It can be seen from the results depicted in Table 7 that the substitution of isoleucine at position 455 in SEQ ID NO:2 with valine provided a 7-fold tolerance to Inhibitor 1. In addition, the corresponding amino acid exchange in the short version of *Scenedesmus obliquus* HPPD (I419V) resulted in a 100-fold tolerance to Inhibitor 1 and those mutants are of particular interest of the present invention.

Furthermore, a variant of SoHPPD-short (SEQ ID NO:4) comprising the combined mutation of glutamine 317 to histidine, alanine 318 exchanged by glycine and glutamate 345 substituted with glutamine resulted in a 50-fold tolerance to Inhibitor 1 compared to untransformed wildtype plants. The single substitution of glutamine 317 by histidine was found to be highly tolerant to the tested HPPD inhibiting herbicide resulting in a tolerance index of 100.

In addition, the highest score of tolerance was assessed for a variant of SoHPPD-short (SEQ ID NO:4), the single mutant carrying the amino acid substitution phenylalanine 363 exchanged by isoleucine. This mutant is of particular interest as the tolerance factor to Inhibitor 1 is 1000-fold improved compared to the non-transgenic control plants. Therefore it is evident that transgenic *Arabidopsis* lines transformed with polynucleotides encoding variants of *Scenedesmus* HPPD are particularly preferred embodiments of the present invention as those plants had an increased tolerance to HPPD-inhibiting herbicides and can be used to generate HPPD-inhibiting herbicide tolerant crop plants.

Transgenic T1 *Arabidopsis* plants were sprayed with the indicated amount of HPPD inhibiting herbicide. The T1 spray application is a fast method to evaluate the potential of transgenic traits even though a segregating population and only one event of respective traits is tested. Exemplary results are depicted in FIG. 3 and it can be seen that in comparison to non-transgenic control plants, all variants of *Scenedesmus* HPPD resulted in a good to excellent tolerance to the HPPD-inhibiting herbicide tested.

Figure 3:
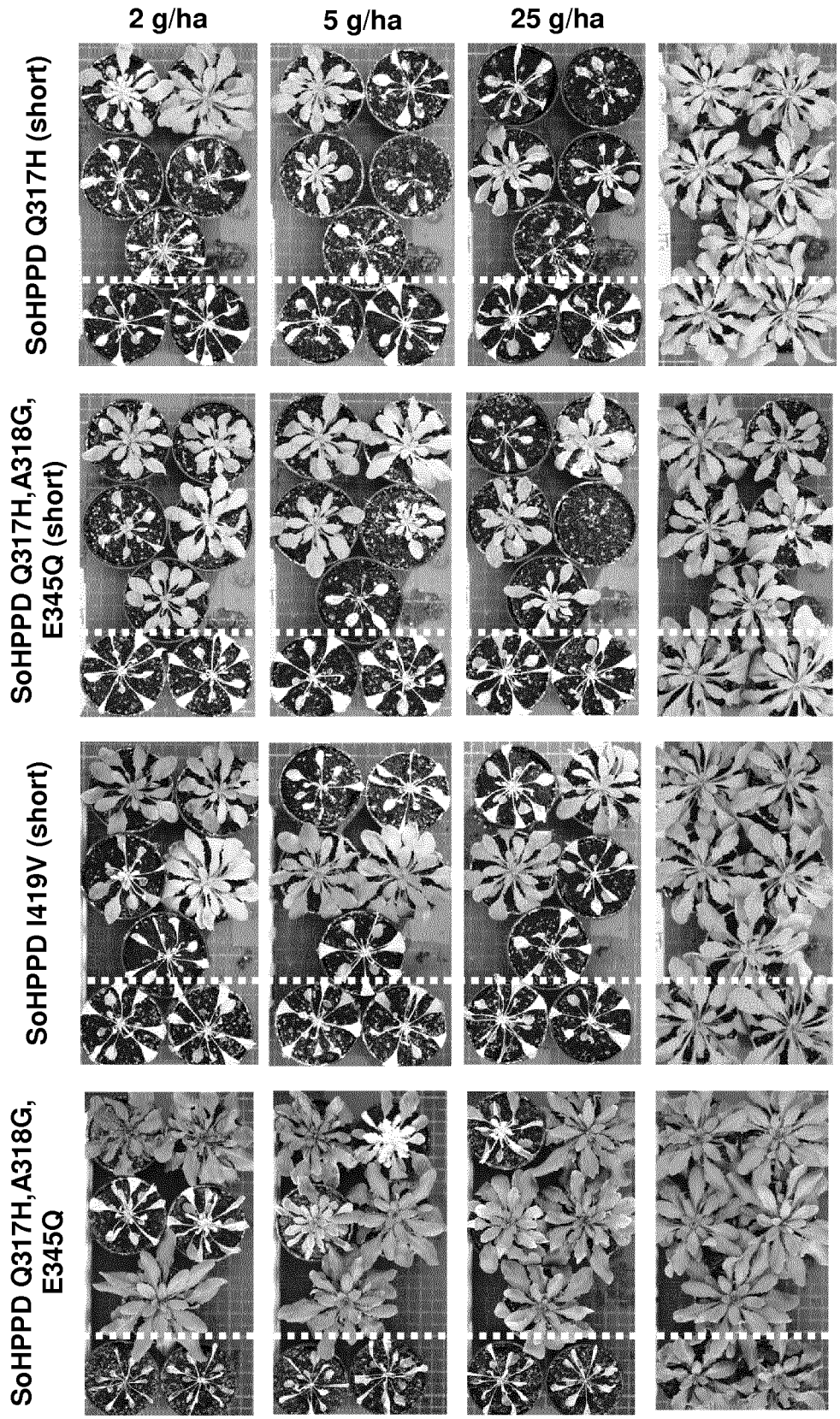
FIG. 3 shows transgenic T1 *Arabdiopsis* plants treated with the indicated spray rate (g ai/ha) of [3-(4,5-dihydroisoxazol-3-yl)-2-methyl-4-methylsulfonyl-phenyl]-(5-hydroxy-1-methyl-pyrazol-4-yl)methanone herbicide. Wildtype plants were sprayed in parallel at each application rate (two lower pots below dashed line) whereas T1 plants are represented by the five upper pots. Pictures were taken 8 days after treatment.
Figure 3:
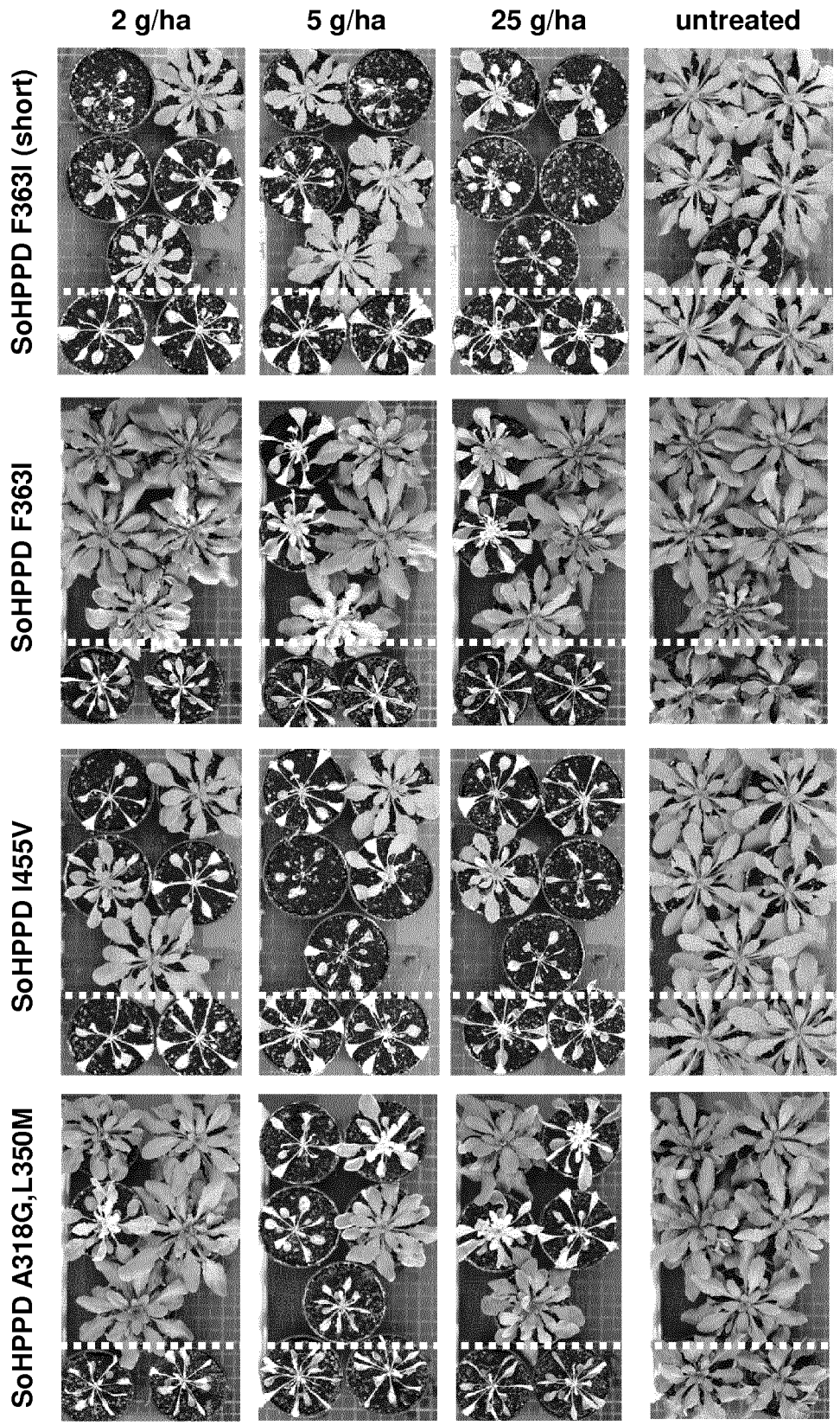

Several conclusions can be derived from FIG. 3. *Scenedesmus* HPPD containing the combined mutation of glutamine 317 to histidine, alanine 318 exchanged by glycine and glutamate 345 substituted with glutamine in SEQ ID NO: 2 (short) and SEQ ID NO:4 was found to be highly resistant to the tested HPPD inhibitor at all application rates.

Furthermore, a good tolerance to Inhibitor 1 was found for the variant of *Scenedesmus* HPPD carrying the combined mutation alanine 318 exchanged by glycine and leucine 350 substituted with methionine. An especially preferred embodiment refers to the *Scenedesmus* HPPD variant in which phenylalanine 363 is exchanged by isoleucine as this mutant is highly tolerant to Inhibitor 1 at the highest application rate and can be used to generate HPPD-inhibiting herbicide tolerant crop plants.

Figure 4:
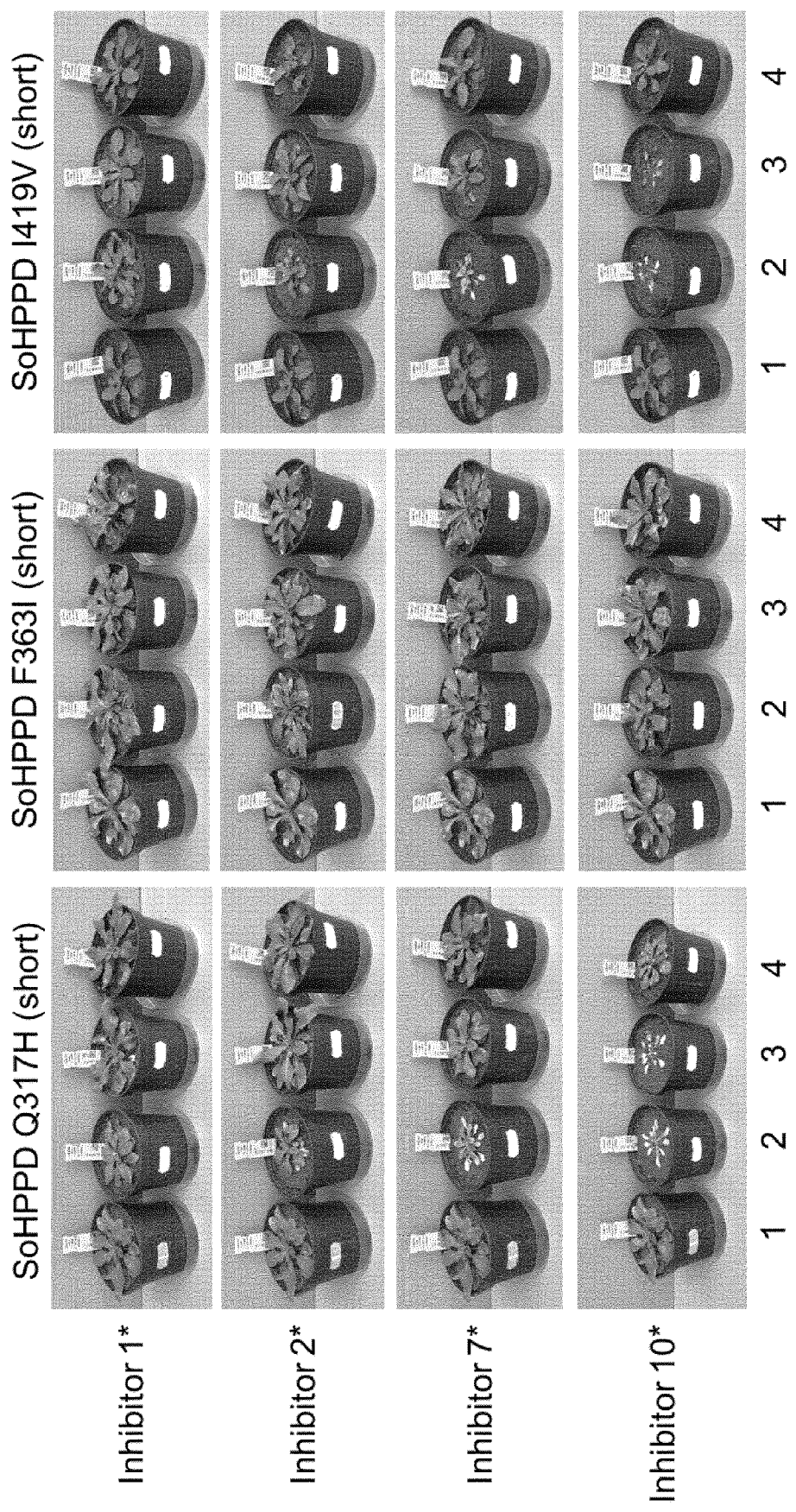
FIG. 4 shows a herbicide spray test with transgenic T2 Arabidopsis plants expressing mutated variants of Scenedesmus HPPD. Non-transgenic control plants were treated in parallel and pictures taken 14 days after treatment. Plants were sprayed with different concentrations of [3-(4,5-dihydroisoxazol-3-yl)-2-methyl-4-methylsulfonyl-phenyl]-(5-hydroxy-1-methyl-pyrazol-4-yl)methanone (Inhibitor 1), 2-(4-methylsulfonyl-2-nitro-benzoyl)cyclohexane-1,3-dione (Inhibitor 2), 2,4-dichloro-6-fluoro-3-methylsulfanyl-N-(1-methyltetrazol-5-yl)benzamide (Inhibitor 7) and 2-chloro-3-methylsulfanyl-N-(1-methyltetrazol-5-yl)-4-(trifluoromethyl)benzamide (Inhibitor 10).

Transgenic T2 *Arabidopsis* plants were sprayed with a range of doses from 1.56-25 g/ha of different HPPD-inhibiting herbicides and injury evaluations were taken two weeks after treatment (FIG. 4). As depicted in Table 8, control plants were severely injured by all doses of herbicides applied, with at least 58% of leaf material being damaged at the lowest application rate and 100% leaf damage at the second application rate.

Compared to the control, plants expressing mutated variants of *Scenedesmus* HPPD were highly tolerant to Inhibitor 1 because all traits and events had no damage (0-8%) at the two lowest application rates and less than 20% of leaf material being damaged after application of 25 g/ha. A similar rating is found for Inhibitor 2 because the tested transgenic events did not show leaf injury after spray application of 1.56 g/ha and 6.25 g/ha, respectively. Using the highest application rate (25 g ai/ha) of Inhibitor 2 resulted in leaf injury with an average damage of 34% for the mutant expressing *Scenedesmus* HPPD Q317H whereas the mutant I419V was more severely damaged resulting in an average injury rate of 75%.

The variant of the *Scenedesmus* HPPD of SEQ ID NO: 4 comprising the single amino acid substitution phenylalanine 363 substituted by isoleucine is a particularly preferred embodiment of the present invention as this mutant was highly resistant to all inhibitors tested. In addition to the outstanding performance of SoHPPD F363I regarding Inhibitor 1 and Inhibitor 2, this particular mutant is highly tolerant to Inhibitors 7 and 11 showing no damage at the highest application rate for the former one and only an average damage of 10% for the latter one, respectively. It can be seen (Table 8 and FIG. 4) that short SoHPPD F363I is particularly useful to generate plants resistant to HPPD-inhibiting herbicides. The corresponding pictures can be seen in FIG. 4.

TABLE 8

Table 8: Greenhouse testing of transgenic *Arabidopsis* plants (T2) comprising polynucleotide sequences encoding mutated variants of *Scenedesmus* HPPD short (SEQ ID NO: 4). Injury evaluations were taken two weeks after herbicide treatment. Representative results are shown in FIG. 4.

| | | | 14 DAT | | | | | |
| | | | SoHPD Q317H | | SoHPPD I419V Event | | SoHPPD F363I | |
| compound | g ai/ha | WT | B | C | G | H | B | C |
| Inhibitor 1* | 25 | 100 | 18 | 10 | 13 | 13 | 0 | 0 |
| | 6.25 | 100 | 0 | 0 | 8 | 0 | 0 | 0 |
| | 1.56 | 75 | 0 | 0 | 5 | 0 | 0 | 0 |
| Inhibitor 2* | 25 | 100 | 33 | 35 | 95 | 58 | 3 | 0 |
| | 6.25 | 100 | 0 | 3 | 0 | 8 | 0 | 0 |
| | 1.56 | 58 | 0 | 0 | 0 | 5 | 0 | 5 |
| Inhibitor 7* | 25 | 100 | 78 | 73 | 40 | 93 | 0 | 0 |
| | 6.25 | 100 | 18 | 8 | 28 | 53 | 5 | 0 |
| | 1.56 | 88 | 0 | 0 | 0 | 5 | 0 | 0 |
| Inhibitor 11* | 25 | 100 | 100 | 100 | 100 | 100 | 15 | 5 |
| | 6.25 | 100 | 99 | 79 | 83 | 100 | 0 | 0 |
| | 1.56 | 100 | 40 | 15 | 58 | 43 | 0 | 8 |

The invention claimed is:

1. An isolated and/or recombinantly produced and/or synthetic nucleic acid molecule comprising a nucleic acid molecule encoding a mutated HPPD polypeptide having 75% or more identity with the amino acid sequence of the HPPD polypeptide sequence of SEQ ID NO: 2 or 4 and conferring increased herbicide tolerance or resistance to a plant cell, plant or part thereof transformed therewith as compared to a corresponding, non-transformed, wild type plant cell, a plant or a part thereof;

wherein the mutated HPPD polypeptide has a substitution of one or more amino acids corresponding to or at positions 30, 39, 54, 57, 84, 210, 212, 223, 243, 247, 249, 251, 264, 291, 306, 317, 318, 319, 321, 326, 327, 331, 341, 342, 345, 350, 363, 367, 373, 374, 375, 379, 405, 412, 414, 419, 421, or 422 of SEQ ID NO:4.

2. A nucleic acid construct which comprises and confers the expression of said nucleic acid molecule of claim 1, comprising one or more regulatory elements.

3. A vector comprising the nucleic acid molecule of claim 1.

4. A mutated HPPD polypeptide encoded by the nucleic acid molecule of claim 1.

5. The isolated and/or recombinantly produced and/or synthetic nucleic acid molecule of claim 1, wherein the nucleic acid molecule encodes a mutated HPPD polypeptide having 85% or more identity with the amino acid sequence of the HPPD polypeptide sequence of SEQ ID NO: 2 or 4,
wherein the mutated HPPD polypeptide has a substitution of one or more amino acids corresponding to or at positions 30, 39, 54, 57, 84, 210, 212, 223, 243, 247, 249, 251, 264, 291, 306, 317, 318, 319, 321, 326, 327, 331, 341, 342, 345, 350, 363, 367, 373, 374, 375, 379, 405, 412, 414, 419, 421, or 422 of SEQ ID NO:4.

6. The isolated and/or recombinantly produced and/or synthetic nucleic acid molecule of claim 1, wherein the nucleic acid molecule encodes a mutated HPPD polypeptide having 90% or more identity with the amino acid sequence of the HPPD polypeptide sequence of SEQ ID NO: 2 or 4,
wherein the mutated HPPD polypeptide has a substitution of one or more amino acids corresponding to or at positions 30, 39, 54, 57, 84, 210, 212, 223, 243, 247, 249, 251, 264, 291, 306, 317, 318, 319, 321, 326, 327, 331, 341, 342, 345, 350, 363, 367, 373, 374, 375, 379, 405, 412, 414, 419, 421, or 422 of SEQ ID NO:4.

7. The isolated and/or recombinantly produced and/or synthetic nucleic acid molecule of claim 1, wherein the nucleic acid molecule encodes a mutated HPPD polypeptide having 95% or more identity with the amino acid sequence of the HPPD polypeptide sequence of SEQ ID NO: 2 or 4,
wherein the mutated HPPD polypeptide has a substitution of one or more amino acids corresponding to or at positions 30, 39, 54, 57, 84, 210, 212, 223, 243, 247, 249, 251, 264, 291, 306, 317, 318, 319, 321, 326, 327, 331, 341, 342, 345, 350, 363, 367, 373, 374, 375, 379, 405, 412, 414, 419, 421, or 422 of SEQ ID NO:4.

* * * * *